US012806292B2

(12) United States Patent
Moullier et al.

(10) Patent No.: US 12,806,292 B2

(45) Date of Patent: Nov. 24, 2026

(54) METHODS OF RECOMBINANT ADENO-ASSOCIATED VIRUS KIDNEY ADMINISTRATION

(71) Applicant: ASKBIO INC., Research Triangle Park, NC (US)

(72) Inventors: Philippe Moullier, Paris (FR); Sherif Gabriel, Research Triangle Park, NC (US); Patrick Deacon, Research Triangle Park, NC (US); Kathleen Boerner, Research Triangle Park, NC (US)

(73) Assignee: ASKBIO INC., Research Triangle Park (NC)

( * ) Notice: Subject to any disclaimer, the term of this patent is extended or adjusted under 35 U.S.C. 154(b) by 0 days.

(21) Appl. No.: 18/955,455

(22) Filed: Nov. 21, 2024

(65) Prior Publication Data

US 2025/0121097 A1 Apr. 17, 2025

Related U.S. Application Data

(63) Continuation of application No. PCT/US2024/031768, filed on May 30, 2024.

(60) Provisional application No. 63/578,838, filed on Aug. 25, 2023, provisional application No. 63/469,766, filed on May 30, 2023.

(51) Int. Cl.

*A61K 48/00* (2006.01)

*C12N 15/86* (2006.01)

(52) U.S. Cl.

CPC .......... *A61K 48/0058* (2013.01); *C12N 15/86* (2013.01); *C12N 2750/14143* (2013.01); *C12N 2750/14171* (2013.01)

(58) Field of Classification Search

CPC .... C12N 15/86; C12N 5/0686; A61K 35/768; A61P 13/12

See application file for complete search history.

(56) References Cited

U.S. PATENT DOCUMENTS

| | | | |
|---|---|---|---|
| 9,193,956 | B2 | 11/2015 | Schaffer et al. |
| 10,077,291 | B2 | 9/2018 | Asokan et al. |
| 10,550,405 | B2 | 2/2020 | Li et al. |
| 11,059,862 | B2 | 7/2021 | Asokan et al. |
| 11,608,510 | B2 | 3/2023 | Pekrun et al. |
| 12,049,478 | B2 | 7/2024 | Asokan et al. |
| 2014/0155468 | A1 | 6/2014 | Gregory et al. |
| 2015/0374851 | A1 | 12/2015 | Lipschutz et al. |
| 2020/0024616 | A1 | 1/2020 | Pekrun et al. |
| 2021/0115091 | A1 | 4/2021 | Asokan et al. |
| 2021/0115473 | A1 | 4/2021 | Bennett et al. |
| 2022/0354969 | A1 | 11/2022 | Nakai et al. |
| 2023/0107173 | A1 | 4/2023 | Haas et al. |

FOREIGN PATENT DOCUMENTS

| | | | | |
|---|---|---|---|---|
| WO | 2008/150459 | A1 | 12/2008 | |
| WO | 2013159036 | A1 | 10/2013 | |
| WO | 2013/170078 | A1 | 11/2013 | |
| WO | 2014144229 | A1 | 9/2014 | |
| WO | 2017/189959 | A1 | 11/2017 | |
| WO | 2017/189963 | A1 | 11/2017 | |
| WO | 2017/189964 | A2 | 11/2017 | |
| WO | 2020/212626 | A1 | 10/2020 | |
| WO | 2020/227515 | A1 | 11/2020 | |
| WO | 2022003357 | A1 | 1/2022 | |
| WO | 2022/155435 | A1 | 7/2022 | |
| WO | 2022175546 | A1 | 8/2022 | |
| WO | WO-2022204535 | A1 * | 9/2022 | ......... A61K 48/0016 |
| WO | 2022/221529 | A1 | 10/2022 | |
| WO | 2023/196619 | A1 | 10/2023 | |
| WO | 2024/050039 | A2 | 3/2024 | |
| WO | 2024206226 | A1 | 10/2024 | |
| WO | 2024226664 | A2 | 10/2024 | |
| WO | 2025/019295 | A2 | 1/2025 | |

OTHER PUBLICATIONS

Rubin et al. Improving Molecular Therapy in the Kidney. Molecular Diagnosis & Therapy 2020, 24:375-396. (Year: 2020).*

Konkalmatt et al. Renal rescue of dopamine D2 receptor function reverses renal injury and high blood pressure. Journal of Clinical Investigation 2016, 1;18:e85888. (Year: 2016).*

Peek et al. Cell and gene therapy for kidney disease. Nature Reviews in Nephrology 2023, 19;7:451-462. (Year: 2023).*

Agarwal et al., "Renal cell markers: lighthouses for managing renal diseases," Am J Physiol Renal Physiol. 321(6): F715-F739 (2021).

Alechinsky et al., "Tannic acid improves renal function recovery after renal warm ischemia-reperfusion in a rat model." Biomolecules 10.3: 439 (2020).

Alshrari et al., "Innovations and development of COVID-19 vaccines: A patent review." Journal of infection and public health 15.1: 123-131 (2022).

Asico et al., "Nephron segment-specific gene expression using AAV vectors." Biochemical and biophysical research communications 497.1: 19-24 (2018).

Baatartsogt et al., "A sensitive and reproducible cell-based assay via secNanoLuc to detect neutralizing antibody against adeno-associated virus vector capsid." Molecular Therapy Methods & Clinical Development 22: 162-171 (2021).

(Continued)

*Primary Examiner* — Christopher M Babic

*Assistant Examiner* — Jennifer S Spence

(74) *Attorney, Agent, or Firm* — Nixon Peabody LLP; Ronald I. Eisenstein; Alissa R. Young

(57) ABSTRACT

The technology described herein is directed to methods of administering a recombinant adeno-associated virus (rAAV) to a kidney of a subject using a retrograde ureter route. Such administration methods can be used to treat a kidney-associated disorder in a subject in need thereof. Also described herein are pharmaceutical compositions comprising a recombinant adeno-associated virus (rAAV) for administration to the kidney.

23 Claims, 50 Drawing Sheets

Specification includes a Sequence Listing.

(56) References Cited

OTHER PUBLICATIONS

Balzer et al., "How many cell types are in the kidney and what do they do?" Annual review of physiology 84.1: 507-531 (2022).
Boletta, "Reversing polycystic kidney disease." Nature Genetics 53.12: 1623-1624 (2021).
Chen et al., "Gene delivery in renal tubular epithelial cells using recombinant adeno-associated viral vectors." Journal of the American Society of Nephrology 14.4: 947-958 (2003).
Chung et al., "Adeno-associated virus-mediated gene transfer to renal tubule cells via a retrograde ureteral approach." Nephron Extra 1.1: 217-223 (2011).
Dalkara et al., "In vivo-directed evolution of a new adeno-associated virus for therapeutic outer retinal gene delivery from the vitreous." Science translational medicine 5.189: 189ra76 (2013).
Davis et al., "Gene therapy research for kidney diseases." Physiological Genomics 51.9: 449-461 (2019).
Dong et al. "Renal plasticity revealed through reversal of polycystic kidney disease in mice." Nature genetics 53.12: 1649-1663 (2021).
Downie et al., "Inherited tubulopathies of the kidney: insights from genetics." Clinical Journal of the American Society of Nephrology 16.4: 620-630 (2021).
Gao et al., "Clades of Adeno-associated viruses are widely disseminated in human tissues." Journal of virology 78.12: 6381-6388 (2004).
Grimm et al., "In vitro and in vivo gene therapy vector evolution via multispecies interbreeding and retargeting of adeno-associated viruses." Journal of virology 82.12: 5887-5911 (2008).
Hemphill et al., "Adeno-associated viral vectors show serotype specific transduction of equine joint tissue explants and cultured monolayers." Scientific reports 4.1: 5861 (2014).
Hinderer et al., "Severe toxicity in nonhuman primates and piglets following high-dose intravenous administration of an adeno-associated virus vector expressing human SMN." Human gene therapy 29.3: 285-298 (2018).
Ikeda et al., "Efficient gene transfer to kidney mesenchymal cells using a synthetic adeno-associated viral vector." Journal of the American Society of Nephrology 29.9: 2287-2297(2018).
Konkalmatt et al., "Renal rescue of dopamine D2 receptor function reverses renal injury and high blood pressure." JCI insight 1.8: e85888 (2016).
Korneyenkov et al., "Next step in gene delivery: modern approaches and further perspectives of AAV tropism modification." Pharmaceutics 13.5: 750 (2021).
Livrozet et al., "An animal model of type A cystinuria due to spontaneous mutation in 129S2/SvPasCrl mice." PLoS One 9.7: e102700 (2014).
Mao et al., "Single point mutation in adeno-associated viral vectors-DJ capsid leads to improvement for gene delivery in vivo." BMC biotechnology 16: 1-8 (2016).
Meliani et al., "Determination of anti-adeno-associated virus vector neutralizing antibody titer with an in vitro reporter system." Human gene therapy methods 26.2: 45-53 (2015).
Moullier et al. "Adenoviral-mediated gene transfer to renal tubular cells in vivo." Kidney international 45.4: 1220-1225 (1994).
Oyama et al., "Effects of tissue pressure on transgene expression characteristics via renal local administration routes from ureter or renal artery in the rat kidney." Pharmaceutics 12.2: 114 (2020).
Pauchard et al., "A practical guide for intra-renal temperature and pressure management during RIRS: what is the evidence telling us." Journal of Clinical Medicine 11.12: 3429 (2022).
Pekrun et al., "Using a barcoded AAV capsid library to select for clinically relevant gene therapy vectors." JCI insight 4.22: e131610 (2019).
Rocca et al., "rAAV9 combined with renal vein injection is optimal for kidney-targeted gene delivery: conclusion of a comparative study." Gene therapy 21.6: 618-628 (2014).
Rubin et al., "Comparison of gene delivery to the kidney by adenovirus, adeno-associated virus, and lentiviral vectors after intravenous and direct kidney injections." Human gene therapy 30.12: 1559-1571 (2019).
Rubin et al., "Improving molecular therapy in the kidney." Molecular diagnosis & therapy 24.4: 375-396 (2020).
Samulski et al., "Rescue of adeno-associated virus from recombinant plasmids: gene correction within the terminal repeats of AAV." Cell 33.1: 135-143 (1983).
Schoenmaker et al., "mRNA-lipid nanoparticle COVID-19 vaccines: Structure and stability." International journal of pharmaceutics 601: 120586 (2021).
Schulz et al., "Binding and neutralizing anti-AAV antibodies: Detection and implications for rAAV-mediated gene therapy." Molecular Therapy 31.3: 616-630 (2023).
Shen et al., "Engraftment of a galactose receptor footprint onto adeno-associated viral capsids improves transduction efficiency." Journal of Biological Chemistry 288.40: 28814-28823 (2013).
Shen. "Understanding and manipulating AAV-glycan interactions." Dissertation. The University of North Carolina at Chapel Hill, (2013).
Shen et al., "Transparenchymal renal pelvis injection of recombinant adeno-associated virus serotype 9 vectors is a practical approach for gene delivery in the kidney." Human gene therapy methods 29.6: 251-258 (2018).
Suzuki et al., "Difference in the lipid nanoparticle technology employed in three approved siRNA (Patisiran) and mRNA (COVID-19 vaccine) drugs." Drug Metabolism and Pharmacokinetics 41: 100424 (2021).
Tenchov et al. "Lipid nanoparticles—from liposomes to mRNA vaccine delivery, a landscape of research diversity and advancement." ACS nano 15.11: 16982-17015 (2021).
Watanabe et al., "Targeting gene expression to specific cells of kidney tubules in vivo, using adenoviral promoter fragments." PLoS One 12.3: e0168638 (2017).
Wang et al. "Impact of pre-existing immunity on gene transfer to nonhuman primate liver with adeno-associated virus 8 vectors." Human Gene Therapy 22: 1389-1401 (2011).
Li et al. "Efficient and Targeted Transduction of Nonhuman Primate Liver with Systemically Delivered Optimized AAV3B Vectors." Mol Ther. 23: 1867-1876 (2015).
Furusho et al., "Enhancing gene transfer to renal tubules and podocytes by context-dependent selection of AAV capsids." bioRxiv (Jul. 29, 2023) available on the world wide web at https://www.biorxiv.org/content/10.1101/2023.07.28.548760v1.
Schreiber. "Hitting the Kidney from All Angles: Using Direct Intrarenal Pelvis Injection Combined with Serotype and Promoter Targeting to Achieve Renal AAV Gene Delivery" Molecular Therapy: Abstract 307 (2016).
Porrett et al. "First clinical-grade porcine kidney xenotransplant using a human decedent model." Am J Transplant 22(4):1037-1053 (2022).

* cited by examiner

Library exposed left kidney

Unexposed right kidney

Punch # 24
Contralateral
(Unexposed)

Punch # 24
Treated

| Kidney gDNA | VG/Diploid Genome |
|---|---|
| Con-RU13 | 0.001 |
| 2G9-RU13 | 0.016 |
| Con-RU14 | 0.000 |
| 2G9-RU14 | 0.059 |

| Protein Kidney | RLU/mg Protein |
|---|---|
| Con-RU13 | 777.8 |
| 2G9-RU13 | 8.81E+6 |
| Con-RU14 | 573.3 |
| 2G9-RU14 | 8.78E+6 |

| Kidney cDNA | Relative Fold-Change |
|---|---|
| Con-RU13 | 3.49 |
| 2G9-RU13 | 7103.7 |
| Con-RU14 | 1.16 |
| 2G9-RU14 | 30733.8 |
| NoRT | 2.15 |

| Liver gDNA | VG/Diploid Genome |
|---|---|
| Con-RU13 | 0.001 |
| 2G9-RU13 | 0.000 |
| Con-RU14 | 0.000 |
| 2G9-RU14 | 0.000 |

| Protein Liver | RLU/mg Protein |
|---|---|
| Con-RU13 | 1186.7 |
| 2G9-RU13 | 10355 |
| Con-RU14 | 400 |
| 2G9-RU14 | 7243.3 |

| Liver cDNA | Relative Fold-Change |
|---|---|
| Con-RU13 | 2.17 |
| 2G9-RU13 | 0.07 |
| Con-RU14 | 1.05 |
| 2G9-RU14 | 1.35 |
| NoRT | 2.15 |

Posterior Superior

Anterior Superior

Posterior Inferior

Anterior Inferior

Anterior Inferior

Anterior Inferior

NHP_RU2 CT

| Sample: | eGFP CT | GAPDH CT |
|---|---|---|
| NHP_Con_RU2 Kidney | 39.64 | 17.12 |
| NHP_Con_RU2 Liver | 39.36 | 18.71 |
| NHP_2G9_RU2 Kidney | **19.76** | 17.12 |
| NHP_2G9_RU2 Liver | 28.27 | 18.23 |
| NHP_Con_RU2 NoRT | 39.78 | 39.80 |
| NHP_2G9_RU2 NoRT | 33.18 | 39.88 |
| NTC | 40 | 40 |

| | NHP_2G9_RU1 | | | |
|---|---|---|---|---|
| Biopsy # | DNA (vg/dg) | RNA (cDNA Relative Fold-Change) | Protein (RLU/mg) | % GFP+ PCT |
| Kidney 1 | 8.44E+00 | 6.79E+06 | 1.68E+08 | |
| Kidney 2 | 1.44E+01 | 1.35E+07 | 1.43E+08 | 8.49E+01 |
| Kidney 3 | 2.93E+01 | 1.36E+07 | 2.23E+08 | |
| Kidney 4 | 6.25E+00 | 4.72E+06 | 5.31E+07 | |
| Kidney 5 | 1.46E+01 | 6.67E+06 | 1.44E+08 | |
| Kidney 6 | 2.12E+01 | 7.45E+06 | 1.67E+08 | |
| Kidney 7 | 3.95E+00 | 4.51E+06 | 3.77E+07 | |
| Kidney 8 | 5.28E+00 | 6.11E+06 | 1.22E+08 | 6.73E+01 |
| Kidney 9 | 1.75E-02 | 1.68E+04 | 6.85E+05 | |
| Kidney 10 | 6.05E+01 | 3.53E+07 | 3.18E+08 | 8.49E+01 |
| Kidney 11 | 2.17E+00 | 2.36E+06 | 6.33E+07 | 6.73E+01 |

| | NHP_2G9_RU2 | | | |
|---|---|---|---|---|
| Biopsy # | DNA (vg/dg) | RNA (cDNA Relative Fold-Change) | Protein (RLU/mg) | % GFP+ PCT |
| Kidney 1 | 4.63E+01 | 1.10E+07 | 2.71E+08 | |
| Kidney 2 | 1.05E+00 | 2.09E+05 | 5.29E+06 | |
| Kidney 3 | 1.24E+00 | 3.81E+04 | 1.08E+06 | 4.15E+01 |
| Kidney 4 | 1.69E+01 | 5.20E+06 | 1.50E+08 | |
| Kidney 5 | 1.02E+01 | 9.71E+05 | 9.71E+07 | |
| Kidney 6 | 6.52E-01 | 4.20E+04 | 1.92E+06 | |
| Kidney 7 | 2.99E+01 | 7.01E+06 | 1.43E+08 | |
| Kidney 8 | 2.56E+01 | 6.02E+06 | 1.93E+08 | |
| Kidney 9 | 5.24E+00 | 2.08E+06 | 5.55E+07 | 6.31E+01 |
| Kidney 10 | 7.12E-01 | 8.69E+04 | 2.25E+06 | 4.15E+01 |
| Kidney 11 | 2.63E+01 | 4.72E+06 | 1.81E+08 | 6.31E+01 |

Lowest Highest

Fig. 7K

| NHP_2G9_RU1 | | | NHP_2G9_RU2 | | |
|---|---|---|---|---|---|
| RANK | Biopsy # | DNA (vg/dg) | RANK | Biopsy # | DNA (vg/dg) |
| 1 | Kidney 10 | **6.05E+01** | 1 | Kidney 1 | **4.63E+01** |
| 2 | Kidney 3 | **2.93E+01** | 2 | Kidney 7 | **2.99E+01** |
| 3 | Kidney 6 | **2.12E+01** | 3 | Kidney 11 | **2.63E+01** |
| 4 | Kidney 5 | **1.46E+01** | 4 | Kidney 8 | **2.56E+01** |
| 5 | Kidney 2 | **1.44E+01** | 5 | Kidney 4 | **1.69E+01** |
| 6 | Kidney 1 | 8.44E+00 | 6 | Kidney 5 | **1.02E+01** |
| 7 | Kidney 4 | 6.25E+00 | 7 | Kidney 9 | 5.24E+00 |
| 8 | Kidney 8 | 5.28E+00 | 8 | Kidney 3 | 1.24E+00 |
| 9 | Kidney 7 | 3.95E+00 | 9 | Kidney 2 | 1.05E+00 |
| 10 | Kidney 11 | 2.17E+00 | 10 | Kidney 10 | 7.12E-01 |
| 11 | Kidney 9 | 1.75E-02 | 11 | Kidney 6 | 6.52E-01 |

vg/dg>1.00E+01
1.00E+01>vg/dg>1.00E+00
1.00E+00>vg/dg>1.00E-01
1.00E-01>vg/dg>1.00E-02
1.00E-02>vg/dg>1.00E-03

Fig. 7L

| NHP_2G9_RU1 | | |
|---|---|---|
| RANK | Biopsy # | Protein (RLU/mg) |
| 1 | Kidney 10 | **3.18E+08** |
| 2 | Kidney 3 | **2.23E+08** |
| 3 | Kidney 1 | **1.68E+08** |
| 4 | Kidney 6 | **1.67E+08** |
| 5 | Kidney 5 | **1.44E+08** |
| 6 | Kidney 2 | **1.43E+08** |
| 7 | Kidney 8 | **1.22E+08** |
| 8 | Kidney 11 | 6.33E+07 |
| 9 | Kidney 4 | 5.31E+07 |
| 10 | Kidney 7 | 3.77E+07 |
| 11 | Kidney 9 | 6.85E+05 |

| NHP_2G9_RU2 | | |
|---|---|---|
| RANK | Biopsy # | Protein (RLU/mg) |
| 1 | Kidney 1 | **2.71E+08** |
| 2 | Kidney 8 | **1.93E+08** |
| 3 | Kidney 11 | **1.81E+08** |
| 4 | Kidney 4 | **1.50E+08** |
| 5 | Kidney 7 | **1.43E+08** |
| 6 | Kidney 5 | 9.71E+07 |
| 7 | Kidney 9 | 5.55E+07 |
| 8 | Kidney 2 | 5.29E+06 |
| 9 | Kidney 10 | 2.25E+06 |
| 10 | Kidney 6 | 1.92E+06 |
| 11 | Kidney 3 | 1.08E+06 |

RLU > 1.00E+08
1.00E+08 > RLU > 1.00E+07
1.00E+07 > RLU > 1.00E+06
1.00E+06>RLU>1.00E+05
1.00E+05>RLU>1.00E+04

Fig. 7M

| Serum Dilution (Interpolated) | Pre_Ru 1 (Entered) | Post_Ru 1 (Entered) |
|---|---|---|
| 512.375 | 0.500 | |
| 75885.430 | | 0.500 |

| Serum Dilution (Interpolated) | Pre_Ru 2 (Entered) | Post_Ru 2 (Entered) |
|---|---|---|
| 15.160 | 0.500 | |
| 2360.453 | | 0.500 |

| Sample | Titer |
|---|---|
| **Ru1- Pre** | **1: 512** |
| Ru1-Post | 1: 75,885 |
| **Ru2-Pre** | **1: 15** |
| Ru2-Post | 1: 2360 |

| Sample: | Average RLU/mg |
|---|---|
| Con-RU26 Kidney | 2.82E+02 |
| Con-RU26 Liver | 1.78E+02 |
| 2G9-RU26 Kidney | 6.20E+05 |
| 2G9-RU26 Liver | 7.34E+03 |

METHODS OF RECOMBINANT ADENO-ASSOCIATED VIRUS KIDNEY ADMINISTRATION

CROSS-REFERENCE TO RELATED APPLICATIONS

This application is a continuation under 35 U.S.C. § 120 of International Application No. PCT/US2024/031768, filed May 30, 2024, which designates the U.S., and which claims benefit under 35 U.S.C. § 119(e) of U.S. Provisional Application No. 63/469,766 filed May 30, 2023, and U.S. Provisional Application No. 63/578,838 filed Aug. 25, 2023, the contents of each of which are incorporated herein by reference in their entireties.

SEQUENCE LISTING

The instant application contains a Sequence Listing which has been submitted in XML format via Patent Center and is hereby incorporated by reference in its entirety. Said XML copy, created on May 30, 2024, is named 046192-000108WOPT_SL.xml and is 51,444 bytes in size.

TECHNICAL FIELD

The technology described herein relates to methods of administering recombinant adeno-associated virus rAAV to the kidney and pharmaceutical compositions comprising rAAV for administration to the kidney.

BACKGROUND

The primary job of the kidney is to filter the blood, removing waste products and excess fluid. The kidneys maintain a healthy balance of water, salts, and minerals. The kidneys also control blood pressure in the body. Kidneys are perfused by approximately 1500 L of blood per day in humans, which translates to 180 L of glomerular filtrate (primary urine) per day and 1 to 2 L of final urine per day.

Kidneys are made up of greater than 1 million filtering units known as nephrons. The nephron comprises the following regions in order of filtrate passage: glomerulus, glomerular capsule (Bowman's capsule), proximal tubule, loop of Henle, distal tubule, and collecting duct. The glomerulus is the site of blood filtration; small fenestrations allow fluids and small molecules to pass through, keeping blood cells and proteins out of the kidney tubules; the filtrate is captured by the glomerular capsule. The proximal tubule (also referred to interchangeably as proximal convoluted tubule (PCT)) filters 65% of primary urine; reabsorbs glucose, amino acids, solutes, and low molecular weight proteins; and maintains acid-base balance by reabsorbing bicarbonate. The loop of Henle reabsorbs water and salts; its descending thin limb reabsorbs water concentrating urine, and its ascending thick limb is permeable to ion exchange. The distal tubule (also referred to interchangeably as distal convoluted tubule (DCT)) regulates extracellular fluid volume and electrolyte homeostasis. The collecting duct reabsorbs more water, with fine tuning to the final urine product. Urine flows out of the collecting duct into minor and major renal calyxes. The urine then travels through the renal pelvis and ureter, is stored in the urinary bladder, and is excreted through the urethra.

Kidney-associated disorders can be treated using genetic vectors, such as a recombinant adeno-associated virus (rAAV). However, it is not beneficial to administer rAAV using the intravenous (IV) route since the virus would transduce other organs (e.g., liver). One alternative administration method is to needle puncture the kidney multiple times; however, this administration method is not clinically favorable. A urologist would likely exclude performing such kidney needle punctures because the kidney is highly vascularized and a puncture may result in excessive bleeding. As the kidney is accessible by vascular tract, another method is to cannulate the renal artery, cannulate the renal vein, attach the cannulas to a pump, and circulate an agent (e.g., rAAV) through the resulting isolated and cannulated vasculature. However, this is a complex surgical procedure that can result in complications and discomfort. There is great need for clinically relevant administration methods to efficiently deliver rAAV to kidneys. There is also need of rAAV that demonstrate tropism and/or efficiency in the kidneys.

SUMMARY

Embodiments of the technology described herein relate to methods of administering a recombinant adeno-associated virus (rAAV) to a kidney of a subject using a retrograde ureter route. Such administration methods can be used to treat a kidney-associated disorder in a subject in need thereof. Also described herein are pharmaceutical compositions comprising a recombinant adeno-associated virus (rAAV) for administration to the kidney.

Also described herein are specific rAAVs that showed high transduction in the kidneys following retrograde ureter administration, including but not limited to an rAAV comprising a capsid selected from Table 1 or FIGS. 4-5. Furthermore, described herein are exemplary parameters for the retrograde ureter administration, including administration volume, timings, and/or renal vessel(s) occlusion.

In multiple aspects, described herein are methods of transducing a sufficient number of the nephrons in a kidney of a subject with a recombinant adeno-associated virus (rAAV) to obtain an effective level of expression (e.g., of the rAAV, of a transgene comprised by the rAAV) in the kidney.

In one aspect, described herein is a method of transducing nephrons in a kidney of a subject with a recombinant adeno-associated virus (rAAV), the method comprising: guiding a catheter through the subject's urethra, bladder, and ureter; and administering a solution comprising the rAAV to the renal pelvis of the kidney through the catheter at a volume of from about 0.13 mL/kg to about 0.33 mL/kg, the kg being the weight of the subject, wherein kidney nephrons comprising nephron cells are transduced with the rAAV at a high efficiency.

In some embodiments of any of the aspects, the solution comprising the rAAV is administered to the kidney for about 0.5 minutes to about 60 minutes.

In some embodiments of any of the aspects, the solution comprising the rAAV is administered to the kidney for about 1 minutes to about 2 minutes.

In some embodiments of any of the aspects, the solution comprising the rAAV is administered at an intra-renal pressure of from about 25 cm $H_2O$ to about 55 cm $H_2O$. In some embodiments of any of the aspects, the solution comprising the rAAV is administered at an intra-renal pressure of from about 27 cm $H_2O$ to about 80 cm $H_2O$.

In some embodiments of any of the aspects, the method results in the transduction of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or more of the nephrons in the kidney with the rAAV.

In some embodiments of any of the aspects, the transduction efficiency of the rAAV of the nephrons in the kidney is at least 2-fold, at least 5-fold, at least 10-fold, at least 50-fold, at least 100-fold, at least 400-fold, at least 1000-fold, or at least 3500-fold increased compared to a corresponding transduction efficiency of corresponding nephrons in another kidney treated by intravenous administration of the solution comprising the rAAV.

In some embodiments of any of the aspects, the rAAV is not AAV9, and the transduction efficiency of the rAAV of the nephrons in the kidney is at least 2-fold, at least 5-fold, at least 10-fold, at least 50-fold, at least 100-fold, at least 400-fold, at least 1000-fold, or at least 3500-fold increased compared to a corresponding transduction efficiency achieved by administering rAAV comprising an AAV9 capsid to another kidney by the same method.

In some embodiments, the nephrons are transduced with an efficiency index that is greater than 1.

In some embodiments of any of the aspects, the rAAV does not comprise an AAV9 capsid, and the transduction efficiency of the rAAV in proximal tubule cells of the nephrons in the kidney is at least 2-fold, at least 5-fold, at least 10-fold, at least 50-fold, at least 100-fold, at least 400-fold, at least 1000-fold, or at least 3500-fold increased compared to a corresponding transduction efficiency in proximal tubule cells achieved by administering rAAV comprising an AAV9 capsid to another kidney by the same method.

In some embodiments of any of the aspects, the method further comprises a step of blocking a renal blood vessel of the kidney selected from the group consisting of a renal artery, a renal vein, and a combination thereof, prior to administering the solution comprising the rAAV.

In some embodiments of any of the aspects, the method further comprises a step of unblocking the renal blood vessel after a period of time of from about 10 minutes to about 60 minutes after administering the solution comprising the rAAV.

In some embodiments of any of the aspects, the method further comprises the kidney is not isolated from systemic circulation.

In some embodiments of any of the aspects, the method further comprises a renal blood vessel selected from the group consisting of a renal artery, a renal vein, and a combination thereof of the kidney is not blocked during performance of the method.

In some embodiments of any of the aspects, the solution comprising the rAAV is administered to the kidney at an intra-renal pressure of from about 25 cm $H_2O$ to about 55 cm $H_2O$. In some embodiments of any of the aspects, the solution comprising the rAAV is administered to the kidney at an intra-renal pressure of from about 27 cm $H_2O$ to about 80 cm $H_2O$.

In some embodiments of any of the aspects, the subject is a human, a non-human primate, a horse, a dog, or a pig.

In some embodiments of any of the aspects, at least about 30% of the nephrons of the kidney are transduced with the rAAV.

In some embodiments of any of the aspects, the volume of the solution comprising the rAAV administered to the subject is from about 0.2 mL/kg to about 0.27 mL/kg.

In some embodiments of any of the aspects, the volume of the solution comprising the rAAV administered to the subject is from about 0.27 mL/kg to about 0.33 mL/mg.

In some embodiments of any of the aspects, the solution comprising the rAAV using a balloon catheter.

In some embodiments of any of the aspects, the renal blood vessel is blocked using a balloon catheter.

In some embodiments of any of the aspects, the renal blood vessel is blocked using a clamp, e.g., after laparoscopy.

In some embodiments of any of the aspects, only one of the renal artery or renal vein of the kidney is blocked.

In some embodiments of any of the aspects, the renal vein of the kidney is not blocked.

In some embodiments of any of the aspects, the method does not comprise a continuous perfusion of an isolated kidney.

In some embodiments of any of the aspects, the method does not comprise a closed circuit comprising the kidney.

In some embodiments of any of the aspects, the method does not comprise a substantially closed system comprising the kidney.

In some embodiments of any of the aspects, the method does not comprise diverting circulation from the kidney.

In some embodiments of any of the aspects, the method does not comprise bypassing the kidney.

In some embodiments of any of the aspects, the method is performed in vivo.

In some embodiments of any of the aspects, the method is not performed ex vivo.

In some embodiments of any of the aspects, the period of time for blocking the at least one renal blood vessel is 15-45 minutes subsequent to the blocking.

In some embodiments of any of the aspects, the period of time for blocking the at least one renal blood vessel is 20-40 minutes subsequent to the blocking.

In some embodiments of any of the aspects, the period of time for blocking the at least one renal blood vessel is about 15-30 minutes subsequent to the blocking.

In some embodiments of any of the aspects, the period of time for blocking the at least one renal blood vessel is about 30 minutes subsequent to the blocking.

In some embodiments of any of the aspects, the volume of the solution comprising the rAAV is from about 0.13 mL/kg to about 0.33 mL/kg, and wherein the period of time for blocking the renal blood vessel is about 15-30 minutes subsequent to the blocking.

In some embodiments of any of the aspects, the volume of the solution comprising the rAAV is from about 0.2 mL/kg to about 0.27 mL/kg, and wherein the period of time for blocking the renal blood vessel is about 15-30 minutes subsequent to the blocking.

In some embodiments of any of the aspects, the volume of the solution comprising the rAAV is from about 0.2 mL/kg to about 0.27 mL/kg, and wherein the period of time for blocking the renal blood vessel is about 30 minutes subsequent to the blocking.

In some embodiments of any of the aspects, the rAAV comprises an AAV capsid protein selected from a serotype provided in Table 1. In some embodiments of any of the aspects, the rAAV comprises an AAV capsid protein selected from serotype AAV1, AAV2, AAV3a, AAV3b, AAV4, AAV5, AAV6, AAV7, AAV8, AAV9, AAV2G9, AAV2.5G9, AAV2.5, AAVrh8, AAVrh10, AAVrh74, AAV10, AAV11, and AAVDJ.

In some embodiments of any of the aspects, the rAAV comprises a capsid protein selected from the group consisting of AAV2G9, AAV2.5, AAVDJ, and AAV2.

In some embodiments of any of the aspects, the capsid protein is AAV2G9.

In some embodiments of any of the aspects, the rAAV comprises a rational polyploid.

In some embodiments of any of the aspects, the solution comprises the rAAV at a concentration of $10^8$ viral genomes per mL (vg/mL) to $10^{15}$ vg/mL.

In some embodiments of any of the aspects, the solution comprises the rAAV at a concentration of $10^8$ vg/mL to $10^{13}$ vg/mL.

In some embodiments of any of the aspects, the solution comprises $1\times10^{13}$ to $2\times10^{13}$ rAAV viral genomes total.

In some embodiments of any of the aspects, the solution comprises $5\times10^{13}$ to $6\times10^{13}$ rAAV viral genomes total.

In some embodiments of any of the aspects, the solution comprises $1\times10^{10}$ viral genomes total.

In some embodiments of any of the aspects, the rAAV comprises a transgene.

In some embodiments of any of the aspects, the transgene is selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof.

In some embodiments of any of the aspects, the transgene is selected from the group consisting of Aquaporin 2 (AQP2); ATPase Na+/K+ Transporting Subunit Alpha 1 (ATP1A1); ATPase H+ Transporting V0 Subunit A4 (ATP6VOA4); ATPase H+ Transporting V1 Subunit B1 (ATP6V1B1); Arginine Vasopressin Receptor 2 (AVPR2); Barttin CLCNK (chloride channel K) Type Accessory Subunit Beta (BSND); Carbonic Anhydrase 2 (CA2); Calcium Sensing Receptor (CaSR); Chloride Voltage-Gated Channel 5 (CLCN5); CLCNKA (Chloride Voltage-Gated Channel Ka); Chloride Voltage-Gated Channel Kb (CLCNKB); Claudin 16 (CLDN16); Claudin 19 (CLDN19); Cyclin And CBS Domain Divalent Metal Cation Transport Mediator 2 (CNNM2); Cullin 3 (CUL3); Cytochrome P450 Family 11 Subfamily B Member 1 (CYP11B1); Cytochrome P450 Family 11 Subfamily B Member 2 (CYP11B2); Cytochrome P450 Family 17 Subfamily A Member 1 (CYP17A1); Cytochrome P450 Family 21 Subfamily A Member 2 (CYP21A2); Epidermal Growth Factor (EGF); Epidermal Growth Factor Receptor (EGFR); Enoyl-CoA Hydratase And 3-Hydroxyacyl CoA Dehydrogenase (EHHADH); FAM111 (family 111) Trypsin Like Peptidase A (FAM111A); Forkhead Box I1 (FOXI1); FXYD Domain/Motif Containing Ion Transport Regulator 2 (FXYD2); Glycine Amidinotransferase (GA™); guanine nucleotide binding protein; alpha stimulating (GNAS); hepatocyte nuclear factor 1 (HNF1) Homeobox B (HNF1B); Hepatocyte Nuclear Factor 4 Alpha (HNF4A); Hydroxysteroid 11-Beta Dehydrogenase 2 (HSD11B2); Hydroxy-Delta-5-Steroid Dehydrogenase, 3 Beta- And Steroid Delta-Isomerase 2 (HSD3B2); Potassium Voltage-Gated Channel Subfamily A Member 1 (KCNA1); Potassium Inwardly Rectifying Channel Subfamily J Member 1 (KCNJ1); Potassium Inwardly Rectifying Channel Subfamily J Member 10 (KCNJ10); Kelch Like Family Member 3 (KLHL3); Melanoma Antigen Gene Family Member D2 (MAGED2); Nuclear Receptor Subfamily 3 Group C Member 2 (NR3C2); Oculocerebrorenal Syndrome Of Lowe (OCRL) Inositol Polyphosphate-5-Phosphatase; Pterin-4 Alpha-Carbinolamine Dehydratase 1 (PCBD1); Phosphate Regulating Endopeptidase X-Linked (PHEX); Sodium Channel Epithelial 1 Subunit Alpha (SCNN1A); Sodium Channel Epithelial 1 Subunit Beta (SCNN1B); Sodium Channel Epithelial 1 Subunit Gamma (SCNN1G); Solute Carrier Family 12 Member 1 (SLC12A1); Solute Carrier Family 12 Member 3 (SLC12A3); Solute Carrier Family 1 Member 1 (SLC1A1); Solute Carrier Family 2 Member 2 (SLC2A2); Solute Carrier Family 34 Member 1 (SLC34A1); Solute Carrier Family 34 Member 3 (SLC34A3); Solute Carrier Family 36 Member 2 (SLC36A2); Solute Carrier Family 3 Member 1 (SLC3A1); Solute Carrier Family 4 Member 1 (SLC4A1); Solute Carrier Family 6 Member 19 (SLC6A19); Solute Carrier Family 6 Member 20 (SLC6A20); Solute Carrier Family 7 Member 7 (SLC7A7); Solute Carrier Family 7 Member 9 (SLC7A9); Transient Receptor Potential Cation Channel Subfamily M Member 6 (TRPM6); WD Repeat Domain 72 (WDR72); With-no-lysine (WNK, Lysine Deficient) Protein Kinase 1 (WNK1); With-no-lysine (WNK, Lysine Deficient) Protein Kinase 4 (WNK4); and combinations thereof.

In some embodiments of any of the aspects, the transgene comprises an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD).

In some embodiments of any of the aspects, circulating serum of the subject does not neutralize the rAAV upon administration.

In some embodiments of any of the aspects, the subject has antibodies that neutralize the rAAV to be administered in the circulating serum and the antibodies do not neutralize the rAAV in the kidney upon administration.

In some embodiments of any of the aspects, a subsequent administration of the rAAV is performed without resulting in a substantial inflammatory response in the kidney.

In some embodiments of any of the aspects, the subsequent administration is at least one day later. In some embodiments of any of the aspects, the subsequent administration is at least one month later.

In some embodiments of any of the aspects, the method transduces proximal tubules of the kidney with the rAAV.

In some embodiments of any of the aspects, the method transduces at least one cell population of a glomerulus, a glomerular capsule, a proximal convoluted tubule, the loop of Henle, a distal convoluted tubule, or the collecting duct of the kidney with the rAAV. In some embodiments of any of the aspects, the method transduces at least one of a glomerulus, a glomerular capsule, a proximal convoluted tubule, the loop of Henle, or a distal convoluted tubule of the kidney with the rAAV.

In some embodiments of any of the aspects, the rAAV comprises a kidney-specific promoter.

In some embodiments of any of the aspects, the kidney-specific promoter is selected from the group consisting of: kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.

In some embodiments of any of the aspects, the kidney-specific promoter is a synthetic promoter.

In some embodiments of any of the aspects, the rAAV has a genome comprising a promoter specific to proximal convoluted tubules and/or collecting ducts.

In one aspect, described herein is a method of treating a kidney-associated disorder in a subject in need thereof, the method comprising administering a recombinant adeno-associated virus (rAAV) to the subject by performing a method as described herein.

In some embodiments of any of the aspects, the kidney-associated disorder is selected from the group consisting of: autosomal dominant polycystic kidney disease (ADPKD); Alport syndrome; autosomal dominant tubulointerstitial kidney disease (ADTKD); medullary cystic kidney disease; nephronophthisis; Bartter Syndrome; Von Hippel-Lindau syndrome; Gitelman syndrome; congenital nephrotic syndrome; primary hyperoxaluria; Dent disease; Thin Basement Membrane Nephropathy; cystinuria; Liddle syndrome; Papillorenal syndrome; and cystinosis.

In some embodiments of any of the aspects, the kidney-associated disorder is selected from the group consisting of: Apparent mineralocorticoid excess, Autosomal dominant hypocalcemia, Autosomal dominant hypomagnesemia, Bartter type 1, Bartter type 2, Bartter type 3, Bartter type 4a, Bartter type 4b, Bartter type 5, Congenital adrenal hyperplasia type 1, Congenital adrenal hyperplasia type 2, Congenital adrenal hyperplasia type 4, Congenital adrenal hyperplasia type 5, Cystinuria A, Cystinuria B, Dent disease type 1, Dent disease type 2/Lowe syndrome, Dicarboxylic aminoaciduria, Distal RTA, EAST/SeSAME syndrome, Fanconi Bickel syndrome, Fanconi renotubular syndrome 1, Fanconi renotubular syndrome 2, Fanconi renotubular syndrome 3, Fanconi renotubular syndrome 4, Gitelman syndrome, Glucocorticoid remediable aldosteronism, Hartnup disorder, Hereditary hypophosphatemic rickets with hypercalciuria, HNF1B-related kidney disease, Hyperphenylalaninemia BH4-deficient, Hypomagnesemia type 1/hypomagnesemia with secondary hypocalcemia, Hypomagnesemia type 2, Hypomagnesemia type 3/familial hypomagnesemia with hypercalciuria and nephrocalcinosis, Hypomagnesemia type 4, Hypomagnesemia type 5/familial hypomagnesemia with hypercalciuria and nephrocalcinosis, Hypomagnesemia, seizures, and mental retardation type 1, Hypomagnesemia, seizures, and mental retardation type 2, Iminoglycinuria, Kenny-Caffey syndrome type 2, Liddle syndrome, Lysinuric protein intolerance, Neonatal inflammatory skin and bowel disease type 2, Nephrogenic diabetes insipidus, Nephrogenic syndrome of inappropriate antidiuresis, Pseudohypoaldosteronism type 1, Pseudohypoaldosteronism type 1A, Pseudohypoaldosteronism type 2b, Pseudohypoaldosteronism type 2c, Pseudohypoaldosteronism type 2d, Pseudohypoaldosteronism type 2e, Renal tubular acidosis type 3, and X-linked hypophosphatemic rickets.

In some embodiments of any of the aspects, the kidney-associated disorder is Cystinuria, and the transgene is SLC3A1 and/or SLC7A9.

In some embodiments of any of the aspects, the kidney-associated disorder is autosomal dominant polycystic kidney disease (ADPKD), and the transgene is PKD1, PKD2, and/or GANAB.

In one aspect, described herein is a method of transducing at least about 10% of the nephrons in a kidney of a subject with a recombinant adeno-associated virus (rAAV), the method comprising: (a) blocking a renal blood vessel of the kidney selected from the group consisting of a renal artery, a renal vein, and a combination thereof; (b) guiding a catheter through the subject's urethra, bladder, and ureter; (c) administering a solution comprising the rAAV to the renal pelvis of the kidney through the catheter at a volume of from about 0.13 mL/kg to about 0.33 mL/kg, the kg being the weight of the subject; and (d) unblocking the renal blood vessel after a period of time of from about 10 minutes to about 60 minutes after administering the solution comprising the rAAV, wherein the method results in the transduction of at least about 10% of the nephrons in the kidney with the rAAV.

In one aspect described herein is a method of transducing at least about 25% of the nephrons in a kidney of a subject with a recombinant adeno-associated virus (rAAV), the method comprising: (a) blocking a renal blood vessel of the kidney selected from the group consisting of a renal artery, a renal vein, and a combination thereof; (b) guiding a catheter through the subject's urethra, bladder, and ureter; (c) administering volume of a solution comprising the rAAV to the renal pelvis of the kidney through the catheter at a volume of from about 0.13 mL/kg to about 0.33 mL/kg, the kg being the weight of the subject; and (d) unblocking the renal blood vessel after a period of time of from about 10 minutes to about 60 minutes subsequent to the blocking and/or after administering the solution comprising the rAAV, wherein the method results in the transduction of at least about 25% of the nephrons in the kidney with the rAAV.

In one aspect, described herein is a method of transducing at least about 25% of the nephrons in a kidney of a subject with a recombinant adeno-associated virus (rAAV), the method comprising: (a) blocking a renal artery of the kidney and not blocking a renal vein of the kidney; (b) guiding a catheter through the subject's urethra, bladder, and ureter; (c) administering a volume of a solution comprising the rAAV to the renal pelvis of the kidney through the catheter; and (d) unblocking the renal artery after a period of time of from about 10 minutes to about 60 minutes subsequent to the blocking and/or after administering the solution comprising the rAAV, wherein the method results in the transduction of at least about 25% of the nephrons in the kidney with the rAAV.

In one aspect, described herein is a method of transducing nephrons in a kidney of a subject, the method comprising: (a) blocking a renal blood vessel selected from the group consisting of a renal artery, a renal vein, and a combination thereof of the kidney; (b) guiding a catheter through the subject's urethra, bladder, and ureter; (c) administering a volume of a solution comprising rAAV to the renal pelvis of the kidney through the catheter, the rAAV not being rAAV9; and (d) unblocking the renal blood vessel after a period of time of from about 10 minutes to about 60 minutes subsequent to the blocking and/or after administering the solution comprising the rAAV, wherein the method results in a transduction efficiency that is at least 2-fold higher compared to a corresponding transduction efficiency achieved by administering rAAV comprising an AAV9 capsid to another kidney by the same method.

In some embodiments of any of the aspects, the rAAV comprises a capsid protein selected from Table 1, excluding AAV9.

In some embodiments of any of the aspects, the rAAV has at least 2-fold higher transduction efficiency in the kidney compared to a corresponding transduction efficiency achieved by administering rAAV comprising an AAV9 capsid to another kidney by the same method.

In some embodiments of any of the aspects, the rAAV has 400-fold higher transduction efficiency in the kidney compared to AAV9. In some embodiments of any of the aspects, the rAAV has 3500-fold higher transduction efficiency in the kidney compared to a corresponding transduction efficiency achieved by administering rAAV comprising an AAV9 capsid to another kidney by the same method.

In one aspect, described herein is a method of transducing at least about 25% of the nephrons in a kidney of a subject with a recombinant adeno-associated virus (rAAV), the method comprising: (a) isolating the kidney from systemic circulation; (b) guiding a catheter through the subject's urethra, bladder, and ureter; (c) administering a solution comprising the rAAV to the renal pelvis of the kidney through the catheter at a volume of from about 0.13 mL/kg to about 0.33 mL/kg, the kg being the weight of the subject; and (d) re-establishing the kidney into systemic circulation after a period of time of from about 10 minutes to about 60 minutes after the isolating and/or after administering the solution comprising the rAAV, wherein the method results in the transduction of at least about 25% of the nephrons in the kidney with the rAAV.

In one aspect, described herein is a method of treating a kidney disorder in a subject in need thereof, the method comprising: administering to a kidney of the subject a first recombinant adeno-associated virus (rAAV) encoding a transgene that is therapeutic toward the kidney disorder; and subsequent to administering the first rAAV, administering to the kidney or a different kidney of the subject a second rAAV encoding the transgene or a different transgene that is therapeutic toward to the kidney disorder, wherein the first rAAV and the second rAAV are cross seroreactive, and wherein the subject does not elicit a significant immune response to the second rAAV in the kidney.

In some embodiments of any of the aspects, at least one solution comprising the first and/or second rAAV is administered to the kidney at an intra-renal pressure of from about 25 cm $H_2O$ to about 55 cm $H_2O$. In some embodiments of any of the aspects, at least one solution comprising the first and/or second rAAV is administered to the kidney at an intra-renal pressure of from about 27 cm $H_2O$ to about 80 cm $H_2O$.

In some embodiments of any of the aspects, a solution comprising the second rAAV is administered after about a week.

In some embodiments of any of the aspects, the first and second rAAVs are administered by an administration method comprising: guiding a catheter through the subject's urethra, bladder, and ureter; and administering a solution comprising the first or second rAAV through the catheter to the renal pelvis of the kidney at a volume of from about 0.13 mL/kg to about 0.33 mL/kg, the kg being the weight of the subject.

In some embodiments of any of the aspects, the first and/or second rAAVs are administered by an administration method comprising: (a) blocking a renal blood vessel of the kidney selected from the group consisting of a renal artery, a renal vein, and a combination thereof; (b) guiding a catheter through the subject's urethra, bladder, and ureter; (c) administering a solution comprising the rAAV through the catheter to the renal pelvis of the kidney or a different kidney at a volume of from about 0.13 mL/kg to about 0.33 mL/kg, the kg being the weight of the subject; and (d) unblocking renal blood vessel after a period of time of from about 10 minutes to about 60 minutes subsequent to the blocking and/or after administering the solution comprising the rAAV.

In some embodiments of any of the aspects, the administration method results in at least about 25% of the nephrons in the kidney being transduced with the rAAV.

In some embodiments of any of the aspects, the subject has neutralizing antibodies toward the first rAAV therapeutic prior to the administering.

In some embodiments of any of the aspects, the capsid protein of the first rAAV is the same serotype as the capsid protein of the second rAAV.

In some embodiments of any of the aspects, the capsid protein of the first rAAV is a different serotype as the capsid protein of the second rAAV.

In some embodiments of any of the aspects, the time period for subsequent administration of the second rAAV is determined based on the efficacy or longevity of the administration of the first rAAV.

In some embodiments of any of the aspects, the first rAAV is administered to a first kidney of the subject, and the second rAAV is administered to a second kidney of the subject.

In some embodiments of any of the aspects, the first rAAV is administered to a first kidney of the subject, and the second rAAV is administered to the first kidney of the subject.

In some embodiments of any of the aspects, the first rAAV is administered to both kidneys of the subject, and the second rAAV is administered to both kidneys of the subject.

In one aspect, described herein is a method of treating a kidney disorder in a subject in need thereof, the subject being seropositive for a recombinant adeno-associated virus (rAAV) therapeutic, the method comprising: administering to a kidney of the subject the rAAV therapeutic encoding a transgene that is therapeutic toward the kidney disorder, wherein the subject does not elicit a significant immune response to the rAAV therapeutic in the kidney.

In some embodiments of any of the aspects, the subject has neutralizing antibodies toward the rAAV therapeutic prior to the administering.

In some embodiments of any of the aspects, the rAAV is administered by an administration method comprising: guiding a catheter through the subject's urethra, bladder, and ureter; and administering a solution comprising the rAAV through the catheter to the renal pelvis of the kidney at a volume of from about 0.13 mL/kg to about 0.33 mL/kg, the kg being the weight of the subject.

In some embodiments of any of the aspects, the rAAV is administered by an administration method comprising: (a) blocking a renal blood vessel of the kidney selected from the group consisting of a renal artery, a renal vein, and a combination thereof; (b) guiding a catheter through the subject's urethra, bladder, and ureter; (c) administering a solution comprising the rAAV through the catheter to the renal pelvis of the kidney through the catheter at a volume of from about 0.13 mL/kg to about 0.33 mL/kg, the kg being the weight of the subject; and (d) unblocking renal blood vessel after a period of time of from about 10 minutes to about 60 minutes subsequent to the blocking and/or after administering the solution comprising the rAAV, wherein the administration method results in at least about 25% of the nephrons in the kidney being transduced with the rAAV.

In one aspect, described herein is a method of transducing at least about 25% of the nephrons in a kidney of a subject with a recombinant adeno-associated virus (rAAV), the method comprising: (a) blocking a renal blood vessel selected from the group consisting of a renal artery, a renal vein, and a combination thereof of the kidney; (b) guiding a catheter through the subject's urethra, bladder, and ureter; (c) administering a solution comprising the rAAV to the renal pelvis of the kidney through the catheter at a volume of from about 0.13 mL/kg to about 0.33 mL/kg, the kg being the weight of the subject, wherein the rAAV comprises a capsid protein selected from Table 1; and (d) unblocking the renal blood vessel after a period of time of from about 10 minutes to about 60 minutes subsequent to the blocking and/or after administering the solution comprising the rAAV, wherein the method results in the transduction of at least about 25% of the nephrons in the kidney with the rAAV.

In one aspect, described herein is a method of treating a kidney-associated disorder in a subject in need thereof, the method comprising administering the 2G9 rAAV to the subject by performing a retrograde ureter administration method as described herein.

In some embodiments of any of the aspects, the rAAV is administered to the kidney at an intra-renal pressure of from about 25 cm $H_2O$ to about 55 cm $H_2O$. In some embodiments of any of the aspects, the rAAV is administered to the kidney at an intra-renal pressure of from about 27 cm $H_2O$ to about 80 cm $H_2O$.

In some embodiments of any of the aspects, the volume of the solution is 0.13 mL/kg to 0.33 mL/kg.

In some embodiments of any of the aspects, the period of time is 30-60 minutes subsequent to the blocking and/or after administering the solution comprising the rAAV.

In some embodiments of any of the aspects, the subject is seropositive for the rAAV prior to the administration of the solution comprising the rAAV.

In some embodiments of any of the aspects, the rAAV is administered in liposomes, nanocapsules, microparticles, microspheres, lipid particles, lipid nanoparticles, or vesicles.

In some embodiments of any of the aspects, the rAAV is administered in lipid nanoparticles (LNPs).

In one aspect, described herein is a pharmaceutical composition comprising a recombinant adeno-associated virus (rAAV) comprising: (a) an AAV capsid protein selected from Table 1; (b) a transgene comprising: (i) a gene selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof; or (ii) an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD); and (c) a pharmaceutically acceptable carrier.

In one aspect, described herein is a pharmaceutical composition comprising a recombinant adeno-associated virus (rAAV) comprising: (a) an AAV capsid protein selected from Table 1; (b) a transgene comprising a gene selected from the group consisting of Aquaporin 2 (AQP2); ATPase Na+/K+ Transporting Subunit Alpha 1 (ATP1A1); ATPase H+ Transporting V0 Subunit A4 (ATP6VOA4); ATPase H+ Transporting V1 Subunit B1 (ATP6V1B1); Arginine Vasopressin Receptor 2 (AVPR2); Barttin CLCNK (chloride channel K) Type Accessory Subunit Beta (BSND); Carbonic Anhydrase 2 (CA2); Calcium Sensing Receptor (CaSR); Chloride Voltage-Gated Channel 5 (CLCN5); CLCNKA (Chloride Voltage-Gated Channel Ka); Chloride Voltage-Gated Channel Kb (CLCNKB); Claudin 16 (CLDN16); Claudin 19 (CLDN19); Cyclin And CBS Domain Divalent Metal Cation Transport Mediator 2 (CNNM2); Cullin 3 (CUL3); Cytochrome P450 Family 11 Subfamily B Member 1 (CYP11B1); Cytochrome P450 Family 11 Subfamily B Member 2 (CYP11B2); Cytochrome P450 Family 17 Subfamily A Member 1 (CYP17A1); Cytochrome P450 Family 21 Subfamily A Member 2 (CYP21A2); Epidermal Growth Factor (EGF); Epidermal Growth Factor Receptor (EGFR); Enoyl-CoA Hydratase And 3-Hydroxyacyl CoA Dehydrogenase (EHHADH); FAM111 (family 111) Trypsin Like Peptidase A (FAM111A); Forkhead Box I1 (FOXI1); FXYD Domain/Motif Containing Ion Transport Regulator 2 (FXYD2); Glycine Amidinotransferase (GATM); guanine nucleotide binding protein; alpha stimulating (GNAS); hepatocyte nuclear factor 1 (HNF1) Homeobox B (HNF1B); Hepatocyte Nuclear Factor 4 Alpha (HNF4A); Hydroxysteroid 11-Beta Dehydrogenase 2 (HSD11B2); Hydroxy-Delta-5-Steroid Dehydrogenase, 3 Beta- And Steroid Delta-Isomerase 2 (HSD3B2); Potassium Voltage-Gated Channel Subfamily A Member 1 (KCNA1); Potassium Inwardly Rectifying Channel Subfamily J Member 1 (KCNJ1); Potassium Inwardly Rectifying Channel Subfamily J Member 10 (KCNJ10); Kelch Like Family Member 3 (KLHL3); Melanoma Antigen Gene Family Member D2 (MAGED2); Nuclear Receptor Subfamily 3 Group C Member 2 (NR3C2); Oculocerebrorenal Syndrome Of Lowe (OCRL) Inositol Polyphosphate-5-Phosphatase; Pterin-4 Alpha-Carbinolamine Dehydratase 1 (PCBD1); Phosphate Regulating Endopeptidase X-Linked (PHEX); Sodium Channel Epithelial 1 Subunit Alpha (SCNN1A); Sodium Channel Epithelial 1 Subunit Beta (SCNN1B); Sodium Channel Epithelial 1 Subunit Gamma (SCNN1G); Solute Carrier Family 12 Member 1 (SLC12A1); Solute Carrier Family 12 Member 3 (SLC12A3); Solute Carrier Family 1 Member 1 (SLC1A1); Solute Carrier Family 2 Member 2 (SLC2A2); Solute Carrier Family 34 Member 1 (SLC34A1); Solute Carrier Family 34 Member 3 (SLC34A3); Solute Carrier Family 36 Member 2 (SLC36A2); Solute Carrier Family 3 Member 1 (SLC3A1); Solute Carrier Family 4 Member 1 (SLC4A1); Solute Carrier Family 6 Member 19 (SLC6A19); Solute Carrier Family 6 Member 20 (SLC6A20); Solute Carrier Family 7 Member 7 (SLC7A7); Solute Carrier Family 7 Member 9 (SLC7A9); Transient Receptor Potential Cation Channel Subfamily M Member 6 (TRPM6); WD Repeat Domain 72 (WDR72); With-no-lysine (WNK, Lysine Deficient) Protein Kinase 1 (WNK1); With-no-lysine (WNK, Lysine Deficient) Protein Kinase 4 (WNK4); and combinations thereof; and (c) a pharmaceutically acceptable carrier In some embodiments of any of the aspects, the pharmaceutically acceptable carrier comprises mannitol.

In some embodiments of any of the aspects, the AAV comprises a capsid protein of AAV2G9.

In some embodiments of any of the aspects, the solution that comprises the rAAV is at a concentration of $10^8$ viral genomes per mL (vg/mL) to $10^{15}$ vg/mL.

In some embodiments of any of the aspects, the solution that comprises the rAAV is at a concentration of $10^8$ viral genomes per mL (vg/mL) to $10^{14}$ vg/mL.

In some embodiments of any of the aspects, the solution that comprises the rAAV is at a concentration of $10^8$ vg/mL to $10^{13}$ vg/mL.

In some embodiments of any of the aspects, the pharmaceutical composition comprises $1\times10^{13}$ to $2\times10^{13}$ rAAV viral genomes total.

In some embodiments of any of the aspects, the pharmaceutical composition comprises $5\times10^{13}$ to $6\times10^{13}$ rAAV viral genomes total.

In some embodiments of any of the aspects, the pharmaceutical composition is in a unit dose of from about 0.13 mL/kg to about 0.33 mL/kg, the kg being the weight of the subject.

In some embodiments of any of the aspects, the pharmaceutical composition is in a unit dose of from about 0.27 mL/kg to about 0.33 mL/kg.

In some embodiments of any of the aspects, the transgene comprises a reporter protein.

In some embodiments of any of the aspects, the genome of the rAAV comprises a kidney-specific promoter.

In some embodiments of any of the aspects, the kidney-specific promoter is selected from the group consisting of: kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.

In some embodiments of any of the aspects, the kidney-specific promoter is a synthetic promoter.

In some embodiments of any of the aspects, the genome of the rAAV comprises a promoter specific to proximal convoluted tubules and/or collecting ducts.

In some embodiments of any of the aspects, the rAAV is formulated for delivery in liposomes, nanocapsules, microparticles, microspheres, lipid particles, lipid nanoparticles, or vesicles.

In some embodiments of any of the aspects, the rAAV is formulated for delivery in lipid nanoparticles (LNPs).

In one aspect, described herein is a method of transducing nephrons in a kidney of a subject with a recombinant adeno-associated virus (rAAV), the method comprising: guiding a catheter through the subject's urethra, bladder, and ureter; and administering a solution comprising the rAAV to the renal pelvis of the kidney at a volume of from about 0.13 mL/kg to about 0.33 mL/kg, the kg being the weight of the subject, wherein the rAAV comprises AAV2G9, and wherein nephrons of the kidney are transduced with the rAAV at a high efficiency.

BRIEF DESCRIPTION OF THE DRAWINGS

FIG. 6A shows immunohistochemistry (IHC) of GFP following administration of AAV2G9 (1.41E+13VG). The images show High-Power Fields (HPF), which are a standard measure for histopathology diagnostic evaluation; the HPFs correspond to 400× magnification. FIG. 6S-6X are bar graphs showing viral quantification following retrograde ureter administration of AAV2G9 to the treated kidney ("2G9") or contralateral kidney ("con") in pig subject RU14: kidney AAV viral copy number (VCN) (FIG. 6S), kidney AAV cDNA (FIG. 6T), kidney AAV protein (FIG. 6U), liver AAV VCN (FIG. 6V), liver AAV cDNA (FIG. 6W), and liver AAV protein (FIG. 6X).

FIG. 7A-7M is a series of images and graphs showing the results of retrograde ureter administration of AAV2G9 in non-human primates (see e.g., Example 3). In FIG. 7A-7F, kidney sections from NHP-RU1 were stained with Periodic acid-Schiff (PAS), and immunohistochemistry was performed for green fluorescent protein GFP (brown staining;

indicates successful transduction of the rAAV in the kidney cells). FIG. 7A shows histology images from the contralateral kidney of NHP-RU1. FIG. 7B shows histology images from the rAAV-administered kidney of NHP-RU1. FIG. 7C shows a high resolution image from the indicated location in the renal cortex of the anterior inferior section from FIG. 7A. FIG. 7D shows a high resolution image from the indicated location in the renal cortex of the anterior inferior section from FIG. 7B. FIG. 7E shows multiple high resolution images from the indicated locations in the renal medulla in the anterior superior section from FIG. 7B. FIG. 7F shows multiple high resolution images from the indicated locations in the renal cortex of the anterior superior section from FIG. 7B; nearly 100% transduction is shown in the proximal convoluted tubules of in the indicated high resolution images. The scale bars in FIG. 7A-7B show 2 mm. The scale bars in the magnified images in FIG. 7C-7F show 200 μm. FIG. 7G is a bar graph showing the vector copy per diploid genome (VCN) in the indicated samples from NHP-RU1 and NHP-RU2; results are quantified in Table 8. FIG. 7H is a bar graph showing eGFP cDNA levels (relative fold-change (log 10) 2^ddCT in the indicated samples from NHP-RU1 and NHP-RU2; results are quantified in Table 9. FIG. 7I shows the RNA analysis for NHP_RU2, comparing eGFP cDNA levels (left bars in each sample) to glyceraldehyde-3-phosphate dehydrogenase (GAPDH) control levels (right bars in each sample) in the indicated samples; "NoRT" indicates no reverse transcriptase, and "NTC" indicates no-template control. FIG. 7J is a bar graph showing the relative light units (RLU) per mg protein in the indicated samples from NHP-RU1 and NHP-RU2; results are quantified in Table 10. FIG. 7K-7M are a series of tables showing biopsy mapping of the AAV2G9-administered kidneys from NHP-RU1 and NHP-RU2; biopsies 1, 2, 3, and 10 were anterior superior; biopsies 7, 8, 9, and 11 were anterior inferior; and biopsies 4, 5, and 6 were kidney midline. FIG. 7K shows viral DNA (vg/dg), eGFP RNA (cDNA relative-fold change), luciferase protein (RLU/mg), and % GFP+ in the proximal convoluted tubules (PCT). Each column (DNA/RNA/Protein) of the tables were analyzed independently. There was consistency for each biopsy across molecular assays and histological staining. FIG. 7L shows biopsy ranks based on transduction (viral DNA vg/dg). FIG. 7M shows biopsy ranks based on functional transduction (luciferase protein RLU/mg).

FIG. 8A shows the analysis process for VISIOPHARM®. FIG. 8B-8E were counterstained for AAV2G9 (GFP—purple staining), proximal convoluted tubules (CD13—yellow staining), and distal convoluted tubules and collecting ducts (CK19—blue staining). FIG. 8B shows histology co-staining images from the contralateral kidney of NHP-RU1, and FIG. 8C shows histology co-staining images from the kidney of NHP-RU1 administered AAV-2G9. FIG. 8D shows histology co-staining images from the contralateral kidney of NHP-RU2, and FIG. 8E shows histology co-staining images from the kidney of NHP-RU2 administered AAV-2G9. Results from FIG. 8B-8E are quantified in Tables 11-12.

FIG. 9A shows a schematic of the transduction inhibition assay. FIG. 9B shows neutralizing antibody levels in the serum of NHP-RU1 pre-administration and post-administration of AAV2G9. FIG. 9C shows neutralizing antibody levels in the serum of NHP-RU2 pre-administration and post-administration of AAV2G9. FIG. 9D shows neutralizing antibody levels in the serum of both NHP-RU1 and NHP-RU2 pre-administration and post-administration of AAV2G9.

In FIG. 10A-10D, kidney sections from RU26 were stained with Periodic acid-Schiff (PAS), and immunohistochemistry was performed for green fluorescent protein GFP (brown staining; indicates successful transduction of the rAAV in the kidney cells). FIG. 10A shows histology images from the contralateral kidney of RU26 (Anterior Inferior (AI) region 1); the scale bar in the left low-magnification image indicates 2 mm, the scale bar in the upper right high-magnification image indicates 200 μm, and the scale bar in the lower right high-magnification image indicates 100 μm. FIG. 10B-10D show histology images from the rAAV-administered kidney of RU26 (AI3 in FIG. 10B, AI4 in FIG. 10C, and All in FIG. 10D); scale bars in the left low-magnification images indicate 2 mm, and scale bars in the right high-magnification images indicate 100 μm. FIG. 10E is a bar graph showing the luciferase activity in relative light units (RLU) per mg protein in the indicated samples from RU26; results are quantified in the table next to the bar graph.

DETAILED DESCRIPTION

Embodiments of the technology described herein relate to methods of administering a recombinant adeno-associated virus (rAAV) to a kidney of a subject using a retrograde ureter route. As used herein, "retrograde ureter route" or "retro-ureteral (RU)" or "retrograde route" or "retrograde route to the ureter" or "retrograde injection through ureter" or "retrograde administration" or "retrograde ureter administration" etc. are used interchangeably and refer to administering a solution against the flow of urine out of the kidney, i.e., by injecting a solution to the ureter (or renal pelvis) and into the nephrons of the kidney, including to the tubules. Such administration methods can be used to treat a kidney-associated disorder in a subject in need thereof. Also described herein are pharmaceutical compositions comprising a recombinant adeno-associated virus (rAAV) for administration to the kidney.

Figure 4:
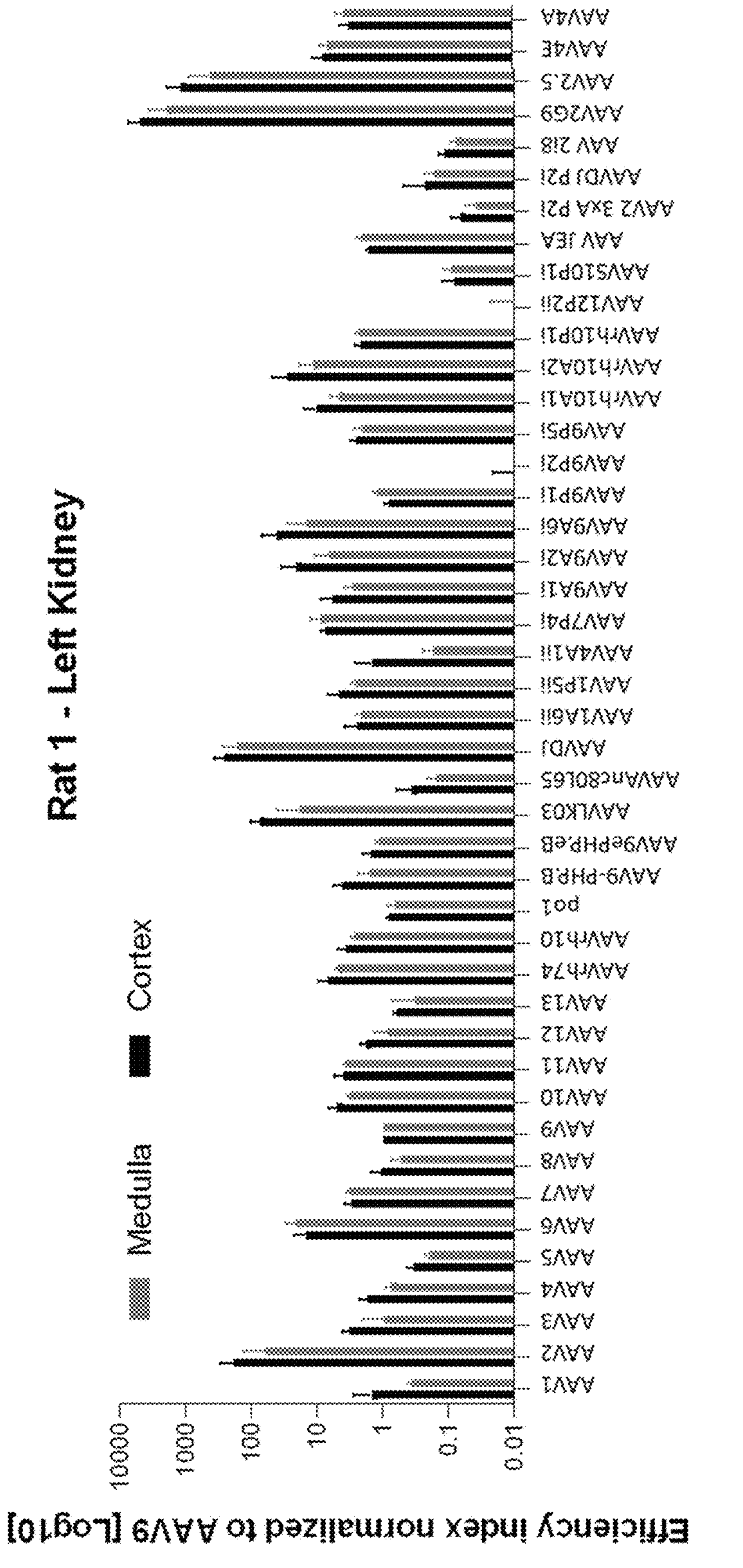
FIG. 4 is a bar graph showing the efficiency index of rAAVs normalized to AAV9 in the kidney medulla (e.g., substantially comprising glomeruli, proximal tubules, and distal tubules) or kidney cortex (e.g., substantially comprising glomeruli, proximal tubules, and distal tubules). The efficiency index of each tested rAAV normalized to AAV9 was calculated as follows in Formula I: (cDNA reads [%]/input [%])/(cDNA AAV9 reads [%]/input AAV9 [%]).
Figure 5:
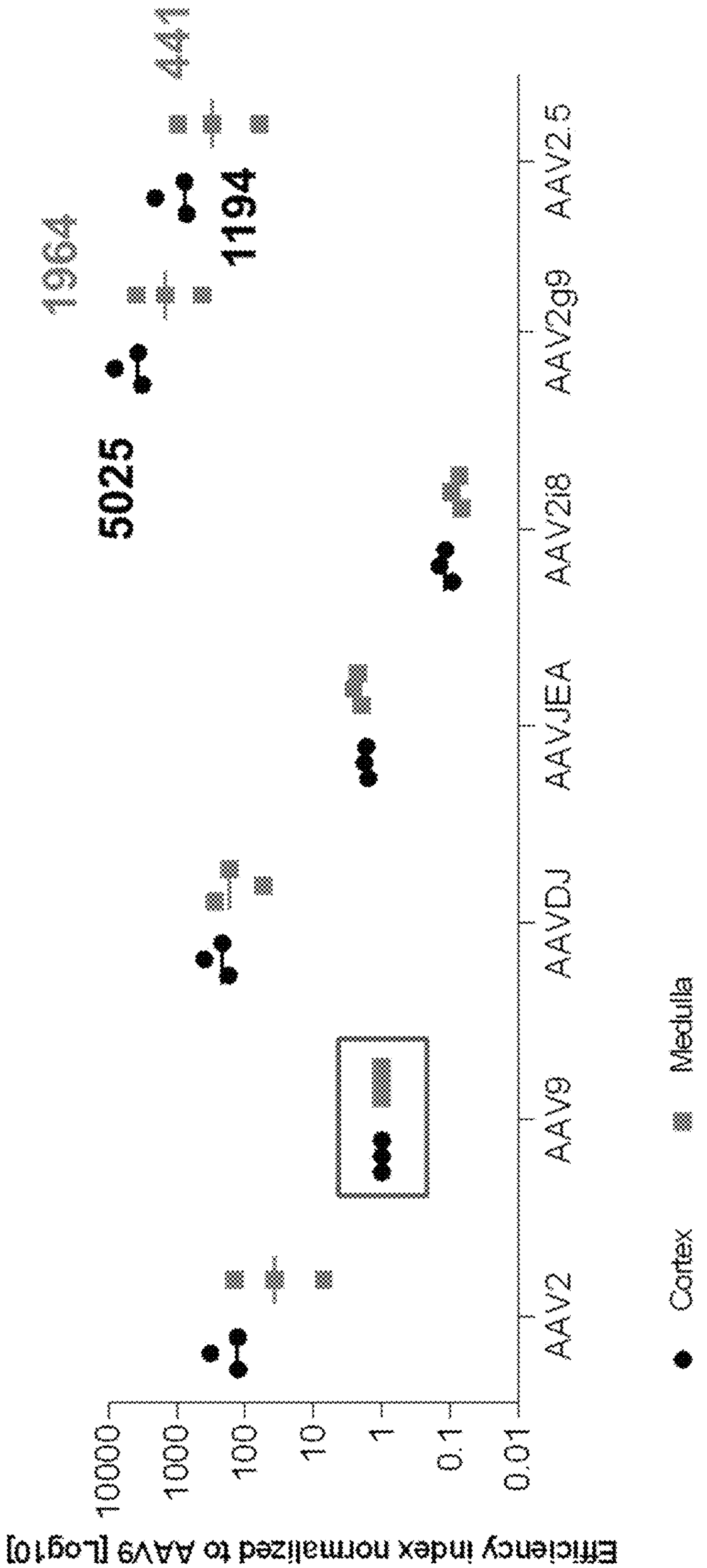
FIG. 5 is a dot plot showing the efficiency index of selected rAAVs from FIG. 4 normalized to AAV9 in the kidney medulla or kidney cortex. The efficiency index of each tested rAAV normalized to AAV9 was calculated as follows: (cDNA reads [%]/input [%])/(cDNA AAV9 reads [%]/input AAV9 [%]).

Also described herein are specific rAAVs that showed high transduction in the kidneys following retrograde ureter administration, including but not limited to an rAAV comprising a capsid selected from those described in Table 1 and FIGS. 4-5. Such specific rAAVs (e.g., AAV2G9, AAV2.5, AAVDJ, AAV2, AAVKP1, AAVKP2, AAVKP3, and AAV2.7m8) have increased levels of kidney transduction compared to AAV9. Furthermore, described herein are exemplary parameters for the retrograde ureter administration, including administration volume, timings, and renal vessel(s) occlusion. The retrograde ureter administration results in increased levels of kidney transduction compared to other administration routes (e.g., intravenous).

Administration and Treatment Methods

In multiple aspects, described herein are methods of administering a recombinant adeno-associated virus (rAAV) to a kidney of a subject and methods of treating a kidney-associated disorder in a subject in need thereof. In one aspect, described herein is a method of transducing a sufficient number of the nephrons in a kidney of a subject with a recombinant adeno-associated virus (rAAV) to obtain an effective level of expression in the kidney, the method comprising administering a volume of a solution comprising the rAAV into a ureter of the kidney in a retrograde route, wherein a solution comprising the rAAV is administered to the kidney for a time sufficient and/or at an intra-renal pressure sufficient to result in a pharmaceutically effective level of rAAV transduction in the nephrons of the kidney.

In one aspect, described herein is a method of transducing nephrons in a kidney of a subject with a recombinant adeno-associated virus (rAAV), the method comprising: guiding a catheter through the subject's urethra, bladder, and ureter; and administering a solution comprising the rAAV to the renal pelvis of the kidney at a volume of from about 0.13 mL/kg to about 0.33 mL/kg, the kg being the weight of the subject, wherein the kidney nephrons comprising nephron cells are transduced with the rAAV at a high efficiency.

In one aspect, described herein is a method of transducing at least about 15% of the nephrons in a kidney of a subject with a recombinant adeno-associated virus (rAAV), the method comprising: administering a volume of a solution comprising the rAAV into a ureter of the kidney in a retrograde route, wherein the volume is from about 0.13 mL/kg to about 0.33 mL/kg, the kg being the weight of the subject. In some embodiments, a solution comprising the rAAV is administered over a period of time from about 0.5 minutes to about 2 minutes. In some embodiments, a solution comprising the rAAV is administered over a period of time from about 1 minute to 60 minutes. In some embodiments, the method further comprises a step of blocking a renal blood vessel of the kidney selected from the group consisting of a renal artery, a renal vein, and a combination thereof, prior to administering the rAAV. In some embodiments, the method further comprises unblocking the renal blood vessel after a period of time of from about 10 minutes to about 60 minutes subsequent to the blocking and/or after administering the solution comprising the rAAV.

In one aspect, described herein is a method of transducing at least about 15% of the nephrons in a kidney of a subject with a recombinant adeno-associated virus (rAAV), the method comprising: (a) blocking a renal blood vessel of the kidney selected from the group consisting of a renal artery, a renal vein, and a combination thereof; (b) administering a volume of a solution comprising the rAAV into a ureter of the kidney in a retrograde route, wherein the volume is from about 0.13 mL/kg to about 0.33 mL/kg, the kg being the weight of the subject; and (c) unblocking the renal blood vessel after a period of time of from about 10 minutes to about 60 minutes subsequent to the blocking and/or after administering the solution comprising the rAAV.

In one aspect, described herein is a method of transducing at least about 20% of the nephrons in a kidney of a subject with the rAAV.

In one aspect, described herein is a method of transducing at least about 25% of the nephrons in a kidney of a subject with the rAAV.

In one aspect, described herein is a method of transducing at least about 25% of the nephrons in a kidney of a subject with a recombinant adeno-associated virus (rAAV), the method comprising: (a) blocking a renal artery of the kidney and not blocking a renal vein of the kidney; (c) administering a volume of a solution comprising the rAAV into a ureter of the kidney in a retrograde route; and (c) unblocking the renal artery after a period of time of from about 10 minutes to about 60 minutes subsequent to the blocking and/or after administering the solution comprising the rAAV. In some embodiments, the method results in the transduction of at least about 25% of the nephrons in the kidney with the rAAV.

In one aspect, described herein is a method of transducing nephrons in a kidney of a subject, the method comprising: (a) blocking a renal blood vessel selected from the group consisting of a renal artery, a renal vein, and a combination thereof of the kidney; (b) administering a volume of a solution comprising rAAV into a ureter of the kidney in a retrograde route, the rAAV not being rAAV9; and (c) unblocking the renal blood vessel after a period of time of from about 10 minutes to about 60 minutes subsequent to the blocking and/or after administering the solution comprising the rAAV. In some embodiments, the method results in a transduction efficiency that is at least 2-fold higher than a corresponding administration using rAAV9 instead of the rAAV. In some embodiments, the rAAV has at least 400-fold or at least 3500-fold higher transduction efficiency than AAV9.

In one aspect, described herein is a method of transducing at least about 30% of the nephrons in a kidney of a subject with the rAAV. In one aspect, described herein is a method of administering a recombinant adeno-associated virus (rAAV) to a kidney of a subject and/or treating a kidney-associated disorder in a subject in need thereof, the method comprising: (a) blocking at least one renal blood vessel selected from the group consisting of a renal artery, a renal vein, and a combination thereof of the kidney; (b) administering a volume of a solution comprising the rAAV into a ureter of the kidney in a retrograde route, wherein the volume is no more than 0.33 mL/kg; and (c) unblocking the at least one renal blood vessel after a period of time subsequent to the blocking and/or after administering the solution comprising the rAAV.

In one aspect, described herein is a method of transducing at least about 15% of the nephrons in a kidney of a subject with a recombinant adeno-associated virus (rAAV), the method comprising: (a) blocking a renal blood vessel selected from the group consisting of a renal artery, a renal vein, and a combination thereof of the kidney; (b) administering a volume of a solution comprising the rAAV into a ureter of the kidney in a retrograde route, wherein the volume is from about 0.13 mL/kg to about 0.33 mL/kg, the kg being the weight of the subject, wherein the rAAV comprises a capsid protein from serotype AAV2G9; and (c) unblocking the renal blood vessel after a period of time of from about 10 minutes to about 60 minutes subsequent to the blocking and/or after administering the solution comprising the rAAV. In some embodiments, the method results in the transduction of at least about 25% of the nephrons in the kidney with the 2G9 rAAV.

In one aspect, described herein is a method of administering a recombinant adeno-associated virus (rAAV) to a kidney of a subject and/or treating a kidney-associated disorder in a subject in need thereof, the method comprising: (a) blocking at least one renal blood vessel selected from the group consisting of a renal artery, a renal vein, and a combination thereof of the kidney; (b) administering a volume of about 0.13 mL/kg to about 0.33 mL/kg of a solution comprising the rAAV into a ureter of the kidney in a retrograde route, wherein the rAAV comprises a capsid protein from serotype AAV2G9; and (c) unblocking the at least one of the renal blood vessel after a period of time subsequent to the blocking and/or after administering the solution comprising the rAAV.

In some embodiments of any of the aspects, the step of "blocking at least one renal blood vessel selected from the group consisting of a renal artery, a renal vein, and a combination thereof of the kidney" or "blocking a renal blood vessel of the kidney selected from the group consisting of a renal artery, a renal vein, and a combination thereof" or "blocking a renal blood vessel selected from the group consisting of a renal artery, a renal vein, and a combination thereof of the kidney" or the like is replaced with a step of "isolating the kidney from systemic circulation."

In some embodiments of any of the aspects, the step of "unblocking the at least one of the renal blood vessel after a period of time" or "unblocking the renal blood vessel after a period of time" or "unblocking the at least one renal blood vessel after a period of time" or the like subsequent to the blocking is replaced with a step of "re-establishing the kidney into systemic circulation after a period of time" subsequent to the isolating.

In one aspect, described herein is a method of transducing at least about 25% of the nephrons in a kidney of a subject with a recombinant adeno-associated virus (rAAV), the method comprising: (a) isolating the kidney from systemic circulation; (b) administering a volume of a solution comprising the rAAV into a ureter of the kidney in a retrograde route, wherein the volume is from about 0.13 mL/kg to about 0.33 mL/kg, the kg being the weight of the subject; and (c) re-establishing the kidney into systemic circulation after a period of time of from about 10 minutes to about 60 minutes subsequent to the isolating. In some embodiments, the method results in the transduction of at least about 25% of the nephrons in the kidney with the rAAV.

In some aspects, described herein is a method of transducing nephrons of a kidney in a subject with a rAAV comprising an AAV2g9 capsid. The method comprises guiding a catheter through the subject's urethra, bladder, and ureter, and administering a solution comprising the rAAV to the renal pelvis of the kidney at a volume of from about 0.13 mL/kg to about 0.33 mL/kg (the kg being the weight of the subject). In various embodiments, an end of the catheter through which the solution is delivered is positioned in the ureter, and the solution is administered in the ureter and flushed into the renal pelvis of the kidney. In other embodiments, an end of the catheter through which the solution is delivered is positioned in the renal pelvis and the solution is administered directly to the renal pelvis of the kidney. As a result of the administration, nephrons of the kidney are transduced with the rAAV at a high efficiency.

In some aspects, described herein is a method of transducing nephrons of a kidney in a subject with a rAAV. The method comprises guiding a catheter through the subject's urethra, bladder, and ureter, and administering a solution comprising the rAAV to the renal pelvis of the kidney at a volume of from about 0.13 mL/kg to about 0.33 mL/kg (the kg being the weight of the subject). In various embodiments, an end of the catheter through which the solution is delivered is positioned in the ureter and the solution is administered in the ureter and flushed into the renal pelvis of the kidney. In other embodiments, an end of the catheter through which the solution is delivered is positioned in the renal pelvis and the solution is administered directly to the renal pelvis of the kidney. As a result of the administration, nephrons of the kidney are transduced with the rAAV at a high efficiency.

As used here, a "high efficiency" means a level of transduction, e.g., a nephron transduction efficiency or nephron component transduction efficiency, that results in detectable and/or measurable levels of rAAV in cells of the kidney. In various embodiments, a high efficiency corresponds to a nephron transduction efficiency or nephron component transduction efficiency of at least 10%, at least 15%, at least 20%, at least 25%, at least 30%, at least 35%, at least 40%, at least 45%, or at least 50%, or more. In some embodiments, a high efficiency corresponds to an efficiency index (as defined herein; see e.g., Formula I) that is greater than 1, e.g., having efficiency higher than what is achieved by administering rAAV comprising an AAV9 capsid. For example, the efficiency index is greater than 1, greater than 2, greater than 3, greater than 4, greater than 5, greater than 6, greater than 7, greater than 8, greater than 9, greater than 10, greater than 20, greater than 30, greater than 40, greater than 50, greater than 60, greater than 70, greater than 80, greater than 90, greater than 100, greater than 200, greater than 300, greater than 400, greater than 500, greater than 600, greater than 700, greater than 800, greater than 900, greater than 1000, greater than 2000, greater than 3000, greater than 4000, greater than 5000. It is understood that each of the individual efficiency indices described herein can be used to define lower and upper values of an efficiency index range. In some embodiments, the efficiency index is between 1 and 6000, between 1 and 5000, between 1 and 4000, between 1 and 3000, between 1 and 2000, between 1 and 1000, between 1 and 900, between 1 and 800, between 1 and 700, between 1 and 600, between 1 and 500, between 1 and 400, between 1 and 300, between 1 and 200, between 1 and 100, between 1 and 90, between 1 and 80, between 1 and 70, between 1 and 60, between 1 and 50, between 1 and 40, between 1 and 30, between 1 and 20, between 1 and 10, between 1 and 9, between 1 and 8, between 1 and 7, between 1 and 6, between 1 and 5, between 1 and 4, between 1 and 3, or between 1 and 2. Such high efficiencies corresponds to a clinically relevant level of transduction. In various embodiments, a clinically relevant level is a therapeutically and/or pharmaceutically effective level.

In some embodiments, the method results in a therapeutically and/or pharmaceutically effective level of rAAV transduction in the nephrons of the kidney, which can vary depending on the specific disease and/or location in the kidney of the transduction. The terms "therapeutically effective" or "pharmaceutically effective" level of transduction refer to the level of transduction sufficient to provide transgene expression (e.g., a transgene encoded by the rAAV genome) in the transduced kidney cells that is sufficient to treat or ameliorate at least one symptom caused by or resulting from a kidney-associated disorder in the subject or to inhibit, slow, minimize, or reverse the progression of a kidney-associated disorder in the subject. In various embodiments, a therapeutically and/or pharmaceutically effective level corresponds to a nephron transduction efficiency or nephron component transduction efficiency of at least 10%, at least 15%, at least 20%, at least 25%, at least 30%, at least 35%, at least 40%, at least 45%, or at least 50%.

In some embodiments, the method results in the transduction of at least about 25% of the nephrons in the kidney with the rAAV. For example, by blocking (e.g., clamping) the renal artery or isolating the kidney from systemic circulation, administering 20 mL to kidney via ureter, holding for 15-30 min, and unblocking (e.g., unclamping) or re-establishing the kidney into systemic circulation, rAAV transduction of the nephrons is at least 30%, which had not previously been described.

As used herein, the terms "transducing a nephron" or "transducing nephrons" interchangeably refer to transducing at least one cell of a nephron, the at least one cell being: a glomerulus cell (including cells of Bowman's capsule); a proximal tubule (also referred to as a proximal convoluted tubule) cell; a cell of the loop of Henle (including descending and/or ascending limbs, and thick and/or thin regions thereof); a distal tubule (also referred to as a distal convoluted tubule) cell; a collecting duct cell; or a combination thereof. Similarly, the terms "transducing a nephron 'component'" or "transducing nephron 'components'" interchangeably refer to transducing at least one cell of a nephron component, the nephron component being: a glomerulus (including Bowman's capsule); a proximal tubule (also referred to as a proximal convoluted tubule); the loop of Henle (including descending and/or ascending limbs, and thick and/or thin regions thereof); a distal tubule (also referred to as a distal convoluted tubule); or a collecting duct.

The terms "nephron transduction efficiency" and "nephron component transduction efficiency" refer to a number of transduced nephrons or nephron components relative to the total number of nephrons or total number of nephron components in a kidney, respectively. Accordingly, a nephron transduction efficiency of 10% means that 10% of the total number of nephrons in the kidney are transduced. For example, in a hypothetical kidney having exactly 1 million (1,000,000) nephrons, a nephron transduction efficiency of 10% means that 100,000 of the 1,000,000 nephrons are transduced. Put another way, in the hypothetical kidney having exactly 1 million (1,000,000) nephrons, the nephron transduction efficiency of 10% means that at least one cell in each of 100,000 individual nephrons of the 1,000,000 total individual nephrons is transduced. Similarly, a proximal tubule transduction percentage of 10% means that 10% of the total number of proximal tubules in the kidney are transduced. For example, in a hypothetical kidney having exactly 1 million (1,000,000) proximal tubules (e.g., one proximal tubule per nephron), a proximal tubule transduction efficiency of 10% means that 100,000 of the 1,000,000 proximal tubules are transduced. Put another way, in the hypothetical kidney having exactly 1 million (1,000,000) nephrons (thus 1,000,0000 proximal tubules), the proximal tubule transduction efficiency of 10% means that at least one cell in each of 100,000 individual proximal tubules of the 1,000,000 total individual proximal tubules is transduced.

Because a transduced nephron component can have more than one cell that is transduced, this aspect can be discussed in terms of a "cellular transduction efficiency." For example, a single nephron can have a nephron cellular transduction efficiency of 30%, which means that 30% of the total number cells making up that single nephron are transduced. Similarly, a single proximal tubule may have a proximal tubule cellular transduction efficiency of 30%, which means 30% of the total number cells in that single proximal tubule are transduced. It is understood that even though 30% of the total number cells in the proximal tubule are transduced, this aspect does not preclude transduction of other components of the same nephron. For example, a cell can have a proximal tubule cellular transduction efficiency of 30% along with specified or unspecified cellular efficiency relating to cells of the loop of Henle (ascending and/or descending limbs, and thick and/or thin regions thereof), cells of the distal tubule, and/or cells of the corresponding collecting duct.

Accordingly, in some aspects, the current technology provides for both a nephron transduction efficiency and a cellular transduction efficiency. As an example, the term "a proximal tubule transduction efficiency of at least 20% and a proximal tubule cellular transduction efficiency of at least 30%" means that at least 20% of the of the total number of proximal tubules in a kidney are transduced and at least 30% of the proximal tubule cells in each of the transduced proximal tubules are transduced, or to put it another way, at least 30% of the proximal tubule cells in at least 20% of the total number proximal tubules in the kidney are transduced.

Descriptions herein, for example, of transduction of a percentage of nephrons in a kidney may refer to a nephron transduction efficiency, a nephron component transduction efficiency, and/or a cellular transduction efficiency.

In some embodiments, the method results in a proximal tubule transduction efficiency of at least 5%, at least 10%, at least 15%, at least 20%, at least 25%, at least 30%, at least 35%, at least 40%, at least 45%, or at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more.

In some embodiments, the method results in a proximal tubule cellular transduction efficiency of at least 5%, at least 10%, at least 15%, at least 20%, at least 25%, at least 30%, at least 35%, at least 40%, at least 45%, or at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more. It is understood that each of the individual percentages described herein can be used to define lower and upper values of a percentage range.

In some embodiments, the method results in a proximal tubule transduction efficiency of at least 30% and a proximal tubule cellular transduction efficiency of at least 30%. In some embodiments, the method results in a proximal tubule transduction efficiency of at least 20% and a proximal tubule cellular transduction efficiency of at least 30%. In some embodiments, the method results in a proximal tubule transduction efficiency of at least 30% and a proximal tubule cellular transduction efficiency of at least 20%. In some embodiments, the method results in a proximal tubule transduction efficiency of at least 20% and a proximal tubule cellular transduction efficiency of at least 20%. In some embodiments, the method results in a proximal tubule transduction efficiency of at least 25% and a proximal tubule cellular transduction efficiency of at least 25%.

In some embodiments, the method results in the transduction of about at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or more of the nephrons in the kidney with the rAAV, or in other words about at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the total number of "nephron cells" (cells of the nephron) in the kidney with the rAAV. In some embodiments, the transduced cells are epithelial cells. It is understood that each of the individual percentages described herein can be used to define lower and upper values of a percentage range.

In some embodiments, the method results in the transduction of about at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or more of the nephrons in the kidney with the rAAV, or in other words about at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the total number of "nephron cells" (e.g., proximal convoluted tubule cells, loop of Henle cells, distal convoluted tubule cells, collecting duct cells, or any combination thereof) in the kidney with the rAAV. It is understood that each of the individual percentages described herein can be used to define lower and upper values of a percentage range. In some embodiments, the transduced cells are epithelial cells from the proximal tubule (see e.g., Example 3). In some embodiments, the transduced cells are epithelial cells from the loop of Henle. In some embodiments, the transduced cells are epithelial cells from the distal convoluted tubule. In some embodiments, the transduced cells are epithelial cells from the collecting duct. In some embodiments, the transduced cells are epithelial cells from the distal convoluted tubule and collecting duct (see e.g., Example 3).

In some embodiments, the transduced cells of the nephrons are epithelial cells from the proximal tubules. Accordingly, the method can include transducing at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the proximal tubules of the kidney or epithelial cells of the proximal tubules of the kidney (see e.g., Table 11). It is understood that each of the individual percentages described herein can be used to define lower and upper values of a percentage range. Transduction of the proximal tubules or epithelial cells of the proximal tubules can be measured using a variety of methods known in the art. As a non-limiting example, the colocalization of the thick brush border (typical and unique to the proximal tubule) and the rAAV reporter gene can be quantified compared to the total number of thick brush border cells. Additional non-limiting examples of markers for proximal tubule epithelial cells include megalin, cubilin, sodium-glucose cotransport 1 (SGLT1), sodium-glucose cotransport 2 (SGLT2), vimentin, Kim-1, Na/Pi, PDZ domain containing 1 (PDZK1), Solute Carrier Family 3 Member 1 (SLC3A1; also referred to as NaS1), stem cells antigen-1 (Sca-1), CD13, and/or aquaporin; see e.g., Agarwal et al. "Renal cell markers: lighthouses for managing renal diseases," Am J Physiol Renal Physiol. 2021 Dec. 1; 321(6):F715-F739, the contents of which are incorporated herein by reference in their entirety.

In some embodiments, the transduced cells of the nephrons are epithelial cells from the loops of Henle. Accordingly, the method can include transducing at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the epithelial cells of the loops of Henle. It is understood that each of the individual percentages described herein can be used to define lower and upper values of a percentage range.

In some embodiments, the method results in a loop of Henle transduction efficiency of at least 30% and a loop of Henle cellular transduction efficiency of at least 30%. In some embodiments, the method results in a loop of Henle transduction efficiency of at least 20% and a loop of Henle cellular transduction efficiency of at least 30%. In some embodiments, the method results in a loop of Henle transduction efficiency of at least 30% and a loop of Henle cellular transduction efficiency of at least 20%. In some embodiments, the method results in a loop of Henle transduction efficiency of at least 20% and a loop of Henle cellular transduction efficiency of at least 20%. In some embodiments, the method results in a loop of Henle transduction efficiency of at least 25% and a loop of Henle cellular transduction efficiency of at least 25%.

In some embodiments, the transduced cells of the nephrons are epithelial cells from the distal convoluted tubules. Accordingly, the method can include transducing at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the epithelial cells of the distal convoluted tubules of the kidney. It is understood that each of the individual percentages described herein can be used to define lower and upper values of a percentage range.

In some embodiments, the method results in a distal tubule transduction efficiency of at least 30% and a distal tubule cellular transduction efficiency of at least 30%. In some embodiments, the method results in a distal tubule transduction efficiency of at least 20% and a distal tubule cellular transduction efficiency of at least 30%. In some embodiments, the method results in a distal tubule transduction efficiency of at least 30% and a distal tubule cellular transduction efficiency of at least 20%. In some embodiments, the method results in a distal tubule transduction efficiency of at least 20% and a distal tubule cellular transduction efficiency of at least 20%. In some embodiments, the method results in a distal tubule transduction efficiency of at least 25% and a distal tubule cellular transduction efficiency of at least 25%.

In some embodiments, the transduced cells of the nephrons are epithelial cells from the collecting ducts. Accordingly, the method can include transducing at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the epithelial cells of the collecting ducts of the kidney. It is understood that each of the individual percentages described herein can be used to define lower and upper values of a percentage range.

In some embodiments, the method results in a collecting duct transduction efficiency of at least 30% and a collecting duct cellular transduction efficiency of at least 30%. In some embodiments, the method results in a collecting duct transduction efficiency of at least 20% and a collecting duct cellular transduction efficiency of at least 30%. In some embodiments, the method results in a collecting duct transduction efficiency of at least 30% and a collecting duct cellular transduction efficiency of at least 20%. In some embodiments, the method results in a collecting duct transduction efficiency of at least 20% and a collecting duct cellular transduction efficiency of at least 20%. In some embodiments, the method results in a collecting duct transduction efficiency of at least 25% and a collecting duct cellular transduction efficiency of at least 25%.

In some embodiments, the transduced cells of the nephrons are epithelial cells from the distal convoluted tubules and/or collecting ducts. Accordingly, the method can include transducing at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the epithelial cells of the distal convoluted tubules and/or collecting ducts of the kidney (see e.g., Table 12). It is understood that each of the individual percentages described herein can be used to define lower and upper values of a percentage range.

In some embodiments, the method results in a distal convoluted tubule and/or collecting duct transduction efficiency of at least 30% and a distal convoluted tubule and/or collecting duct cellular transduction efficiency of at least 30%. In some embodiments, the method results in a distal convoluted tubule and/or collecting duct transduction efficiency of at least 20% and a distal convoluted tubule and/or collecting duct cellular transduction efficiency of at least 30%. In some embodiments, the method results in a distal convoluted tubule and/or collecting duct transduction efficiency of at least 30% and a distal convoluted tubule and/or collecting duct cellular transduction efficiency of at least 20%. In some embodiments, the method results in a distal convoluted tubule and/or collecting duct transduction efficiency of at least 20% and a distal convoluted tubule and/or collecting duct cellular transduction efficiency of at least 20%. In some embodiments, the method results in a distal convoluted tubule and/or collecting duct transduction efficiency of at least 25% and a distal convoluted tubule and/or collecting duct cellular transduction efficiency of at least 25%.

In some embodiments, the transduction percentage of the nephrons can represent transduction percentage of all the proximal tubules in the kidney. As a non-limiting example, transduction of 30% of the nephrons refers to transduction of 30% of the proximal tubules or proximal tubule cells per treated kidney. In some embodiments, at least 30% of the nephrons or nephron cells per treated kidney are transduced, and other nephrons can be transduced at locations other than the proximal tubule. In some embodiments, the nephron transduction percentage in a kidney can be higher than the proximal tubules transduction percentage, e.g., when accounting for transduction in the proximal tubules and other locations of the nephron.

In some embodiments, the method results in the transduction of cells and/or nephrons in at least one pyramid and/or associated cortex region of the kidney. Renal pyramids are kidney tissues that are shaped like cones in the medulla; a kidney can contain between 7 and 18 pyramids. Each pyramid ends in a papilla, where collecting ducts drain urine into the minor and major calyxes, which combine into the renal pelvis and then ureter. The superficial cortex region includes proximal and distal tubules connected to loops of Henle and collecting ducts in the deeper medullary pyramids. In some embodiments, the method results in the transduction of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or more of cells and/or nephrons in at least one pyramid and/or associated cortex region of the kidney. In some embodiments, the method results in the transduction of at least one cell or at least one nephron in at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, 90-100%, 95-100%, or more of the pyramids and/or associated cortex regions of the kidney. It is understood that each of the individual percentages described herein can be used to define lower and upper values of a percentage range.

In some embodiments, the volume of the solution comprising the rAAV is from about 0.13 mL/kg to about 0.33 mL/kg of the subject. The "kg" (kilograms) indicates the weight of the subject. The volume of 0.13 mL/kg to about 0.33 mL/kg is equivalent to 10 mL to 25 mL in a 75 kg subject. In some embodiments, the volume can be adjusted according to the weight of the subject. For example, instead of administering 25 mL maximal volume to a 75 kg subject, 30 mL maximal volume can be administered to a 90 kg subject. In some embodiments, the subject weighs 60 kg to 90 kg. Volumes below 0.13 mL/kg may not be sufficient to elicit sufficient transduction in the kidney. On the other hand, volumes above 0.33 mL/kg may damage the kidney.

In some embodiments, the volume of the solution comprising the rAAV is from about 0.13 mL/kg to about 0.35 mL/kg. In some embodiments, the volume of the solution comprising the rAAV is from about 0.13 mL/kg to about 0.33 mL/kg, from about 0.15 mL/kg to about 0.30 mL/kg, or from about 0.2 mL/kg to about 0.25 mL/kg. In some embodiments, the volume of the solution comprising the rAAV is from about 0.27 mL/kg to about 0.33 mL/kg. In some embodiments, the volume of the solution comprising the rAAV is from about 0.2 mL/kg to about 0.27 mL/kg. In some embodiments, the volume of the solution comprising the rAAV is about 0.24 mL/kg. In some embodiments, the volume of the solution comprising the rAAV is from about 0.13 mL/kg to about 0.35 mL/kg, about 0.15 mL/kg to about 0.35 mL/kg, about 0.2 mL/kg to about 0.35 mL/kg, from about 0.25 mL/kg to about 0.35 mL/kg, from about 0.3 mL/kg to about 0.35 mL/kg, from about 0.13 mL/kg to about 0.30 mL/kg, from about 0.13 mL/kg to about 0.25 mL/kg, or from about 0.13 mL/kg to about 0.2 mL/kg. In some embodiments, the volume of the solution comprising the rAAV is 0.13 mL/kg, 0.14 mL/kg, 0.15 mL/kg, 0.16 mL/kg, 0.17 mL/kg, 0.18 mL/kg, 0.19 mL/kg, 0.2 mL/kg, 0.21 mL/kg, 0.22 mL/kg, 0.23 mL/kg, 0.24 mL/kg, 0.25 mL/kg, 0.26 mL/kg, 0.27 mL/kg, 0.28 mL/kg, 0.29 mL/kg, 0.3 mL/kg, 0.31 mL/kg, 0.32 mL/kg, 0.33 mL/kg, 0.34 mL/kg, 0.35 mL/kg, 0.05-0.15 mL/kg, 0.10-0.20 mL/kg, 0.15-0.25 mL/kg, 0.20-0.30 mL/kg, 0.25-0.35 mL/kg, 0.05-0.10 mL/kg, 0.10-0.15 mL/kg, 0.15-0.20 mL/kg, 0.20-0.25 mL/kg, 0.25-0.30 mL/kg, 0.30-0.35 mL/kg, 0.05-0.35 mL/kg, 0.10-0.35 mL/kg, 0.15-0.35 mL/kg, 0.20-0.35 mL/kg, 0.05-0.20 mL/kg, 0.05-0.25 mL/kg, or 0.05-0.30 mL/kg. It is understood that each of the individual volumes described herein can be used to define lower and upper values of a volume range.

In some embodiments, the volume of the solution comprising the rAAV is a volume selected from the group consisting of at least 0.05 mL/kg, at least 0.1 mL/kg, at least 0.13 mL/kg, at least 0.14 mL/kg, at least 0.15 mL/kg, at least 0.16 mL/kg, at least 0.17 mL/kg, at least 0.18 mL/kg, at least 0.19 mL/kg, at least 0.20 mL/kg, at least 0.21 mL/kg, at least 0.22 mL/kg, at least 0.23 mL/kg, at least 0.24 mL/kg, at least 0.25 mL/kg, at least 0.26 mL/kg, at least 0.27 mL/kg, at least 0.28 mL/kg, at least 0.29 mL/kg, at least 0.30 mL/kg, at least 0.31 mL/kg, at least 0.32 mL/kg, at least 0.33 mL/kg, at least 0.34 mL/kg, and at least 0.35 mL/kg. In some embodiments, the volume of the solution comprising the rAAV is a volume selected from the group consisting of at most 0.30 mL/kg, at most 0.31 mL/kg, at most 0.32 mL/kg, at most 0.33 mL/kg, at most 0.34 mL/kg, or at most 0.35 mL/kg. It is understood that each of the individual volumes described herein can be used to define lower and upper values of a volume range.

In some embodiments, heparin is administered to the subject prior to, during, or after the retrograde rAAV administration, e.g., to prevent blood coagulation during the procedure.

In some embodiments, a solution comprising the rAAV is administered to the kidney at an intra-renal pressure that results in pyelotubular reflux and pyelovenous backflow with no fornix rupture. The term "pyelotubular reflux" (also referred to interchangeably as "intrarenal reflux") refers to urinary reflux (i.e., a backward or return flow) from renal pelvis and calyces into the collecting ducts; pyelotubular reflux can be seen as a blush of the renal pyramid on voiding cystourethrography. The term "pyelovenous backflow" (also referred to as "pyelovenous reflux") refers to drainage of fluid from the renal pelvis of a kidney into the renal venous system; pyelovenous backflow can occur when abnormal amounts of intra-renal pressure occur in a direction opposite to normal. The term "renal fornix" (or "fornix") refers to the thin pointed projections, arising from the lateral aspects of each minor calyx, and extending a short distance into the renal columns; each fornix contacts the renal pyramid on its inner surface. Rupture of the renal fornix can be due to increased renal pelvis pressure; rupture of one or more renal fornices can lead to peri-renal or retro-peritoneal extravasation (leakage) of urine.

The normal intrarenal pressure (IRP) range is 0 cm $H_2O$ to 20 cm $H_2O$. An IRP between 27 cm $H_2O$ to 41 cm $H_2O$ results in pyelotubular reflux. An IRP between 41 cm $H_2O$ to 68 cm $H_2O$ results in pyelovenous backflow. An IRP below 27 cm $H_2O$ does not result in pyelotubular reflux or pyelovenous backflow and is thus not an effective IRP for the methods described herein. An IRP between 81 cm $H_2O$ to 95 cm $H_2O$ can result in fornix rupture. As such, the methods described herein use an IRP that is 80 cm $H_2O$ or less. An above-normal IRP (e.g., for an extended time period, e.g., multiple days) can be associated with infectious and hemorrhagic complications, as well as kidney damage. See e.g., Pauchard et al. "A Practical Guide for Intra-Renal Temperature and Pressure Management during Rirs: What Is the Evidence Telling Us," J Clin Med. 2022 June; 11(12): 3429; the contents of which are incorporated herein by reference in its entirety.

In some embodiments, the administered volume and resultant intrarenal pressure are determined in a subject, such as a human, a non-human primate, or a pig, which is a relevant animal model for human translation due to their anatomical and physiological similarities to humans. Intrarenal pressure can be measured by methods known in the art, such as a sensor wire (e.g., a wire including a pressure sensor; e.g., placed into the renal cavities) and the like.

When working with an irrigation flow (i.e., flow rate) greater than 6 mL/min, the ureter behaves like an open tube, resulting in a linear relationship between flow and pressure. In some embodiments, about 0.13 mL/kg to about 0.35 mL/kg of the rAAV solution are administered over a time period from about 0.5 minutes (30 seconds) to about 2 minutes (120 seconds). The time for administration of the rAAV can be shorter for smaller volumes and/or smaller subjects (e.g., 5 mL/min for 2.5 mL in about 0.5-1.0 minutes for an 8-12 kg subject) or longer for larger volumes and/or larger subjects (e.g., 9 mL/min for 18 mL in about 1-2 minutes for a 60-80 kg subject). A shorter time period for administration of the rAAV can reduce risk of damage to the fornix structure of the kidney. In some embodiments, a solution comprising the rAAV is administered for a time sufficient to reach a desired intrarenal pressure (e.g., from about 25 cm $H_2O$ to about 55 cm $H_2O$, or from about 27 cm $H_2O$ to about 80 cm $H_2O$). In some embodiments, about 0.13 mL/kg to about 0.35 mL/kg of the rAAV solution are administered over a time period from about 10 minutes to about 60 minutes, resulting in a flow rate from between about 0.167 mL/min to about 2.5 mL/min. In some embodiments, the flow rate is below 6 mL/min. In some embodiments, the ureter does not behave like an open tube when the rAAV solution is administered. In some embodiments, the volume of the administered solution significantly affects efficacy of the treatment, while the flow rate does not significantly affect efficacy of the treatment.

In some embodiments, a solution comprising the rAAV is administered to the kidney at an intra-renal pressure of from about 25 cm $H_2O$ to about 55 cm $H_2O$. In some embodiments, a solution comprising the rAAV is administered to the kidney at an intra-renal pressure of about 46 cm $H_2O$. In some embodiments, a solution comprising the rAAV is administered to the kidney at an intra-renal pressure of about 45 cm $H_2O$. In some embodiments, a solution comprising the rAAV is administered to the kidney at an intra-renal pressure of from about 27 cm $H_2O$ to about 80 cm $H_2O$. In some embodiments, a solution comprising the rAAV is administered to the kidney at an intra-renal pressure of from about 27 cm $H_2O$ to about 41 cm $H_2O$. In some embodiments, a solution comprising the rAAV is administered to the kidney at an intra-renal pressure of from about 41 cm $H_2O$ to about 68 cm $H_2O$. In some embodiments, a solution comprising the rAAV is administered to the kidney at an intra-renal pressure of from about 68 cm $H_2O$ to about 80 cm $H_2O$. In some embodiments, a solution comprising the rAAV is administered to the kidney at an intra-renal pressure of about at least 20 cm $H_2O$, at least 25 cm $H_2O$, at least 30 cm $H_2O$, at least 35 cm $H_2O$, at least 40 cm $H_2O$, at least 45 cm $H_2O$, at least 50 cm $H_2O$, at least 55 cm $H_2O$, at least 60 cm $H_2O$, at least 65 cm $H_2O$, at least 70 cm $H_2O$, or at least 75 cm $H_2O$. In some embodiments, a solution comprising the rAAV is administered to the kidney at an intra-renal pressure of about at most 25 cm $H_2O$, at most 30 cm $H_2O$, at most 35 cm $H_2O$, at most 40 cm $H_2O$, at most 45 cm $H_2O$, at most 50 cm $H_2O$, at most 55 cm $H_2O$, at most 60 cm $H_2O$, at most 65 cm $H_2O$, at most 70 cm $H_2O$, at most 75 cm $H_2O$, or at most 80 cm $H_2O$. In some embodiments, a solution comprising the rAAV is administered to the kidney at an intra-renal pressure range of about 20-30 cm $H_2O$, 25-35 cm $H_2O$, 30-40 cm $H_2O$, 35-45 cm $H_2O$, 40-50 cm $H_2O$, 45-55 cm $H_2O$, 50-60 cm $H_2O$, 55-65 cm $H_2O$, 60-70 cm $H_2O$, 65-75 cm $H_2O$, 70-80 cm $H_2O$, 20-40 cm $H_2O$, 20-50 cm $H_2O$, 20-60 cm $H_2O$, 20-70 cm $H_2O$, 20-80 cm $H_2O$, 25-85 cm $H_2O$, 30-80 cm $H_2O$, 40-80 cm $H_2O$, 50-80 cm $H_2O$, or 60-80 cm $H_2O$. It is understood that each of the individual intrarenal pressures described herein can be used to define lower and upper values of an intrarenal pressure range.

In some embodiments, the solution comprising the rAAV is administered in the retrograde route to the ureter using a catheter or cannula. As used herein, the terms "catheter" and "cannula" are used interchangeably to refer to a hollow tube that can inserted into, for example, a body cavity, a blood vessel, the urethra, the ureter, etc.; in some embodiments, the catheter is thin (e.g., at most 5, 6, 7, 8, 9, 10, 11, 12 mm in diameter) and/or flexible. In some embodiments, the catheter is made from a material that does not trigger an immune response (e.g., latex, silicone, TEFLON, polyvinyl chloride, etc.) and/or is treated to reduce infection (e.g., silver-coated catheter). In some embodiments, any solutions or pharmaceutical composition described herein (e.g., comprising at least one rAAV) can be manually delivered into the ureter using a plunger associated with a catheter or cannula. In some embodiments, any solutions or pharmaceutical composition described herein (e.g., comprising at least one rAAV) can be manually delivered into the ureter using an automatic injection, e.g., pump (syringe pump, peristaltic pump, etc.).

In some embodiments, a catheter can be used to administer the rAAV solution to the kidney. The catheter can be inserted through the subject's urethra, through the bladder, and up through a ureter of the kidney to a desired location within the ureter, e.g., at, near, or in the renal pelvis. In some embodiments, the catheter used to administer the solution comprising the rAAV is a balloon catheter. In some embodiments, the balloon catheter is inflated to block the ureter and prevent, inhibit, or minimize urine and/or rAAV backflow downstream of the balloon, e.g., from the bladder, back toward the kidney, before, during, and/or after administration of the solution comprising the rAAV. In some embodiments, the balloon catheter is deflated to unblock the ureter after the period of time, e.g., after 10-60 minutes subsequent to the blocking and/or after administering the solution comprising the rAAV. In some embodiments, the catheter used to administer the solution comprising the rAAV is a non-balloon catheter and/or the ureter is not blocked during administration of the solution comprising the rAAV.

In some embodiments, the administering the volume of the solution comprising rAAV into the ureter of the kidney in the retrograde route is performed by injecting the rAAV, e.g., a composition comprising the rAAV, into the ureter. The injecting can be performed using a syringe coupled to and in fluid communication with the catheter. The injecting is performed over an injection time period of from about 1 second (s) to about 5 minutes (min), from about 1 second to about 4 minutes, from about 1 second to about 3 minutes, from about 1 second to about 2 minutes, from about 1 second to about 1 minute, from about 0.5 minutes (30 seconds) to about 0.75 minutes (45 seconds), from about 0.5 minutes (30 seconds) to about 1 minute (60 seconds), from about 1 minute (60 seconds) to about 2 minutes (120 seconds), from about 0.5 minutes (30 seconds) to about 2 minutes (120 seconds), for example, for about 1 s, about 2 s, about 3 s, about 4 s, about 5 s, about 6 s, about 7 s, about 8 s, about 9 s, about 10 s, about 11 s, about 12 s, about 13 s, about 14 s, about 15 s, about 16 s, about 17 s, about 18 s, about 19 s, about 20 s, about 21 s, about 22 s, about 23 s, about 24 s, about 25 s, about 26 s, about 27 s, about 28 s, about 29 s, about 30 s, about 31 s, about 32 s, about 33 s, about 34 s, about 35 s, about 36 s, about 37 s, about 38 s, about 39 s, about 40 s, about 41 s, about 42 s, about 43 s, about 44 s, about 45 s, about 46 s, about 47 s, about 48 s, about 49 s, about 50 s, about 51 s, about 52 s, about 53 s, about 54 s, about 55 s, about 56 s, about 57 s, about 58 s, about 59 s, about 1 min, about 1.25 min, about 1.5 min, about 1.75 min, about 2 min, about 2.25 min, about 2.5 min, about 2.75 min, about 3 min, about 3.25 min, about 3.5 min, about 3.75 min, about 4 min, about 4.25 min, about 4.5 min, about 4.75 min, or about 5 min. In some embodiments, the injection time period is less than or equal to about 5 min, less than or equal to about 4 min, less than or equal to about 3 min, less than or equal to about 2 min, or less than or equal to about 1 min. It is understood that each of the individual times described herein can be used to define lower and upper values of a time range.

In other embodiments, the administering the volume of the solution comprising rAAV does not comprise a continuous perfusion of the composition comprising rAAV that extends beyond about 5 minutes. In some embodiments, a solution comprising the rAAV is administered using a retrograde ureter route (e.g., using a syringe coupled to and in fluid communication with a catheter in the ureter) to a kidney reversibly, i.e., temporarily, isolated from systemic circulation over a time period of at most 5 minutes, and the isolated kidney is re-established into systemic circulation after a period of time of from about 10 minutes to about 60 minutes after the isolating. In some embodiments, the isolation period is replaced with a blocking period (e.g., using a balloon catheter or clamp) of about of from about 10 minutes to about 60 minutes after the blocking, and a solution comprising the rAAV is administered using a retrograde ureter route (e.g., using a syringe coupled to and in fluid communication with a catheter in the ureter) to the blocked kidney over a time period of at most 5 minutes. The at most 5-minute administration of the rAAV can be performed at any time during the 10-minute to 60-minute isolation or blocking period of the kidney. For example, the rAAV administration is performed at about minutes 0-5, about minutes 5-10, about minutes 10-15, about minutes 15-20, about minutes 20-25, about minutes 25-30, about minutes 30-35, about minutes 35-40, about minutes 40-45, about minutes 45-50, about minutes 50-55, or about minutes 55-60 of the 10 minute to 60 minute kidney isolation or blocking period. In some embodiments, a solution comprising the rAAV is administered in discontinuous increments, e.g., about 1-minute injection followed by about 1-minute of isolation or blocking without injection, rejected iteratively until the entire rAAV volume has been administered.

As described herein, prior to and during administration of the solution comprising the rAAV to the kidney, the kidney is reversibly isolated from the subject's systemic circulation. As used herein, the term "systemic circulation" refers to a flow of blood through a subject's vascular system from the heart to organs and tissues throughout the body (including kidneys) and back to the heart. Via beating of the heart, oxygenated blood is carried through arteries to organs and tissues where the arteries transition into arterioles and then to capillaries where gas exchange occurs. Deoxygenated blood is then transferred from the capillaries to venules, which transition into veins, and then back to the heart. With specific regard to a kidney, the vascular system includes a renal artery, which supplies oxygenated blood to the kidney, and a renal vein, which carries deoxygenated blood away from the kidney. By "isolating the kidney from systemic circulation," it is meant that blood flow through a particular kidney is slowed, minimized, substantially stopped, or stopped. Isolating a kidney from systemic circulation can be achieved by blocking at least one renal blood vessel (i.e., the renal artery and/or renal vein) of the kidney and/or by diverting the circulation away from the kidney, for example, by way of an external circuit, such that systemic blood flow does not continuously enter the "isolated kidney" by way of the renal artery. Accordingly, any agent delivered to the systemic circulation will not enter and/or circulate through the kidney when the kidney is "isolated." Isolating a kidney from systemic circulation results in reduced or no urine production in nephrons of the kidney, thus in the kidney itself. Accordingly, urine production is minimized or decreased relative to a kidney that has not been isolated from systemic circulation or stopped, which allows for a more effective backflow of the retrograde ureter rAAV administration in the urinary tract.

In some embodiments, the method comprises blocking at least one renal blood vessel of the kidney. By blocking at least one renal blood vessel, the kidney is isolated from systemic circulation. In some embodiments, only the renal artery is blocked and the renal vein is not blocked. In other embodiments, only the renal vein is blocked and the renal artery is not blocked. In yet other embodiments, both the renal artery and the renal vein are blocked. Accordingly, only one of the renal blood vessels can be blocked or both of the renal blood vessels can be blocked. Blocking a renal blood vessel can be performed by methods known in the art, including by occluding or clamping. Blocking a renal blood vessel by occluding or clamping isolates the kidney from systemic circulation without the formation or introduction of an external or secondary circuit. Accordingly, in some embodiments, the at least one kidney is isolated from systemic circulation without an external or secondary circuit. In some embodiments, neither the renal artery nor the renal vein are blocked.

Occluding the at least one renal blood vessel comprises introducing an occlusion into the at least one blood vessel, such that the flow of blood through the at least one renal blood vessel is slowed, minimized, substantially stopped, or stopped. Such an occlusion can be introduced by use of a catheter, such as a dilation catheter, a balloon catheter, or a perfusion catheter as non-limiting examples. In some embodiments, the catheter is inserted into an accessible artery or vein, such as the femoral artery, femoral vein, internal jugular vein, and the like, as determined by a medical professional. In some embodiments, the catheter is inserted percutaneously. Accordingly, the catheter can be directed internally to a desired location of a targeted blood vessel, such as the renal artery or renal vein. For example, in some embodiments, a balloon catheter is percutaneously directed to a desired renal blood vessel and is then inflated to block the renal blood vessel, which slows, minimizes, substantially stops, or stops blood supply to the kidney and isolates the kidney from systemic circulation. When both renal blood vessels are to be blocked, separate balloon catheters are directed to each individual renal blood vessel. Blocking the at least one renal blood vessel is performed prior to administration of the solution comprising the rAAV. As discussed herein, the at least one renal blood vessel is unblocked after a time period of from about 10 minutes to about 60 minutes subsequent to the blocking and/or after administering the solution comprising the rAAV. The blocking period and the isolating period, whichever period is implied, are measured from moment of blocking or isolating, i.e., subsequent to the blocking or isolating and/or after administering the solution comprising the rAAV. Unblocking the at least one renal blood vessel is performed by, for example, deflating the balloon of the catheter, which reestablishes blood flow to the kidney and reintroduces the kidney to systemic circulation.

Clamping the at least one renal blood vessel comprises clamping the at least one blood vessel, such that the flow of blood through the at least one renal blood vessel is slowed, minimized, substantially stopped, or stopped. Non-limiting examples of suitable clamps include renal artery clamps, artery clamps, vascular clamps, artery clips, vascular clips, renal vein clamps, renal vein clips, Dieffenbach clamps, and hemostats. Such a clamp can be introduced through an incision made in the subject. For example, in some embodiments, a clamp is directed to and placed on a desired renal blood vessel. The clamp squeezes and blocks the renal blood vessel, which slows, minimizes, substantially stops, or stops blood supply to the kidney and isolates the kidney from systemic circulation. When both renal blood vessels are to be blocked, separate clamps are directed to each individual renal blood vessel. Blocking the at least one renal blood vessel is performed prior to administration of the solution comprising the rAAV. As discussed herein, the at least one renal blood vessel is unblocked after a time period of from about 10 minutes to about 60 minutes subsequent to the blocking and/or after administering the solution comprising the rAAV. Unblocking the at least one renal blood vessel is performed by, for example, unclamping or releasing the clamp, which reestablishes blood flow to the kidney and reintroduces the kidney to systemic circulation.

In some embodiments, the method comprises introducing an external or secondary circuit to isolate the kidney from systemic circulation. In some embodiments, the method for using an external circuit to isolate the kidney comprises: (a) positioning a perfusion catheter in the renal artery of the kidney; (b) positioning a recovery catheter in the renal vein of the kidney, wherein the perfusion catheter and the recovery catheter together with a membrane oxygenation device form a closed external perfusion circuit through the kidney; and (c) causing a perfusate to flow through the external circuit, wherein the external circuit isolates perfusion through the kidney from the systemic circulation of the subject. Positioning the perfusion and recovery catheters can include blocking the renal artery and/or the renal vein, respectively, for example, by use of a balloon catheter. See e.g., International Patent Publication WO2022175546A1, the contents of which are incorporated herein by reference in their entirety. The perfusate can be, for example, blood donated from the subject or from another subject prior to the performance of the method. Such a use of an external circuit to isolate the kidney from systemic circulation can also be referred to as an "isolated perfused kidney (IPK)." In some embodiments, the IPK is maintained in a physiological environment without ischemia. In some embodiments, the flow rate of the perfusate circulated through the closed circuit does not deviate significantly from the patient's own blood flow rate in order to avoid ischemia and/or under perfusion. In some embodiments, the blood from the recovery catheter in the renal vein is recirculated back to the perfusion catheter in the renal artery to form an external circuit. The rAAV can be administered via a retrograde route through a ureter while the kidney is isolated from systemic circulation by way of the external circuit.

In some embodiments, the method for re-establishing the kidney into systemic circulation comprises disassembling the external circuit, for example, by: (a) removing the perfusion catheter from the renal artery of the kidney; (b) removing the recovery catheter from the renal vein of the kidney; and (c) allowing blood from systemic circulation to flow into the renal artery and out of the renal vein back into systemic circulation. Because the external circuit allows for a continuous supply of oxygen to the kidney, re-establishing the kidney to the systemic circulation can be performed at a time period longer than kidney isolation methods that impart ischemia to the kidney.

In some embodiments, the method does not comprise a continuous perfusion of the kidney. In some embodiments, the method does not comprise a closed circuit comprising the kidney. In some embodiments, the method does not comprise a substantially closed system comprising the kidney. In some embodiments, the method does not comprise diverting circulation from the kidney. In some embodiments, the method does not comprise bypassing the kidney. In some embodiments, the method is performed in vivo. In some embodiments, the method is not performed ex vivo.

In some embodiments, the method comprises a continuous perfusion of the kidney. In some embodiments, the method comprises a closed circuit comprising the kidney. In some embodiments, the method comprises a substantially closed system comprising the kidney. In some embodiments, the method comprises diverting circulation from the kidney. In some embodiments, the method comprises bypassing the kidney. In some embodiments, the method is not performed in vivo. In some embodiments, the method is performed ex vivo.

In some embodiments, during the period of time of isolating the kidney from systemic circulation, for example, by blocking the at least one renal blood vessel, the isolated kidney is maintained under normothermic "warm" conditions (i.e., body temperature). Non-limiting examples of normothermic conditions for the isolated kidney include about 36 °C, about 36.1 °C, about 36.2 °C, about 36.3 °C, about 36.4 °C, about 36.5 °C, about 36.6 °C, about 36.7 °C, about 36.8 °C, about 36.9 °C, about 37 °C, about 37.1 °C, about 37.2 °C, about 37.3 °C, about 37.4 °C, about 37.5 °C, about 37.6 °C, about 37.7 °C, about 37.8 °C, about 37.9 °C, or about 36.0 °C-38.0 °C.

In some embodiments, the period of time for isolating the kidney from systemic circulation, for example, by blocking the at least one renal blood vessel, is such that the kidney does not undergo substantial ischemic damage (e.g., build-up of metabolic waste products, inability to maintain cell membranes, mitochondrial damage, and/or leakage of autolyzing proteolytic enzymes into the kidney cell and surrounding kidney tissues). In some embodiments, the period of time for isolating the kidney from systemic circulation is about 15 minutes subsequent to the isolating. In some embodiments, the period of time for isolating the kidney from systemic circulation is 10-60 minutes subsequent to the isolating. In some embodiments, the period of time for isolating the kidney from systemic circulation is 30-60 minutes subsequent to the isolating. In some embodiments, the period of time for isolating the kidney from systemic circulation is 30-45 minutes subsequent to the isolating. In some embodiments, the period of time for isolating the kidney from systemic circulation is 15-45 minutes subsequent to the isolating. In some embodiments, the period of time for isolating the kidney from systemic circulation is 20-40 minutes subsequent to the isolating. In some embodiments, the period of time for isolating the kidney from systemic circulation is about 15-30 minutes subsequent to the isolating. In some embodiments, the period of time for isolating the kidney from systemic circulation is about 30 minutes subsequent to the isolating. In some embodiments, the period of time for isolating the kidney from systemic circulation is no more than 45 minutes (min) subsequent to the isolating. In some embodiments, the period of time for isolating the kidney from systemic circulation is at least 10 min, at least 11 min, at least 12 min, at least 13 min, at least 14 min, at least 15 min, at least 16 min, at least 17 min, at least 18 min, at least 19 min, at least 20 min, at least 21 min, at least 22 min, at least 23 min, at least 24 min, at least 25 min, at least 26 min, at least 27 min, at least 28 min, at least 29 min, at least 30 min, at least 31 min, at least 32 min, at least 33 min, at least 34 min, at least 35 min, at least 36 min, at least 37 min, at least 38 min, at least 39 min, at least 40 min, at least 41 min, at least 42 min, at least 43 min, at least 44 min, at least 45 min, at least 46 min, at least 47 min, at least 48 min, at least 49 min, at least 50 min, at least 51 min, at least 52 min, at least 53 min, at least 54 min, at least 55 min, at least 56 min, at least 57 min, at least 58 min, or at least 59 min subsequent to the isolating. It is understood that each of the individual times described herein can be used to define lower and upper values of a time range.

In some embodiments, the period of time for isolating the kidney from systemic circulation is at most 10 min, at most 11 min, at most 12 min, at most 13 min, at most 14 min, at most 15 min, at most 16 min, at most 17 min, at most 18 min, at most 19 min, at most 20 min, at most 21 min, at most 22 min, at most 23 min, at most 24 min, at most 25 min, at most 26 min, at most 27 min, at most 28 min, at most 29 min, at most 30 min, at most 31 min, at most 32 min, at most 33 min, at most 34 min, at most 35 min, at most 36 min, at most 37 min, at most 38 min, at most 39 min, at most 40 min, at most 41 min, at most 42 min, at most 43 min, at most 44 min, at most 45 min, at most 46 min, at most 47 min, at most 48 min, at most 49 min, at most 50 min, at most 51 min, at most 52 min, at most 53 min, at most 54 min, at most 55 min, at most 56 min, at most 57 min, at most 58 min, at most 59 min, or at most 60 min subsequent to the isolating. It is understood that each of the individual times described herein can be used to define lower and upper values of a time range.

In some embodiments, the period of time for isolating the kidney from systemic circulation is about 10 min, about 11 min, about 12 min, about 13 min, about 14 min, about 15 min, about 16 min, about 17 min, about 18 min, about 19 min, about 20 min, about 21 min, about 22 min, about 23 min, about 24 min, about 25 min, about 26 min, about 27 min, about 28 min, about 29 min, about 30 min, about 31 min, about 32 min, about 33 min, about 34 min, about 35 min, about 36 min, about 37 min, about 38 min, about 39 min, about 40 min, about 41 min, about 42 min, about 43 min, about 44 min, about 45 min, about 46 min, about 47 min, about 48 min, about 49 min, about 50 min, about 51 min, about 52 min, about 53 min, about 54 min, about 55 min, about 56 min, about 57 min, about 58 min, about 59 min, or about 60 min subsequent to the isolating. It is understood that each of the individual times described herein can be used to define lower and upper values of a time range.

In some embodiments, the volume of the solution comprising the rAAV is from 0.13 mL/kg to about 0.35 mL/kg, about 0.2 mL/kg to about 0.35 mL/kg, from about 0.25 mL/kg to about 0.35 mL/kg, from about 0.3 mL/kg to about 0.35 mL/kg, from about 0.2 mL/kg to about 0.30 mL/kg, or from about 0.2 mL/kg to about 0.25 mL/kg; and the period of time for isolating the kidney from systemic circulation, for example, by blocking the at least one renal blood vessel or establishing an external circuit comprising the kidney, is 10-60 minutes subsequent to the isolating. In some embodiments, the volume of the solution comprising the rAAV is from about 0.13 mL/kg to about 0.35 mL/kg, about 0.2 mL/kg to about 0.35 mL/kg, from about 0.25 mL/kg to about 0.35 mL/kg, from about 0.3 mL/kg to about 0.35 mL/kg, from about 0.2 mL/kg to about 0.30 mL/kg, or from about 0.2 mL/kg to about 0.25 mL/kg; and the period of time for isolating the kidney from systemic circulation, for example, by blocking the at least one renal blood vessel or establishing an external circuit comprising the kidney, is about 30 minutes subsequent to the isolating, or about 15-30 minutes subsequent to the isolating.

In some embodiments, the method of treatment can comprise first diagnosing a subject or patient who can benefit from treatment by the methods described herein and/or a pharmaceutical composition described herein. In some embodiments, such diagnosis comprises detecting or measuring an abnormal level of an analyte in a sample from the subject or patient associated with a kidney-associated disorder. In some embodiments, the method further comprises administering an rAAV to the kidney of the subject.

In some embodiments, the subject has previously been determined to have an abnormal level of an analyte or marker described herein relative to a reference. In some embodiments, the reference level can be the level in a sample of similar cell type, sample type, sample processing, and/or obtained from a subject of similar age, sex and other demographic parameters as the sample/subject. In some embodiments, the test sample and control reference sample are of the same type, that is, obtained from the same biological source, and comprising the same composition, e.g., the same number and type of cells.

The term “sample” or “test sample” as used herein denotes a sample taken or isolated from a biological organism, e.g., a blood or plasma sample from a subject. In some embodiments of any of the aspects, the technology described herein encompasses several examples of a biological sample. In some embodiments of any of the aspects, the biological sample is cells, or tissue, or peripheral blood, or bodily fluid. Exemplary biological samples include, but are not limited to, a biopsy (e.g., from the kidney); blood; serum; plasma; or urine. The term also includes a mixture of the above-mentioned samples. The term “test sample” also includes untreated or pretreated (or pre-processed) biological samples. In some embodiments of any of the aspects, a test sample can comprise cells from a subject.

In some embodiments, the reference can be a level of the analyte in a population of subjects who do not have or are not diagnosed as having, and/or do not exhibit signs or symptoms of a kidney-associated disorder. In some embodiments, the reference can also be a level of expression of the analyte in a control sample, a pooled sample of control individuals or a numeric value or range of values based on the same. In some embodiments of any of the aspects, the reference can be the level of an analyte in a sample obtained from the same subject at an earlier point in time, e.g., the methods described herein can be used to determine if a subject’s sensitivity or response to the rAAV therapy is changing over time.

In some embodiments of any of the aspects, the step of determining if the subject has an abnormal level of an analyte described herein can comprise i) obtaining or having obtained a sample from the subject and ii) performing or having performed an assay on the sample obtained from the subject to determine/measure the level of the analyte in the subject. In some embodiments of any of the aspects, the step of determining if the subject has an abnormal level of an analyte described herein can comprise performing or having performed an assay on a sample obtained from the subject to determine/measure the level of analyte in the subject. In some embodiments of any of the aspects, the step of determining if the subject has an abnormal level of an analyte described herein can comprise ordering or requesting an assay on a sample obtained from the subject to determine/measure the level of the analyte in the subject. In some embodiments of any of the aspects, the step of determining if the subject has an abnormal level of an analyte described herein can comprise receiving the results of an assay on a sample obtained from the subject to determine/measure the level of the analyte in the subject. In some embodiments of any of the aspects, the step of determining if the subject has an abnormal level of an analyte described herein can comprise receiving a report, results, or other means of identifying the subject as a subject with a decreased level of the analyte.

In one aspect of any of the embodiments, described herein is a method of treating a kidney-associated disorder in a subject in need thereof, the method comprising: a) determining if the subject has an abnormal level of an analyte described herein; and b) instructing or directing that the subject be administered a solution comprising an rAAV or a pharmaceutical composition as described herein if the level of the analyte is abnormal relative to a reference. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

In some embodiments of any of the aspects, the solution (or pharmaceutical composition) comprising the rAAV described herein is administered as a monotherapy, e.g., another treatment for the kidney-associated disorder is not administered to the subject.

In some embodiments of any of the aspects, the methods described herein can further comprise administering a second agent and/or treatment to the subject, e.g., as part of a combinatorial therapy. Non-limiting examples of a second agent and/or treatment can include a treatment for a kidney-associated disorder, such as blood pressure medication (e.g., angiotensin converting enzyme (ACE) such as ramipril, enalapril and lisinopril); medication for diabetes or a high albumin to creatinine ratio (ACR) (e.g., dapagliflozin); medication for cardiovascular disease (e.g., a statin such as atorvastatin or simvastatin); medication to lower potassium (e.g., sodium zirconium cyclosilicate); reduced fluid intake; diuretics (e.g., furosemide); anemia medication (e.g., erythropoietin); calcium supplements; steroids (e.g., cyclophosphamide); dialysis (e.g., hemodialysis, peritoneal dialysis); lifestyle changes (e.g., ceasing smoking; eating a healthy, balanced diet; restricting salt intake, e.g., to less than 6 g a day; doing regular exercise, e g., at least 150 minutes a week; reducing alcohol intake, e.g., no more than the recommended limit of 14 units of alcohol a week; losing weight if overweight or obese; avoiding over-the-counter non-steroidal anti-inflammatory drugs (NSAIDs), such as ibuprofen); and/or a kidney transplant (e.g., of a kidney not transduced by the rAAV).

By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In some embodiments of any of the aspects, the methods described herein can further comprise administering a second agent and/or treatment to the subject, e.g., as part of an immune suppression therapy. In some embodiments, at least one immune suppression agent is DEPO-MEDROL® (methylprednisolone acetate) and/or Tacrolimus (calcineurin-inhibitor). In some embodiments, the at least one immune suppression agent is selected from the group consisting of: Prednisone, Cyclosporine, Tacrolimus, Azathioprine, Mycophenolate mofetil, Sirolimus, Everolimus, Alemtuzumab, and is DEPO-MEDROL® (methylprednisolone acetate). In some embodiments, the at least one immune suppression agent is administered about 7 days prior to, about 6 days prior to, about 5 days prior to, about 4 days prior to, about 3 days prior to, about 2 days prior to, about 1 day prior to, the same day as, about 1 day after, about 2 days after, about 3 days after, about 4 days after, about 5 days after, about 6 days after, about 7 days after, about 8 days after, about 9 days after, about 10 days after, about 11 days after, about 12 days after, about 13 days after, about 14 days after, about 15 days after, about 16 days after, about 17 days after, about 18 days after, about 19 days after, about 20 days, or more, after retro-ureteral administration of the rAAV. In some embodiments, the at least one immune suppression agent is administered if at least one transgene is immunogenic; as non-limiting examples, GFP, mCherry, HA1, and luciferase, and some variants thereof are known to be immunogenic. In some embodiments, the transgene(s) are not immunogenic and do not comprise immunogenic markers, and at least one immune suppression agent is not administered.

Recombinant Adeno-Associated Virus (rAAV)

Described herein are methods of administering a recombinant adeno-associated virus (rAAV) to a kidney of a subject. Recombinant AAV (rAAV) vectors are typically composed of, at a minimum, a transgene and its regulatory sequences, and 5' and 3' AAV inverted terminal repeats (ITRs). The transgene can comprise, as described further herein, one or more regions that encode one or more inhibitory RNAs (e.g., miRNAs) comprising a nucleic acid that targets an endogenous mRNA of a subject. The transgene can also comprise a region encoding, for example, a protein and/or an expression control sequence (e.g., a poly-A tail), as described further herein. The isolated nucleic acid (e.g., the recombinant AAV vector) can be packaged into a capsid protein and administered to a subject (e.g., using retrograde ureter administration) and/or delivered to a selected target cell, such as a kidney cells.

In some embodiments, the rAAV comprises a capsid selected from the capsids described in Table 1. In other embodiments, the rAAV comprises a capsid selected from the capsids described in Table 1, but excluding AAV9. The exemplary capsids provided in Table 1 include representative AAV VP1 sequences, which further contain the respective VP2 and VP3 sequences, as is known in the art. Each of the references that is recited in Table 1 (including non-patent literature and patent literature) is herein incorporated by reference in its entirety.

TABLE 1

Exemplary descriptions of capsids and sequences

| Serotype and where capsid sequence is published and/or described | Serotype and where capsid sequence is published and/or described |
|---|---|
| AAV1 (see SEQ ID NO: 11 in US20150159173 and SEQ ID NO: 202 in US20150315612) | AAVI (see SEQ ID NO: 1 in US20160017295, SEQ ID NO: 64 in US20030138772, SEQ ID NO: 27 in US20150159173, and SEQ ID NO: 5 in US7198951) |
| AAV1 (see SEQ ID NO: 6 in US20030138772) | AAV1.3 (see SEQ ID NO: 14 in US20030138772) |
| AAV2 (see SEQ ID NO: 7 in US20150159173 and SEQ ID NO: 211 in US20150315612) | AAV2 (see SEQ ID NO: 70 in US20030138772, SEQ ID NO: 23 in US20150159173, and SEQ ID NO: 4 in US6156303) |
| AAV2 (see SEQ ID NO: 8 in US6156303) | AAV2 (see SEQ ID NO: 7 in US20030138772) |
| AAV2 (see SEQ ID NO: 3 in US6156303) | AAV2.5T (see SEQ ID NO: 42 in US9233131) |
| AAV3 (see SEQ ID NO: 12 in US20150159173) | AAV3 (see SEQ ID NO: 71 in US20030138772, SEQ ID NO: 28 in US20150159173, and SEQ ID NO: 6 in US7198951) |
| AAV3.3b (See SEQ ID NO: 72 in US20030138772) | AAV3-3 (See SEQ ID NO: 200 US20150315612) |
| AAV3-3 (See SEQ ID NO: 217 US20150315612) | AAV3a ((See SEQ ID NO: 5 in US6156303) |
| AAV3a (See SEQ ID NO: 9 in US6156303) | AAV3b (See SEQ ID NO: 6 in US6156303) |
| AAV3b (See SEQ ID NO: 10 in US6156303) | AAV3b (See SEQ ID NO: 1 in US6156303) |
| AAV4 (See SEQ ID NO: 17 US20140348794) | AAV4 ((See SEQ ID NO: 5 in US20140348794) |
| AAV4 (See SEQ ID NO: 3 in US20140348794) | AAV4 (See SEQ ID NO: 14 in US20140348794) |
| AAV4 (See SEQ ID NO: 15 in US20140348794) | AAV4 (See SEQ ID NO: 1 in US20140348794) |
| AAV4 (See SEQ ID NO: 12 in US20140348794) | AAV4 (See SEQ ID NO: 1 in US20140348794) |
| AAV4 (See SEQ ID NO: 7 in US20140348794) | AAV4 (See SEQ ID NO: 8 in US20140348794) |
| AAV4 (See SEQ ID NO: 9 in US20140348794) | AAV4 (See SEQ ID NO: 2 in US20140348794) |
| AAV4 (See SEQ ID NO: 10 in US20140348794) | AAV4 (See SEQ ID NO: 11 in US20140348794) |
| AAV4 (See SEQ ID NO: 18 in US20140348794) | AAV4 (See SEQ ID NO: 63 in US20030138772 and SEQ ID NO: 4 in US20160017295) |
| AAV4 (See SEQ ID NO: 4 in US20140348794) | AAV4 (See SEQ ID NO: 16 in US20140348794) |
| AAV4 (See SEQ ID NO: 20 in US20140348794) | AAV4 (See SEQ ID NO: 6 in US20140348794) |
| AAV4 (See SEQ ID NO: 1 in US20140348794) | AAV42.2 (See SEQ ID NO: 9 in US20030138772) |
| AAV42.2 (See SEQ ID NO: 102 in US20030138772) | AAV42.3b (See SEQ ID NO: 36 in US20030138772) |

TABLE 1-continued

| Exemplary descriptions of capsids and sequences | |
|---|---|
| Serotype and where capsid sequence is published and/or described | Serotype and where capsid sequence is published and/or described |
| AAV42.3B (See SEQ ID NO: 107 in US20030138772) | AAV42.4 (See SEQ ID NO: 33 in US20030138772) |
| AAV42.4 (See SEQ ID NO: 88 in US20030138772) | AAV42.8 (See SEQ ID NO: 27 in US20030138772) |
| AAV42.8 (See SEQ ID NO: 85 in US20030138772) | AAV43.1 (See SEQ ID NO: 39 in US20030138772) |
| AAV43.1 (See SEQ ID NO: 92 in US20030138772) | AAV43.12 (See SEQ ID NO: 41 in US20030138772) |
| AAV43.12 (See SEQ ID NO: 93 in US20030138772) | AAV5 (see SEQ ID NO: 1 in US7427396) |
| AAV5 (see SEQ ID NO: 114 in US20030138772) | AAV5 (see SEQ ID NO: 5 in US20160017295, SEQ ID NO: 2 in US7427396, and SEQ ID NO: 216 in US20150315612) |
| AAV5 (see SEQ ID NO: 199 in US20150315612) | AAV6 (see SEQ ID NO: 65 in US20030138772, SEQ ID NO: 29 in US20150159173, SEQ ID NO: 6 in US20160017295, and SEQ ID NO: 7 in US6156303) |
| AAV6 (see SEQ ID NOS:2, 7, and 11 in US6156303) | AAV6 (see SEQ ID NOS:203 and 220 in US20150315612) |
| AAV7 (see SEQ ID NO: 14 in US20150159173) | AAV7 (see SEQ ID NO: 183 in US20150315612) |
| AAV7 (see SEQ ID NO: 2 in US20030138772, SEQ ID NO: 30 in US20150159173, SEQ ID NO: 181 in US20150315612, and SEQ ID NO: 7 in US20160017295) | AAV7 (see SEQ ID NO: 3 in US20030138772) |
| AAV7 (see SEQ ID NO: 1 in US20030138772 and SEQ ID NO: 180 in US20150315612) | AAV7 (see SEQ ID NO: 213 US20150315612) |
| AAV7 (see SEQ ID NO: 222 in US20150315612) | AAV7 (see SEQ ID NO: 2 in US8906675) |
| AAV8 (See SEQ ID NO: 15 in US20150159173) | AAV8 (See SEQ ID NO: 7 in US20150376240) |
| AAV8 (See SEQ ID NO: 4 in US20030138772; SEQ ID NO: 182 in US20150315612) | AAV8 (See SEQ ID NO: 95 in US20030138772, SEQ ID NO: 1 in US20140359799) |
| AAV8 (See SEQ ID NO: 31 in US20150159173) | AAV8 (See, e.g., SEQ ID NO: 8 in US20160017295, or SEQ ID NO: 7 in US7198951, or SEQ ID NO: 223 in US20150315612) |
| AAV8 (See SEQ ID NO: 8 in US20150376240) | AAV8 (See SEQ ID NO: 214 in US20150315612) |
| AAV-8b (See SEQ ID NO: 5 in US20150376240) | AAV-8b (See SEQ ID NO: 3 in US20150376240) |
| AAV-8h (See SEQ ID NO: 6 in US20150376240) | AAV-8h (See SEQ ID NO: 4 in US20150376240) |
| AAV9 (See SEQ ID NO: 5 in US20030138772) | AAV9 (See SEQ ID NO: 1 in US7198951) |
| AAV9 (See SEQ ID NO: 9 in US20160017295) | AAV9 (See SEQ ID NO: 100 in US20030138772 and SEQ ID NO: 2 in US7198951) |
| AAV9 (See SEQ ID NO: 3 in US7198951) | AAV9 (AAVhu.14) (See SEQ ID NO: 3 in US20150315612) |
| AAV9 (AAVhu.14) (See SEQ ID NO: 123 in US20150315612) | AAV10 (see SEQ ID NO: 117 in US20030138772) |
| AAV10 (SEQ ID NO: 9 in WO2015121501) | AAV10 (SEQ ID NO: 8 in WO2015121501) |
| AAV11 (SEQ ID NO: 118 in US20030138772) | AAV12 (SEQ ID NO: 119 in US20030138772) |
| AAVA3.1 (See SEQ ID NO: 120 in US20030138772) | AAVA3.3 (See SEQ ID NO: 57 in US20030138772) |
| AAVA3.3 (See SEQ ID NO: 66 in US20030138772) | AAVA3.4 (See SEQ ID NO: 54 in US20030138772) |
| AAVA3.4 (See SEQ ID NO: 68 in US20030138772) | AAVA3.5 (See SEQ ID NO: 55 in US20030138772) |
| AAVA3.5 (See SEQ ID NO: 69 in US20030138772) | AAVA3.7 (See SEQ ID NO: 56 in US20030138772) |
| AAVA3.7 (See SEQ ID NO: 67 in US20030138772) | AAV29. (See SEQ ID NO: 11 in (AAVbb. 1) 161 US20030138772) |
| AAVC2 (See SEQ ID NO: 61 in US20030138772) | AAVCh.5 (See SEQ ID NO: 46 in US20150159173); SEQ ID NO: 234 in US20150315612) |
| AAV24.1 (See SEQ ID NO: 101 in US20030138772) | AAVcy.2 (AAV13.3) (See SEQ ID NO: 15 in US20030138772) |
| AAV27.3 (See SEQ ID NO: 104 in US20030138772) | AAVcy.3 (AAV24.1) (See SEQ ID NO: 16 in US20030138772) |
| AAVcy.5 (See SEQ ID NO: 227 in US20150315612) | AAVcy.4 (AAV27.3) (See SEQ ID NO: 17 in US20030138772) |
| AAVcy.5 (AAV7.2) (See SEQ ID NO: 18 in US20030138772) | AAV7.2 (See SEQ ID NO: 103 in US20030138772) |

TABLE 1-continued

| Exemplary descriptions of capsids and sequences | |
|---|---|
| Serotype and where capsid sequence is published and/or described | Serotype and where capsid sequence is published and/or described |
| AAVcy.6 (AAV16.3) (See SEQ ID NO: 10 in US20030138772) | AAV16.3 (See SEQ ID NO: 105 in US20030138772) |
| AAVcy.5 (See SEQ ID NO: 24 in US20150159173) | AAVcy.5 (See SEQ ID NO: 8 in US20150159173) |
| AAVCy.5R2 (See SEQ ID NO: 24 modified with G13D and D403N in US20150159173) | AAVCy.5Rl (See SEQ ID NO: 24 modified with G13D in US20150159173) |
| AAVCy.5R4 (See SEQ ID NO: 24 modified with G13D, D403N, R51K, N158K, and P161Q in US20150159173) | AAVCy.5R3 (See SEQ ID NO: 24 modified with G13D, D403N, and R51K in US20150159173) |
| AAVDJ (See SEQ ID NO: 2 in US20140359799) | AAVDJ (See SEQ ID NO: 3 in US20140359799 and SEQ ID NO: 2 in US7588772) |
| AAVDJ-8 (See SEQ ID NO: 1 modified with R587Q and R590T in US7588772) | AAVDJ (See SEQ ID NO: 1 in US7588772) |
| AAVH2 (See SEQ ID NO: 26 in US20030138772) | AAVF5 (See SEQ ID NO: 110 in US20030138772) |
| AAVhEl. 1 (See SEQ ID NO: 44 in US9233131) | AAVH6 (See SEQ ID NO: 25 in US20030138772) |
| AAVhErl. 16 (See SEQ ID NO: 48 in US9233131) | AAVhErl.14 (See SEQ ID NO: 46 in US9233131) |
| AAVhErl.23 (AA VhEr2.29) (See SEQ ID NO: 53 in US9233131) | AAVhErl.18 (See SEQ ID NO: 49 in US9233131) |
| AAVhErl.36 (See SEQ ID NO: 52 in US9233131) | AAVhErl.35 (See SEQ ID NO: 50 in US9233131) |
| AAVhErl.7 (See SEQ ID NO: 51 in US9233131) | AAVhErl.5 (See SEQ ID NO: 45 in US9233131) |
| AAVhEr2.16 (See SEQ ID NO: 55 in US9233131) | AAVhErl.8 (See SEQ ID NO: 47 in US9233131) |
| AAVhEr2.31 (See SEQ ID NO: 58 in US9233131) | AAVhEr2.30 (See SEQ ID NO: 56 in US9233131) |
| AAVhEr2.4 (See SEQ ID NO: 54 in US9233131) | AAVhEr2.36 (See SEQ ID NO: 57 in US9233131) |
| AAVhu.l (See SEQ ID NO: 46 in US20150315612) | AAVhEr3.1 (See SEQ ID NO: 59 in US9233131) |
| AAVhu.1O (AAV16.8) (See SEQ ID NO: 56 in US20150315612) | AAVhu.l (See SEQ ID NO: 144 in US20150315612) |
| AAVhu.11 (AAV16.12) (See SEQ ID NO: 57 in US20150315612) | AAVhu.1O (AAV16.8) (See SEQ ID NO: 156 in US20150315612) |
| AAVhu. 12 (See SEQ ID NO: 59 in US20150315612) | AAVhu.ll (AAV16.12) (See SEQ ID NO: 153 in US20150315612) |
| AAVhu.13 (See SEQ ID NO: 16 in US2015015917 and ID NO: 71 in US20150315612) | AAVhu.12 (See SEQ ID NO: 154 in US20150315612) |
| AAVhu.13 (See SEQ ID NO: 32 in US20150159173 and ID NO: 129 US20150315612) | AAVhu.136.1 (See SEQ ID NO: 165 in US20150315612) |
| AAVhu. 140.2 (See SEQ ID NO: 167 in US20150315612) | AAVhu. 140.1 (See SEQ ID NO: 166 in US20150315612) |
| AAVhu. 15 (See SEQ ID NO: 147 in US20150315612) | AAVhu. 145.6 (See SEQ ID NO: 178 in US20150315612) |
| AAVhu. 156.1 (See SEQ ID NO: 179 in US20150315612) | AAVhu.15 (AAV33.4) (See SEQ ID NO: 50 in US20150315612) |
| AAVhu.16 (AAV33.8) (See SEQ ID NO: 51 in US20150315612) | AAVhu. 16 (See SEQ ID NO: 148 in US20150315612) |
| AAVhu.17 (AAV33.12) (See SEQ ID NO: 4 in US20150315612) | AAVhu. 17 (See SEQ ID NO: 83 in US20150315612) |
| AAVhu. 172.2 (See SEQ ID NO: 172 in US20150315612) | AAVhu. 172.1 (See SEQ ID NO: 171 in US20150315612) |
| AAVhu. 173.8 (See SEQ ID NO: 175 in US20150315612) | AAVhu. 173.4 (See SEQ ID NO: 173 in US20150315612) |
| AAVhu. 18 (See SEQ ID NO: 149 in US20150315612) | AAVhu.18 (See SEQ ID NO: 52 in US20150315612) |
| AAVhu. 19 (See SEQ ID NO: 133 in US20150315612) | AAVhu. 19 (See SEQ ID NO: 62 in US20150315612) |
| AAVhu.2 (See SEQ ID NO: 143 in US20150315612) | AAVhu.2 (See SEQ ID NO: 48 in US20150315612) |
| AAVhu.20 (See SEQ ID NO: 134 in US20150315612) | AAVhu.20 (See SEQ ID NO: 63 in US20150315612) |
| AAVhu.21 (See SEQ ID NO: 135 in US20150315612) | AAVhu.21 (See SEQ ID NO: 65 in US20150315612) |
| AAVhu.22 239 (See SEQ ID NO: 138 in US20150315612) | AAVhu.22 (See SEQ ID NO: 67 in US20150315612) |
| AAVhu.23.2 (See SEQ ID NO: 137 in US20150315612) | AAVhu.23 (See SEQ ID NO: 60 in US20150315612) |

TABLE 1-continued

| Exemplary descriptions of capsids and sequences | |
|---|---|
| Serotype and where capsid sequence is published and/or described | Serotype and where capsid sequence is published and/or described |
| AAVhu.24 (See SEQ ID NO: 136 in US20150315612) | AAVhu.24 (See SEQ ID NO: 66 in US20150315612) |
| AAVhu.25 (See SEQ ID NO: 146 in US20150315612) | AAVhu.25 (See SEQ ID NO: 49 in US20150315612) |
| AAVhu.26 (See SEQ ID NO: 33 in US20150159173, and SEQ ID NOS: 61 and 139 in US20150315612) | AAVhu.26 (See SEQ ID NO: 17 in US20150159173 and SEQ ID NO: 61 in US20150315612) |
| AAVhu.27 (See SEQ ID NO: 140 in US20150315612) | AAVhu.27 (See SEQ ID NO: 64 in US20150315612) |
| AAVhu.28 (See SEQ ID NO: 130 in US20150315612) | AAVhu.28 (See SEQ ID NO: 68 in US20150315612) |
| AAVhu.29 (See SEQ ID NO: 42 in US20150159173 and SEQ ID NO: 132 in US20150315612) | AAVhu.29 (See SEQ ID NO: 69 in US20150315612) |
| AAVhu.29 (See SEQ ID NO: 225 in US20150315612) | AAVhu.29R (See SEQ ID NO: 42 with G396E in US20150159173) |
| AAVhu.3 (See SEQ ID NO: 44 in US20150315612) | AAVhu.3 (See SEQ ID NO: 145 in US20150315612) |
| AAVhu.30 (See SEQ ID NO: 70 in US20150315612) | AAVhu.30 (See SEQ ID NO: 131 in US20150315612) |
| AAVhu.31 (See SEQ ID NO: 1 in US20150315612) | AAVhu.31 (See SEQ ID NO: 121 in US20150315612) |
| AAVhu.32 (See SEQ ID NO: 2 in US20150315612) | AAVhu.32 (See SEQ ID NO: 122 in US20150315612) |
| AAVhu.33 (See SEQ ID NO: 75 in US20150315612) | AAVhu.33 (See SEQ ID NO: 124 in US20150315612) |
| AAVhu.34 (See SEQ ID NO: 72 in US20150315612) | AAVhu.34 (See SEQ ID NO: 125 in US20150315612) |
| AAVhu.35 (See SEQ ID NO: 73 in US20150315612) | AAVhu.35 (See SEQ ID NO: 164 in US20150315612) |
| AAVhu.36 (See SEQ ID NO: 74 in US20150315612) | AAVhu.36 (See SEQ ID NO: 126 in US20150315612) |
| AAVhu.37 (See SEQ ID NO: 34 in US20150159173 and SEQ ID NO: 88 in US20150315612) | AAVhu.37 (AAV106.1) (See SEQ ID NO: 10 in US20150315612 and SEQ ID NO: 18 in US20150159173) |
| AAVhu.38 (See SEQ ID NO: 161 in US20150315612) | AAVhu.39 (See SEQ ID NO: 102 in US20150315612) |
| AAVhu.39 (AAVLG-9) (See SEQ ID NO: 24 in US20150315612 | AAVhu.4 (See SEQ ID NO: 47 in US20150315612) |
| AAVhu.4 (See SEQ ID NO: 141 in US20150315612) | AAVhu.40 (See SEQ ID NO: 87 in US20150315612) |
| AAVhu.40 (AAV114.3) (See SEQ ID NO: 11 in US20150315612) | AAVhu.41 (See SEQ ID NO: 91 in US20150315612) |
| AAVhu.41 (AAV127.2) (See SEQ ID NO: 6 in US20150315612) | AAVhu.42 (See SEQ ID NO: 85 in US20150315612) |
| AAVhu.42 (AAV127.5) (See SEQ ID NO: 8 in US20150315612) | AAVhu.43 (See SEQ ID NO: 160 in US20150315612) |
| AAVhu.43 (See SEQ ID NO: 236 in US20150315612) | AAVhu.43 (AAV128.1) (See SEQ ID NO: 80 in US20150315612) |
| AAVhu.44 (See SEQ ID NO: 45 in US20150159173 and SEQ ID NO: 158 in US20150315612) | AAVhu.44Rl (See SEQ ID NO: 45 modified with E137K in US20150159173) |
| AAVhu.44 (AAV128.3) (See SEQ ID NO: 81 in US20150315612) | AAVhu.44R3 (See SEQ ID NO: 45 modified with E137K, P446L, and G609D in US20150159173) |
| AAVhu.44R2 (See SEQ ID NO: 45 modified with E137K and P446L in US20150159173) | AAVhu.45 (See SEQ ID NO: 127 in US20150315612) |
| AAVhu.45 (See SEQ ID NO: 76 in US20150315612) | AAVhu.46 (See SEQ ID NO: 159 in US20150315612) |
| AAVhu.46 (See SEQ ID NO: 82 in US20150315612) | AAVhu.47 (See SEQ ID NO: 77 in US20150315612) |
| AAVhu.46 (See SEQ ID NO: 224 in US20150315612) | AAVhu.48 (See SEQ ID NO: 38 in US20150159173) |
| AAVhu.47 (See SEQ ID NO: 128 in US20150315612) | AAVhu.48 (AAV130.4) (See SEQ ID NO: 78 in US20150315612) |
| AAVhu.48 (See SEQ ID NO: 157 in US20150315612) | AAVhu.48R2 (See SEQ ID NO: 38 modified with G277S and E322K in US20150159173) |
| AAVhu.48Rl (See SEQ ID NO: 38 modified with G277S in US20150159173) | AAVhu.49 (See SEQ ID NO: 209 in US20150315612) |
| AAVhu.48R3 (See SEQ ID NO: 38 modified with G277S, E322K, and S552N in US20150159173) | AAVhu.5 (See SEQ ID NO: 45 in US20150315612) |
| AAVhu.49 (See SEQ ID NO: 189 in US20150315612) | AAVhu.51 (See SEQ ID NO: 208 in US20150315612) |

TABLE 1-continued

Exemplary descriptions of capsids and sequences

| Serotype and where capsid sequence is published and/or described | Serotype and where capsid sequence is published and/or described |
|---|---|
| AAVhu.5 (See SEQ ID NO: 142 in US20150315612) | AAVhu.52 (See SEQ ID NO: 210 in US20150315612) |
| AAVhu.51 (See SEQ ID NO: 190 in US20150315612) | AAVhu.53 (See SEQ ID NO: 19 in US20150159173) |
| AAVhu.52 (See SEQ ID NO: 191 in US20150315612) | AAVhu.53 (AAV145.1) (See SEQ ID NO: 176 in US20150315612) |
| AAVhu.53 (See SEQ ID NO: 35 in US20150159173) | AAVhu.54 (AAV145.5) (See SEQ ID NO: 177 in US20150315612) |
| AAVhu.54 (See SEQ ID NO: 188 in US20150315612) | AAVhu.56 (See SEQ ID NO: 205 in US20150315612) |
| AAVhu.55 (See SEQ ID NO: 187 in US20150315612) | AAVhu.56 (AAV145.6) (See SEQ ID NO: 192 in US20150315612) |
| AAVhu.56 (AAV145.6) (See SEQ ID NO: 168 in US20150315612) | AAVhu.57 (See SEQ ID NO: 169 in US20150315612) |
| AAVhu.57 (See SEQ ID NO: 206 in US20150315612) | AAVhu.58 (See SEQ ID NO: 207 in US20150315612) |
| AAVhu.57 (See SEQ ID NO: 193 in US20150315612) | AAVhu.6 (AAV3.1) (See SEQ ID NO: 5 in US20150315612) |
| AAVhu.58 (See SEQ ID NO: 194 in US20150315612) | AAVhu.60 (See SEQ ID NO: 184 in US20150315612) |
| AAVhu.6 (AAV3.1) (See SEQ ID NO: 84 in US20150315612) | AAVhu.61 (See SEQ ID NO: 185 in US20150315612) |
| AAVhu.60 (AAV161.10) (See SEQ ID NO: 170 in US20150315612) | AAVhu.63 (See SEQ ID NO: 204 in US20150315612) |
| AAVhu.61 (AAV161.6) (See SEQ ID NO: 174 in US20150315612) | AAVhu.64 (See SEQ ID NO: 212 in US20150315612) |
| AAVhu.63 (See SEQ ID NO: 195 in US20150315612) | AAVhu.66 (See SEQ ID NO: 197 in US20150315612) |
| AAVhu.64 (See SEQ ID NO: 196 in US20150315612) | AAVhu.67 (See SEQ ID NO: 198 in US20150315612) |
| AAVhu.67 (See SEQ ID NO: 215 in US20150315612) | AAVhu.7 (See SEQ ID NO: 150 in US20150315612) |
| AAVhu.7 (See SEQ ID NO: 226 in US20150315612) | AAVhu.71 (See SEQ ID NO: 79 in US20150315612) |
| AAVhu.7 (AAV7.3) (See SEQ ID NO: 55 in US20150315612) | AAVhu.8 (See SEQ ID NO: 12 in US20150315612) |
| AAVhu.8 (See SEQ ID NO: 53 in US20150315612) | AAVhu.9 (AAV3.1) (See SEQ ID NO: 58 in US20150315612) |
| AAVhu.8 (See SEQ ID NO: 151 in US20150315612) | AAV-LK01 (See SEQ ID NO: 2 in US20150376607) |
| AAVhu.9 (AAV3.1) (See SEQ ID NO: 155 in US20150315612) | AAV-LK02 (See SEQ ID NO: 3 in US20150376607) |
| AAV-LK01 (See SEQ ID NO: 29 in US20150376607) | AAV-LK03 (See SEQ ID NO: 4 in US20150376607) |
| AAV-LK02 (See SEQ ID NO: 30 in US20150376607) | AAV-LK04 (See SEQ ID NO: 32 in US20150376607) |
| AAV-LK03 (See SEQ ID NO: 12 in WO2015121501 and SEQ ID NO: 31 in US20150376607) | AAV-LK05 (See SEQ ID NO: 33 in US20150376607) |
| AAV-LK04 (See SEQ ID NO: 5 in US20150376607) | AAV-LK06 (See SEQ ID NO: 34 in US20150376607) |
| AAV-LK05 (See SEQ ID NO: 6 in US20150376607) | AAV-LK07 (See SEQ ID NO: 35 in US20150376607) |
| AAV-LK06 (See SEQ ID NO: 7 in US20150376607) | AAV-LK08 (See SEQ ID NO: 36 in US20150376607) |
| AAV-LK07 (See SEQ ID NO: 8 in US20150376607) | AAV-LK09 (See SEQ ID NO: 37 in US20150376607) |
| AAV-LK08 (See SEQ ID NO: 9 in US20150376607) | AAV-LK10 (See SEQ ID NO: 38 in US20150376607) |
| AAV-LK09 (See SEQ ID NO: 10 in US20150376607) | AAV-LK11 (See SEQ ID NO: 39 in US20150376607) |
| AAV-LK10 (See SEQ ID NO: 11 in US20150376607) | AAV-LK12 (See SEQ ID NO: 40 in US20150376607) |
| AAV-LK11 (See SEQ ID NO: 12 in US20150376607) | AAV-LK13 (See SEQ ID NO: 41 in US20150376607) |
| AAV-LK12 (See SEQ ID NO: 13 in US20150376607) | AAV-LK14 (See SEQ ID NO: 42 in US20150376607) |
| AAV-LK13 (See SEQ ID NO: 14 in US20150376607) | AAV-LK15 (See SEQ ID NO: 43 in US20150376607) |
| AAV-LK14 (See SEQ ID NO: 15 in US20150376607) | AAV-LK16 (See SEQ ID NO: 44 in US20150376607) |
| AAV-LK15 (See SEQ ID NO: 16 in US20150376607) | AAV-LK17 (See SEQ ID NO: 45 in US20150376607) |
| AAV-LK16 (See SEQ ID NO: 17 in US20150376607) | AAV-LK18 (See SEQ ID NO: 46 in US20150376607) |

TABLE 1-continued

| Exemplary descriptions of capsids and sequences | |
|---|---|
| Serotype and where capsid sequence is published and/or described | Serotype and where capsid sequence is published and/or described |
| AAV-LK17 (See SEQ ID NO: 18 in US20150376607) | AAV-LK19 (See SEQ ID NO: 47 in US20150376607) |
| AAV-LK18 (See SEQ ID NO: 19 in US20150376607) | AAV-PAEC (See SEQ ID NO: 48 in US20150376607) |
| AAV-LK19 (See SEQ ID NO: 20 in US20150376607) | AAV-PAEC11 (See SEQ ID NO: 54 in US20150376607) |
| AAV-PAEC (See SEQ ID NO: 1 in US20150376607) | AAV-PAEC 12 (See SEQ ID NO: 51 in US20150376607) |
| AAV-PAEC11 (See SEQ ID NO: 26 in US20150376607) | AAV-PAEC 13 (See SEQ ID NO: 49 in US20150376607) |
| AAV-PAEC 12 (See SEQ ID NO: 27 in US20150376607) | AAV-PAEC2 (See SEQ ID NO: 56 in US20150376607) |
| AAV-PAEC 13 (See SEQ ID NO: 28 in US20150376607) | AAV-PAEC4 (See SEQ ID NO: 55 in US20150376607) |
| AAV-PAEC2 (See SEQ ID NO: 21 in US20150376607) | AAV-PAEC6 (See SEQ ID NO: 52 in US20150376607) |
| AAV-PAEC4 (See SEQ ID NO: 22 in US20150376607) | AAV-PAEC7 (See SEQ ID NO: 53 in US20150376607) |
| AAV-PAEC6 (See SEQ ID NO: 23 in US20150376607) | AAV-PAEC8 (See SEQ ID NO: 50 in US20150376607) |
| AAV-PAEC7 (See SEQ ID NO: 24 in US20150376607) | AAVpi.1 (See SEQ ID NO: 93 in US20150315612) |
| AAV-PAEC8 (See SEQ ID NO: 25 in US20150376607) | AAVpi.2 (see SEQ ID NO: 30 in US20150315612) |
| AAVpi.l (See SEQ ID NO: 28 in US20150315612) | AAVpi.3 (See SEQ ID NO: 29 in US20150315612) |
| AAVpi.2 (See SEQ ID NO: 95 in US20150315612) | AAVrh.10 (See SEQ ID NO: 9 in US20150159173) |
| AAVpi.3 (See SEQ ID NO: 94 in US20150315612) | AAV44.2 (See SEQ ID NO: 59 in US20030138772) |
| AAVrh.10 (See SEQ ID NO: 25 in US20150159173) | AAV42.1B (See SEQ ID NO: 90 in US20030138772) |
| AAVrh.10 (AAV44.2) (See SEQ ID NO: 81 in US20030138772) | AAVrh.13 (See SEQ ID NO: 10 in US20150159173) |
| AAVrh.12 (AAV42.1b) (See SEQ ID NO: 30 in US20030138772) | AAVrh.13 (See SEQ ID NO: 228 in US20150315612) |
| AAVrh.13 (See SEQ ID NO: 26 in US20150159173) | AAV42.3A (See SEQ ID NO: 87 in US20030138772) |
| AAVrh.13R (See SEQ ID NO: 26 modified with E538K in US20150159173 | AAV42.5A (See SEQ ID NO: 89 in US20030138772) |
| AAVrh.14 (AAV42.3a) (See SEQ ID NO: 32 in US20030138772) | AAV42.5B (See SEQ ID NO: 91 in US20030138772) |
| AAVrh.17 (AAV42.5a) (See SEQ ID NO: 34 in US20030138772) | AAV42.6B (See SEQ ID NO: 112 in US20030138772) |
| AAVrh.18 (AAV42.5b) (See SEQ ID NO: 29 in US20030138772) | AAVrh.2 (See SEQ ID NO: 39 in US20150159173) |
| AAVrh.19 (AAV42.6b) (See SEQ ID NO: 38 in US20030138772) | AAVrh.20 (See SEQ ID NO: 1 in US20150159173) |
| AAVrh.2 (See SEQ ID NO: 231 in US20150315612) | AAVrh.21 (AAV42.10) (See SEQ ID NO: 35 in US20030138772) |
| AAV42.10 (See SEQ ID NO: 106 in US20030138772) | AAVrh.22 (AAV42.11) (See SEQ ID NO: 37 in US20030138772) |
| AAV42.11 (See SEQ ID NO: 108 in US20030138772) | AAVrh.23 (AAV42.12) (See SEQ ID NO: 58 in US20030138772) |
| AAV42.12 (See SEQ ID NO: 113 in US20030138772) | AAVrh.24 (AAV42.13) (See SEQ ID NO: 31 in US20030138772) |
| AAV42.13 (See SEQ ID NO: 86 in US20030138772) | AAVrh.25 (AAV42.15) (See SEQ ID NO: 28 in US20030138772) |
| AAV42.15 (See SEQ ID NO: 84 in US20030138772) | AAVrh.31 (AAV223.1) (See SEQ ID NO: 48 in US20030138772) |
| AAVrh.2R (See SEQ ID NO: 39 modified with V651I in US20150159173) | AAVrh.32 (AAVC1) (See SEQ ID NO: 19 in 446 US20030138772) |
| AAVCI (See SEQ ID NO: 60 in US20030138772) | AAVrh.51 (AAV2-5) (See SEQ ID NO: 104 in US20150315612) |
| AAVrh.32/33 (See SEQ ID NO: 2 in US20150159173) | AAVrh.52 (AAV3-9) (See SEQ ID NO: 96 in US20150315612) |
| AAVrh.52 (AAV3-9) (See SEQ ID NO: 18 in US20150315612) | AAVrh.53 (AAV3-11) (See SEQ ID NO: 17 in US20150315612) |
| AAVrh.53 (See SEQ ID NO: 97 in US20150315612) | AAVrh.54 (See SEQ ID NO: 40 in US20150315612) |
| AAVrh.53 (AAV3-11) (See SEQ ID NO: 186 in US20150315612) | AAVrh.55 (AAV4-19) (See SEQ ID NO: 117 in US20150315612) |
| AAVrh.54 (See SEQ ID NO: 49 in US20150159173 and SEQ ID NO: 116 in US20150315612) | AAVrh.56 (See SEQ ID NO: 152 in US20150315612) |

TABLE 1-continued

Exemplary descriptions of capsids and sequences

| Serotype and where capsid sequence is published and/or described | Serotype and where capsid sequence is published and/or described |
|---|---|
| AAVrh.55 (See SEQ ID NO: 37 in US20150315612) | AAVrh.57 (See SEQ ID NO: 105 in US20150315612) |
| AAVrh.56 (See SEQ ID NO: 54 in US20150315612) | AAVrh.58 (See SEQ ID NO: 48 in US20150159173 and SEQ ID NO: 106 in US20150315612) |
| AAVrh.57 (See SEQ ID NO: 26 in US20150315612) | AAVrh.58 (See SEQ ID NO: 232 in US20150315612) |
| AAVrh.58 (See SEQ ID NO: 27 in US20150315612) | AAVrh.59 (See SEQ ID NO: 110 in US20150315612) |
| AAVrh.59 (See SEQ ID NO: 42 in US20150315612) | AAVrh.60 (See SEQ ID NO: 120 in US20150315612) |
| AAVrh.60 (See SEQ ID NO: 31 in US20150315612) | AAVrh.61 (AAV2-3) (See SEQ ID NO: 21 in US20150315612) |
| AAVrh.61 (See SEQ ID NO: 107 in US20150315612) | AAVrh.62 (AAV2-15) (See SEQ ID NO: 114 in US20150315612) |
| AAVrh.62 (AAV2-15) (See SEQ ID NO: 33 in US20150315612) | AAVrh.64 (See SEQ ID NO: 43 in US20150159173 and SEQ ID NO: 99 in US20150315612) |
| AAVrh.64 (See SEQ ID NO: 15 in US20150315612) | AAVrh.64 (See SEQ ID NO: 233 in US20150315612) |
| AAVRh.64Rl (See SEQ ID NO: 43 modified with R697W in US20150159173 | AAVRh.64R2 (See SEQ ID NO: 43 modified with R697W and V686E in US20150159173 |
| AAVrh.65 (See SEQ ID NO: 35 in US20150315612) | AAVrh.65 (See SEQ ID NO: 112 in US20150315612) |
| AAVrh.67 (See SEQ ID NO: 36 in US20150315612) | AAVrh.67 (See SEQ ID NO: 230 in US20150315612) |
| AAVrh.67 (See SEQ ID NO: 47 in US20150159173 and SEQ ID NO: 47 in US20150315612) | AAVrh.68 (See SEQ ID NO: 100 in US20150315612) |
| AAVrh.68 (See SEQ ID NO: 16 in US20150315612) | AAVrh.69 (See SEQ ID NO: 119 in US20150315612) |
| AAVrh.69 (See SEQ ID NO: 39 in US20150315612) | AAVrh.70 (See SEQ ID NO: 98 in US20150315612) |
| AAVrh.70 (See SEQ ID NO: 20 in US20150315612) | AAVrh.72 (See SEQ ID NO: 9 in US20150315612) |
| AAVrh.71 (See SEQ ID NO: 162 in US20150315612) | AAVrh.74 (See SEQ ID NO: 6 in US20150159173) |
| AAVrh.73 (See SEQ ID NO: 5 in US20150159173) | AAVrh.8 (See SEQ ID NO: 235 in US20150315612) |
| AAVrh.8 (See SEQ ID NO: 41 in US20150159173) | AAVrh.8R A586R mutant (See SEQ ID NO: 10 in WO2015168666) |
| AAVrh.8R (See SEQ ID NO: 9 in US20150159173, WO2015168666) | BAAV (bovine AAV) (See SEQ ID NO: 8 in US9193769) |
| AAVrh.8R R533A mutant (See SEQ ID NO: 11 in WO2015168666) | BAAV (bovine AAV) (See SEQ ID NO: 4 in US9193769) |
| BAAV (bovine AAV) (See SEQ ID NO: 10 in US9193769) | BAAV (bovine AAV) (See SEQ ID NO: 6 in US9193769) |
| BAAV (bovine AAV) (See SEQ ID NO: 2 in US9193769) | BAAV (bovine AAV) (See SEQ ID NO: 5 in US9193769) |
| BAAV (bovine AAV) (See SEQ ID NO: 1 in US9193769) | BAAV (bovine AAV) (See SEQ ID NO: 11 in US9193769) |
| BAAV (bovine AAV) (See SEQ ID NO: 3 in US9193769) | BAAV (bovine AAV) (See SEQ ID NO: 6 in US7427396) |
| BAAV (bovine AAV) (See SEQ ID NO: 5 in US7427396) | BAAV (bovine AAV) (See SEQ ID NO: 9 in US9193769) |
| BAAV (bovine AAV) (See SEQ ID NO: 7 in US9193769) | BNP61 AAV (See SEQ ID NO: 2 in US20150238550) |
| BNP61 AAV (See SEQ ID NO: 1 in US20150238550) | BNP63 AAV (See SEQ ID NO: 4 in US20150238550) |
| BNP62 AAV (See SEQ ID NO: 3 in US20150238550) | caprine AAV (See SEQ ID NO: 4 in US7427396) |
| caprine AAV (See SEQ ID NO: 3 in US7427396) | AAAV (Avian AAV) (See SEQ ID NO: 12 in US9238800) |
| true type AAV (ttAAV) (See SEQ ID NO: 2 in WO2015121501) | AAAV (Avian AAV) (See SEQ ID NO: 6 in US9238800) |
| AAAV (Avian AAV) (See SEQ ID NO: 2 in US9238800) | AAAV (Avian AAV) (See SEQ ID NO: 8 in US9238800) |
| AAAV (Avian AAV) (See SEQ ID NO: 4 in US9238800) | AAAV (Avian AAV) (See SEQ ID NO: 10 in US9238800) |
| AAAV (Avian AAV) (See SEQ ID NO: 14 in US9238800) | AAAV (Avian AAV) (See SEQ ID NO: 5 in US9238800) |
| AAAV (Avian AAV) (See SEQ ID NO: 15 in US9238800) | AAAV (Avian AAV) (See SEQ ID NO: 3 in US9238800) |
| AAAV (Avian AAV) (See SEQ ID NO: 9 in US9238800) | AAAV (Avian AAV) (See SEQ ID NO: 11 in US9238800) |

TABLE 1-continued

| Exemplary descriptions of capsids and sequences | |
|---|---|
| Serotype and where capsid sequence is published and/or described | Serotype and where capsid sequence is published and/or described |
| AAAV (Avian AAV) (See SEQ ID NO: 7 in US9238800) | AAAV (Avian AAV) (See SEQ ID NO: 1 in US9238800) |
| AAAV (Avian AAV) (See SEQ ID NO: in US9238800) | AAV Shuffle 100-1 (See SEQ ID NO: 11 in US20160017295) |
| AAV Shuffle 100-1 (See SEQ ID NO: 23 in US20160017295) | AAV Shuffle 100-2 (See SEQ ID NO: 29 in US20160017295) |
| AAV Shuffle 100-2 (See SEQ ID NO: 37 in US20160017295) | AAV Shuffle 100-3 (See SEQ ID NO: 12 in US20160017295) |
| AAV Shuffle 100-3 (See SEQ ID NO: 24 in US20160017295) | AAV Shuffle 100-7 (See SEQ ID NO: 13 in US20160017295) |
| AAV Shuffle 100-7 (See SEQ ID NO: 25 in US20160017295) | AAV Shuffle 10-2 (See SEQ ID NO: 26 in US20160017295) |
| AAV Shuffle 10-2 (See SEQ ID NO: 34 in US20160017295) | AAV Shuffle 10-6 (See SEQ ID NO: 27 in US20160017295) |
| AAV Shuffle 10-6 (See SEQ ID NO: 35 in US20160017295) | AAV Shuffle 10-8 (See SEQ ID NO: 28 in US20160017295) |
| AAV Shuffle 10-8 (See SEQ ID NO: 36 in US20160017295) | AAV SM 100-10 (See SEQ ID NO: 33 in US20160017295) |
| AAV SM 100-10 (See SEQ ID NO: 41 in US20160017295) | AAV SM 100-3 (See SEQ ID NO: 32 in US20160017295) |
| AAV SM 100-3 (See SEQ ID NO: 40 in US20160017295) | AAV SM 10-1 (See SEQ ID NO: 30 in US20160017295) |
| AAV SM 10-1 (See SEQ ID NO: 38 in US20160017295) | AAV SM 10-2 (See SEQ ID NO: 22 in US20160017295) |
| AAV SM 10-2 (See SEQ ID NO: 10 in US20160017295) | AAV SM 10-8 (See SEQ ID NO: 31 in US20160017295) |
| AAV SM 10-8 (See SEQ ID NO: 39 in US20160017295) | AAV CBr-7.1 (See SEQ ID NO: 54 in WO2016065001) |
| AAV CBr-7.1 (See SEQ ID NO: 4 in WO2016065001) | AAV CBr-7.10 (See SEQ ID NO: 61 in WO2016065001) |
| AAV CBr-7.10 (See SEQ ID NO: 11 in WO2016065001) | AAV CBr-7.2 (See SEQ ID NO: 55 in WO2016065001) |
| AAV CBr-7.2 (See SEQ ID NO: 5 in WO2016065001) | AAV CBr-7.3 (See SEQ ID NO: 56 in WO2016065001) |
| AAV CBr-7.3 (See SEQ ID NO: 6 in WO2016065001) | AAV CBr-7.4 (See SEQ ID NO: 57 in WO2016065001) |
| AAV CBr-7.4 (See SEQ ID NO: 7 in WO2016065001) | AAV CHt-6.6 (See SEQ ID NO: 35 in WO2016065001) |
| AAV CBr-7.5 (See SEQ ID NO: 8 in WO2016065001) | AAV CHt-6.7 (See SEQ ID NO: 36 in WO2016065001) |
| AAV CHt-6.6 (See SEQ ID NO: 85 in WO2016065001) | AAV CHt-6.8 (See SEQ ID NO: 37 in WO2016065001) |
| AAV CHt-6.7 (See SEQ ID NO: 86 in WO2016065001) | AAV CHt-Pl (See SEQ ID NO: 29 in WO2016065001) |
| AAV CHt-6.8 (See SEQ ID NO: 87 in WO2016065001) | AAV CHt-P2 (See SEQ ID NO: 1 in WO2016065001) |
| AAV CHt-Pl (See SEQ ID NO: 79 in WO2016065001) | AAV CHt-P5 (See SEQ ID NO: 2 in WO2016065001) |
| AAV CHt-P2 (See SEQ ID NO: 51 in WO2016065001) | AAV CHt-P6 (See SEQ ID NO: 30 in WO2016065001) |
| AAV CHt-P5 (See SEQ ID NO: 52 in WO2016065001) | AAV CHt-P8 (See SEQ ID NO: 31 in WO2016065001) |
| AAV CHt-P6 (See SEQ ID NO: 80 in WO2016065001) | AAV CHt-P9 (See SEQ ID NO: 3 in WO2016065001) |
| AAV CHt-P8 (See SEQ ID NO: 81 in WO2016065001) | AAV CKd-1 (See SEQ ID NO: 57 in US8734809) |
| AAV CHt-P9 (See SEQ ID NO: 53 in WO2016065001) | AAV CKd-10 (See SEQ ID NO: 58 in US8734809) |
| AAV CKd-1 (See SEQ ID NO: 131 in US8734809) | AAV CKd-2 (See SEQ ID NO: 59 in US8734809) |
| AAV CKd-10 (See SEQ ID NO: 132 in US8734809) | AAV CKd-3 (See SEQ ID NO: 60 in US8734809) |
| AAV CKd-2 (See SEQ ID NO: 133 in US8734809) | AAV CKd-4 (See SEQ ID NO: 61 in US8734809) |
| AAV CKd-3 (See SEQ ID NO: 134 in US8734809) | AAV CKd-6 (See SEQ ID NO: 62 in US8734809) |
| AAV CKd-4 (See SEQ ID NO: 135 in US8734809) | AAV CKd-7 (See SEQ ID NO: 63 in US8734809) |
| AAV CKd-6 (See SEQ ID NO: 136 in US8734809) | AAV CKd-8 (See SEQ ID NO: 64 in US8734809) |
| AAV CKd-7 (See SEQ ID NO: 137 in US8734809) | AAV CKd-B 1 (See SEQ ID NO: 73 in US8734809) |
| AAV CKd-8 (See SEQ ID NO: 138 in US8734809) | AAV CKd-B2 (See SEQ ID NO: 74 in US8734809) |

TABLE 1-continued

| Exemplary descriptions of capsids and sequences | |
|---|---|
| Serotype and where capsid sequence is published and/or described | Serotype and where capsid sequence is published and/or described |
| AAV CKd-B 1 (See SEQ ID NO: 147 in US8734809) | AAV CKd-B3 (See SEQ ID NO: 75 in US8734809) |
| AAV CKd-B2 (See SEQ ID NO: 148 in US8734809) | AAV CKd-B3 (See SEQ ID NO: 149 in US8734809) |
| AAV CKd-B3 (See SEQ ID NO: in US8734809 | AAV CLv-1 (See SEQ ID NO: 139 in US8734809) |
| AAV CLv-1 (See SEQ ID NO: 65 in US8734809) | AAV Civ 1-10 (See SEQ ID NO: 178 in US8734809) |
| AAV CLvl-1 (See SEQ ID NO: 171 in US8734809) | AAV CLv-12 (See SEQ ID NO: 66 in US8734809) |
| AAV CLvl-2 (See SEQ ID NO: 172 in US8734809) | AAV CLv1-3 (See SEQ ID NO: 173 in US8734809) |
| AAV CLv-12 (See SEQ ID NO: 140 in US8734809) | AAV CLv-13 (See SEQ ID NO: 141 in US8734809) |
| AAV CLv-13 (See SEQ ID NO: 67 in US8734809) | AAV Civ 1-7 (See SEQ ID NO: 175 in US8734809) |
| AAV CLvl-4 (See SEQ ID NO: 174 in US8734809) | AAV Civ 1-9 (See SEQ ID NO: 177 in US8734809) |
| AAV Civ 1-8 (See SEQ ID NO: 176 in US8734809) | AAV CLv-2 (See SEQ ID NO: 142 in US8734809) |
| AAV CLv-2 (See SEQ ID NO: 68 in US8734809) | AAV CLv-3 (See SEQ ID NO: 143 in US8734809) |
| AAV CLv-3 (See SEQ ID NO: 69 in US8734809) | AAV CLv-4 (See SEQ ID NO: 144 in US8734809) |
| AAV CLv-4 (See SEQ ID NO: 70 in US8734809) | AAV CLv-6 (See SEQ ID NO: 145 in US8734809) |
| AAV CLv-6 (See SEQ ID NO: 71 in US8734809) | AAV CLv-8 (See SEQ ID NO: 146 in US8734809) |
| AAV CLv-8 (See SEQ ID NO: 72 in US8734809) | AAV CLv-DI (See SEQ ID NO: 96 in US8734809) |
| AAV CLv-DI (See SEQ ID NO: 22 in US8734809) | AAV CLv-D2 (See SEQ ID NO: 97 in US8734809) |
| AAV CLv-D2 (See SEQ ID NO: 23 in US8734809) | AAV CLv-D3 (See SEQ ID NO: 98 in US8734809) |
| AAV CLv-D3 (See SEQ ID NO: 24 in US8734809) | AAV CLv-D4 (See SEQ ID NO: 99 in US8734809) |
| AAV CLv-D4 (See SEQ ID NO: 25 in US8734809) | AAV CLv-D5 (See SEQ ID NO: 100 in US8734809) |
| AAV CLv-D5 (See SEQ ID NO: 26 in US8734809) | AAV CLv-D6 (See SEQ ID NO: 101 in US8734809) |
| AAV CLv-D6 (See SEQ ID NO: 27 in US8734809) | AAV CLv-D7 (See SEQ ID NO: 102 in US8734809) |
| AAV CLv-D7 (See SEQ ID NO: 28 in US8734809) | AAV CLv-D8 (See SEQ ID NO: 103 in US8734809); AAV CLv-KI 762, see SEQ ID NO: 18 in WO2016065001) |
| AAV CLv-D8 (See SEQ ID NO: 29 in US8734809) | AAV CLv-K3 (See SEQ ID NO: 19 in WO2016065001) |
| AAV CLv-KI (See SEQ ID NO: 68 in WO2016065001) | AAV CLv-K6 (See SEQ ID NO: 20 in WO2016065001) |
| AAV CLv-K3 (See SEQ ID NO: 69 in WO2016065001) | AAV CLv-L4 (See SEQ ID NO: 15 in WO2016065001) |
| AAV CLv-K6 (See SEQ ID NO: 70 in WO2016065001) | AAV CLv-L5 (See SEQ ID NO: 16 in WO2016065001) |
| AAV CLv-L4 (See SEQ ID NO: 65 in WO2016065001) | AAV CLv-L6 (See SEQ ID NO: 17 in WO2016065001) |
| AAV CLv-L5 (See SEQ ID NO: 66 in WO2016065001) | AAV CLv-MI (See SEQ ID NO: 21 in WO2016065001) |
| AAV CLv-L6 (See SEQ ID NO: 67 in WO2016065001) | AAV CLv-Mll (See SEQ ID NO: 22 in WO2016065001) |
| AAV CLv-MI (See SEQ ID NO: 71 in WO2016065001) | AAV CLv-M2 (See SEQ ID NO: 23 in WO2016065001) |
| AAV CLv-MI 1 (See SEQ ID NO: 72 in WO2016065001) | AAV CLv-M5 (See SEQ ID NO: 24 in WO2016065001) |
| AAV CLv-M2 (See SEQ ID NO: 73 in WO2016065001) | AAV CLv-M6 (See SEQ ID NO: 25 in WO2016065001) |
| AAV CLv-M5 (See SEQ ID NO: 74 in WO2016065001) | AAV CLv-M7 (See SEQ ID NO: 26 in WO2016065001) |
| AAV CLv-M6 (See SEQ ID NO: 75 in WO2016065001) | AAV CLv-M8 (See SEQ ID NO: 27 in WO2016065001) |
| AAV CLv-M7 (See SEQ ID NO: 76 in WO2016065001) | AAV CLv-M9 (See SEQ ID NO: 28 in WO2016065001) |
| AAV CLv-M8 (See SEQ ID NO: 77 in WO2016065001) | AAV CLv-RI (See SEQ ID NO: 30 in US8734809) |
| AAV CLv-M9 (See SEQ ID NO: 78 in WO2016065001) | AAV CLv-R2 (See SEQ ID NO: 31 in US8734809) |

TABLE 1-continued

Exemplary descriptions of capsids and sequences

| Serotype and where capsid sequence is published and/or described | Serotype and where capsid sequence is published and/or described |
|---|---|
| AAV CLv-RI (See SEQ ID NO: 104 in US8734809) | AAV CLv-R3 (See SEQ ID NO: 32 in US8734809) |
| AAV CLv-R2 (See SEQ ID NO: 105 in US8734809) | AAV CLv-R4 (See SEQ ID NO: 33 in US8734809) |
| AAV CLv-R3 (See SEQ ID NO: 106 in US8734809) | AAV CLv-R5 (See SEQ ID NO: 34 in US8734809) |
| AAV CLv-R4 (See SEQ ID NO: 107 in US8734809) | AAV CLv-R6 (See SEQ ID NO: 35 in US8734809) |
| AAV CLv-R5 (See SEQ ID NO: 108 in US8734809) | AAV CLv-R7 (See SEQ ID NO: 110 in US8734809) |
| AAV CLv-R6 (See SEQ ID NO: 109 in US8734809); AAV CLv-R7 802 (see SEQ ID NO: 36 in US8734809) | AAV CLv-R8 (See SEQ ID NO: 111 in US8734809) |
| AAV CLv-R8 (See SEQ ID NO: 37 in US8734809) | AAV CLv-R9 (See SEQ ID NO: 112 in US8734809) |
| AAV CLv-R9 (See SEQ ID NO: 38 in US8734809) | AAV CSp-1 (See SEQ ID NO: 119 in US8734809) |
| AAV CSp-1 (See SEQ ID NO: 45 in US8734809) | AAV CSp-10 (See SEQ ID NO: 120 in US8734809) |
| AAV CSp-10 (See SEQ ID NO: 46 in US8734809) | AAV CSp-11 (See SEQ ID NO: 121 in US8734809) |
| AAV CSp-11 (See SEQ ID NO: 47 in US8734809) | AAV CSp-2 (See SEQ ID NO: 122 in US8734809) |
| AAV CSp-2 (See SEQ ID NO: 48 in US8734809) | AAV CSp-3 (See SEQ ID NO: 123 in US8734809) |
| AAV CSp-3 (See SEQ ID NO: 49 in US8734809) | AAV CSp-4 (See SEQ ID NO: 124 in US8734809) |
| AAV CSp-4 (See SEQ ID NO: 50 in US8734809) | AAV CSp-6 (See SEQ ID NO: 125 in US8734809) |
| AAV CSp-6 (See SEQ ID NO: 51 in US8734809) | AAV CSp-7 (See SEQ ID NO: 126 in US8734809) |
| AAV CSp-7 (See SEQ ID NO: 52 in US8734809) | AAV CSp-8 (See SEQ ID NO: 127 in US8734809) |
| AAV CSp-8 (See SEQ ID NO: 53 in US8734809) | AAV CSp-8.10 (See SEQ ID NO: 88 in WO2016065001) |
| AAV CSp-8.10 (See SEQ ID NO: 38 in WO2016065001) | AAV CSp-8.2 (See SEQ ID NO: 89 in WO2016065001) |
| AAV CSp-8.2 (See SEQ ID NO: 39 in WO2016065001) | AAV CSp-8.4 (See SEQ ID NO: 90 in WO2016065001) |
| AAV CSp-8.4 (See SEQ ID NO: 40 in WO2016065001) | AAV CSp-8.5 (See SEQ ID NO: 91 in WO2016065001) |
| AAV CSp-8.5 (See SEQ ID NO: 41 in WO2016065001) | AAV CSp-8.6 (See SEQ ID NO: 92 in WO2016065001) |
| AAV CSp-8.6 (See SEQ ID NO: 42 in WO2016065001) | AAV CSp-8.7 (See SEQ ID NO: 93 in WO2016065001) |
| AAV CSp-8.7 (See SEQ ID NO: 43 in WO2016065001) | AAV CSp-8.8 (See SEQ ID NO: 94 in WO2016065001) |
| AAV CSp-8.8 (See SEQ ID NO: 44 in WO2016065001) | AAV CSp-8.9 (See SEQ ID NO: 95 in WO2016065001) |
| AAV CSp-8.9 (See SEQ ID NO: 45 in WO2016065001) | AAV CSp-9 (See SEQ ID NO: 128 in US8734809) |
| AAV CSp-9 842 (See SEQ ID NO: 54 in US8734809) | AAV.VR-355 (See SEQ ID NO: 181 in US8734809) |
| AAV.hu.48R3 (See SEQ ID NO: 183 in US8734809) | AAV3B (See SEQ ID NO: 98 in WO2016065001) |
| AAV3B (See SEQ ID NO: 48 in WO2016065001) | AAV4 (See SEQ ID NO: 99 in WO2016065001) |
| AAV4 (See SEQ ID NO: 49 in WO2016065001) | AAV5 (See SEQ ID NO: 100 in WO2016065001) |
| AAV5 (See SEQ ID NO: 50 in WO2016065001) | AAVF1/HSC1 (See SEQ ID NO: 2 in WO2016049230) |
| AAVF1/HSC1 (See SEQ ID NO: 20 in WO2016049230) | AAVF11/HSC11 (See SEQ ID NO: 4 in WO2016049230) |
| AAVF11/HSC11 (See SEQ ID NO: 26 in WO2016049230) | AAVF12/HSC12 (See SEQ ID NO: 12 in WO2016049230) |
| AAVF12/HSC12 (See SEQ ID NO: 30 in WO2016049230) | AAVF13/HSC13 (See SEQ ID NO: 14 in WO2016049230) |
| AAVF13/HSC13 (See SEQ ID NO: 31 in WO2016049230) | AAVF14/HSC14 (See SEQ ID NO: 15 in WO2016049230) |
| AAVF14/HSC14 (See SEQ ID NO: 32 in WO2016049230) | AAVF15/HSC15 (See SEQ ID NO: 16 in WO2016049230) |
| AAVF15/HSC15 (See SEQ ID NO: 33 in WO2016049230) | AAVF16/HSC16 (See SEQ ID NO: 17 in WO2016049230) |
| AAVF16/HSC16 (See SEQ ID NO: 34 in WO2016049230) | AAVF17/HSC17 (See SEQ ID NO: 13 in WO2016049230) |

TABLE 1-continued

| Exemplary descriptions of capsids and sequences | |
|---|---|
| Serotype and where capsid sequence is published and/or described | Serotype and where capsid sequence is published and/or described |
| AAVF17/HSC17 (See SEQ ID NO: 35 in WO2016049230) | AAVF2/HSC2 (See SEQ ID NO: 3 in WO2016049230) |
| AAVF2/HSC2 (See SEQ ID NO: 21 in WO2016049230) | AAVF3/HSC3 (See SEQ ID NO: 5 in WO2016049230) |
| AAVF3/HSC3 (See SEQ ID NO: 22 in WO2016049230) | AAVF4/HSC4 (See SEQ ID NO: 6 in WO2016049230) |
| AAVF4/HSC4 (See SEQ ID NO: 23 in WO2016049230) | AAVF5/HSC5 (See SEQ ID NO: 11 in WO2016049230) |
| AAVF5/HSC5 (See SEQ ID NO: 25 in WO2016049230) | AAVF6/HSC6 (See SEQ ID NO: 7 in WO2016049230) |
| AAVF6/HSC6 (See SEQ ID NO: 24 in WO2016049230) | AAVF7/HSC7 (See SEQ ID NO: 8 in WO2016049230) |
| AAVF7/HSC7 (See SEQ ID NO: 27 in WO2016049230) | AAVF8/HSC8 (See SEQ ID NO: 9 in WO2016049230) |
| AAVF8/HSC8 (See SEQ ID NO: 28 in WO2016049230) | AAVF9/HSC9 882 (see SEQ ID NO: 29 in WO2016049230) |
| AAVF9/HSC9 (See SEQ ID NO: 10 in WO2016049230) | AAV Anc80L65 (see SEQ ID NO: 23 in WO/2017/019994) |
| AAVpol (see SEQ ID NO: 24 in US8420372) | AAVIP5ii (see *Mol. Ther.* 2020 April 8; 28(4): 1016-1032 and SEQ ID NOS:5 and 11 in US20200370039 with corresponding description) |
| AAVIA6ii (see *Mol. Ther.* 2020 April 8; 28(4): 1016-1032 and SEQ ID NOS:8 and 14 in US20200370039 with corresponding description) | AAV7P4i (see *Mol. Ther.* 2020 April 8; 28(4): 1016-1032 and SEQ ID NOS:4 and 10 in US20200370039 with corresponding description) |
| AAV4A lii (see *Mol. Ther.* 2020 April 8; 28(4): 1016-1032 and SEQ ID NOS:6 and 12 in US20200370039 with corresponding description) | AAV9A2i (see *Mol. Ther.* 2020 April 8; 28(4): 1016-1032 and SEQ ID NOS:7 and 13 in US20200370039 with corresponding description) |
| AAV9Ali (see *Mol. Ther.* 2020 April 8; 28(4): 1016-1032 and SEQ ID NOS:6 and 12 in US20200370039 with corresponding description) | AAV9Pli (see *Mol. Ther.* 2020 April 8; 28(4): 1016-1032) |
| AAV9A6i (see *Mol. Ther.* 2020 April 8; 28(4): 1016-1032 and SEQ ID NOS:8 and 14 in US20200370039 with corresponding description) | AAV9P5i (see *Mol. Ther.* 2020 April 8; 28(4): 1016-1032 and SEQ ID NOS:5 and 11 in US20200370039 with corresponding description) |
| AAV9P2i (see *Mol. Ther.* 2020 April 8; 28(4): 1016-1032 and SEQ ID NOS:3 and 9 in US20200370039 with corresponding description) | AAVrh 10A2i (see *Mol. Ther.* 2020 April 8; 28(4): 1016-1032 and SEQ ID NOS:7 and 13 in US20200370039 with corresponding description) |
| AAVrh10Ali (see *Mol. Ther.* 2020 April 8; 28(4): 1016-1032 and SEQ ID NOS:6 and 12 in US20200370039 with corresponding description) | AAVS10Pli (see *Mol. Ther.* 2020 April 8; 28(4): 1016-1032) |
| AAVrh 10Pli (see *Mol. Ther.* 2020 April 8; 28(4): 1016-1032) | AAV2 3xA P2i (see *Mol. Ther.* 2020 April 8; 28(4): 1016-1032 and SEQ ID NOS:3 and 9 in US20200370039 with corresponding description) |
| AAV12P2ii (see *Mol. Ther.* 2020 April 8; 28(4): 1016-1032 and SEQ ID NOS:3 and 9 in US20200370039 with corresponding description) | AAVDJ P2i (see *Mol. Ther.* 2020 April 8; 28(4): 1016-1032 and SEQ ID NOS:3 and 9 in US20200370039 with corresponding description) |
| AAV2i8g9 (See *J Biol Chem.* 2013 Oct 4; 288(40): 28814-28823) | AAV 218 (see SEQ ID NO: 29 in US10548947) |
| AAV2g9 (See descriptions in WO2014144229 and *J Biol Chem.* 2013 Oct 4; 288(40): 28814-28823; and SEQ ID NO: 24 US20220354969 (without A266S)) | AAV2.5 (See SEQ ID NO: 2 in WO/2022/159871, SEQ ID NO: 16 in US9012224, and SEQ ID NO: 1 in US11639509) |
| AAV2.5g9 (see SEQ ID NO: 2 in US11639509 and SEQ ID NO: 2 in WO/2020/219656) | AAV 2110 (see SEQ ID NO: 11 and its corresponding description in US9475845) |
| AAV219 (see SEQ ID NO: 10 and its corresponding description in US9475845) | MyoAAV3A (see SEQ ID NO: 22 and corresponding description in WO/2022/020616) |
| MyoAAVIA (see SEQ ID NO: 12 and corresponding description in WO/2022/020616) | MyoAAV3C (see SEQ ID NO: 24 and corresponding description in WO/2022/020616) |
| MyoAAV3B (see SEQ ID NO: 23 and corresponding description in WO/2022/020616) | MyoAAV3E (see SEQ ID NO: 26 and corresponding description in WO/2022/020616) |
| MyoAAV3D (see SEQ ID NO: 25 and corresponding description in WO/2022/020616) | MyoAAV4A (see SEQ ID NO: 28 and corresponding description in WO/2022/020616) |
| MyoAAV3F (see SEQ ID NO: 27 and corresponding description in WO/2022/020616) | MyoAAV4C (see SEQ ID NO: 30 and corresponding description in WO/2022/020616) |
| MyoAAV4B (see SEQ ID NO: 29 and corresponding description in WO/2022/020616) | MyoAAV4E (see SEQ ID NO: 32 and corresponding description in WO/2022/020616) |
| MyoAAV4D (see SEQ ID NO: 31 and corresponding description in WO/2022/020616) | AAV9-P1(589) (AAVMYO) (see SEQ ID NO: 16 in US20210363193) |
| AAV9-P1(588) (AAVMYO) (see SEQ ID NO: 12 in US20210363193) | AAV9-P3(589) (see SEQ ID NO: 20 in US20210363193) |
| AAV9-P3(588) (see SEQ ID NO: 18 in US20210363193) | AAVSI-P1 (see SEQ ID NO: 30 in 20210363193) |
| AAVSI (see SEQ ID NO: 30 without Pl peptide in 20210363193) | AAVS10-P1 (see SEQ ID NO: 28 in 20210363193) |
| AAVS10 (see SEQ ID NO: 28 without Pl peptide in 20210363193) | AAV.cc44 (see SEQ ID NO: 5 in WO2021226267) |

TABLE 1-continued

| Exemplary descriptions of capsids and sequences | |
|---|---|
| Serotype and where capsid sequence is published and/or described | Serotype and where capsid sequence is published and/or described |
| AAV.cc47 (see SEQ ID NO: 8 in WO2021226267) | AAV.cc84 (see SEQ ID NO: 14 in WO2021226267) |
| AAV.cc81 (see SEQ ID NO: 11 in WO2021226267) | AAVRec3 (see SEQ ID NO: 3 in US20210371880) |
| AAVRec2 (see SEQ ID NO: 2 in US20210371880) | AAV-Olig001 (see SEQ ID NO: 2 in US9636370) |
| AAVLC.VI (see SEQ ID NO: 6 in WO2022051633) | AAV-Olig003 (see SEQ ID NO: 4 in US9636370) |
| AAV-Olig002 (see SEQ ID NO: 3 in US9636370) | AAV.PHP.B (see SEQ ID NO: 3 in US11149256 and SEQ ID NO: 7 in WO2019200016) |
| AAV.PHP.S (see SEQ IDNO: 4 in US11149256) | AAV9.24 (AAV9 with W503R; see Table 6 in US9409953) |
| AAV9-PHP.eB (See SEQ ID NOS:4 and 46 in US20170166926 and SEQ ID NO: 5 in US11149256) | AAV9.47 (AAV9 with S414N, G453D, K557E, and T582I; see Table 6 in US9409953) |
| AAV9.45 (AAV9 with N498Y and L602F; see Table 6 in US9409953) | AAV9.68 (AAV9 with P504T; see Table 6 in US9409953) |
| AAV9.61 (AAV9 with N498Y; see Table 6 in US9409953) | AAVXL12 (see SEQ ID NOS: 1 and 4 in US20210246467) |
| AAV9.84 (AAV9 with P468T and E500D; see Table 6 in US9409953) | AAVXL32.1 (see SEQ ID NOS:3 and 6 in US20210246467) |
| AAVXL32 (see SEQ ID NOS:2 and 5 in US20210246467) | AAVKP1 (see *JCI Insight.* 2019 Nov 14; 4(22): e131610; SEQ ID NOS: 1 and 14 in US11608510; and SEQ ID NO: 39 in US20220354969) |
| AAVKP2 (see *JCI Insight.* 2019 Nov 14; 4(22): e131610; SEQ ID NOS: 5 and 18 in US11608510; and SEQ ID NO: 40 in US20220354969) | AAVKP3 (see *JCI Insight.* 2019 Nov 14; 4(22): e131610; SEQ ID NOS: 2 and 15 in US11608510; and SEQ ID NO: 40 in US20220354969) |
| AAV2.7m8 (see Sci Transl Med. 2013 Jun 12; 5(189): 189ra76-189ra76 and SEQ ID NO: 13 and its corresponding description in US9193956; SEQ ID NO: 13 in US20230057380; and SEQ ID NO: 34 in US20220354969) | AAVNP40 (see SEQ ID NO: 25 in US20220354969) |
| AAVsh10 (see SEQ ID NO: 35 US20220354969) | AAVAnc80 (see SEQ ID NO: 33 in US20220354969) |
| AAVbovine (see SEQ ID NO. 12 in US20220184227 | AAV2R585E (see SEQ ID NO: in US11866462) |

In some embodiments, the rAAV comprises one or more AAV capsid protein selected from serotype AAV1, AAV2, AAV3a, AAV3b, AAV4, AAV5, AAV6, AAV7, AAV8, AAV9, AAV2G9, AAV2.5G9, AAV2.5, AAVrh8, AAVrh10, AAVrh74, AAV10, AAV11, and AAVDJ.

In some embodiments, the rAAV comprises one or more AAV capsid protein selected from serotype AAV1, AAV2, AAV3a, AAV3b, AAV4, AAV5, AAV6, AAV7, AAV8, AAV2G9, AAV2.5G9, AAV2.5, AAVrh8, AAVrh10, AAVrh74, AAV10, AAV11, and AAVDJ.

In some embodiments, the rAAV comprises one or more AAV capsid protein selected from serotype AAV1, AAV2, AAV3, AAV4, AAV5, AAV6, AAV7, AAV8, AAV9, AAV10, AAV11, AAV12, AAV13, AAVrh74, AAVrh10, pol, AAV9-PHP.B, AAV9-PHP.eB, AAVLK03, AAVAnc80L65, AAVDJ, AAV1A6ii, AAV1P5ii, AAV4A1ii, AAV7P4i, AAV9A1i, AAV9A2i, AAV9A6i, AAV9P1i, AAV9P2i, AAV9P5i, AAVrh10A1i, AAVrh10A2i, AAVrh10P1i, AAV12P2ii, AAVS10P1i, AAV JEA, AAV2 3xA P2i, AAVDJ P2i, AAV2i8, AAV2G9, AAV2.5, AAV4E, and AAV4A.

In some embodiments, the rAAV comprises an AAV capsid protein selected from AAV2, AAV6, AAVLK03, AAVDJ, AAV9A2i, AAV9A6i, AAVrh10A2i, AAV2g9, or AAV2.5 (see e.g., FIG. 4). In some embodiments, the rAAV comprises an AAV capsid protein selected from AAV2, AAVDJ, AAVJEA (minimal), AAV2g9, or AAV2.5 (see e.g., FIG. 5).

In some embodiments, the rAAV comprises a capsid selected from the group consisting of: AAV2G9, AAV2.5, AAVDJ, and AAV2. In some embodiments, the rAAV does not comprise a capsid protein from serotype AAV9. In some embodiments, the rAAV is not rAAV9. In some embodiments, the rAAV demonstrates tropism for the kidneys, in that it has the ability to preferentially and productively infect kidney cells and/or tissues.

In some embodiments, the rAAV comprises an AAV capsid protein selected from AAV2, AAV6, AAVLK03, AAVDJ, AAV9A2i, AAV9A6i, AAVrh10A2i, AAV2g9, AAV2.5, AAVKP1, AAVKP2, AAVKP3, and AAV2.7m8.

In some embodiments, the rAAV does not comprise an AAV9 capsid.

In some embodiments, the rAAV comprises a capsid selected from the group consisting of: AAV2G9, AAV2.5, AAVDJ, AAV2, AAVKP1, AAVKP2, AAVKP3, and AAV2.7m8. In some embodiments, the rAAV comprises a capsid selected from the group consisting of: AAVKP1, AAVKP2, AAVKP3, AAVDJ, AAV2G9, and AAV2.7m8. In some embodiments, the rAAV comprises a capsid selected from the group consisting of: AAVKP1, AAVKP2, and AAVKP3. In some embodiments, the rAAV comprises a capsid of AAV2.7m8. In some embodiments, the rAAV comprises a capsid of AAV-DJ.

In some embodiments, the rAAV administered using the retrograde ureter route has at least 10-fold higher transduction efficiency in the kidneys (e.g., cells of the nephrons, proximal tubules, loops of Henle, distal convoluted tubules, and/or collecting ducts) as compared to transduction efficiency in the kidneys of the rAAV administered using another route, such intravenously, intraperitoneally, via an intrarenal artery or intrarenal vein route, retro-orbitally, via direct kidney injection, or subcapsularly. In some embodiments, the rAAV administered using the retrograde ureter route has at least 2-fold, at least 5-fold, at least 10-fold, at least 25-fold, at least 50-fold, at least 75-fold, at least 100-fold, at least 200-fold, at least 300-fold, at least 400-fold, at least 500-fold, at least 600-fold, at least 700-fold, at least 800-fold, at least 900-fold, at least 1000-fold, at least 1100-fold, at least 1200-fold, at least 1300-fold, at least 1400-fold, at least 1500-fold, at least 1600-fold, at least 1700-fold, at least 1800-fold, at least 1900-fold, at least 2000-fold, at least 2100-fold, at least 2200-fold, at least 2300-fold, at least 2400-fold, at least 2500-fold, at least 2600-fold, at least 2700-fold, at least 2800-fold, at least 2900-fold, at least 3000-fold, at least 3100-fold, at least 3200-fold, at least 3300-fold, at least 3400-fold, or at least 3500-fold higher transduction efficiency in the kidneys (e.g., cells of the nephrons, proximal tubules, loops of Henle, distal convoluted tubules, and/or collecting ducts) compared to transduction efficiency in the kidneys of the rAAV administered using another route (e.g., IV).

In some embodiments, the rAAV has at least 3500-fold higher transduction efficiency in the kidneys (e.g., cells of the nephrons, proximal tubules, loops of Henle, distal convoluted tubules, and/or collecting ducts) compared to AAV9 (e.g., administered using the retrograde route as described herein). In some embodiments, the rAAV has at least 100-fold higher transduction efficiency in the kidneys (e.g., nephrons, proximal tubules) compared to AAV9. In some embodiments, the rAAV has at least 800-fold higher transduction efficiency in the kidneys (e.g., cells of the nephrons, proximal tubules, loops of Henle, distal convoluted tubules, and/or collecting ducts) compared to AAV9. In some embodiments, the rAAV has at least 2-fold, at least 5-fold, at least 10-fold, at least 25-fold, at least 50-fold, at least 75-fold, at least 100-fold, at least 200-fold, at least 300-fold, at least 400-fold, at least 500-fold, at least 600-fold, at least 700-fold, at least 800-fold, at least 900-fold, at least 1000-fold, at least 1100-fold, at least 1200-fold, at least 1300-fold, at least 1400-fold, at least 1500-fold, at least 1600-fold, at least 1700-fold, at least 1800-fold, at least 1900-fold, at least 2000-fold, at least 2100-fold, at least 2200-fold, at least 2300-fold, at least 2400-fold, at least 2500-fold, at least 2600-fold, at least 2700-fold, at least 2800-fold, at least 2900-fold, at least 3000-fold, at least 3100-fold, at least 3200-fold, at least 3300-fold, at least 3400-fold, or at least 3500-fold higher transduction efficiency in the kidneys (e.g., cells of the nephrons, proximal tubules, loops of Henle, distal convoluted tubules, and/or collecting ducts) compared to AAV9.

In some embodiments, the rAAV comprises a rational polyploid. As used herein, the term "rational polyploid" refers to AAV vectors which are composed of capsids from two or more AAV serotypes, which can take advantages from individual serotypes for an altered behavior such as tropism, transduction or antigenicity. Some of these polyploid viruses have the ability to change the tropism and transduction efficiency, as well as escape the neutralization by neutralizing antibodies (Nabs). Previously described methodology permits the rational design and production of virions. Such virions are sometimes referred to as "rational polyploid" virions to refer to the fact that the capsid proteins VP1, VP2, and VP3 come from at least two different serotypes, but not all the same serotype. The term "haploid" is sometimes used to refer to a virion where the capsid proteins VP1, VP2 and VP3 are from at least two different serotypes, and the term "triploid" is used to commonly refer to a virion where the capsid proteins VP1, VP2 and VP3 are from three different serotypes. In particular, such rational polyploid, e.g., rational haploid virions and their method of production are disclosed in U.S. Pat. No. 10,550,405, which is incorporated herein in its entirety by reference.

In some embodiments, the rAAV comprises a capsid protein from serotype AAV2G9 or variants thereof. The AAV2G9 capsid comprises amino acids substitutions that introduce a new glycan binding site into the AAV capsid protein. The AAV2G9 capsid protein comprises the Gal binding footprint from AAV9 onto the AAV2 VP3. The AAV2G9 capsid protein was generated by substituting amino acid residues directly involved or flanking the Gal recognition site on the AAV9 VP3 capsid protein subunit onto corresponding residues on the VP3 subunit of AAV2 (e.g., AAV2 VP3 numbering: A266S, Q464V, A467P, D469N, I470M, R471A, D472V, S474G, Y500F, and/or S501A). See e.g., Shen et al. "Engraftment of a Galactose Receptor Footprint onto Adeno-associated Viral Capsids Improves Transduction Efficiency," The Journal Of Biological Chemistry vol. 288, no. 40, pp. 28814-28823, Oct. 4, 2013; Shen, "Understanding And Manipulating AAV-Glycan Interactions," University of North Carolina at Chapel Hill dissertation (2013) (available on the world wide web at cdr.lib.unc.edu/concem/dissertations/pc289j203); International Patent Publication WO2014144229A1; U.S. Pat. No. 10,077,291 B2; U.S. Pat. No. 11,059,862 B2; US Patent Publication 20210115091 A1; the contents of each of which are incorporated herein by reference in their entireties.

In some embodiments, the AAV2G9 VP3 capsid protein or variant thereof comprises the A266S variation. In some embodiments, the AAV2G9 VP3 capsid protein or variant thereof does not comprise the A266S variation. In some embodiments, the AAV2G9 VP3 capsid protein or variant thereof comprises the A266S, Q464V, A467P, D469N, I470M, R471A, D472V, S474G, Y500F, and S501A variations. In some embodiments, the AAV2G9 VP3 capsid protein or variant thereof comprises the Q464V, A467P, D469N, I470M, R471A, D472V, S474G, Y500F, and S501A variations. There is an insubstantial difference between 2G9 capsids with or without the A266S variation. 2G9 can also include other variations that do not affect its general properties (e.g., tropism, transduction efficacy in the kidney (e.g., PCT), etc.)

In some embodiments, the AAV2G9 VP3 capsid protein or variant thereof comprises at least one variation of the AAV9 VP3 capsid protein (see e.g., SEQ ID NO: 2) inserted into the AAV2 VP3 capsid protein (see e.g., SEQ ID NO: 1), inserted at the following position(s): A266S, Q464V, A467P, D469N, I470M, R471A, D472V, S474G, Y500F, and/or S501A (AAV2 VP3 numbering).

AAV2 VP3 capsid protein (see e.g., SEQ ID NO: 65 of WO2014144229), 735 amino acids (aa),

SEQ ID NO: 1

MAADGYLPDWLEDTLSEGIRQWWKLKPGPPPPKPAERHKDDSRGLVLPGYKYLGPFNGLDK

GEPVNEADAAALEHDKAYDRQLDSGDNPYLKYNHADAEFQERLKEDTSFGGNLGRAVFQA

-continued

KKRVLEPLGLVEEPVKTAPGKKRPVEHSPVEPDSSSGTGKAGQQPARKRLNFGQTGDADSVP

DPQPLGQPPAAPSGLGTNTMATGSGAPMADNNEGADGVGNSSGNWHCDSTWMGDRVITTS

TRTWALPTYNNHLYKQISSQSGASNDNHYFGYSTPWGYFDFNRFHCHFSPRDWQRLINNNW

GFRPKRLNFKLFNIQVKEVTQNDGTTTIANNLTSTVQVFTDSEYQLPYVLGSAHQGCLPPFPA

DVFMVPQYGYLTLNNGSQAVGRSSFYCLEYFPSQMLRTGNNFTFSYTFEDVPFHSSYAHSQS

LDRLMNPLIDQYLYYLSRTNTPSGTTTQSRLQFSQAGASDIRDQSRNWLPGPCYRQQRVSKT

SADNNNSEYSWTGATKYHLNGRDSLVNPGPAMASHKDDEEKFFPQSGVLIFGKQGSEKTNV

DIEKVMITDEEEIRTTNPVATEQYGSVSTNLQRGNRQAATADVNTQGVLPGMVWQDRDVYL

QGPIWAKIPHTDGHFHPSPLMGGFGLKHPPPQILIKNTPVPANPSTTFSAAKFASFITQYSTGQ

VSVEIEWELQKENSKRWNPEIQYTSNYNKSVNVDFTVDTNGVYSEPRPIGTRYLTRNL

AAV9 VP3 capsid protein (see e.g., SEQ ID NO: 75 of WO2014144229), 736 aa,

SEQ ID NO: 2

MAADGYLPDWLEDNLSEGIREWWALKPGAPQPKANQQHQDNARGLVLPGYKYLGPGNGL

DKGEPVNAADAAALEHDKAYDQQLKAGDNPYLKYNHADAEFQERLKEDTSFGGNLGRAVF

QAKKRLLEPLGLVEEAAKTAPGKKRPVEQSPQEPDSSAGIGKSGAQPAKKRLNFGQTGDTES

VPDPQPIGEPPAAPSGVGSLTMASGGGAPVADNNEGADGVGSSSGNWHCDSQWLGDRVITT

STRTWALPTYNNHLYKQISNSTSGGSSNDNAYFGYSTPWGYFDFNRFHCHFSPRDWQRLINN

NWGFRPKRLNFKLFNIQVKEVTDNNGVKTIANNLTSTVQVFTDSDYQLPYVLGSAHEGCLPP

FPADVFMIPQYGYLTLNDGSQAVGRSSFYCLEYFPSQMLRTGNNFQFSYEFENVPFHSSYAHS

QSLDRLMNPLIDQYLYYLSKTINGSGQNQQTLKFSVAGPSNMAVQGRNYIPGPSYRQQRVST

TVTQNNNSEFAWPGASSWALNGRNSLMNPGPAMASHKEGEDRFFPLSGSLIFGKQGTGRDN

VDADKVMITNEEEIKTTNPVATESYGQVATNHQSAQAQAQTGWVQNQGILPGMVWQDRDV

YLQGPIWAKIPHTDGNFHPSPLMGGFGMKHPPPQILIKNTPVPADPPTAFNKDKLNSFITQYST

GQVSVEIEWELQKENSKRWNPEIQYTSNYYKSNNVEFAVNTEGVYSEPRPIGTRYLTRNL

In some embodiments, the AAV2G9 VP3 capsid protein or variant thereof comprises SEQ ID NO: 3, SEQ ID NO: 4, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 3 or SEQ ID NO: 4, which maintains the same function, or a functional fragment thereof.

exemplary AAV2G9 VP3 capsid protein, the following variations are noted in bold, underlined text: A266S, Q464V, A467P, D469N, I470M, R471A, D472V, S474G, Y500F, and S501A (AAV2 VP3 numbering).,

SEQ ID NO: 3

MAADGYLPDWLEDTLSEGIRQWWKLKPGPPPPKPAERHKDDSRGLVLPGYKYLGPFNGLDK

GEPVNEADAAALEHDKAYDRQLDSGDNPYLKYNHADAEFQERLKEDTSFGGNLGRAVFQA

KKRVLEPLGLVEEPVKTAPGKKRPVEHSPVEPDSSSGTGKAGQQPARKRLNFGQTGDADSVP

DPQPLGQPPAAPSGLGTNTMATGSGAPMADNNEGADGVGNSSGNWHCDSTWMGDRVITTS

TRTWALPTYNNHLYKQISSQSGSSNDNHYFGYSTPWGYFDFNRFHCHFSPRDWQRLINNNW

GFRPKRLNFKLFNIQVKEVTQNDGTTTIANNLTSTVQVFTDSEYQLPYVLGSAHQGCLPPFPA

DVFMVPQYGYLTLNNGSQAVGRSSFYCLEYFPSQMLRTGNNFTFSYTFEDVPFHSSYAHSQS

LDRLMNPLIDQYLYYLSRTNTPSGTTTQSRLQFSVAGPSNMAVQGNWLPGPCYRQQRVSK

-continued

TSADNNNSE__FA__WTGATKYHLNGRDSLVNPGPAMASHKDDEEKFFPQSGVLIFGKQGSEKTN

VDIEKVMITDEEEIRTTNPVATEQYGSVSTNLQRGNRQAATADVNTQGVLPGMVWQDRDVY

LQGPIWAKIPHTDGHFHPSPLMGGFGLKHPPPQILIKNTPVPANPSTTFSAAKFASFITQYSTGQ

VSVEIEWELQKENSKRWNPEIQYTSNYNKSVNVDFTVDINGVYSEPRPIGTRYLTRNL exemplary AAV2G9 VP3 capsid protein, the following variations are noted in bold, underlined text: Q464V, A467P, D469N, I470M, R471A, D472V, S474G, Y500F, and S501A (AAV2 VP3 numbering); see e.g., SEQ ID NO: 24 of US20220354969.,

SEQ ID NO: 4

MAADGYLPDWLEDTLSEGIRQWWKLKPGPPPPKPAERHKDDSRGLVLPGYKYLGPFNGLDK

GEPVNEADAAALEHDKAYDRQLDSGDNPYLKYNHADAEFQERLKEDTSFGGNLGRAVFQA

KKRVLEPLGLVEEPVKTAPGKKRPVEHSPVEPDSSSGTGKAGQQPARKRLNFGQTGDADSVP

DPQPLGQPPAAPSGLGTNTMATGSGAPMADNNEGADGVGNSSGNWHCDSTWMGDRVITTS

TRTWALPTYNNHLYKQISSQSGASNDNHYFGYSTPWGYFDFNRFHCHFSPRDWQRLINNNW

GFRPKRLNFKLFNIQVKEVTQNDGTTTIANNLTSTVQVFTDSEYQLPYVLGSAHQGCLPPFPA

DVFMVPQYGYLTLNNGSQAVGRSSFYCLEYFPSQMLRTGNNFTFSYTFEDVPFHSSYAHSQS

LDRLMNPLIDQYLYYLSRTNTPSGTTTQSRLQFS__V__AG__P__S__NMAV__Q__G__RNWLPGPCYRQQRVSK

TSADNNNSE__FA__WTGATKYHLNGRDSLVNPGPAMASHKDDEEKFFPQSGVLIFGKQGSEKTN

VDIEKVMITDEEEIRTTNPVATEQYGSVSTNLQRGNRQAATADVNTQGVLPGMVWQDRDVY

LQGPIWAKIPHTDGHFHPSPLMGGFGLKHPPPQILIKNTPVPANPSTTFSAAKFASFITQYSTGQ

VSVEIEWELQKENSKRWNPEIQYTSNYNKSVNVDFTVDTNGVYSEPRPIGTRYLTRNL

In some embodiments, the AAV2G9 VP3 capsid protein or variant thereof comprises SVAGPSNMAVQGR (SEQ ID NO: 15) at positions corresponding to amino acids 464-476 of AAV9 VP3 SEQ ID NO: 2. In some embodiments, the AAV2G9 VP3 capsid protein or variant thereof comprises EFAW (SEQ ID NO: 16) at positions corresponding to amino acids 500-503 of AAV9 VP3 SEQ ID NO: 2.

In some embodiments, the rAAV comprises a capsid protein from serotype AAV2.5. AAV2.5 is a chimera composed of AAV2 with 5 amino acid substitutions from AAV1 (which uses α-2,3- and α-2,6-N-linked sialic acid as major receptors). AAV2.5 contained four AAV1 substitutions (N705A, Q263A, V708A and T716N, AAV2 numbering) and one insertion of T265 from AAV1. See e.g., Komeyenkov et al., "Next Step in Gene Delivery: Modem Approaches and Further Perspectives of AAV Tropism Modification." Pharmaceutics 2021 May, 13(5): 750; Hemphill et al. "Adeno-Associated Viral Vectors Show Serotype Specific Transduction of Equine Joint Tissue Explants and Cultured Monolayers," Scientific Reports volume 4, Article number: 5861 (2014); the contents of each of which are incorporated herein by reference in their entireties.

In some embodiments, the rAAV comprises a capsid protein from serotype AAVDJ. AAV-DJ is a highly recombinogenic hybrid vector created from experiments involving DNA shuffling of eight AAV serotypes. AAV-DJ is a chimera of AAV type 2/type 8/type 9. AAV2 and AAV8 are the closest parental vectors of AAV-DJ. It has been reported that mutations on the 137/251/503 ubiquitination or phosphorylation sites of the AAV2 or AAV8 capsid lead to dramatic enhancement of gene delivery (K137R/T251A/S503A). See e.g., Grimm et al. "In Vitro and In Vivo Gene Therapy Vector Evolution via Multispecies Interbreeding and Retargeting of Adeno-Associated Viruses," J Virol. 2008 June; 82(12): 5887-5911; Mao et al. "Single point mutation in adeno-associated viral vectors-DJ capsid leads to improvement for gene delivery in vivo," BMC Biotechnology volume 16, Article number: 1 (2016); the contents of each of which are incorporated herein by reference in their entireties.

In some embodiments, the rAAV comprises a capsid protein from serotype AAV2. A molecular clone for AAV2 was isolated in 1983. In some embodiments, the rAAV does not comprise a capsid protein from serotype AAV9. AAV9 was isolated from human DNA in 2004. See e.g., Samulski et al. "Rescue of adeno-associated virus from recombinant plasmids: gene correction within the terminal repeats of AAV," Cell 1983 May, 33(1):135-43; Guo et al. "Clades of Adeno-associated viruses are widely disseminated in human tissues," J Virol. 2004 June, 78(12):6381-8; the contents of each of which are incorporated herein by reference in their entireties.

In some embodiments, the solution comprises rAAV at a concentration that is effective to treat the kidney-associated disorder. In some embodiments, the solution comprises rAAV at a concentration of $10^8$ viral genomes per mL (vg/mL) to $10^{15}$ vg/mL, $10^9$ vg/mL to $10^{11}$ vg/mL, $10^{10}$ vg/mL to $10^{15}$ vg/mL, $10^{11}$ vg/mL to $10^{11}$ vg/mL, $10^{12}$ vg/mL to $10^{11}$ vg/mL, $10^{13}$ vg/mL to $10^{15}$ vg/mL, $10^{11}$ vg/mL to $10^{12}$ vg/mL, $10^{12}$ vg/mL to $10^{13}$ vg/mL, $10^{13}$ vg/mL to $10^{14}$ vg/mL, $10^{14}$ vg/mL to $10^{15}$ vg/mL, $10^8$ vg/mL to $10^{14}$ vg/mL, $10^8$ vg/mL to $10^{13}$ vg/mL, $10^8$ vg/mL to $10^{12}$ vg/mL, $10^8$ vg/mL to $10^{11}$ vg/mL, $10^8$ vg/mL to $10^{10}$ vg/mL, or $10^8$ vg/mL to $10^9$ vg/mL. In some embodiments, the solution comprises rAAV at a concentration of $10^8$ vg/mL to $10^{13}$ vg/mL. In some embodiments, the solution comprises rAAV at a concentration of at least $10^8$ vg/mL, at least $10^9$ vg/mL, at least $10^{10}$ vg/mL, at least $10^{11}$ vg/mL, at least $10^{12}$ vg/mL, at least $10^{13}$ vg/mL, at least $10^{14}$ vg/mL, at least $10^{11}$ vg/mL, or more. In some embodiments, the solution comprises rAAV at a concentration of at most $10^9$ vg/mL, at most $10^{10}$ vg/mL, at most $10^{11}$ vg/mL, at most $10^{12}$ vg/mL, at most $10^{13}$ vg/mL, at most $10^{14}$ vg/mL, or at most $10^{11}$ vg/mL. In some embodiments, the rAAV is at a concentration of about $5.2\times10^{10}$ vg/kg, e.g., in a 75 kg subject. In some embodiments, the solution comprises rAAV at a concentration of about $1\times10^{10}$ vg/kg, about $2\times10^{10}$ vg/kg, about $3\times10^{10}$ vg/kg, about $4\times10^{10}$ vg/kg, about $5\times10^{10}$ vg/kg, about $6\times10^{10}$ vg/kg, about $7\times10^{10}$ vg/kg, about $8\times10^{10}$ vg/kg, about $9\times10^{10}$ vg/kg, e.g., in a 75 kg subject. It is understood that each of the individual rAAV concentrations described herein can be used to define lower and upper values of an rAAV concentration range.

In some embodiments, the solution comprises, per 75 kg subject, $1\times10^{11}$ to $1\times10^{14}$ vg total, $1\times10^{11}$ to $1\times10^{13}$ vg total, $1\times10^{11}$ to $1\times10^{12}$ vg total, $1\times10^{12}$ to $1\times10^{13}$ vg total, $1\times10^{12}$ to $1\times10^{4}$ vg total, $1\times10^{13}$ to $1\times10^{14}$ vg total, $1\times10^{13}$ to $6\times10^{13}$ vg total, $2\times10^{13}$ to $5\times10^{13}$ vg total, or $1\times10^{13}$ to $2\times10^{13}$ rAAV viral genomes total. In some embodiments, the solution comprises $5\times10^{13}$ to $6\times10^{13}$ rAAV viral genomes total. In some embodiments, the solution comprises at least $1\times10^{13}$, at least $2\times10^{13}$, at least $3\times10^{13}$, at least $4\times10^{13}$, at least $5\times10^{13}$, at least $6\times10^{13}$, at least $7\times10^{13}$, at least $8\times10^{13}$, at least $9\times10^{13}$, or more rAAV viral genomes total. In some embodiments, the solution comprises at most $1\times10^{13}$, at most $2\times10^{13}$, at most $3\times10^{13}$, at most $4\times10^{13}$, at most $5\times10^{13}$, at most $6\times10^{13}$, at most $7\times10^{13}$ at most $8\times10^{13}$, at most $9\times10^{13}$, or more rAAV viral genomes total. In some embodiments, the solution comprises about $1\times10^{11}$ vg total, about $2\times10^{11}$ vg total, about $3\times10^{11}$ vg total, about $4\times10^{11}$ vg total, about $5\times10^{11}$ vg total, about $6\times10^{11}$ vg total, about $7\times10^{11}$ vg total, about $8\times10^{11}$ vg total, about $9\times10^{11}$ vg total, about $10\times10^{11}$ vg total, about $1\times10^{12}$ vg total, about $2\times10^{12}$ vg total, about $3\times10^{12}$ vg total, about $4\times10^{12}$ vg total, about $5\times10^{12}$ vg total, about $6\times10^{12}$ vg total, about $7\times10^{12}$ vg total, about $8\times10^{12}$ vg total, about $9\times10^{12}$ vg total, about $10\times10^{12}$ vg total, about $1\times10^{13}$ vg total, about $2\times10^{13}$ vg total, about $3\times10^{13}$ vg total, about $4\times10^{13}$ vg total, about $5\times10^{13}$ vg total, about $6\times10^{13}$ vg total, about $7\times10^{13}$ vg total, about $8\times10^{13}$ vg total, about $9\times10^{13}$ vg total, about $10\times10^{13}$ vg total, or about $1\times10^{14}$ vg total. It is understood that each of the individual rAAV amounts described herein can be used to define lower and upper values of an rAAV amount range.

In some embodiments, the solution comprises $1\times10^{10}$ viral genomes total. In some embodiments, the solution comprises $1\times10^{10}$ viral genomes total (e.g., $4\times10^{8}$ vg/mL to $1\times10^{9}$ vg/mL).

In some embodiments, the genome of the rAAV comprises a transgene. As used herein, the term "transgene" refers to a gene or other nucleic acid sequence, which is transduced into the genome of the subject using the rAAV. In order to transduce cells, an rAAV vector enters a cell and delivers its single-stranded DNA genome to the nucleus, where the genome becomes double-stranded before transcription and integration into the subject's cell genome.

In some embodiments, the transgene comprises a reporter protein. Non-limiting examples of such reporter proteins a fluorescent protein (e.g., GPF, mCherry, etc.), luciferase, alkaline phosphatase, beta-galactosidase, beta-lactamase, horseradish peroxidase, a detectable tag (such as c-Myc, HA, VSV-G, HSV, FLAG, V5, HIS, or biotin), and variants thereof. In some embodiments, the transgene comprises a barcode that can be identified by sequencing.

In some embodiments, the transgene is therapeutic for a kidney-associated disorder. In some embodiments, the kidney-associated disorder, for which the transgene is therapeutic, is selected from the group consisting of autosomal dominant polycystic kidney disease (ADPKD); Alport syndrome; autosomal dominant tubulointerstitial kidney disease (ADTKD); medullary cystic kidney disease; nephronophthisis; Bartter Syndrome; Von Hippel-Lindau syndrome; Gitelman syndrome; congenital nephrotic syndrome; primary hyperoxaluria; Dent disease; Thin Basement Membrane Nephropathy; cystinuria; Liddle syndrome; Papillorenal syndrome; and cystinosis, as described in Table 2A.

TABLE 2A

Exemplary kidney-associated disorders (adapted from Rubin et al. 2020, "Improving molecular therapy in the kidney," Mol Diagn Ther. 24(4): 375-396, the contents of which are incorporated herein by reference in their entirety.

| Disorder | Underlying Genes | cDNA Size (bp) | Exemplary Gene Therapy Strategy |
|---|---|---|---|
| ADPKD | PKD1 | 14,138 | Gene addition |
| | PKD2 | 5056 | Gene addition |
| | GANAB | 3906 | Gene addition |
| ARPKD | PKHD1 | 16,282 | Gene addition |
| Alport syndrome | COL4A3 | 8097 | Gene addition |
| | COL4A4 | 9895 | Gene addition |
| | COL4A5 | 6483 | Gene addition |
| ADTKD/Medullary cystic kidney disease | MUC1 (type I) | Variable | Gene addition |
| | UMOD | 2477 | Gene knockdown |
| | REN | 1462 | Gene knockdown |
| | HNF1B | 2790 | Gene addition |
| | SEC61A1 | 1871 | Gene addition |
| Nephronophthisis | NPHP1 | 3756 | Gene addition |
| Bartter Syndrome | SLC12A1 | 4707 | Gene addition |
| | KCNJ1 (type II) | 4074 | Gene addition |
| | CLCNKB (type III and IV) | 1544 | Gene addition |
| | BSND (type IV) | 3472 | Gene addition |
| | CLCNKA (type IV) | 2581 | Gene addition |
| | MAGED2 (type V) | 2066 | Gene addition |
| Von Hippel-Lindau syndrome | VHL | 3737 | Gene addition |
| Gitelman syndrome | SLC12A3 | 3119 | Gene addition |
| | CLCNKB | 1544 | Gene addition |
| Congenital nephrotic syndrome | NPHS1 | 4276 | Gene addition |
| | NPHS2 | 1855 | Gene addition |
| Primary hyperoxaluria | AGXT (type I) | 1865 | Gene addition |
| | GRHPR (type II) | 1280 | Gene addition |
| | HOGA1 (type III) | 2488 | Gene addition |
| Dent disease | CLCN5 (type I) | 10,108 | Gene addition |
| | OCRL (type II) | 5138 | Gene addition |
| | COL4A3 | 8097 | Gene addition |
| Thin Basement Membrane Nephropathy | COL4A4 | 9895 | Gene addition |
| | COL4A5 | 6483 | Gene addition |
| Cystinuria | SLC3A1 | 1737 | Gene addition |
| | SLC7A9 | 1752 | Gene addition |
| Liddle syndrome | SCNN1A | 3481 | Gene knockdown |
| | SCNN1B | 2597 | Gene knockdown |

In some embodiments, the transgene comprises a gene that when expressed (e.g., at about a physiological level) in the subject is effective to treat a kidney-associated disorder. In some embodiments, the transgene comprises a gene selected from the group consisting of Alanine-Glyoxylate Aminotransferase (AGXT; e.g., type I); Bartter Syndrome, Infantile, With Sensorineural Deafness (BSND; e.g., type IV); Chloride Voltage-Gated Channel 5 (CLCN5; e.g., type I); Chloride Voltage-Gated Channel Ka (CLCNKA; e.g., type IV); Chloride Voltage-Gated Channel Kb (CLCNKB; e.g., type III and IV); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR; e.g., type II); Hepatic Nuclear Factor 1 (HNF1) Homeobox B (HNF1B); 4-Hydroxy-2-Oxoglutarate Aldolase 1 (HOGA1; e.g., type III); Potassium Inwardly Rectifying Channel Subfamily J Member 1 (KCNJ1; e.g., type II); MAGED2 (type V); Mucin 1 (MUC1; e.g., type I); Nephrocystin 1 (NPHP1); Nephrin (NPHS1); Nephrosis 2 (NPHS2; Podocin); Inositol Polyphosphate-5-Phosphatase (OCRL; e.g., type II); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and any combination thereof.

In some embodiments, the kidney-associated disorder, for which the transgene is therapeutic, is selected from the group consisting of: Apparent mineralocorticoid excess, Autosomal dominant hypocalcemia, Autosomal dominant hypomagnesemia, Bartter type 1, Bartter type 2, Bartter type 3, Bartter type 4a, Bartter type 4b, Bartter type 5, Congenital adrenal hyperplasia type 1, Congenital adrenal hyperplasia type 2, Congenital adrenal hyperplasia type 4, Congenital adrenal hyperplasia type 5, Cystinuria A, Cystinuria B, Dent disease type 1, Dent disease type 2/Lowe syndrome, Dicarboxylic aminoaciduria, Distal RTA, EAST/SeSAME syndrome, Fanconi Bickel syndrome, Fanconi renotubular syndrome 1, Fanconi renotubular syndrome 2, Fanconi renotubular syndrome 3, Fanconi renotubular syndrome 4, Gitelman syndrome, Glucocorticoid remediable aldosteronism, Hartnup disorder, Hereditary hypophosphatemic rickets with hypercalciuria, HNF1B-related kidney disease, Hyperphenylalaninemia BH4-deficient, Hypomagnesemia type 1/hypomagnesemia with secondary hypocalcemia, Hypomagnesemia type 2, Hypomagnesemia type 3/familial hypomagnesemia with hypercalciuria and nephrocalcinosis, Hypomagnesemia type 4, Hypomagnesemiatype 5/familial hypomagnesemia with hypercalciuria and nephrocalcinosis, Hypomagnesemia, seizures, and mental retardation type 1, Hypomagnesemia, seizures, and mental retardation type 2, Iminoglycinuria, Kenny-Caffey syndrome type 2, Liddle syndrome, Lysinuric protein intolerance, Neonatal inflammatory skin and bowel disease type 2, Nephrogenic diabetes insipidus, Nephrogenic syndrome of inappropriate antidiuresis, Pseudohypoaldosteronism type 1, Pseudohypoaldosteronism type IA, Pseudohypoaldosteronism type 2b, Pseudohypoaldosteronism type 2c, Pseudohypoaldosteronism type 2d, Pseudohypoaldosteronism type 2e, Renal tubular acidosis type 3, and X-linked hypophosphatemic rickets, as described in Table 2B3.

TABLE 2B

Exemplary kidney-associated disorders (adapted from Downie et al. 2020, "Inherited tubulopathies of the kidney," Clin J Am Soc Nephrol. 16(4): 620-630, the contents of which are incorporated herein by reference in their entirety). Listed are exemplary renal tubulopathies grouped by affected nephron segment, the underlying gene(s), and encoded protein(s), as well as their Online Mendelian Inheritance in Man (OMIM) entry number. AD, autosomal dominant; AR, autosomal recessive; XLR, x-linked recessive; RTA, renal tubular acidosis.

| Disorder | Inheritance | Gene | Protein | OMIM |
|---|---|---|---|---|
| | | Proximal tubule | | |
| Fanconi renotubular syndrome 1 | AD | GATM | L-ARGININE:GLYCINE AMIDINOTRANSFERASE | #134600 |
| Fanconi renotubular syndrome 2 | AR | SLC34A1 | NaPi2A | #182309 |
| Fanconi renotubular syndrome 3 | AD | EHHADH | PBFE | #607037 |
| Fanconi renotubular syndrome 4 | AD | HNF4A | HNF-4 | #600281 |
| Fanconi Bickel syndrome | AR | SLC2A2 | GLUT-2 | #138160 |
| Dent disease type 1 | XLR | CLCN5 | CLC-5 | #300008 |
| Dent disease type 2/ Lowe syndrome | XLR | OCRL | OCRL | #300535 |
| Renal tubular acidosis type 3 | AR | CA2 | Carbonic anhydrase 2 | #611492 |
| Hereditary hypophosphatemic rickets with hypercalciuria | AR | SLC34A3 | NaPi2c | #241530 |
| X-linked hypophosphatemic rickets | XLD | PHEX | PHEX | #307800 |
| Cystinuria A | AD | SLC3A1 | rBAT | #104614 |
| Cystinuria B | AR | SLC7A9 | b(0, +)AT1 | #604144 |
| Lysinuric protein intolerance | AR | SLC7A7 | y(+)LAT1 | #222700 |
| Hartnup disorder | AR | SLC6A19 | B(0)AT1 | #234500 |
| Iminoglycinuria | AR/digenic | SLC36A2 + SLC6A20/ SLC6A19 | SLC36A2 + SLC6A20/ SLC6A19 | #242600 |
| Dicarboxylic aminoaciduria | AR | SLC1A1 | | #222730 |
| | | Thick ascending limb | | |
| Bartter type 1 | AR | SLC12A1 | NKCC2 | #600839 |
| Bartter type 2 | AR | KCNJ1 | ROMK | #600359 |
| Bartter type 3 | AR | CLCNKB | CLC-Kb | #602023 |
| Bartter type 4a | AR | BSND | Barttin | #606412 |

TABLE 2B-continued

Exemplary kidney-associated disorders (adapted from Downie et al. 2020, "Inherited tubulopathies of the kidney," Clin J Am Soc Nephrol. 16(4): 620-630, the contents of which are incorporated herein by reference in their entirety). Listed are exemplary renal tubulopathies grouped by affected nephron segment, the underlying gene(s), and encoded protein(s), as well as their Online Mendelian Inheritance in Man (OMIM) entry number. AD, autosomal dominant; AR, autosomal recessive; XLR, x-linked recessive; RTA, renal tubular acidosis.

| Disorder | Inheritance | Gene | Protein | OMIM |
|---|---|---|---|---|
| Bartter type 4b | Digenic | CLCNKA + CLCNKB | CLC-Ka + CLC-Kb | #602024 |
| Bartter type 5 | XR | MAGED2 | MAGED2 | #601199 |
| Hypomagnesemia type 3/familial hypomagnesemia with hypercalciuria and nephrocalcinosis | AR | CLDN16 | Claudin 16 | #603959 |
| Hypomagnesemia type 5/familial hypomagnesemia with hypercalciuria and nephrocalcinosis | AR | CLDN19 | Claudin 19 | #610036 |
| Autosomal dominant hypocalcemia | AD | CaSR | Calcium-sensing receptor | #601198 |
| Kenny-Caffey syndrome type 2 | AD | FAM111A | FAM111A | #127000 |
| Distal convoluted tubule | | | | |
| Gitelman syndrome | AR | SLC12A3 | NCCT | #600968 |
| EAST/SeSAME syndrome | AR | KCNJ10 | Kir4.1 | #602028 |
| Pseudohypoaldosteronism type 2b | AD | WNK4 | WNK4 | #601844 |
| Pseudohypoaldosteronism type 2c | AD | WNK1 | WNK1 | #605232 |
| Pseudohypoaldosteronism type 2d | AD/AR | KLHL3 | KLHL3 | #614495 |
| Pseudohypoaldosteronism type 2e | AD | CUL3 | CUL3 | #614496 |
| Hypomagnesemia type 1/hypomagnesemia with secondary hypocalcemia | AR | TRPM6 | TRPM6 | #607009 |
| Hypomagnesemia type 2 | AD | FXYD2 | Na-K-ATPase | #154020 |
| Autosomal dominant hypomagnesemia | AD | KCNA1 | Kv1.1 | #176260 |
| HNF1B-related kidney disease | AD | HNF1B | HNF1B | #137920 |
| Hyperphenylalanine mia BH4-deficient | AR | PCBD1 | PCDB1 | #264070 |
| Hypomagnesemia type 4 | AR | EGF | EGF | #611718 |
| Neonatal inflammatory skin and bowel disease type 2 | AR | EGFR | EGFR | #616069 |
| Hypomagnesemia, seizures, and mental retardation type 1 | AD/AR | CNNM2 | CNNM2 | #613882 |
| Hypomagnesemia, seizures, and mental retardation type 2 | De novo | ATP1A1 | ATP1A1 | #618314 |
| Collecting duct | | | | |
| Pseudohypoaldosteronism type 1 | AR | SCNN1A | ENaC α subunit | #600228 |
| Pseudohypoaldosteronism type 1 | AR | SCNN1B | ENaC β subunit | #600760 |
| Pseudohypoaldosteronism type 1 | AR | SCNN1G | ENaC γ subunit | #600761 |
| Pseudohypoaldosteronism type 1A | AD | NR3C2 | MR | #600983 |
| Liddle syndrome | AD | SCNN1B | ENaC β subunit | #600760 |
| Liddle syndrome | AD | SCNN1G | ENaC γ subunit | #600761 |
| Apparent mineralocorticoid excess | AR | HSD11B2 | 11-β-HSD2 | #614232 |

TABLE 2B-continued

Exemplary kidney-associated disorders (adapted from Downie et al. 2020, "Inherited tubulopathies of the kidney," Clin J Am Soc Nephrol. 16(4): 620-630, the contents of which are incorporated herein by reference in their entirety). Listed are exemplary renal tubulopathies grouped by affected nephron segment, the underlying gene(s), and encoded protein(s), as well as their Online Mendelian Inheritance in Man (OMIM) entry number. AD, autosomal dominant; AR, autosomal recessive; XLR, x-linked recessive; RTA, renal tubular acidosis.

| Disorder | Inheritance | Gene | Protein | OMIM |
|---|---|---|---|---|
| Glucocorticoid remediable aldosteronism | AD | CYP11B1/CYP11B2 | 11-β-hydroxylase/ALDOS | #610613 |
| Congenital adrenal hyperplasia type 1 | AR | CYP21A2 | 21-hydroxylase | #613815 |
| Congenital adrenal hyperplasia type 2 | AR | HSD3B2 | 3-β-HSD2 | #613890 |
| Congenital adrenal hyperplasia type 4 | AR | CYP11B1 | 11-β-hydroxylase | #610613 |
| Congenital adrenal hyperplasia type 5 | AR | CYP17A1 | 17-α-hydroxylase | #609300 |
| Nephrogenic diabetes insipidus | XLR | AVPR2 | AVPR2 | #300538 |
| Nephrogenic diabetes insipidus | AR/AD | AQP2 | AQP-2 | #107777 |
| Nephrogenic syndrome of inappropriate antidiuresis | XLR | AVPR2 | V2R | #300538 |
| Nephrogenic syndrome of inappropriate antidiuresis | AD | GNAS | G-as | |
| Distal RTA | AD/AR | SLC4A1 | AE1 | #109270 |
| Distal RTA | AR | ATP6V1B1 | V-ATPase subunit B1 | #192132 |
| Distal RTA | AR | ATP6V0A4 | V-ATPase subunit a4 | #605239 |
| Distal RTA | AR | FOXI1 | Forkhead box protein I1 | #601093 |
| Distal RTA | AR | WDR72 | WD repeat-containing protein 72 | #613214 |

In some embodiments, the kidney-associated disorder, for which the transgene is therapeutic, is associated with the proximal tubule and is selected from the group consisting of: Cystinuria A, Cystinuria B, Dent disease type 1, Dent disease type 2/Lowe syndrome, Dicarboxylic aminoaciduria, Fanconi Bickel syndrome, Fanconi renotubular syndrome 1, Fanconi renotubular syndrome 2, Fanconi renotubular syndrome 3, Fanconi renotubular syndrome 4, Hartnup disorder, Hereditary hypophosphatemic rickets with hypercalciuria, Iminoglycinuria, Lysinuric protein intolerance, Renal tubular acidosis type 3, and X-linked hypophosphatemic rickets.

In some embodiments, the kidney-associated disorder, for which the transgene is therapeutic, is associated with the thick ascending limb of the loop of Henle and is selected from the group consisting of: Autosomal dominant hypocalcemia, Bartter type 1, Bartter type 2, Bartter type 3, Bartter type 4a, Bartter type 4b, Bartter type 5, Hypomagnesemia type 3/familial hypomagnesemia with hypercalciuria and nephrocalcinosis, Hypomagnesemia type 5/familial hypomagnesemia with hypercalciuria and nephrocalcinosis, and Kenny-Caffey syndrome type 2.

In some embodiments, the kidney-associated disorder, for which the transgene is therapeutic, is associated with the distal convoluted tubule and is selected from the group consisting of: Autosomal dominant hypomagnesemia, EAST/SeSAME syndrome, Gitelman syndrome, HNF1B-related kidney disease, Hyperphenylalaninemia BH4-deficient, Hypomagnesemia type 1/hypomagnesemia with secondary hypocalcemia, Hypomagnesemia type 2, Hypomagnesemia type 4, Hypomagnesemia, seizures, and mental retardation type 1, Hypomagnesemia, seizures, and mental retardation type 2, Neonatal inflammatory skin and bowel disease type 2, Pseudohypoaldosteronism type 2b, Pseudohypoaldosteronism type 2c, Pseudohypoaldosteronism type 2d, and Pseudohypoaldosteronism type 2e.

In some embodiments, the kidney-associated disorder, for which the transgene is therapeutic, is associated with the collecting duct and is selected from the group consisting of: Apparent mineralocorticoid excess, Congenital adrenal hyperplasia type 1, Congenital adrenal hyperplasia type 2, Congenital adrenal hyperplasia type 4, Congenital adrenal hyperplasia type 5, Distal RTA, Glucocorticoid remediable aldosteronism, Liddle syndrome, Nephrogenic diabetes insipidus, Nephrogenic syndrome of inappropriate antidiuresis, Pseudohypoaldosteronism type 1, and Pseudohypoaldosteronism type 1A In some embodiments, the transgene comprises a gene that when expressed (e.g., at about a physiological level) in the subject is effective to treat a kidney-associated disorder. In some embodiments, the transgene comprises a gene selected from the group consisting of Aquaporin 2 (AQP2); ATPase Na+/K+ Transporting Subunit Alpha 1 (ATP1A1); ATPase H+ Transporting V0 Subunit A4 (ATP6V0A4); ATPase H+ Transporting V1 Subunit B1 (ATP6V1B1); Arginine Vasopressin Receptor 2 (AVPR2); Barttin CLCNK (chloride channel K) Type Accessory Subunit Beta (BSND); Carbonic Anhydrase 2 (CA2); Calcium Sensing Receptor (CaSR); Chloride Voltage-Gated Channel 5 (CLCN5); CLCNKA (Chloride Voltage-Gated Channel Ka); Chloride Voltage-Gated Channel Kb (CLCNKB); Claudin 16 (CLDN16); Claudin 19 (CLDN19); Cyclin And CBS Domain Divalent Metal Cation Transport Mediator 2 (CNNM2); Cullin 3 (CUL3); Cytochrome P450 Family 11 Subfamily B Member 1 (CYP11B1); Cytochrome P450 Family 11 Subfamily B Member 2 (CYP11B2); Cytochrome P450 Family 17 Subfamily A Member 1 (CYP17A1); Cytochrome P450 Family 21 Subfamily A Member 2 (CYP21A2); Epidermal Growth Factor (EGF); Epidermal Growth Factor Receptor (EGFR); Enoyl-CoA Hydratase And 3-Hydroxyacyl CoA Dehydrogenase (EHHADH); FAM111 (family 111) Trypsin Like Peptidase A (FAM111A); Forkhead Box I1 (FOXI1); FXYD Domain/Motif Containing Ion Transport Regulator 2 (FXYD2); Glycine Amidinotransferase (GATM); guanine nucleotide binding protein; alpha stimulating (GNAS); hepatocyte nuclear factor 1 (HNF1) Homeobox B (HNF1B); Hepatocyte Nuclear Factor 4 Alpha (HNF4A); Hydroxysteroid 11-Beta Dehydrogenase 2 (HSD11B2); Hydroxy-Delta-5-Steroid Dehydrogenase, 3 Beta- And Steroid Delta-Isomerase 2 (HSD3B2); Potassium Voltage-Gated Channel Subfamily A Member 1 (KCNA1); Potassium Inwardly Rectifying Channel Subfamily J Member 1 (KCNJ1); Potassium Inwardly Rectifying Channel Subfamily J Member 10 (KCNJ10); Kelch Like Family Member 3 (KLHL3); Melanoma Antigen Gene Family Member D2 (MAGED2); Nuclear Receptor Subfamily 3 Group C Member 2 (NR3C2); Oculocerebrorenal Syndrome Of Lowe (OCRL) Inositol Polyphosphate-5-Phosphatase; Pterin-4 Alpha-Carbinolamine Dehydratase 1 (PCBD1); Phosphate Regulating Endopeptidase X-Linked (PHEX); Sodium Channel Epithelial 1 Subunit Alpha (SCNN1A); Sodium Channel Epithelial 1 Subunit Beta (SCNN1B); Sodium Channel Epithelial 1 Subunit Gamma (SCNN1G); Solute Carrier Family 12 Member 1 (SLC12A1); Solute Carrier Family 12 Member 3 (SLC12A3); Solute Carrier Family 1 Member 1 (SLC1A1); Solute Carrier Family 2 Member 2 (SLC2A2); Solute Carrier Family 34 Member 1 (SLC34A1); Solute Carrier Family 34 Member 3 (SLC34A3); Solute Carrier Family 36 Member 2 (SLC36A2); Solute Carrier Family 3 Member 1 (SLC3A1); Solute Carrier Family 4 Member 1 (SLC4A1); Solute Carrier Family 6 Member 19 (SLC6A19); Solute Carrier Family 6 Member 20 (SLC6A20); Solute Carrier Family 7 Member 7 (SLC7A7); Solute Carrier Family 7 Member 9 (SLC7A9); Transient Receptor Potential Cation Channel Subfamily M Member 6 (TRPM6); WD Repeat Domain 72 (WDR72); With-no-lysine (WNK, Lysine Deficient) Protein Kinase 1 (WNK1); With-no-lysine (WNK, Lysine Deficient) Protein Kinase 4 (WNK4); and any combination thereof.

In some embodiments, the transgene comprises a gene encoding a polypeptide that when expressed (e.g., at about a physiological level) in the subject is effective to treat a kidney-associated disorder. In some embodiments, the transgene comprises a gene encoding for a polypeptide selected from the group consisting of 11-β-HSD2, 11-β-hydroxylase, 17-α-hydroxylase, 21-hydroxylase, 3-β-HSD2, AE1, Aldosterone synthase (ALDOS), AQP-2, ATP1A1, AVPR2, B(0)AT1, b(0, +)AT1, Barttin, Calcium-sensing receptor, Carbonic anhydrase 2, Claudin16, Claudin19, CLC-5, CLC-Ka+CLC-Kb, CLC-Kb, CNNM2, CUL3, EGF, EGFR, ENaC α subunit, EnaC β subunit, EnaC γ subunit, FAM111A, Forkhead box protein I1, GLUT-2, G-α s, HNF1B, HNF-4, Kir4.1, KLHL3, Kv1.1, L-ARGININE: GLYCINE AMIDINOTRANSFERASE, MAGED2, MR, Na-K-ATPase, NaPi2A, NaPi2c, NCCT, NKCC2, OCRL, PBFE, PCDB1, PHEX, rBAT, ROMK, SLC36A2+SLC6A20/SLC6A19, TRPM6, V2R, V-ATPase subunit a4, V-ATPase subunit B1, WD repeat-containing protein 72, WNK1, WNK4, y(+)LAT1, and any combination thereof.

In some embodiments, the kidney-associated disorder is Cystinuria (e.g., Cystinuria A, Cystinuria B). Cystinuria is an inherited autosomal recessive disease characterized by high concentrations of the amino acid cystine in the urine, leading to the formation of cystine stones in the kidneys, ureters, and bladder. Cystinuria is a type of aminoaciduria. Cystine is a dimer of cysteines. Symptoms of polycystic kidney disease include, but are not limited to crystalluria (crystals in urine); aminoaciduria (urine containing abnormally high levels of amino acids, e.g., cystine); pain in the side or back (e.g., often on one side); pain while urinating; blood in the urine; sharp pain in the side or back; pain near the groin, pelvis, or abdomen; nausea and vomiting; flank pain; loin pain; recurrent abdominal pain; recurrent urinary tract infections; and/or fever.

In some embodiments, the transgene is SLC3A1 and/or SLC7A9. SLC3A1 and SLC7A9 are subunits of an amino acid transporter (the b0,+ transporter system) that functions to resorb cystine from the urine in the kidney tubules. In some embodiments, the kidney-associated disorder is Cystinuria A, and the transgene is SLC3A1. In some embodiments, the kidney-associated disorder is Cystinuria B, and the transgene is SLC7A9.

In some embodiments, the transgene comprises SEQ ID NO: 5, SEQ ID NO: 6, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 5, SEQ ID NO: 6, which maintains the same function when expressed as a protein (e.g., cystine transport), or a functional fragment thereof, or a codon-optimized version of the nucleic acid.

Solute Carrier Family 3 Member 1 (SLC3A1), also known as: ATR1, CSNU1, D2H, NBAT, RBAT; positions 57-2114 of NCBI ref NM_000341.4, CCDS1819.1, human, 2058 nucleotides (nt),

SEQ ID NO: 5

ATGGCTGAAGATAAAAGCAAGAGAGACTCCATCGAGATGAGTATGAAGGGATGCCAGA

CAAACAACGGGTTTGTCCATAATGAAGACATTCTGGAGCAGACCCCGGATCCAGGAAGC

TCAACAGACAACCTGAAGCACAGCACCAGGGGCATCCTTGGCTCCCAGGAGCCCGACTT

CAAGGGCGTCCAGCCCTATGCGGGGATGCCCAAGGAGGTGCTGTTCCAGTTCTCTGGCCA

GGCCCGCTACCGCATACCTCGGGAGATCCTCTTCTGGCTCACAGTGGCTTCTGTGCTGGT

GCTCATCGCGGCCACCATAGCCATCATTGCCCTCTCTCCAAAGTGCCTAGACTGGTGGCA

GGAGGGGCCCATGTACCAGATCTACCCAAGGTCTTTCAAGGACAGTAACAAGGATGGGA

ACGGAGATCTGAAAGGTATTCAAGATAAACTGGACTACATCACAGCTTTAAATATAAAA

-continued

ACTGTTTGGATTACTTCATTTTATAAATCGTCCCTTAAAGATTTCAGATATGGTGTTGAAG

ATTTCCGGGAAGTTGATCCCATTTTTGGAACGATGGAAGATTTTGAGAATCTGGTTGCAG

CCATACATGATAAAGGTTTAAAATTAATCATCGATTTCATACCAAACCACACGAGTGATA

AACATATTTGGTTTCAATTGAGTCGGACACGGACAGGAAAATATACTGATTATTATATCT

GGCATGACTGTACCCATGAAAATGGCAAAACCATTCCACCCAACAACTGGTTAAGTGTG

TATGGAAACTCCAGTTGGCACTTTGACGAAGTGCGAAACCAATGTTATTTTCATCAGTTT

ATGAAAGAGCAACCTGATTTAAATTTCCGCAATCCTGATGTTCAAGAAGAAATAAAAGA

AATTTTACGGTTCTGGCTCACAAAGGGTGTTGATGGTTTTAGTTTGGATGCTGTTAAATTC

CTCCTAGAAGCAAAGCACCTGAGAGATGAGATCCAAGTAAATAAGACCCAAATCCCGGA

CACGGTCACACAATACTCGGAGCTGTACCATGACTTCACCACCACGCAGGTGGGAATGC

ACGACATTGTCCGCAGCTTCCGGCAGACCATGGACCAATACAGCACGGAGCCCGGCAGA

TACAGGTTCATGGGGACTGAAGCCTATGCAGAGAGTATTGACAGGACCGTGATGTACTA

TGGATTGCCATTTATCCAAGAAGCTGATTTTCCCTTCAACAATTACCTCAGCATGCTAGA

CACTGTTTCTGGGAACAGCGTGTATGAGGTTATCACATCCTGGATGGAAAACATGCCAGA

AGGAAAATGGCCTAACTGGATGATTGGTGGACCAGACAGTTCACGGCTGACTTCGCGTTT

GGGGAATCAGTATGTCAACGTGATGAACATGCTTCTTTTCACACTCCCTGGAACTCCTAT

AACTTACTATGGAGAAGAAATTGGAATGGGAAATATTGTAGCCGCAAATCTCAATGAAA

GCTATGATATTAATACCCTTCGCTCAAAGTCACCAATGCAGTGGGACAATAGTTCAAATG

CTGGTTTTTCTGAAGCTAGTAACACCTGGTTACCTACCAATTCAGATTACCACACTGTGA

ATGTTGATGTCCAAAAGACTCAGCCCAGATCGGCTTTGAAGTTATATCAAGATTTAAGTC

TACTTCATGCCAATGAGCTACTCCTCAACAGGGGCTGGTTTTGCCATTTGAGGAATGACA

GCCACTATGTTGTGTACACAAGAGAGCTGGATGGCATCGACAGAATCTTTATCGTGGTTC

TGAATTTTGGAGAATCAACACTGTTAAATCTACATAATATGATTTCGGGCCTTCCCGCTA

AAATGAGAATAAGGTTAAGTACCAATTCTGCCGACAAAGGCAGTAAAGTTGATACAAGT

GGCATTTTTCTGGACAAGGGAGAGGGACTCATCTTTGAACACAACACGAAGAATCTCCTT

CATCGCCAAACAGCTTTCAGAGATAGATGCTTTGTTTCCAATCGAGCATGCTATTCCAGT

GTACTGAACATACTGTATACCTCGTGTTAG

Solute Carrier Family 7 Member 9 (SLC7A9), also known as B(0, +)-type amino acid transporter 1, BAT1, or CSNU3; positions 108-1571 of NCBI ref NM_001126335.2, CCDS12425.1, human, 1464 nt,

SEQ ID NO: 6

ATGGGGGATACTGGCCTGAGAAAGCGGAGAGAGGATGAGAAGTCGATCCAGAGCCAAG

AGCCTAAGACCACCAGTCTCCAAAAGGAGCTGGGCCTCATCAGTGGCATCTCCATCATCG

TGGGCACCATCATTGGCTCTGGGATCTTCGTTTCCCCCAAGTCTGTGCTCAGCAACACGG

AAGCTGTGGGGCCCTGCCTCATCATATGGGCGGCTTGCGGGGTCCTCGCGACGCTGGGTG

CCCTGTGCTTTGCGGAGCTTGGCACAATGATCACCAAGTCAGGGGGAGAGTATCCCTACC

TGATGGAGGCCTACGGGCCCATCCCCGCCTACCTCTTCTCCTGGGCCAGCCTGATCGTCA

TTAAGCCCACGTCCTTCGCCATCATCTGCCTCAGCTTCTCCGAGTATGTGTGTGCGCCCTT

CTATGTGGGCTGCAAGCCTCCTCAAATCGTTGTGAAATGCCTGGCCGCCGCCGCCATCTT

GTTCATCTCGACAGTGAACTCACTGAGCGTGCGGCTGGGAAGCTACGTCCAGAACATCTT

CACCGCGGCCAAGCTGGTGATCGTGGCCATCATCATCATCAGCGGGCTGGTGCTCCTGGC

CCAAGGAAACACAAAGAATTTTGATAATTCTTTCGAGGGCGCCCAGCTGTCTGTGGGAG

-continued

CCATCAGCCTGGCGTTTTACAATGGACTCTGGGCCTATGATGGATGGAATCAACTCAATT

ACATCACAGAAGAACTTAGAAACCCTTACAGAAACCTGCCTTTGGCCATTATCATCGGGA

TCCCCCTGGTGACGGCGTGCTACATCCTCATGAACGTGTCCTACTTCACCGTGATGACTG

CCACCGAACTCCTGCAGTCCCAGGCGGTGGCTGTGACATTTGGTGACCGTGTTCTCTATC

CTGCTTCTTGGATCGTTCCACTTTTTGTGGCATTTTCAACCATCGGTGCTGCTAACGGGAC

CTGCTTCACAGCGGGCAGACTCATTTACGTGGCGGGCCGGGAGGGTCACATGCTCAAAG

TGCTTTCTTACATCAGCGTCAGGCGCCTCACTCCAGCCCCCGCCATCATCTTTTATGGTAT

CATAGCAACGATTTATATCATCCCTGGTGACATAAACTCGTTAGTCAATTATTTCAGCTTT

GCCGCATGGCTGTTTTATGGCCTGACGATTCTAGGACTCATCGTGATGAGATTTACAAGG

AAAGAGCTGGAAAGGCCTATCAAGGTGCCCGTAGTCATTCCCGTCTTGATGACACTCATC

TCTGTGTTTTTGGTTCTGGCTCCAATCATCAGCAAGCCCACCTGGGAGTACCTCTACTGTG

TGCTGTTTATATTAAGCGGCCTTTTATTTTACTTCCTGTTTGTCCACTACAAGTTTGGATG

GGCTCAGAAAATCTCAAAGCCGATTACCATGCACCTTCAGATGCTAATGGAAGTGGTCCC

ACCGGAGGAAGACCCTGAGTAA

In some embodiments, the transgene encodes for a polypeptide comprising SEQ ID NO: 7, SEQ ID NO: 8, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 7, SEQ ID NO: 8, which maintains the same function (e.g., cystine transport), or a functional fragment thereof.

Solute Carrier Family 3 Member 1 (SLC3A1), NCBI ref NP_000332.2, human, 685 amino acids (aa),

SEQ ID NO: 7

MAEDKSKRDSIEMSMKGCQTNNGFVHNEDILEQTPDPGSSTDNLKHSTRGILGSQEPDFKGV

QPYAGMPKEVLFQFSGQARYRIPREILFWLTVASVLVLIAATIAIIALSPKCLDWWQEGPMYQ

IYPRSFKDSNKDGNGDLKGIQDKLDYITALNIKTVWITSFYKSSLKDFRYGVEDFREVDPIFGT

MEDFENLVAAIHDKGLKLIIDFIPNHTSDKHIWFQLSRTRTGKYTDYYIWHDCTHENGKTIPP

NNWLSVYGNSSWHFDEVRNQCYFHQFMKEQPDLNFRNPDVQEEIKEILRFWLTKGVDGFSL

DAVKFLLEAKHLRDEIQVNKTQIPDTVTQYSELYHDFTTTQVGMHDIVRSFRQTMDQYSTEP

GRYRFMGTEAYAESIDRTVMYYGLPFIQEADFPFNNYLSMLDTVSGNSVYEVITSWMENMP

EGKWPNWMIGGPDSSRLTSRLGNQYVNVMNMLLFTLPGTPITYYGEEIGMGNIVAANLNES

YDINTLRSKSPMQWDNSSNAGFSEASNTWLPTNSDYHTVNVDVQKTQPRSALKLYQDLSLL

HANELLLNRGWFCHLRNDSHYVVYTRELDGIDRIFIVVLNFGESTLLNLHNMISGLPAKMRIR

LSTNSADKGSKVDTSGIFLDKGEGLIFEHNTKNLLHRQTAFRDRCFVSNRACYSSVLNILYTS

C

Solute Carrier Family 7 Member 9 (SLC7A9), NCBI ref NP_001119807.1, human, 487 aa,

SEQ ID NO: 8

MGDTGLRKRREDEKSIQSQEPKTTSLQKELGLISGISIIVGTIIGSGIFVSPKSVLSNTEAVGPCLI

IWAACGVLATLGALCFAELGTMITKSGGEYPYLMEAYGPIPAYLFSWASLIVIKPTSFAIICLSF

SEYVCAPFYVGCKPPQIVVKCLAAAAILFISTVNSLSVRLGSYVQNIFTAAKLVIVAIIIISGLVL

LAQGNTKNFDNSFEGAQLSVGAISLAFYNGLWAYDGWNQLNYITEELRNPYRNLPLAIIIGIP

LVTACYILMNVSYFTVMTATELLQSQAVAVTFGDRVLYPASWIVPLFVAFSTIGAANGTCFT

-continued

AGRLIYVAGREGHMLKVLSYISVRRLTPAPAIIFYGIIATIYIIPGDINSLVNYFSFAAWLFYGLT

ILGLIVMRFTRKELERPIKVPVVIPVLMTLISVFLVLAPIISKPTWEYLYCVLFILSGLLFYFLFV

HYKFGWAQKISKPITMHLQMLMEVVPPEEDPE

In some embodiments, the kidney-associated disorder is autosomal dominant polycystic kidney disease (ADPKD). ADPKD is an inherited condition that causes small fluid-filled sacs called cysts displacing normal renal tubules in the kidneys. Cysts can develop from any nephron segment, but the cysts most often form in the distal nephron (e.g., distal convoluted tubules) and the collecting duct (CD). Symptoms of polycystic kidney disease include, but are not limited to abdominal pain or tenderness, blood in the urine, excessive urination at night, flank pain on one or both sides, drowsiness, joint pain, nail abnormalities, high blood pressure, back or side pain, a feeling of fullness in the abdomen, enlarged liver, heart murmurs, and/or growths in the kidneys or abdomen. In some embodiments, the transgene is PKD1, PKD2, and/or GANAB. The PKD1 and PKD2 genes encode the proteins polycystin-1 and polycystin-2, respectively. These two proteins interact to regulate cells in the kidneys and liver, are a part of the process to form tubular structures, and influence growth and fluid secretion function. Mutations of the PKD1 or PKD2 gene creates cells with abnormal functions and ultimately result in the cyst growth that is common in ADPKD. GANAB encodes the alpha subunit of glucosidase II and a member of the glycosyl hydrolase 31 family of proteins. The heterodimeric enzyme glucosidase II plays a role in protein folding and quality control by cleaving glucose residues from immature glycoproteins in the endoplasmic reticulum. Mutations in the GANAB gene can cause autosomal-dominant polycystic kidney and liver disease.

In some embodiments, the transgene comprises one of SEQ ID NOs: 9-10, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 9-10, which maintains the same function when expressed as a protein (e.g., regulate kidney cells, influence formation of kidney tubular structures, and influence kidney fluid secretion function), or a functional fragment thereof, or a codon-optimized version of the nucleic acid.

polycystin-1 (PKD1), also known as: PBP, PC1, Pc-1, TRPP1; positions 210-13118 of NCBI ref NM_000296.4, CCDS45385.1, human, 12,909 nt,
SEQ ID NO: 9

ATGCCGCCCGCCGCGCCCGCCCGCCTGGCGCTGGCCCTGGGCCTGGGCCTGTGGCTCGGG

GCGCTGGCGGGGGGCCCCGGGCGCGGCTGCGGGCCCTGCGAGCCCCCCTGCCTCTGCGG

CCCAGCGCCCGGCGCCGCCTGCCGCGTCAACTGCTCGGGCCGCGGGCTGCGGACGCTCG

GTCCCGCGCTGCGCATCCCCGCGGACGCCACAGCGCTAGACGTCTCCCACAACCTGCTCC

GGGCGCTGGACGTTGGGCTCCTGGCGAACCTCTCGGCGCTGGCAGAGCTGGATATAAGC

AACAACAAGATTTCTACGTTAGAAGAAGGAATATTTGCTAATTTATTTAATTTAAGTGAA

ATAAACCTGAGTGGGAACCCGTTTGAGTGTGACTGTGGCCTGGCGTGGCTGCCGCGATG

GGCGGAGGAGCAGCAGGTGCGGGTGGTGCAGCCCGAGGCAGCCACGTGTGCTGGGCCTG

GCTCCCTGGCTGGCCAGCCTCTGCTTGGCATCCCCTTGCTGGACAGTGGCTGTGGTGAGG

AGTATGTCGCCTGCCTCCCTGACAACAGCTCAGGCACCGTGGCAGCAGTGTCCTTTTCAG

CTGCCCACGAAGGCCTGCTTCAGCCAGAGGCCTGCAGCGCCTTCTGCTTCTCCACCGGCC

AGGGCCTCGCAGCCCTCTCGGAGCAGGGCTGGTGCCTGTGTGGGGCGGCCCAGCCCTCC

AGTGCCTCCTTTGCCTGCCTGTCCCTCTGCTCCGGCCCCCCGCCACCTCCTGCCCCCACCT

GTAGGGGCCCCACCCTCCTCCAGCACGTCTTCCCTGCCTCCCCAGGGGCCACCCTGGTGG

GGCCCCACGGACCTCTGGCCTCTGGCCAGCTAGCAGCCTTCCACATCGCTGCCCCGCTCC

CTGTCACTGCCACACGCTGGGACTTCGGAGACGGCTCCGCCGAGGTGGATGCCGCTGGG

CCGGCTGCCTCGCATCGCTATGTGCTGCCTGGGCGCTATCACGTGACGGCCGTGCTGGCC

CTGGGGGCCGGCTCAGCCCTGCTGGGGACAGACGTGCAGGTGGAAGCGGCACCTGCCGC

CCTGGAGCTCGTGTGCCCGTCCTCGGTGCAGAGTGACGAGAGCCTCGACCTCAGCATCCA

GAACCGCGGTGGTTCAGGCCTGGAGGCCGCCTACAGCATCGTGGCCCTGGGCGAGGAGC

CGGCCCGAGCGGTGCACCCGCTCTGCCCCTCGGACACGGAGATCTTCCCTGGCAACGGG

CACTGCTACCGCCTGGTGGTGGAGAAGGCGGCCTGGCTGCAGGCGCAGGAGCAGTGTCA

-continued

GGCCTGGGCCGGGGCCGCCCTGGCAATGGTGGACAGTCCCGCCGTGCAGCGCTTCCTGG

TCTCCCGGGTCACCAGGAGCCTAGACGTGTGGATCGGCTTCTCGACTGTGCAGGGGGTGG

AGGTGGGCCCAGCGCCGCAGGGCGAGGCCTTCAGCCTGGAGAGCTGCCAGAACTGGCTG

CCCGGGGAGCCACACCCAGCCACAGCCGAGCACTGCGTCCGGCTCGGGCCCACCGGGTG

GTGTAACACCGACCTGTGCTCAGCGCCGCACAGCTACGTCTGCGAGCTGCAGCCCGGAG

GCCCAGTGCAGGATGCCGAGAACCTCCTCGTGGGAGCGCCCAGTGGGGACCTGCAGGGA

CCCCTGACGCCTCTGGCACAGCAGGACGGCCTCTCAGCCCCGCACGAGCCCGTGGAGGT

CATGGTATTCCCGGGCCTGCGTCTGAGCCGTGAAGCCTTCCTCACCACGGCCGAATTTGG

GACCCAGGAGCTCCGGCGGCCCGCCCAGCTGCGGCTGCAGGTGTACCGGCTCCTCAGCA

CAGCAGGGACCCCGGAGAACGGCAGCGAGCCTGAGAGCAGGTCCCCGGACAACAGGAC

CCAGCTGGCCCCCGCGTGCATGCCAGGGGGACGCTGGTGCCCTGGAGCCAACATCTGCTT

GCCGCTGGACGCCTCCTGCCACCCCCAGGCCTGCGCCAATGGCTGCACGTCAGGGCCAG

GGCTACCCGGGGCCCCCTATGCGCTATGGAGAGAGTTCCTCTTCTCCGTTCCCGCGGGGC

CCCCCGCGCAGTACTCGGTCACCCTCCACGGCCAGGATGTCCTCATGCTCCCTGGTGACC

TCGTTGGCTTGCAGCACGACGCTGGCCCTGGCGCCCTCCTGCACTGCTCGCCGGCTCCCG

GCCACCCTGGTCCCCGGGCCCCGTACCTCTCCGCCAACGCCTCGTCATGGCTGCCCCACT

TGCCAGCCCAGCTGGAGGGCACTTGGGCCTGCCCTGCCTGTGCCCTGCGGCTGCTTGCAG

CCACGGAACAGCTCACCGTGCTGCTGGGCTTGAGGCCCAACCCTGGACTGCGGCTGCCTG

GGCGCTATGAGGTCCGGGCAGAGGTGGGCAATGGCGTGTCCAGGCACAACCTCTCCTGC

AGCTTTGACGTGGTCTCCCCAGTGGCTGGGCTGCGGGTCATCTACCCTGCCCCCCGCGAC

GGCCGCCTCTACGTGCCCACCAACGGCTCAGCCTTGGTGCTCCAGGTGGACTCTGGTGCC

AACGCCACGGCCACGGCTCGCTGGCCTGGGGGCAGTGTCAGCGCCCGCTTTGAGAATGT

CTGCCCTGCCCTGGTGGCCACCTTCGTGCCCGGCTGCCCCTGGGAGACCAACGATACCCT

GTTCTCAGTGGTAGCACTGCCGTGGCTCAGTGAGGGGGAGCACGTGGTGGACGTGGTGG

TGGAAAACAGCGCCAGCCGGGCCAACCTCAGCCTGCGGGTGACGGCGGAGGAGCCCATC

TGTGGCCTCCGCGCCACGCCCAGCCCCGAGGCCCGTGTACTGCAGGGAGTCCTAGTGAG

GTACAGCCCCGTGGTGGAGGCCGGCTCGGACATGGTCTTCCGGTGGACCATCAACGACA

AGCAGTCCCTGACCTTCCAGAACGTGGTCTTCAATGTCATTTATCAGAGCGCGGCGGTCT

TCAAGCTCTCACTGACGGCCTCCAACCACGTGAGCAACGTCACCGTGAACTACAACGTA

ACCGTGGAGCGGATGAACAGGATGCAGGGTCTGCAGGTCTCCACAGTGCCGGCCGTGCT

GTCCCCCAATGCCACGCTAGCACTGACGGCGGGCGTGCTGGTGGACTCGGCCGTGGAGG

TGGCCTTCCTGTGGACCTTTGGGGATGGGGAGCAGGCCCTCCACCAGTTCCAGCCTCCGT

ACAACGAGTCCTTCCCGGTTCCAGACCCCTCGGTGGCCCAGGTGCTGGTGGAGCACAATG

TCATGCACACCTACGCTGCCCCAGGTGAGTACCTCCTGACCGTGCTGGCATCTAATGCCT

TCGAGAACCTGACGCAGCAGGTGCCTGTGAGCGTGCGCGCCTCCCTGCCCTCCGTGGCTG

TGGGTGTGAGTGACGGCGTCCTGGTGGCCGGCCGGCCCGTCACCTTCTACCCGCACCCGC

TGCCCTCGCCTGGGGGTGTTCTTTACACGTGGGACTTCGGGGACGGCTCCCCTGTCCTGA

CCCAGAGCCAGCCGGCTGCCAACCACACCTATGCCTCGAGGGGCACCTACCACGTGCGC

CTGGAGGTCAACAACACGGTGAGCGGTGCGGCGGCCCAGGCGGATGTGCGCGTCTTTGA

GGAGCTCCGCGGACTCAGCGTGGACATGAGCCTGGCCGTGGAGCAGGGCGCCCCCGTGG

-continued

TGGTCAGCGCCGCGGTGCAGACGGGCGACAACATCACGTGGACCTTCGACATGGGGGAC

GGCACCGTGCTGTCGGGCCCGGAGGCAACAGTGGAGCATGTGTACCTGCGGGCACAGAA

CTGCACAGTGACCGTGGGTGCGGCCAGCCCCGCCGGCCACCTGGCCCGGAGCCTGCACG

TGCTGGTCTTCGTCCTGGAGGTGCTGCGCGTTGAACCCGCCGCCTGCATCCCCACGCAGC

CTGACGCGCGGCTCACGGCCTACGTCACCGGGAACCCGGCCCACTACCTCTTCGACTGGA

CCTTCGGGGATGGCTCCTCCAACACGACCGTGCGGGGGTGCCCGACGGTGACACACAAC

TTCACGCGGAGCGGCACGTTCCCCCTGGCGCTGGTGCTGTCCAGCCGCGTGAACAGGGC

GCATTACTTCACCAGCATCTGCGTGGAGCCAGAGGTGGGCAACGTCACCCTGCAGCCAG

AGAGGCAGTTTGTGCAGCTCGGGGACGAGGCCTGGCTGGTGGCATGTGCCTGGCCCCCG

TTCCCCTACCGCTACACCTGGGACTTTGGCACCGAGGAAGCCGCCCCCACCCGTGCCAGG

GGCCCTGAGGTGACGTTCATCTACCGAGACCCAGGCTCCTATCTTGTGACAGTCACCGCG

TCCAACAACATCTCTGCTGCCAATGACTCAGCCCTGGTGGAGGTGCAGGAGCCCGTGCTG

GTCACCAGCATCAAGGTCAATGGCTCCCTTGGGCTGGAGCTGCAGCAGCCGTACCTGTTC

TCTGCTGTGGGCCGTGGGCGCCCCGCCAGCTACCTGTGGGATCTGGGGGACGGTGGGTG

GCTCGAGGGTCCGGAGGTCACCCACGCTTACAACAGCACAGGTGACTTCACCGTTAGGG

TGGCCGGCTGGAATGAGGTGAGCCGCAGCGAGGCCTGGCTCAATGTGACGGTGAAGCGG

CGCGTGCGGGGGCTCGTCGTCAATGCAAGCCGCACGGTGGTGCCCCTGAATGGGAGCGT

GAGCTTCAGCACGTCGCTGGAGGCCGGCAGTGATGTGCGCTATTCCTGGGTGCTCTGTGA

CCGCTGCACGCCCATCCCTGGGGGTCCTACCATCTCTTACACCTTCCGCTCCGTGGGCAC

CTTCAATATCATCGTCACGGCTGAGAACGAGGTGGGCTCCGCCCAGGACAGCATCTTCGT

CTATGTCCTGCAGCTCATAGAGGGGCTGCAGGTGGTGGGCGGTGGCCGCTACTTCCCCAC

CAACCACACGGTACAGCTGCAGGCCGTGGTTAGGGATGGCACCAACGTCTCCTACAGCT

GGACTGCCTGGAGGGACAGGGGCCCGGCCCTGGCCGGCAGCGGCAAAGGCTTCTCGCTC

ACCGTGCTCGAGGCCGGCACCTACCATGTGCAGCTGCGGGCCACCAACATGCTGGGCAG

CGCCTGGGCCGACTGCACCATGGACTTCGTGGAGCCTGTGGGGTGGCTGATGGTGGCCG

CCTCCCCGAACCCAGCTGCCGTCAACACAAGCGTCACCCTCAGTGCCGAGCTGGCTGGTG

GCAGTGGTGTCGTATACACTTGGTCCTTGGAGGAGGGGCTGAGCTGGGAGACCTCCGAG

CCATTTACCACCCATAGCTTCCCCACACCCGGCCTGCACTTGGTCACCATGACGGCAGGG

AACCCGCTGGGCTCAGCCAACGCCACCGTGGAAGTGGATGTGCAGGTGCCTGTGAGTGG

CCTCAGCATCAGGGCCAGCGAGCCCGGAGGCAGCTTCGTGGCGGCCGGGTCCTCTGTGC

CCTTTTGGGGGCAGCTGGCCACGGGCACCAATGTGAGCTGGTGCTGGGCTGTGCCCGGC

GGCAGCAGCAAGCGTGGCCCTCATGTCACCATGGTCTTCCCGGATGCTGGCACCTTCTCC

ATCCGGCTCAATGCCTCCAACGCAGTCAGCTGGGTCTCAGCCACGTACAACCTCACGGCG

GAGGAGCCCATCGTGGGCCTGGTGCTGTGGGCCAGCAGCAAGGTGGTGGCGCCCGGGCA

GCTGGTCCATTTTCAGATCCTGCTGGCTGCCGGCTCAGCTGTCACCTTCCGCCTGCAGGTC

GGCGGGGCCAACCCCGAGGTGCTCCCCGGGCCCCGTTTCTCCCACAGCTTCCCCCGCGTC

GGAGACCACGTGGTGAGCGTGCGGGGCAAAAACCACGTGAGCTGGGCCCAGGCGCAGG

TGCGCATCGTGGTGCTGGAGGCCGTGAGTGGGCTGCAGGTGCCCAACTGCTGCGAGCCT

GGCATCGCCACGGGCACTGAGAGGAACTTCACAGCCCGCGTGCAGCGCGGCTCTCGGGT

CGCCTACGCCTGGTACTTCTCGCTGCAGAAGGTCCAGGGCGACTCGCTGGTCATCCTGTC

GGGCCGCGACGTCACCTACACGCCCGTGGCCGCGGGGCTGTTGGAGATCCAGGTGCGCG

-continued

CCTTCAACGCCCTGGGCAGTGAGAACCGCACGCTGGTGCTGGAGGTTCAGGACGCCGTC

CAGTATGTGGCCCTGCAGAGCGGCCCCTGCTTCACCAACCGCTCGGCGCAGTTTGAGGCC

GCCACCAGCCCCAGCCCCCGGCGTGTGGCCTACCACTGGGACTTTGGGGATGGGTCGCC

AGGGCAGGACACAGATGAGCCCAGGGCCGAGCACTCCTACCTGAGGCCTGGGGACTACC

GCGTGCAGGTGAACGCCTCCAACCTGGTGAGCTTCTTCGTGGCGCAGGCCACGGTGACC

GTCCAGGTGCTGGCCTGCCGGGAGCCGGAGGTGGACGTGGTCCTGCCCCTGCAGGTGCT

GATGCGGCGATCACAGCGCAACTACTTGGAGGCCCACGTTGACCTGCGCGACTGCGTCA

CCTACCAGACTGAGTACCGCTGGGAGGTGTATCGCACCGCCAGCTGCCAGCGGCCGGGG

CGCCCAGCGCGTGTGGCCCTGCCCGGCGTGGACGTGAGCCGGCCTCGGCTGGTGCTGCC

GCGGCTGGCGCTGCCTGTGGGGCACTACTGCTTTGTGTTTGTCGTGTCATTTGGGGACAC

GCCACTGACACAGAGCATCCAGGCCAATGTGACGGTGGCCCCCGAGCGCCTGGTGCCCA

TCATTGAGGGTGGCTCATACCGCGTGTGGTCAGACACACGGGACCTGGTGCTGGATGGG

AGCGAGTCCTACGACCCCAACCTGGAGGACGGCGACCAGACGCCGCTCAGTTTCCACTG

GGCCTGTGTGGCTTCGACACAGAGGGAGGCTGGCGGGTGTGCGCTGAACTTTGGGCCCC

GCGGGAGCAGCACGGTCACCATTCCACGGGAGCGGCTGGCGGCTGGCGTGGAGTACACC

TTCAGCCTGACCGTGTGGAAGGCCGGCCGCAAGGAGGAGGCCACCAACCAGACGGTGCT

GATCCGGAGTGGCCGGGTGCCCATTGTGTCCTTGGAGTGTGTGTCCTGCAAGGCACAGGC

CGTGTACGAAGTGAGCCGCAGCTCCTACGTGTACTTGGAGGGCCGCTGCCTCAATTGCAG

CAGCGGCTCCAAGCGAGGGCGGTGGGCTGCACGTACGTTCAGCAACAAGACGCTGGTGC

TGGATGAGACCACCACATCCACGGGCAGTGCAGGCATGCGACTGGTGCTGCGGCGGGGC

GTGCTGCGGGACGGCGAGGGATACACCTTCACGCTCACGGTGCTGGGCCGCTCTGGCGA

GGAGGAGGGCTGCGCCTCCATCCGCCTGTCCCCCAACCGCCCGCCGCTGGGGGGCTCTTG

CCGCCTCTTCCCACTGGGCGCTGTGCACGCCCTCACCACCAAGGTGCACTTCGAATGCAC

GGGCTGGCATGACGCGGAGGATGCTGGCGCCCCGCTGGTGTACGCCCTGCTGCTGCGGC

GCTGTCGCCAGGGCCACTGCGAGGAGTTCTGTGTCTACAAGGGCAGCCTCTCCAGCTACG

GAGCCGTGCTGCCCCCGGGTTTCAGGCCACACTTCGAGGTGGGCCTGGCCGTGGTGGTGC

AGGACCAGCTGGGAGCCGCTGTGGTCGCCCTCAACAGGTCTTTGGCCATCACCCTCCCAG

AGCCCAACGGCAGCGCAACGGGGCTCACAGTCTGGCTGCACGGGCTCACCGCTAGTGTG

CTCCCAGGGCTGCTGCGGCAGGCCGATCCCCAGCACGTCATCGAGTACTCGTTGGCCCTG

GTCACCGTGCTGAACGAGTACGAGCGGGCCCTGGACGTGGCGGCAGAGCCCAAGCACGA

GCGGCAGCACCGAGCCCAGATACGCAAGAACATCACGGAGACTCTGGTGTCCCTGAGGG

TCCACACTGTGGATGACATCCAGCAGATCGCTGCTGCGCTGGCCCAGTGCATGGGGCCCA

GCAGGGAGCTCGTATGCCGCTCGTGCCTGAAGCAGACGCTGCACAAGCTGGAGGCCATG

ATGCTCATCCTGCAGGCAGAGACCACCGCGGGCACCGTGACGCCCACCGCCATCGGAGA

CAGCATCCTCAACATCACAGGAGACCTCATCCACCTGGCCAGCTCGGACGTGCGGGCAC

CACAGCCCTCAGAGCTGGGAGCCGAGTCACCATCTCGGATGGTGGCGTCCCAGGCCTAC

AACCTGACCTCTGCCCTCATGCGCATCCTCATGCGCTCCCGCGTGCTCAACGAGGAGCCC

CTGACGCTGGCGGGCGAGGAGATCGTGGCCCAGGGCAAGCGCTCGGACCCGCGGAGCCT

GCTGTGCTATGGCGGCGCCCCAGGGCCTGGCTGCCACTTCTCCATCCCCGAGGCTTTCAG

CGGGGCCCTGGCCAACCTCAGTGACGTGGTGCAGCTCATCTTTCTGGTGGACTCCAATCC

-continued

CTTTCCCTTTGGCTATATCAGCAACTACACCGTCTCCACCAAGGTGGCCTCGATGGCATTC

CAGACACAGGCCGGCGCCCAGATCCCCATCGAGCGGCTGGCCTCAGAGCGCGCCATCAC

CGTGAAGGTGCCCAACAACTCGGACTGGGCTGCCCGGGGCCACCGCAGCTCCGCCAACT

CCGCCAACTCCGTTGTGGTCCAGCCCCAGGCCTCCGTCGGTGCTGTGGTCACCCTGGACA

GCAGCAACCCTGCGGCCGGGCTGCATCTGCAGCTCAACTATACGCTGCTGGACGGCCACT

ACCTGTCTGAGGAACCTGAGCCCTACCTGGCAGTCTACCTACACTCGGAGCCCCGGCCCA

ATGAGCACAACTGCTCGGCTAGCAGGAGGATCCGCCCAGAGTCACTCCAGGGTGCTGAC

CACCGGCCCTACACCTTCTTCATTTCCCCGGGGAGCAGAGACCCAGCGGGGAGTTACCAT

CTGAACCTCTCCAGCCACTTCCGCTGGTCGGCGCTGCAGGTGTCCGTGGGCCTGTACACG

TCCCTGTGCCAGTACTTCAGCGAGGAGGACATGGTGTGGCGGACAGAGGGGCTGCTGCC

CCTGGAGGAGACCTCGCCCCGCCAGGCCGTCTGCCTCACCCGCCACCTCACCGCCTTCGG

CGCCAGCCTCTTCGTGCCCCCAAGCCATGTCCGCTTTGTGTTTCCTGAGCCGACAGCGGA

TGTAAACTACATCGTCATGCTGACATGTGCTGTGTGCCTGGTGACCTACATGGTCATGGC

CGCCATCCTGCACAAGCTGGACCAGTTGGATGCCAGCCGGGGCCGCGCCATCCCTTTCTG

TGGGCAGCGGGGCCGCTTCAAGTACGAGATCCTCGTCAAGACAGGCTGGGGCCGGGGCT

CAGGTACCACGGCCCACGTGGGCATCATGCTGTATGGGGTGGACAGCCGGAGCGGCCAC

CGGCACCTGGACGGCGACAGAGCCTTCCACCGCAACAGCCTGGACATCTTCCGGATCGC

CACCCCGCACAGCCTGGGTAGCGTGTGGAAGATCCGAGTGTGGCACGACAACAAAGGGC

TCAGCCCTGCCTGGTTCCTGCAGCACGTCATCGTCAGGGACCTGCAGACGGCACGCAGCG

CCTTCTTCCTGGTCAATGACTGGCTTTCGGTGGAGACGGAGGCCAACGGGGGCCTGGTGG

AGAAGGAGGTGCTGGCCGCGAGCGACGCAGCCCTTTTGCGCTTCCGGCGCCTGCTGGTG

GCTGAGCTGCAGCGTGGCTTCTTTGACAAGCACATCTGGCTCTCCATATGGGACCGGCCG

CCTCGTAGCCGTTTCACTCGCATCCAGAGGGCCACCTGCTGCGTTCTCCTCATCTGCCTCT

TCCTGGGCGCCAACGCCGTGTGGTACGGGGCTGTTGGCGACTCTGCCTACAGCACGGGG

CATGTGTCCAGGCTGAGCCCGCTGAGCGTCGACACAGTCGCTGTTGGCCTGGTGTCCAGC

GTGGTTGTCTATCCCGTCTACCTGGCCATCCTTTTTCTCTTCCGGATGTCCCGGAGCAAGG

TGGCTGGGAGCCCGAGCCCCACACCTGCCGGGCAGCAGGTGCTGGACATCGACAGCTGC

CTGGACTCGTCCGTGCTGGACAGCTCCTTCCTCACGTTCTCAGGCCTCCACGCTGAGGCC

TTTGTTGGACAGATGAAGAGTGACTTGTTTCTGGATGATTCTAAGAGTCTGGTGTGCTGG

CCCTCCGGCGAGGGAACGCTCAGTTGGCCGGACCTGCTCAGTGACCCGTCCATTGTGGGT

AGCAATCTGCGGCAGCTGGCACGGGGCCAGGCGGGCCATGGGCTGGGCCCAGAGGAGG

ACGGCTTCTCCCTGGCCAGCCCCTACTCGCCTGCCAAATCCTTCTCAGCATCAGATGAAG

ACCTGATCCAGCAGGTCCTTGCCGAGGGGGTCAGCAGCCCAGCCCCTACCCAAGACACC

CACATGGAAACGGACCTGCTCAGCAGCCTGTCCAGCACTCCTGGGGAGAAGACAGAGAC

GCTGGCGCTGCAGAGGCTGGGGGAGCTGGGGCCACCCAGCCCAGGCCTGAACTGGGAAC

AGCCCCAGGCAGCGAGGCTGTCCAGGACAGGACTGGTGGAGGGTCTGCGGAAGCGCCTG

CTGCCGGCCTGGTGTGCCTCCCTGGCCCACGGGCTCAGCCTGCTCCTGGTGGCTGTGGCT

GTGGCTGTCTCAGGGTGGGTGGGTGCGAGCTTCCCCCCGGGCGTGAGTGTTGCGTGGCTC

CTGTCCAGCAGCGCCAGCTTCCTGGCCTCATTCCTCGGCTGGGAGCCACTGAAGGTCTTG

CTGGAAGCCCTGTACTTCTCACTGGTGGCCAAGCGGCTGCACCCGGATGAAGATGACAC

CCTGGTAGAGAGCCCGGCTGTGACGCCTGTGAGCGCACGTGTGCCCCGCGTACGGCCAC

-continued

CCCACGGCTTTGCACTCTTCCTGGCCAAGGAAGAAGCCCGCAAGGTCAAGAGGCTACAT

GGCATGCTGCGGAGCCTCCTGGTGTACATGCTTTTTCTGCTGGTGACCCTGCTGGCCAGC

TATGGGGATGCCTCATGCCATGGGCACGCCTACCGTCTGCAAAGCGCCATCAAGCAGGA

GCTGCACAGCCGGGCCTTCCTGGCCATCACGCGGTCTGAGGAGCTCTGGCCATGGATGGC

CCACGTGCTGCTGCCCTACGTCCACGGGAACCAGTCCAGCCCAGAGCTGGGGCCCCCAC

GGCTGCGGCAGGTGCGGCTGCAGGAAGCACTCTACCCAGACCCTCCCGGCCCCAGGGTC

CACACGTGCTCGGCCGCAGGAGGCTTCAGCACCAGCGATTACGACGTTGGCTGGGAGAG

TCCTCACAATGGCTCGGGGACGTGGGCCTATTCAGCGCCGGATCTGCTGGGGGCATGGTC

CTGGGGCTCCTGTGCCGTGTATGACAGCGGGGGCTACGTGCAGGAGCTGGGCCTGAGCC

TGGAGGAGAGCCGCGACCGGCTGCGCTTCCTGCAGCTGCACAACTGGCTGGACAACAGG

AGCCGCGCTGTGTTCCTGGAGCTCACGCGCTACAGCCCGGCCGTGGGGCTGCACGCCGCC

GTCACGCTGCGCCTCGAGTTCCCGGCGGCCGGCCGCGCCCTGGCCGCCCTCAGCGTCCGC

CCCTTTGCGCTGCGCCGCCTCAGCGCGGGCCTCTCGCTGCCTCTGCTCACCTCGGTGTGCC

TGCTGCTGTTCGCCGTGCACTTCGCCGTGGCCGAGGCCCGTACTTGGCACAGGGAAGGGC

GCTGGCGCGTGCTGCGGCTCGGAGCCTGGGCGCGGTGGCTGCTGGTGGCGCTGACGGCG

GCCACGGCACTGGTACGCCTCGCCCAGCTGGGTGCCGCTGACCGCCAGTGGACCCGTTTC

GTGCGCGGCCGCCCGCGCCGCTTCACTAGCTTCGACCAGGTGGCGCAGCTGAGCTCCGCA

GCCCGTGGCCTGGCGGCCTCGCTGCTCTTCCTGCTTTTGGTCAAGGCTGCCCAGCAGCTA

CGCTTCGTGCGCCAGTGGTCCGTCTTTGGCAAGACATTATGCCGAGCTCTGCCAGAGCTC

CTGGGGGTCACCTTGGGCCTGGTGGTGCTCGGGGTAGCCTACGCCCAGCTGGCCATCCTG

CTCGTGTCTTCCTGTGTGGACTCCCTCTGGAGCGTGGCCCAGGCCCTGTTGGTGCTGTGCC

CTGGGACTGGGCTCTCTACCCTGTGTCCTGCCGAGTCCTGGCACCTGTCACCCCTGCTGTG

TGTGGGGCTCTGGGCACTGCGGCTGTGGGGCGCCCTACGGCTGGGGGCTGTTATTCTCCG

CTGGCGCTACCACGCCTTGCGTGGAGAGCTGTACCGGCCGGCCTGGGAGCCCCAGGACT

ACGAGATGGTGGAGTTGTTCCTGCGCAGGCTGCGCCTCTGGATGGGCCTCAGCAAGGTC

AAGGAGTTCCGCCACAAAGTCCGCTTTGAAGGGATGGAGCCGCTGCCCTCTCGCTCCTCC

AGGGGCTCCAAGGTATCCCCGGATGTGCCCCCACCCAGCGCTGGCTCCGATGCCTCGCAC

CCCTCCACCTCCTCCAGCCAGCTGGATGGGCTGAGCGTGAGCCTGGGCCGGCTGGGGAC

AAGGTGTGAGCCTGAGCCCTCCCGCCTCCAAGCCGTGTTCGAGGCCCTGCTCACCCAGTT

TGACCGACTCAACCAGGCCACAGAGGACGTCTACCAGCTGGAGCAGCAGCTGCACAGCC

TGCAAGGCCGCAGGAGCAGCCGGGCGCCCGCCGGATCTTCCCGTGGCCCATCCCCGGGC

CTGCGGCCAGCACTGCCCAGCCGCCTTGCCCGGGCCAGTCGGGGTGTGGACCTGGCCACT

GGCCCCAGCAGGACACCCCTTCGGGCCAAGAACAAGGTCCACCCCAGCAGCACTTAG polycystin-2 (PKD2), also known as: PC2, PKD4, Pc-2, APKD2, TRPP2;
positions 100-3006 of NCBI ref NM_000297.4, CCDS3627.1, human, 2907 nt,
SEQ ID NO: 10

ATGGTGAACTCCAGTCGCGTGCAGCCTCAGCAGCCCGGGGACGCCAAGCGGCCGCCCGC

GCCCCGCGCGCCGGACCCGGGCCGGCTGATGGCTGGCTGCGCGGCCGTGGGCGCCAGCC

TCGCCGCCCCGGGCGGCCTCTGCGAGCAGCGGGGCCTGGAGATCGAGATGCAGCGCATC

CGGCAGGCGGCCGCGCGGGACCCCCGGCCGGAGCCGCGGCCTCCCCTTCTCCTCCGCTC

TCGTCGTGCTCCCGGCAGGCGTGGAGCCGCGATAACCCCGGCTTCGAGGCCGAGGAGGA

GGAGGAGGAGGTGGAAGGGGAAGAAGGCGGAATGGTGGTGGAGATGGACGTAGAGTGG

-continued

CGCCCGGGCAGCCGGAGGTCGGCCGCCTCCTCGGCCGTGAGCTCCGTGGGCGCGCGGAG

CCGGGGGCTTGGGGGCTACCACGGCGCGGGCCACCCGAGCGGGAGGCGGCGCCGGCGA

GAGGACCAGGGCCCGCCGTGCCCCAGCCCAGTCGGCGGCGGGGACCCGCTGCATCGCCA

CCTCCCCCTGGAAGGGCAGCCGCCCCGAGTGGCCTGGGCGGAGAGGCTGGTTCGCGGGC

TGCGAGGTCTCTGGGGAACAAGACTCATGGAGGAAAGCAGCACTAACCGAGAGAAATA

CCTTAAAAGTGTTTTACGGGAACTGGTCACATACCTCCTTTTTCTCATAGTCTTGTGCATC

TTGACCTACGGCATGATGAGCTCCAATGTGTACTACTACACCCGGATGATGTCACAGCTC

TTCCTAGACACCCCCGTGTCCAAAACGGAGAAAACTAACTTTAAAACTCTGTCTTCCATG

GAAGACTTCTGGAAGTTCACAGAAGGCTCCTTATTGGATGGGCTGTACTGGAAGATGCA

GCCCAGCAACCAGACTGAAGCTGACAACCGAAGTTTCATCTTCTATGAGAACCTGCTGTT

AGGGGTTCCACGAATACGGCAACTCCGAGTCAGAAATGGATCCTGCTCTATCCCCCAGG

ACTTGAGAGATGAAATTAAAGAGTGCTATGATGTCTACTCTGTCAGTAGTGAAGATAGG

GCTCCCTTTGGGCCCCGAAATGGAACCGCTTGGATCTACACAAGTGAAAAAGACTTGAA

TGGTAGTAGCCACTGGGGAATCATTGCAACTTATAGTGGAGCTGGCTATTATCTGGATTT

GTCAAGAACAAGAGAGGAAACAGCTGCACAAGTTGCTAGCCTCAAGAAAAATGTCTGGC

TGGACCGAGGAACCAGGGCAACTTTTATTGACTTCTCAGTGTACAACGCCAACATTAACC

TGTTCTGTGTGGTCAGGTTATTGGTTGAATTCCCAGCAACAGGTGGTGTGATTCCATCTTG

GCAATTTCAGCCTTTAAAGCTGATCCGATATGTCACAACTTTTGATTTCTTCCTGGCAGCC

TGTGAGATTATCTTTTGTTTCTTTATCTTTTACTATGTGGTGGAAGAGATATTGGAAATTC

GCATTCACAAACTACACTATTTCAGGAGTTTCTGGAATTGTCTGGATGTTGTGATCGTTGT

GCTGTCAGTGGTAGCTATAGGAATTAACATATACAGAACATCAAATGTGGAGGTGCTAC

TACAGTTTCTGGAAGATCAAAATACTTTCCCCAACTTTGAGCATCTGGCATATTGGCAGA

TACAGTTCAACAATATAGCTGCTGTCACAGTATTTTTTGTCTGGATTAAGCTCTTCAAATT

CATCAATTTTAACAGGACCATGAGCCAGCTCTCGACAACCATGTCTCGATGTGCCAAAGA

CCTGTTTGGCTTTGCTATTATGTTCTTCATTATTTTCCTAGCGTATGCTCAGTTGGCATACC

TTGTCTTTGGCACTCAGGTCGATGACTTCAGTACTTTCCAAGAGTGTATCTTCACTCAATT

CCGTATCATTTTGGGCGATATCAACTTTGCAGAGATTGAGGAAGCTAATCGAGTTTTGGG

ACCAATTTATTTCACTACATTTGTGTTCTTTATGTTCTTCATTCTTTTGAATATGTTTTTGG

CTATCATCAATGATACTTACTCTGAAGTGAAATCTGACTTGGCACAGCAGAAAGCTGAAA

TGGAACTCTCAGATCTTATCAGAAAGGGCTACCATAAAGCTTTGGTCAAACTAAAACTGA

AAAAAAATACCGTGGATGACATTTCAGAGAGTCTGCGGCAAGGAGGAGGCAAGTTAAAC

TTTGACGAACTTCGACAAGATCTCAAAGGGAAGGGCCATACTGATGCAGAGATTGAGGC

AATATTCACAAAGTACGACCAAGATGGAGACCAAGAACTGACCGAACATGAACATCAGC

AGATGAGAGACGACTTGGAGAAAGAGAGGGAGGACCTGGATTTGGATCACAGTTCTTTA

CCACGTCCCATGAGCAGCCGAAGTTTCCCTCGAAGCCTGGATGACTCTGAGGAGGATGA

CGATGAAGATAGCGGACATAGCTCCAGAAGGAGGGGAAGCATTTCTAGTGGCGTTTCTT

ACGAAGAGTTTCAAGTCCTGGTGAGACGAGTGGACCGGATGGAGCATTCCATCGGCAGC

ATAGTGTCCAAGATTGACGCCGTGATCGTGAAGCTAGAGATTATGGAGCGAGCCAAACT

GAAGAGGAGGGAGGTGCTGGGAAGGCTGTTGGATGGGGTGGCCGAGGATGAAAGGCTG

GGTCGTGACAGTGAAATCCATAGGGAACAGATGGAACGGCTAGTACGTGAAGAGTTGGA

-continued

```
ACGCTGGGAATCCGATGATGCAGCTTCCCAGATCAGTCATGGTTTAGGCACGCCAGTGG

GACTAAATGGTCAACCTCGCCCCAGAAGCTCCCGCCCATCTTCCTCCCAATCTACAGAAG

GCATGGAAGGTGCAGGTGGAAATGGGAGTTCTAATGTCCACGTATGA
```

In some embodiments, the transgene encodes for a polypeptide comprising one of SEQ ID NOs: 11-12, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of one of SEQ ID NOs: 11-12, which maintains the same function (e.g., regulate kidney cells, influence formation of kidney tubular structures, and influence kidney fluid secretion function), or a functional fragment thereof.

```
polycystin-1 (PKD1), NCBI ref NP_000287.4, human, 4302 aa,
                                                            SEQ ID NO: 11
MPPAAPARLALALGLGLWLGALAGGPGRGCGPCEPPCLCGPAPGAACRVNCSGRGLRTLGP

ALRIPADATALDVSHNLLRALDVGLLANLSALAELDISNNKISTLEEGIFANLFNLSEINLSGNP

FECDCGLAWLPRWAEEQQVRVVQPEAATCAGPGSLAGQPLLGIPLLDSGCGEEYVACLPDN

SSGTVAAVSFSAAHEGLLQPEACSAFCFSTGQGLAALSEQGWCLCGAAQPSSASFACLSLCS

GPPPPPAPTCRGPTLLQHVFPASPGATLVGPHGPLASGQLAAFHIAAPLPVTATRWDFGDGSA

EVDAAGPAASHRYVLPGRYHVTAVLALGAGSALLGTDVQVEAAPAALELVCPSSVQSDESL

DLSIQNRGGSGLEAAYSIVALGEEPARAVHPLCPSDTEIFPGNGHCYRLVVEKAAWLQAQEQ

CQAWAGAALAMVDSPAVQRFLVSRVTRSLDVWIGFSTVQGVEVGPAPQGEAFSLESCQNW

LPGEPHPATAEHCVRLGPTGWCNTDLCSAPHSYVCELQPGGPVQDAENLLVGAPSGDLQGP

LTPLAQQDGLSAPHEPVEVMVFPGLRLSREAFLTTAEFGTQELRRPAQLRLQVYRLLSTAGTP

ENGSEPESRSPDNRTQLAPACMPGGRWCPGANICLPLDASCHPQACANGCTSGPGLPGAPYA

LWREFLFSVPAGPPAQYSVTLHGQDVLMLPGDLVGLQHDAGPGALLHCSPAPGHPGPRAPY

LSANASSWLPHLPAQLEGTWACPACALRLLAATEQLTVLLGLRPNPGLRLPGRYEVRAEVG

NGVSRHNLSCSFDVVSPVAGLRVIYPAPRDGRLYVPTNGSALVLQVDSGANATATARWPGG

SVSARFENVCPALVATFVPGCPWETNDTLFSVVALPWLSEGEHVVDVVVENSASRANLSLR

VTAEEPICGLRATPSPEARVLQGVLVRYSPVVEAGSDMVFRWTINDKQSLTFQNVVFNVIYQ

SAAVFKLSLTASNHVSNVTVNYNVTVERMNRMQGLQVSTVPAVLSPNATLALTAGVLVDS

AVEVAFLWTFGDGEQALHQFQPPYNESFPVPDPSVAQVLVEHNVMHTYAAPGEYLLTVLAS

NAFENLTQQVPVSVRASLPSVAVGVSDGVLVAGRPVTFYPHPLPSPGGVLYTWDFGDGSPVL

TQSQPAANHTYASRGTYHVRLEVNNTVSGAAAQADVRVFEELRGLSVDMSLAVEQGAPVV

VSAAVQTGDNITWTFDMGDGTVLSGPEATVEHVYLRAQNCTVTVGAASPAGHLARSLHVL

VFVLEVLRVEPAACIPTQPDARLTAYVTGNPAHYLFDWTFGDGSSNTTVRGCPTVTHNFTRS

GTFPLALVLSSRVNRAHYFTSICVEPEVGNVTLQPERQFVQLGDEAWLVACAWPPFPYRYTW

DFGTEEAAPTRARGPEVTFIYRDPGSYLVTVTASNNISAANDSALVEVQEPVLVTSIKVNGSL

GLELQQPYLFSAVGRGRPASYLWDLGDGGWLEGPEVTHAYNSTGDFTVRVAGWNEVSRSE

AWLNVTVKRRVRGLVVNASRTVVPLNGSVSFSTSLEAGSDVRYSWVLCDRCTPIPGGPTISY

TFRSVGTFNIIVTAENEVGSAQDSIFVYVLQLIEGLQVVGGGRYFPTNHTVQLQAVVRDGTNV

SYSWTAWRDRGPALAGSGKGFSLTVLEAGTYHVQLRATNMLGSAWADCTMDFVEPVGWL

MVAASPNPAAVNTSVTLSAELAGGSGVVYTWSLEEGLSWETSEPFTTHSFPTPGLHLVTMTA

GNPLGSANATVEVDVQVPVSGLSIRASEPGGSFVAAGSSVPFWGQLATGTNVSWCWAVPGG

SSKRGPHVTMVFPDAGTFSIRLNASNAVSWVSATYNLTAEEPIVGLVLWASSKVVAPGQLVH

FQILLAAGSAVTFRLQVGGANPEVLPGPRFSHSFPRVGDHVVSVRGKNHVSWAQAQVRIVVL
```

-continued

EAVSGLQVPNCCEPGIATGTERNFTARVQRGSRVAYAWYFSLQKVQGDSLVILSGRDVTYTP

VAAGLLEIQVRAFNALGSENRTLVLEVQDAVQYVALQSGPCFTNRSAQFEAATSPSPRRVAY

HWDFGDGSPGQDTDEPRAEHSYLRPGDYRVQVNASNLVSFFVAQATVTVQVLACREPEVD

VVLPLQVLMRRSQRNYLEAHVDLRDCVTYQTEYRWEVYRTASCQRPGRPARVALPGVDVS

RPRLVLPRLALPVGHYCFVFVVSFGDTPLTQSIQANVTVAPERLVPIIEGGSYRVWSDTRDLV

LDGSESYDPNLEDGDQTPLSFHWACVASTQREAGGCALNFGPRGSSTVTIPRERLAAGVEYT

FSLTVWKAGRKEEATNQTVLIRSGRVPIVSLECVSCKAQAVYEVSRSSYVYLEGRCLNCSSGS

KRGRWAARTFSNKTLVLDETTTSTGSAGMRLVLRRGVLRDGEGYTFTLTVLGRSGEEEGCA

SIRLSPNRPPLGGSCRLFPLGAVHALTTKVHFECTGWHDAEDAGAPLVYALLLRRCRQGHCE

EFCVYKGSLSSYGAVLPPGFRPHFEVGLAVVVQDQLGAAVVALNRSLAITLPEPNGSATGLT

VWLHGLTASVLPGLLRQADPQHVIEYSLALVTVLNEYERALDVAAEPKHERQHRAQIRKNIT

ETLVSLRVHTVDDIQQIAAALAQCMGPSRELVCRSCLKQTLHKLEAMMLILQAETTAGTVTP

TAIGDSILNITGDLIHLASSDVRAPQPSELGAESPSRMVASQAYNLTSALMRILMRSRVLNEEP

LTLAGEEIVAQGKRSDPRSLLCYGGAPGPGCHFSIPEAFSGALANLSDVVQLIFLVDSNPFPFG

YISNYTVSTKVASMAFQTQAGAQIPIERLASERAITVKVPNNSDWAARGHRSSANSANSVVV

QPQASVGAVVTLDSSNPAAGLHLQLNYTLLDGHYLSEEPEPYLAVYLHSEPRPNEHNCSASR

RIRPESLQGADHRPYTFFISPGSRDPAGSYHLNLSSHFRWSALQVSVGLYTSLCQYFSEEDMV

WRTEGLLPLEETSPRQAVCLTRHLTAFGASLFVPPSHVRFVFPEPTADVNYIVMLTCAVCLVT

YMVMAAILHKLDQLDASRGRAIPFCGQRGRFKYEILVKTGWGRGSGTTAHVGIMLYGVDSR

SGHRHLDGDRAFHRNSLDIFRIATPHSLGSVWKIRVWHDNKGLSPAWFLQHVIVRDLQTARS

AFFLVNDWLSVETEANGGLVEKEVLAASDAALLRFRRLLVAELQRGFFDKHIWLSIWDRPPR

SRFTRIQRATCCVLLICLFLGANAVWYGAVGDSAYSTGHVSRLSPLSVDTVAVGLVSSVVVY

PVYLAILFLFRMSRSKVAGSPSPTPAGQQVLDIDSCLDSSVLDSSFLTFSGLHAEAFVGQMKS

DLFLDDSKSLVCWPSGEGTLSWPDLLSDPSIVGSNLRQLARGQAGHGLGPEEDGFSLASPYSP

AKSFSASDEDLIQQVLAEGVSSPAPTQDTHMETDLLSSLSSTPGEKTETLALQRLGELGPPSPG

LNWEQPQAARLSRTGLVEGLRKRLLPAWCASLAHGLSLLLVAVAVAVSGWVGASFPPGVS

VAWLLSSSASFLASFLGWEPLKVLLEALYFSLVAKRLHPDEDDTLVESPAVTPVSARVPRVRP

PHGFALFLAKEEARKVKRLHGMLRSLLVYMLFLLVTLLASYGDASCHGHAYRLQSAIKQEL

HSRAFLAITRSEELWPWMAHVLLPYVHGNQSSPELGPPRLRQVRLQEALYPDPPGPRVHTCS

AAGGFSTSDYDVGWESPHNGSGTWAYSAPDLLGAWSWGSCAVYDSGGYVQELGLSLEESR

DRLRFLQLHNWLDNRSRAVFLELTRYSPAVGLHAAVTLRLEFPAAGRALAALSVRPFALRRL

SAGLSLPLLTSVCLLLFAVHFAVAEARTWHREGRWRVLRLGAWARWLLVALTAATALVRL

AQLGAADRQWTRFVRGRPRRFTSFDQVAQLSSAARGLAASLLFLLLVKAAQQLRFVRQWSV

FGKTLCRALPELLGVTLGLVVLGVAYAQLAILLVSSCVDSLWSVAQALLVLCPGTGLSTLCP

AESWHLSPLLCVGLWALRLWGALRLGAVILRWRYHALRGELYRPAWEPQDYEMVELFLRR

LRLWMGLSKVKEFRHKVRFEGMEPLPSRSSRGSKVSPDVPPPSAGSDASHPSTSSSQLDGLSV

SLGRLGTRCEPEPSRLQAVFEALLTQFDRLNQATEDVYQLEQQLHSLQGRRSSRAPAGSSRGP

SPGLRPALPSRLARASRGVDLATGPSRTPLRAKNKVHPSST polycystin-2 (PKD2), NCBI ref NP_000288.1, human, 968 aa,

SEQ ID NO: 12

MVNSSRVQPQQPGDAKRPPAPRAPDPGRLMAGCAAVGASLAAPGGLCEQRGLEIEMQRIRQ

AAARDPPAGAAASPSPPLSSCSRQAWSRDNPGFEAEEEEEEVEGEEGGMVVEMDVEWRPGS

-continued

RRSAASSAVSSVGARSRGLGGYHGAGHPSGRRRRREDQGPPCPSPVGGGDPLHRHLPLEGQP

PRVAWAERLVRGLRGLWGTRLMEESSTNREKYLKSVLRELVTYLLFLIVLCILTYGMMSSNV

YYYTRMMSQLFLDTPVSKTEKTNFKTLSSMEDFWKFTEGSLLDGLYWKMQPSNQTEADNRS

FIFYENLLLGVPRIRQLRVRNGSCSIPQDLRDEIKECYDVYSVSSEDRAPFGPRNGTAWIYTSE

KDLNGSSHWGIIATYSGAGYYLDLSRTREETAAQVASLKKNVWLDRGTRATFIDFSVYNANI

NLFCVVRLLVEFPATGGVIPSWQFQPLKLIRYVTTFDFFLAACEIIFCFFIFYYVVEEILEIRIHK

LHYFRSFWNCLDVVIVVLSVVAIGINIYRTSNVEVLLQFLEDQNTFPNFEHLAYWQIQFNNIA

AVTVFFVWIKLFKFINFNRTMSQLSTTMSRCAKDLFGFAIMFFIIFLAYAQLAYLVFGTQVDD

FSTFQECIFTQFRIILGDINFAEIEEANRVLGPIYFTTFVFFMFFILLNMFLAIINDTYSEVKSDLA

QQKAEMELSDLIRKGYHKALVKLKLKKNTVDDISESLRQGGGKLNFDELRQDLKGKGHTDA

EIEAIFTKYDQDGDQELTEHEHQQMRDDLEKEREDLDLDHSSLPRPMSSRSFPRSLDDSEEDD

DEDSGHSSRRRGSISSGVSYEEFQVLVRRVDRMEHSIGSIVSKIDAVIVKLEIMERAKLKRREV

LGRLLDGVAEDERLGRDSEIHREQMERLVREELERWESDDAASQISHGLGTPVGLNGQPRPR

SSRPSSSQSTEGMEGAGGNGSSNVHV

In some embodiments, the transgene comprises SEQ ID NO: 13, or a nucleic acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 13, which maintains the same function when expressed as a protein (e.g., cleaving glucose residues from immature glycoproteins), or a functional fragment thereof, or a codon-optimized version of the nucleic acid.

Glucosidase II Alpha Subunit (GANAB), also known as: G2AN, GIIA, PKD3, GLUII, GIIalpha; positions 15-2573 of NCBI ref NM_001278192.2, CCDS60818.1, human, 2559 nucleotides (nt),

SEQ ID NO: 13

ATGGCGGCGGTAGCGGCAGTGGCGGCGCGTAGGAGGCGGCTTTCTGTCTCTGGTCGTGA

TGAGAACAGTGTGGAGTTAACCATGGCTGAGGGACCCTACAAGATCATCTTGACAGCAC

GGCCATTCCGCCTTGACCTACTAGAGGACCGAAGTCTTTTGCTTAGTGTCAATGCCCGAG

GACTCTTGGAGTTTGAGCATCAGAGGGCCCCTAGGGTCTCTTTCTCGGATAAGGTTAATC

TCACGCTTGGTAGCATATGGGATAAGATCAAGAACCTTTTCTCTAGGCAAGGATCAAAA

GACCCAGCTGAGGGCGATGGGGCCCAGCCTGAGGAAACACCCAGGGATGGCGACAAGC

CAGAGGAGACTCAGGGGAAGGCAGAGAAAGATGAGCCAGGAGCCTGGGAGGAGACATT

CAAAACTCACTCTGACAGCAAGCCGTATGGCCCCATGTCTGTGGGTTTGGACTTCTCTCT

GCCAGGCATGGAGCATGTCTATGGGATCCCTGAGCATGCAGACAACCTGAGGCTGAAGG

TCACTGAGGGTGGGGAGCCATATCGCCTCTACAATTTGGATGTGTTCCAGTATGAGCTGT

ACAACCCAATGGCCTTGTATGGGTCTGTGCCTGTGCTCCTGGCACACAACCCTCATCGCG

ACTTGGGCATCTTCTGGCTCAATGCTGCAGAGACCTGGGTTGATATATCTTCCAACACTG

CCGGGAAGACCCTGTTTGGGAAGATGATGGACTACCTGCAGGGCTCTGGGGAGACCCCA

CAGACAGATGTTCGCTGGATGTCAGAGACTGGCATCATTGACGTCTTCCTGCTGCTGGGG

CCCTCCATCTCTGATGTTTTCCGGCAATATGCTAGTCTCACAGGAACCCAGGCGTTGCCC

CCACTCTTCTCCCTCGGCTACCACCAGAGCCGTTGGAACTACCGGGACGAGGCTGATGTG

CTGGAAGTGGATCAGGGCTTTGATGATCACAACCTGCCCTGTGATGTCATCTGGCTAGAC

ATTGAACATGCTGATGGCAAGCGGTATTTCACCTGGGACCCCAGTCGCTTCCCTCAGCCC

CGCACCATGCTTGAGCGCTTGGCTTCTAAGAGGCGGAAGCTGGTGGCCATCGTAGACCCC

CACATCAAGGTGGACTCCGGCTACCGAGTTCACGAGGAGCTGCGGAACCTGGGGCTGTA

-continued

TGTTAAAACCCGGGATGGCTCTGACTATGAGGGCTGGTGCTGGCCAGGCTCAGCTGGTTA

CCCTGACTTCACTAATCCCACGATGAGGGCCTGGTGGGCTAACATGTTCAGCTATGACAA

TTATGAGGGCTCAGCTCCCAACCTCTTTGTCTGGAATGACATGAACGAACCATCTGTGTT

CAATGGTCCTGAGGTCACCATGCTCAAGGATGCCCAGCATTATGGGGGCTGGGAGCACC

GGGATGTGCATAACATCTATGGCCTTTATGTGCACATGGCGACTGCTGATGGGCTGAGAC

AGCGCTCTGGGGGCATGGAACGCCCCTTTGTCCTGGCCAGGGCCTTCTTCGCTGGCTCCC

AGCGCTTTGGAGCCGTGTGGACAGGGGACAACACTGCCGAGTGGGACCATTTGAAGATC

TCTATTCCTATGTGTCTCAGCTTGGGGCTGGTGGGACTTTCCTTCTGTGGGGCGGATGTGG

GTGGCTTCTTCAAAAACCCAGAGCCAGAGCTGCTTGTGCGCTGGTACCAGATGGGTGCTT

ACCAGCCATTCTTCCGGGCACATGCCCACTTGGACACTGGGCGACGAGAGCCATGGCTGT

TACCATCTCAGCACAATGATATAATCCGAGATGCCTTGGGCCAGCGATATTCTTTGCTGC

CCTTCTGGTACACCCTCTTATATCAGGCCCATCGGGAAGGCATTCCTGTCATGAGGCCCC

TGTGGGTGCAGTACCCTCAGGATGTGACTACCTTCAATATAGATGATCAGTACTTGCTTG

GGGATGCGTTGCTGGTTCACCCTGTATCAGACTCTGGAGCCCATGGTGTCCAGGTCTATC

TGCCTGGCCAAGGGGAGGTGTGGTATGACATTCAAAGCTACCAGAAGCATCATGGTCCC

CAGACCCTGTACCTGCCTGTAACTCTAAGCAGTATCCCTGTGTTCCAGCGTGGAGGGACA

ATCGTGCCTCGATGGATGCGAGTGCGGCGGTCTTCAGAATGTATGAAGGATGACCCCATC

ACTCTCTTTGTTGCACTTAGCCCTCAGGGTACAGCTCAAGGAGAGCTCTTTCTGGATGAT

GGGCACACGTTCAACTATCAGACTCGCCAAGAGTTCCTGCTGCGTCGATTCTCATTCTCT

GGCAACACCCTTGTCTCCAGCTCAGCAGACCCTGAAGGACACTTTGAGACACCAATCTGG

ATTGAGCGGGTGGTGATAATAGGGGCTGGAAAGCCAGCAGCTGTGGTACTCCAGACAAA

AGGATCTCCAGAAAGCCGCCTGTCCTTCCAGCATGACCCTGAGACCTCTGTGTTGGTCCT

GCGCAAGCCTGGCATCAATGTGGCATCTGATTGGAGTATTCACCTGCGATAA

In some embodiments, the transgene encodes for a polypeptide comprising SEQ ID NO: 14, or an amino acid sequence that is at least 70%, at least 75%, at least 80%, at least 85%, at least 90%, at least 90%, at least 91%, at least 92%, at least 93%, at least 94%, at least 95%, at least 96%, at least 97%, at least 98%, or at least 99% identical to the sequence of SEQ ID NO: 14, which maintains the same function (e.g., cleaving glucose residues from immature glycoproteins), or a functional fragment thereof.

glucosidase II alpha subunit (GANAB), NCBI ref NP_001265121.1,
human, 852 aa,

SEQ ID NO: 14

MAAVAAVAARRRRLSVSGRDENSVELTMAEGPYKIILTARPFRLDLLEDRSLLLSVNARGLL

EFEHQRAPRVSFSDKVNLTLGSIWDKIKNLFSRQGSKDPAEGDGAQPEETPRDGDKPEETQG

KAEKDEPGAWEETFKTHSDSKPYGPMSVGLDFSLPGMEHVYGIPEHADNLRLKVTEGGEPY

RLYNLDVFQYELYNPMALYGSVPVLLAHNPHRDLGIFWLNAAETWVDISSNTAGKTLFGKM

MDYLQGSGETPQTDVRWMSETGIIDVFLLLGPSISDVFRQYASLTGTQALPPLFSLGYHQSRW

NYRDEADVLEVDQGFDDHNLPCDVIWLDIEHADGKRYFTWDPSRFPQPRTMLERLASKRRK

LVAIVDPHIKVDSGYRVHEELRNLGLYVKTRDGSDYEGWCWPGSAGYPDFTNPTMRAWWA

NMFSYDNYEGSAPNLFVWNDMNEPSVFNGPEVTMLKDAQHYGGWEHRDVHNIYGLYVHM

ATADGLRQRSGGMERPFVLARAFFAGSQRFGAVWTGDNTAEWDHLKISIPMCLSLGLVGLS

-continued

```
FCGADVGGFFKNPEPELLVRWYQMGAYQPFFRAHAHLDTGRREPWLLPSQHNDIIRDALGQ

RYSLLPFWYTLLYQAHREGIPVMRPLWVQYPQDVTTFNIDDQYLLGDALLVHPVSDSGAHG

VQVYLPGQGEVWYDIQSYQKHHGPQTLYLPVTLSSIPVFQRGGTIVPRWMRVRRSSECMKD

DPITLFVALSPQGTAQGELFLDDGHTFNYQTRQEFLLRRFSFSGNTLVSSSADPEGHFETPIWIE

RVVIIGAGKPAAVVLQTKGSPESRLSFQHDPETSVLVLRKPGINVASDWSIHLR
```

In some embodiments, the transgene encodes a human protein. In some embodiments, the transgene encodes a mammalian protein. In some embodiments, the transgene encodes protein from the same species as the subject. In some embodiments, the transgene encodes protein from a different species than the subject.

In some embodiments, the transgene comprises an inhibitor of a gene or protein, such that when expression of such a gene or protein is reduced, such reduction is effective to treat a kidney-associated disorder. In some embodiments, the transgene comprises an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD). In some embodiments, the inhibitor is an inhibitory nucleic acid. In some embodiments, the inhibitory nucleic acid is selected from the group consisting of: miRNA, siRNA, shRNA, RNAi, anti-sense oligonucleotide, crRNA, and gRNA. In some embodiments, the inhibitor is a protein that inhibits a gene or protein selected from the group consisting of: REN, SCNN1A, SCNN1B, and UMOD.

In some embodiments, the rAAV genome comprises at least one transgene. In some embodiments, the rAAV genome comprises 1, 2, 3, 4, 5, or more transgenes. Such multiple transgenes can be expressed using the same or different promoters. In some embodiments, the rAAV genome comprises any combination of (a) a reporter gene, (b) a gene that when expressed in the subject is effective to treat a kidney-associated disorder, and/or (c) an inhibitor of a gene or protein such that inhibition is effective to treat a kidney-associated disorder. In some embodiments, the rAAV genome comprises any combination of (a) a reporter gene and (b) a gene that when expressed in the subject is effective to treat a kidney-associated disorder. In some embodiments, the rAAV genome comprises any combination of (b) a gene that when expressed in the subject is effective to treat a kidney-associated disorder and (c) an inhibitor of a gene or protein such that inhibition is effective to treat a kidney-associated disorder. In some embodiments, the rAAV genome comprises any combination of (a) a reporter gene and (c) an inhibitor of a gene or protein such that inhibition is effective to treat a kidney-associated disorder. In some embodiments, the rAAV genome comprises any combination of (a) a reporter gene, (b) a gene that when expressed in the subject is effective to treat a kidney-associated disorder, and (c) an inhibitor of a gene or protein such that inhibition is effective to treat a kidney-associated disorder.

In some embodiments, the rAAV genome further comprises at least one inverted terminal repeat (ITR). Generally, ITR sequences are about 145 bp in length. Preferably, substantially the entire sequences encoding the ITRs are used in the rAAV genome, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV3a, AAV3b, AAV4, AAV5, AAV6, AAV7, AAV8, AAV9, AAV10, AAV11, AAVrh8, AAVrh10, and variants thereof. In some embodiments, the isolated nucleic acid comprises a region (e.g., a first region) encoding an AAV2 ITR. In some embodiments, the isolated nucleic acid comprises a region (e.g., a first region) encoding an AAV9 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV3a, AAV3b, AAV4, AAV5, AAV6, AAV7, AAV8, AAV9, AAV10, AAV11, AAVrh8, AAVrh10, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) Molecular Therapy 16(10): 1648-1656.

Kidney-Associated Disorders

In some embodiments, the methods described herein relate to treating a subject having or diagnosed as having a kidney-associated disorder. In some aspects, the method of treating a kidney-associated disorder in a subject in need thereof comprises administering a recombinant adeno-associated virus (rAAV) to the subject by performing a retrograde ureter administration method as described further herein. Subjects having a kidney-associated disorder can be identified by a physician using current methods of diagnosing the kidney-associated disorder. Symptoms and/or complications of the kidney-associated disorder which characterize these conditions and aid in diagnosis are well known in the art and include but are not limited to, nausea and vomiting, muscle cramps, loss of appetite, swelling via feet and ankles, dry and/or itchy skin, shortness of breath, trouble sleeping, urinating either too much or too little, metallic taste in mouth, chills, etc. Tests that may aid in a diagnosis of a kidney-associated disorder include, but are not limited to, a blood test (e.g., eGFR; serum creatinine test; blood urea nitrogen (BUN) test; urine test; kidney ultrasound; kidney biopsy; and the like. A family history of a kidney-associated disorder, or exposure to risk factors for a kidney-associated disorder (e.g., diabetes; high blood pressure; cardiovascular disease; smoking; obesity; being black, Native American or Asian American; abnormal kidney structure) can also aid in determining if a subject is likely to have a kidney-associated disorder or in making a diagnosis of a kidney-associated disorder.

In some embodiments, the kidney-associated disorder is selected from the group consisting of: autosomal dominant polycystic kidney disease (ADPKD); Alport syndrome; autosomal dominant tubulointerstitial kidney disease (ADTKD); medullary cystic kidney disease; nephronophthisis; Bartter Syndrome; Von Hippel-Lindau syndrome; Gitelman syndrome; congenital nephrotic syndrome; primary hyperoxaluria; Dent disease; Thin Basement Membrane Nephropathy; cystinuria; Liddle syndrome; Papillorenal syndrome; and cystinosis; see e.g., Rubin et al. 2020, "Improving molecular therapy in the kidney," Mol Diagn Ther. 24(4): 375-396; the contents of which are incorporated herein by reference in their entirety.

In some embodiments, the kidney-associated disorder is selected from the group consisting of: Apparent mineralocorticoid excess, Autosomal dominant hypocalcemia, Autosomal dominant hypomagnesemia, Bartter type 1, Bartter type 2, Bartter type 3, Bartter type 4a, Bartter type 4b, Bartter type 5, Congenital adrenal hyperplasia type 1, Congenital adrenal hyperplasia type 2, Congenital adrenal hyperplasia type 4, Congenital adrenal hyperplasia type 5, Cystinuria A, Cystinuria B, Dent disease type 1, Dent disease type 2/Lowe syndrome, Dicarboxylic aminoaciduria, Distal RTA, EAST/SeSAME syndrome, Fanconi Bickel syndrome, Fanconi renotubular syndrome 1, Fanconi renotubular syndrome 2, Fanconi renotubular syndrome 3, Fanconi renotubular syndrome 4, Gitelman syndrome, Glucocorticoid remediable aldosteronism, Hartnup disorder, Hereditary hypophosphatemic rickets with hypercalciuria, HNF1B-related kidney disease, Hyperphenylalaninemia BH4-deficient, Hypomagnesemia type 1/hypomagnesemia with secondary hypocalcemia, Hypomagnesemia type 2, Hypomagnesemia type 3/familial hypomagnesemia with hypercalciuria and nephrocalcinosis, Hypomagnesemia type 4, Hypomagnesemia type 5/familial hypomagnesemia with hypercalciuria and nephrocalcinosis, Hypomagnesemia, seizures, and mental retardation type 1, Hypomagnesemia, seizures, and mental retardation type 2, Iminoglycinuria, Kenny-Caffey syndrome type 2, Liddle syndrome, Lysinuric protein intolerance, Neonatal inflammatory skin and bowel disease type 2, Nephrogenic diabetes insipidus, Nephrogenic syndrome of inappropriate antidiuresis, Pseudohypoaldosteronism type 1, Pseudohypoaldosteronism type 1A, Pseudohypoaldosteronism type 2b, Pseudohypoaldosteronism type 2c, Pseudohypoaldosteronism type 2d, Pseudohypoaldosteronism type 2e, Renal tubular acidosis type 3, and X-linked hypophosphatemic rickets, see e.g., Downie et al. 2020, "Inherited tubulopathies of the kidney," Clin J Am Soc Nephrol. 16(4): 620-630, the contents of which are incorporated herein by reference in their entirety.

In some embodiments, the methods described herein comprise administering an effective amount of compositions described herein, e.g. a solution or pharmaceutical composition comprising an rAAV, to a subject in order to alleviate a symptom of a kidney-associated disorder. As used herein, "alleviating a symptom of a kidney-associated disorder" is ameliorating any condition or symptom associated with the kidney-associated disorder. As compared with an equivalent untreated control, such reduction is by at least 5%, 10%, 20%, 40%, 50%, 60%, 80%, 90%, 95%, 99% or more as measured by any standard technique.

For example, for Cystinuria, the subjects can be evaluated for a decreased incidence of Cystinuria symptoms (e.g., crystalluria (crystals in urine); aminoaciduria (urine containing abnormally high levels of amino acids, e.g., cystine); pain in the side or back (e.g., often on one side); pain while urinating; blood in the urine; sharp pain in the side or back; pain near the groin, pelvis, or abdomen; nausea and vomiting; flank pain; loin pain; recurrent abdominal pain; recurrent urinary tract infections; and/or fever), any of which can indicate rAAV transduction efficiency in the kidneys sufficient to treat Cystinuria.

As another example, for polycystic kidney disease (e.g., ADPKD), the subjects can be evaluated for a decreased incidence of PKD symptoms (e.g., abdominal pain or tenderness, blood in the urine, excessive urination at night, flank pain on one or both sides, drowsiness, joint pain, nail abnormalities, high blood pressure, back or side pain, a feeling of fullness in the abdomen, enlarged liver, heart murmurs, and/or growths in the kidneys or abdomen), any of which can indicate rAAV transduction efficiency in the kidneys sufficient to treat polycystic kidney disease (e.g., ADPKD).

The term "effective amount" as used herein refers to the amount of a solution or pharmaceutical composition comprising an rAAV needed to improve or alleviate at least one or more symptom of the kidney-associated disorder, and relates to a sufficient amount of the solution or pharmacological composition to provide the desired effect. The terms "therapeutically effective amount" or "pharmaceutically effective amount" therefore refers to an amount of a solution or pharmaceutical composition comprising an rAAV that is sufficient to provide a particular anti-kidney-associated disorder effect when administered to atypical subject. An effective amount as used herein, in various contexts, would also include an amount sufficient to delay the development of a symptom of the disorder, alter the course of a symptom (for example but not limited to, slowing the progression of a symptom of the disorder), or reverse a symptom of the disorder. Thus, it is not generally practicable to specify an exact "effective amount." However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the minimal effective dose and/or maximal tolerated dose. The dosage can vary depending upon the dosage form employed and the protocol of administration utilized. A therapeutically effective dose can be estimated initially from cell culture assays. Also, a dose can be formulated in animal models to achieve a dosage range between the minimal effective dose and the maximal tolerated dose. The effects of any particular dosage can be monitored by a suitable bioassay. The dosage can be determined by a physician and adjusted, as necessary, to suit observed effects of the treatment.

In some embodiments, the subject is a human. In some embodiments, the subject is a non-human primate. In some embodiments, the subject is a non-human mammal. In some embodiments, the subject is a pig, which is a relevant animal model for human translation due to its anatomical and physiological similarities to humans. In some embodiments, the subject is any animal in need of a treatment of a kidney-associated disorder.

In some embodiments, the kidney-associated disorder is treated when the rAAV transduces a cell in the kidney, leading to the expression of a transgene and/or an inhibitor of a gene or protein by the kidney cell, which is effective to treat the kidney-associated disorder. In order to transduce cells, an rAAV vector enters the kidney cell and delivers its single-stranded DNA genome to the nucleus, where the genome becomes double-stranded before transcription and integration into the subject's cell genome. Transduction by the rAAV of the kidney cell can be detected by a variety of methods, including but not limited to, sequencing for rAAV genomes (or a bar code therein) or expression of an rAAV-delivered reporter gene or transgene (e.g., RNA or protein-based assays such as RT-qPCR, ELISA, histological staining, or flow cytometry). In some embodiments, the rAAV transduction can be detected using anti-rAAV serology (e.g., in the urine or blood) or occurrence of symptoms related to a kidney-associated disorder (for which the rAAV was administered to treat).

In some embodiments, the rAAV transduces nephrons of the kidney. In some embodiments, the rAAV transduces a nephron portion selected from the group consisting of: a glomerulus, a glomerular capsule, a proximal convoluted tubule, the loop of Henle, or a distal convoluted tubule of a nephron of the kidney. In some embodiments, the rAAV transduces proximal convoluted tubules of the kidney. In some embodiments, the rAAV transduces collecting ducts of the kidney. In some embodiments, the rAAV transduces proximal convoluted tubules and collecting ducts of the kidney. In some embodiments, the rAAV transduces a kidney tubule selected from the group consisting of: a glomerulus (e.g., a glomerular capsule), a proximal tubule (PT), thin descending limb of the loop of Henle (DL), thin ascending limb of the loop of Henle (AL), thick ascending limb of the loop of Henle (TALH), macula densa (MD), a distal convoluted tubule (DCT), connecting tubule (CNT), or collecting duct (CT) of the kidney.

In some embodiments, the rAAV transduces a kidney cell selected from the group consisting of vasculature cells (e.g., glomerular endothelium); mesangium, smooth muscle cells (SMCs), or juxtaglomerular cells (JGs) (e.g., mesangial cells, SMCs, pericytes, and/or JGs); podocytes (e.g., adult podocytes and/or podocyte progenitors); proximal tubule (PT) cells (e.g., Pan-PT, proximal convoluted tubule, proximal straight tubule, PT progenitors, and/or injured PT); Loop of Henle (LOH), macula densa (MD) cells (e.g., descending thin limb of LOH, ascending thin limb of LOH, thick ascending limb of LOH, and/or macula densa (MD)); distal convoluted tubule (DCT) or connecting tubule (CNT) cells (e.g. DCT1, DCT2, and/or CNT); and/or collecting duct (CD) cells (e.g., CD-principal cells, Pan-CD-intercalated cells, CD-intercalated cells (type A), CD-intercalated cells (type B), and/or CD-transitional cells).

In some embodiments, the rAAV transduces a kidney cell selected from the group consisting of glomerular endothelium, mesangial cells, SMCs, pericytes, JGs, adult podocytes, podocyte progenitors, Pan-PT, proximal convoluted tubule, proximal straight tubule, PT progenitors, injured PT, descending thin limb of LOH, ascending thin limb of LOH, thick ascending limb of LOH, macula densa (MD), DCT1, DCT2, CNT, CD-principal cells, Pan-CD-intercalated cells, CD-intercalated cells (type A), CD-intercalated cells (type B), and/or CD-transitional cells.

In some embodiments, the rAAV transduces a kidney cell selected from the group consisting of vasculature cells, including but not limited to glomerular endothelium (non-limiting examples of glomerular endothelium-specific marker genes include Plat, Emcn, Tsapn7, Mapt, Kdr, Smad6, Ehd3, Lpl, Flt1, Fb/n2, Mgp, Trpv4, Bmx); mesangium/smooth muscle cells (SMCs)/juxtaglomerular cells (JGs), including but not limited to mesangial cells (non-limiting examples of mesangial cell-specific marker genes include Serpine2, Fhl2, Des, Prkca, Art3, Nt5e, Pdgfrb), SMCs (non-limiting examples of SMC-specific marker genes include Tagln, Myh11, Acta2, Gata3, Rergl, Map3k7c1), pericytes (non-limiting examples of pericyte-specific marker genes include Vim, Tagln, Myh11, Pdgfrb), and/or JGs (non-limiting examples of JG-specific marker genes include Reni, Akr1b7, Rgs5); podocytes, including but not limited to adult podocytes (non-limiting examples of adult podocyte-specific marker genes include Nphs1, Nphs2, Synpo, Cdkn1c, Wt1), and/or podocyte progenitors (non-limiting examples of podocyte progenitor-specific marker genes include Wti, Foxc2, Mafb, Efnb2, Foxl1); proximal tubule (PT) cells, including but not limited to Pan-PT (non-limiting examples of Pan-PT-specific marker genes include Slc34a1, Lrp2, Hxyd2, Hrsp12, Acsm1, Acsm2, Cpt1a, Acox3, Slc26a6, Slc9a3, Glud1, Pck1, Aqp8, Hnf4a, Ppara), proximal convoluted tubule (non-limiting examples of proximal convoluted tubule-specific marker genes include Slc5a2, Slc5a12, Adra1a, Slc6a19, Slc7a8, Slc7a9), proximal straight tubule (non-limiting examples of proximal straight tubule-specific marker genes include Atp11a, Slc13a3, Slc16a9, Slc27a2, Slc7a13, Slc22a6 (S2 segment), Slc1a1), PT progenitors (non-limiting examples of PT progenitor-specific marker genes include Notch2, Lgr4), and/or injured PT (non-limiting examples of injured PT-specific marker genes include Havcr1, Krt20, Hspa1a, Vcam1, Dcdc2a, Sema5a); Loop of Henle (LOH)/macula densa (MD) cells, including but not limited to descending thin limb of LOH (non-limiting examples of descending thin limb of LOH-specific marker genes include Fst, Aqp1, Slc14a2, Bst1, Epha7, Cryab, Tshz2, Cald1, Bst1, Lypd2), ascending thin limb of LOH (non-limiting examples of ascending thin limb of LOH-specific marker genes include Epha7, Mx2, Clcnka), thick ascending limb of LOH (non-limiting examples of thick ascending limb of LOH-specific marker genes include Slc12a1, Umod, Tmem207, Foxq1, Cldn10, Ptger3, Kcnj1, Enox1, Thsd4, Mt2, Slc5a3), and/or macula densa (MD) (non-limiting examples of MD-specific marker genes include Enox1, Thsd4, Nos1, Avpr1a); distal convoluted tubule (DCT)/connecting tubule (CNT) cells, including but not limited to DCT1 (non-limiting examples of DCT1-specific marker genes include Pvalb, Slc12a3, Trpm7, Wnk1, Wnk4, Stk39, Calb1, Slc8a1, Egf Trpm6, Cnnm2, Atp1a1, Atp1a2, Atp1a3, Atp1a4, Fxyd2), DCT2 (non-limiting examples of DCT2-specific marker genes include Slc12a3, Trpm7, Wnk1, Wnk4, KlhN3, Stk39, Calb1, Slc8a1, Egf Trpm6, Cnnm2, Atp1a1, Atp1a2, Atp1a3, Atp1a4, Klk1, Trpv5, Trpm6, S100g, Atp2b1, Atp2b4, Scnn1b, Scnn1g, Kcne1, Fxyd2), and/or CNT (non-limiting examples of CNT-specific marker genes include Calb1, Slc8a1, Egf Klk1, Trpv5, Trpm6, S100g, Atp2b1, Scnn1b, Scnn1g, Kcne7); and/or collecting duct (CD) cells, including but not limited to CD-principal cells (non-limiting examples of CD-principal cell-specific marker genes include Scnn1b, Scnn1g, Aqp2, Avpr2, Hsd11b2, Rhbg, Elf5, Fxyd4, Aqp3, Apela, Kcne7, Npnt, Kcnj10), Pan-CD-intercalated cells (non-limiting examples of pan-CD-intercalated cell-specific marker genes include Tcfcp2l1, Foxi, Atp6v1g3, Atp6v0d2, Insr, Atp6v1b1), CD-intercalated cells (type A) (non-limiting examples of CD-intercalated cell (type A)-specific marker genes include Atp4a, Slc4a1, Aqp6, Kit, Adgrf5, Mme), CD-intercalated cells (type B) (non-limiting examples of CD-intercalated cell (type B)-specific marker genes include Slc26a4, Hmx2, Spink8), and/or CD-transitional cells (non-limiting examples of CD-transitional cell-specific marker genes include Agp2, Hsd11b2, Rhbg, Atp6v1g3, Atp6v0d2, Insr, Atp6v1b1, Atp6v1b1, Parm1, Sec23b). See e.g., of Balzer, "How Many Cell Types are in the Kidney and What Do they Do? Annu Rev Physiol. 2022 Feb. 10; 84: 507-531; the contents of which are incorporated herein by reference in their entirety.

In some embodiments, the genome of the rAAV comprises a kidney-specific promoter, which can be operably linked to at least one transgene. As used herein, the term "kidney-specific promoter" refers to a promoter that is activated preferentially in cells of the kidney and/or leads to the expression of genes in kidney cells at level that is increased compared to cells and tissues outside of the kidney. In some embodiments, the kidney-specific promoter activation is increased in kidney cells compared to non-kidney cells (e.g., liver, heart, muscle, brain, lung, eye, joint cells, etc.) at least about 10%, at least about 20%, or at least about 30%, or at least about 40%, or at least about 50%, or at least about 60%, or at least about 70%, or at least about 80%, or at least about 90% increased or up to and including a 100% increase or any increase between 10-100%, or at least about a 2-fold, or at least about a 3-fold, or at least about a 4-fold, or at least about a 5-fold or at least about a 10-fold increase, or any increase between 2-fold and 10-fold, or any increase between 10-fold and 100-fold or greater. In some embodiments, the kidney-specific promoter is operably linked to at least one transgene, e.g., (a) a reporter gene, (b) a gene that when expressed in the subject is effective to treat a kidney-associated disorder, and/or (c) an inhibitor of a gene or protein such that inhibition is effective to treat a kidney-associated disorder.

In some embodiments, the genome of the rAAV comprises a promoter (and/or other regulatory element, such as an enhancer) specific to the proximal convoluted tubule. In some embodiments, the genome of the rAAV comprises a promoter specific to the collecting duct. In some embodiments, the genome of the rAAV comprises a promoter specific to the proximal convoluted tubule and the collecting duct.

In some embodiments, the kidney-specific promoter is for a gene that is naturally expressed specifically in kidney cells or tissues. In some embodiments, the kidney-specific promoter is selected from the group consisting of: the kidney-specific cadherin (KSPC) gene promoter; the Na+/glucose co-transporter (SGLT2) gene promoter; the sodium potassium, 2 chloride co-transporter (NKCC2) gene promoter; and the E-cadherin (ECAD) gene promoter. The KSPC gene promoter specifically activates expression in the entire nephron. The SGLT2 gene promoter specifically activates expression in the S1 and S2 segments of the proximal tubule. The NKCC2 gene promoter specifically activates expression in the thick ascending limb of Henle's loop (TALH). The ECAD gene promoter specifically activates expression in the collecting duct (CD). See e.g., Asico et al. "Nephron segment-specific gene expression using AAV vectors," Biochem Biophys Res Commun. 2018 Feb. 26, 497(1): 19-24; the contents of which are incorporated herein by reference in their entirety.

In some embodiments, the kidney-specific promoter is a synthetic promoter. In some embodiments, the synthetic promoter comprises portions of at least one natural kidney-specific promoter (e.g., KSPC, SGLT2, NKCC2, or ECAD gene promoters). In some embodiments, the synthetic promoter comprises synthetic sequences. In some embodiments, the synthetic promoter comprises portions of at least one natural kidney-specific promoter (e.g., KSPC, SGLT2, NKCC2, or ECAD gene promoters) and synthetic sequences. Such a synthetic promoter sequence can be designed to be selectively active in proximal tubules, distal convoluted tubules, and/or collecting ducts of the kidney. Promoter sequences can be tested in vitro for specific activation (e.g., expression of a reporter protein) in kidney cells, e.g., using kidney (e.g., 293 cells, renal proximal tubular epithelial cells (PTEC) cells, Madin-Darby Canine Kidney (MDCK) cells, primary kidney cells, etc.) v. non-kidney cells (e.g., liver, heart, muscle, brain, lung, eye, joint cells, etc.). Promoter sequences that show increased activation in kidney cells compared to non-kidney cells can be further screened in animal models, such as mice, pigs, or non-human primates. Specific activation of the promoter sequence in vivo can be evaluated using co-staining for tissue markers and reporter reporters (e.g., histology, flow cytometry, etc.).

In some embodiments, the genome of the rAAV comprises a ubiquitous promoter, which can be operably linked to at least one transgene. As used herein, the term "ubiquitous promoter" refers to a promoter that is activated in all cells of the subject, including both kidney and non-kidney cells. In some embodiments, the ubiquitous promoter is selected from the group consisting of: cytomegalovirus (CMV), beta actin (β-Act), chicken beta-actin promoter (CAG), elongation factor-1 alpha (EF1), Early Growth Response 1 (EGR1), Eukaryotic Initiation Factor 4A1 (eIF4A1), Ferritin Heavy Chain (FerH), Ferritin Light Chain (FerL), Glyceraldehyde 3-Phosphate Dehydrogenase (GAPDH), Glucose-Regulated Protein 78 (GRP78), Glucose-Regulated Protein 94 (GRP94), Heat Shock Protein 70 (HSP70), Beta-Kinesin (O-Kin), Phosphoglycerate Kinase 1 (PGK-1), Rosa26, or Ubiquitin B promoters, or composites or combinations thereof.

As used herein, a coding sequence (e.g., of at least one transgene) and regulatory sequences (e.g., a kidney-specific promoter) are said to be "operably" or "operatively" linked or joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the polypeptides described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

In some embodiments, one or more of the recombinantly expressed transgene(s) can be integrated into the genome of the cell. Such genome integration can allow for stable expression of a nucleic acid or protein effective to treat the kidney-associated disorder.

Subsequent Administration Methods

Described herein are methods comprising subsequent administration or re-administration of rAAV (comprising a capsid of the same or different serotype) after a period of time. Such a re-administration can be performed because at least the first administration does not elicit an immune response to the rAAV in the kidney.

In some embodiments, circulating serum of the subject does not neutralize the rAAV upon administration or re-administration. In some embodiments, the subject has antibodies that neutralize the rAAV to be administered in the circulating serum. In some embodiments, the circulating serum antibodies do not neutralize the rAAV in the kidney upon administration. In some embodiments, the subject is seropositive for the rAAV prior to the administration of the solution comprising the rAAV. In some embodiments, neutralizing antibodies are not present in the kidney fluids and/or urine, even if neutralizing antibodies are circulating in the serum. In some embodiments, a subsequent administration of an rAAV as described herein can be performed without resulting in a substantial inflammatory response in the kidney. In some embodiments, the subsequent administration is at least one day later. In some embodiments, the subsequent administration is at least one month later.

In one aspect, described herein is a method of treating a kidney disorder in a subject in need thereof, the method comprising: administering to a kidney of the subject a first recombinant adeno-associated virus (rAAV) encoding a transgene that is therapeutic toward the kidney disorder; and subsequent to administering the first rAAV, administering to the kidney or a different kidney of the subject a second rAAV encoding the transgene or a different transgene that is therapeutic toward to the kidney disorder. In some embodiments, the first rAAV and the second rAAV are cross seroreactive. As used herein, the term “cross seroreactive” refers to rAAVs that bind to the same antibody. In some embodiments, the subject does not elicit a significant immune response to the second rAAV in the kidney. As used herein, the term “a significant immune response” refers to an immune response to the second rAAV that results in decreased efficacy or transduction of the first and/or second rAAV.

In one aspect, described herein is a method of treating a kidney disorder in a subject in need thereof, the subject being seropositive for a recombinant adeno-associated virus (rAAV) therapeutic, the method comprising: administering to a kidney of the subject the rAAV therapeutic encoding a transgene that is therapeutic toward the kidney disorder. In some embodiments, the subject does not elicit a significant adverse immune response to the rAAV therapeutic in the kidney.

In some embodiments, the first and second rAAVs are administered by an administration method comprising: guiding a catheter through the subject’s urethra, bladder, and ureter; and administering a solution comprising the first or second rAAV to the renal pelvis of the kidney at a volume of from about 0.13 mL/kg to about 0.33 mL/kg, the kg being the weight of the subject.

In some embodiments, the first and second rAAVs are administered by an administration method comprising: (a) blocking a renal blood vessel of the kidney selected from the group consisting of a renal artery, a renal vein, and a combination thereof; (b) administering a volume of a solution comprising the first or second rAAV into a ureter of the kidney or a second ureter to the different kidney in a retrograde route, wherein the volume is from about 0.13 mL/kg to about 0.33 mL/kg, the kg being the weight of the subject; and (c) unblocking renal blood vessel after a period of time of from about 10 minutes to about 60 minutes subsequent to the blocking and/or after administering the solution comprising the first and/or second rAAV.

In some embodiments, the first and second rAAVs are administered by an administration method comprising: (a) isolating the kidney from systemic circulation; (b) administering a volume of a solution comprising the first or second rAAV into a ureter of the kidney or a second ureter to the different kidney in a retrograde route, wherein the volume is from about 0.13 mL/kg to about 0.33 mL/kg, the kg being the weight of the subject; and (c) re-establishing the kidney into systemic circulation after a period of time of from about 10 minutes to about 60 minutes subsequent to the isolating.

In some embodiments, at least one solution comprising the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure of from about 25 cm $H_2O$ to about 55 cm $H_2O$. In some embodiments, at least one solution comprising the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure of from about 27 cm $H_2O$ to about 80 cm $H_2O$. In some embodiments, at least one solution comprising the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure of from about 27 cm $H_2O$ to about 41 cm $H_2O$. In some embodiments, at least one solution comprising the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure of from about 41 cm $H_2O$ to about 68 cm $H_2O$. In some embodiments, at least one solution comprising the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure of from about 68 cm $H_2O$ to about 80 cm $H_2O$.

In some embodiments, at least one solution comprising the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure of about at least 20 cm $H_2O$, at least 25 cm $H_2O$, at least 30 cm $H_2O$, at least 35 cm $H_2O$, at least 40 cm $H_2O$, at least 45 cm $H_2O$, at least 50 cm $H_2O$, at least 55 cm $H_2O$, at least 60 cm $H_2O$, at least 65 cm $H_2O$, at least 70 cm $H_2O$, or at least 75 cm $H_2O$. In some embodiments, the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure of about at most 25 cm $H_2O$, at most 30 cm $H_2O$, at most 35 cm $H_2O$, at most 40 cm $H_2O$, at most 45 cm $H_2O$, at most 50 cm $H_2O$, at most 55 cm $H_2O$, at most 60 cm $H_2O$, at most 65 cm $H_2O$, at most 70 cm $H_2O$, at most 75 cm $H_2O$, or at most 80 cm $H_2O$. In some embodiments, at least one solution comprising the first rAAV and/or second rAAV (and/or third rAAV, fourth rAAV, fifth rAAV, sixth rAAV, seventh rAAV, eighth rAAV, ninth rAAV, tenth rAAV, or more) is administered to the kidney at an intra-renal pressure range of about 20-30 cm $H_2O$, 25-35 cm $H_2O$, 30-40 cm $H_2O$, 35-45 cm $H_2O$, 40-50 cm $H_2O$, 45-55 cm $H_2O$, 50-60 cm $H_2O$, 55-65 cm $H_2O$, 60-70 cm $H_2O$, 65-75 cm $H_2O$, 70-80 cm $H_2O$, 20-40 cm $H_2O$, 20-50 cm $H_2O$, 20-60 cm $H_2O$, 20-70 cm $H_2O$, 20-80 cm $H_2O$, 25-85 cm $H_2O$, 30-80 cm $H_2O$, 40-80 cm $H_2O$, 50-80 cm $H_2O$, or 60-80 cm $H_2O$. It is understood that each of the individual intrarenal pressures described herein can be used to define lower and upper values of an intrarenal pressure range.

In some embodiments, the administration method results in at least about 15% of the nephrons in the kidney being transduced with the first and/or second rAAV. In some embodiments, the method results in the transduction of about at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or more of the nephrons in the kidney with the first and/or second rAAV.

In one aspect, described herein is a method of transducing at least about 15% of the nephrons in a kidney of a subject with a recombinant adeno-associated virus (rAAV), the method comprising: (a) blocking a renal blood vessel selected from the group consisting of a renal artery, a renal vein, and a combination thereof of the kidney; (b) administering a volume of a first solution comprising a first rAAV into a ureter of the kidney in a retrograde route, wherein the volume of the first solution is from about 0.13 mL/kg to about 0.33 mL/kg, the kg being the weight of the subject; (c) unblocking the renal blood vessel after a first blocking time period of from about 10 minutes to about 60 minutes subsequent to the first blocking; and (d) administering a volume of a second solution comprising the first rAAV or a second rAAV by repeating steps (a)-(c) using the first blocking time period or a second blocking time period of from about 10 minutes to about 60 minutes subsequent to the second blocking, after a time period for subsequent administration, wherein the volume of the second solution is from about 0.13 mL/kg to about 0.33 mL/kg. In some embodiments, neither the first solution nor the second solution elicits an immune response in the kidney.

In one aspect, described herein is a method of administering a recombinant adeno-associated virus (rAAV) to a kidney of a subject and/or treating a kidney-associated disorder in a subject in need thereof, (a) blocking at least one renal blood vessel selected from the group consisting of a renal artery, a renal vein, and a combination thereof of the kidney; (b) administering a volume of a first solution comprising a first rAAV into a ureter of the kidney in a retrograde route; (c) unblocking the at least one renal blood vessel after a first blocking time period subsequent to the first blocking; and (d) administering a volume of a second solution comprising the first rAAV or a second rAAV by repeating steps (a)-(c), after a time period for subsequent administration. In some embodiments, neither the first solution nor the second solution elicits an immune response in the kidney.

In one aspect, described herein is a method of transducing at least about 25% of the nephrons in a kidney of a subject with a recombinant adeno-associated virus (rAAV), the method comprising: (a) blocking a renal blood vessel selected from the group consisting of a renal artery, a renal vein, and a combination thereof of the kidney; (b) administering a volume of a first solution comprising a first rAAV into a ureter of the kidney in a retrograde route, wherein the volume of the first solution is from about 0.13 mL/kg to about 0.33 mL/kg, the kg being the weight of the subject; (c) unblocking the renal blood vessel after a first blocking time period of from about 10 minutes to about 60 minutes subsequent to the first blocking; and (d) administering a volume of a second solution comprising the first rAAV or a second rAAV by repeating steps (a)-(c) using the first blocking time period or a second blocking time period of from about 10 minutes to about 60 minutes subsequent to the second blocking, after a time period for subsequent administration, wherein the volume of the second solution is from about 0.13 mL/kg to about 0.33 mL/kg. In some embodiments, neither the first solution nor the second solution elicits an immune response in the kidney.

In some embodiments of any of the aspects, the step of "blocking at least one renal blood vessel selected from the group consisting of a renal artery, a renal vein, and a combination thereof of the kidney" or "blocking a renal blood vessel of the kidney selected from the group consisting of a renal artery, a renal vein, and a combination thereof" or "blocking a renal blood vessel selected from the group consisting of a renal artery, a renal vein, and a combination thereof of the kidney" or the like is replaced with a step of "isolating the kidney from systemic circulation."

In some embodiments of any of the aspects, the step of "unblocking the renal blood vessel after a first blocking time period" or "unblocking the at least one renal blood vessel after a first blocking time period" or the like subsequent to the first blocking is replaced with a step of "re-establishing the kidney into systemic circulation after a first isolating time period" subsequent to the first isolating.

In some embodiments of any of the aspects, the "first blocking period" is replaced with a "first isolating period." The first blocking period and the first isolating period, whichever period is implied, are measured from moment of blocking or isolating. In some embodiments of any of the aspects, the "second blocking period" is replaced with a "second isolating period." In some embodiments of any of the aspects, the first rAAV administration comprises blocking at least one renal blood vessel, and the second rAAV administration comprises isolating the kidney from systemic circulation. In some embodiments of any of the aspects, the second rAAV administration comprises blocking at least one renal blood vessel, and the first rAAV administration comprises isolating the kidney from systemic circulation. In some embodiments of any of the aspects, the first and second rAAV administrations comprise blocking at least one renal blood vessel. In some embodiments of any of the aspects, the first and second rAAV administrations comprise isolating the kidney from systemic circulation.

In some embodiments, steps (a)-(c) are repeated using a first rAAV, a second rAAV, a third rAAV, a fourth rAAV, a fifth rAAV, a sixth rAAV, a seventh rAAV, an eighth rAAV, a ninth rAAV, a tenth rAAV, or more. In some embodiments, steps (a)-(c) are repeated 1, 2, 3, 4, 5, 6, 7, 8, 9, 10, or more times, e.g., using the same or different rAAV, or a combination thereof.

In some embodiments, the capsid of the first rAAV is the same serotype as the capsid of the second rAAV. In some embodiments, the capsid of the first rAAV is a different serotype as the capsid of the second rAAV. In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the capsids described in Table 1. In other embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the group consisting of: AAV1, AAV2, AAV3, AAV4, AAV5, AAV6, AAV7, AAV8, AAV9, AAV10, AAV11, AAV12, AAV13, AAVrh74, AAVrh10, pol, AAV9-PHP.B, AAV9-PHP.eB, AAVLK03, AAVAnc80L65, AAVDJ, AAV1A6ii, AAV1P5ii, AAV4A1ii, AAV7P4i, AAV9A1i, AAV9A2i, AAV9A6i, AAV9P1i, AAV9P2i, AAV9P5i, AAVrh10A1i, AAVrh10A2i, AAVrh10P1i, AAV12P2ii, AAVS10P1i, AAV JEA, AAV2 3xA P2i, AAVDJ P2i, AAV2i8, AAV2G9, AAV2.5, AAV4E, and AAV4A. It is understood that the capsids can be all the same, all different, or some being the same and some different.

In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the capsids described in Table 1. In other embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the group consisting of: AAV1, AAV2, AAV3a, AAV3b, AAV4, AAV5, AAV6, AAV7, AAV8, AAV9, AAV2G9, AAV2.5G9, AAV2.5, AAVrh8, AAVrh10, AAVrh74, AAV10, AAV11, and AAVDJ. It is understood that the capsids can be all the same, all different, or some being the same and some different.

In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the capsids described in Table 1. In other embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the group consisting of: AAV2, AAV6, AAVLK03, AAVDJ, AAV9A2i, AAV9A6i, AAVrh10A2i, AAV2g9, and AAV2.5 (see e.g., FIG. 4). In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the group consisting of: AAV2, AAVDJ, AAVJEA (minimal), AAV2g9, or AAV2.5 (see e.g., FIG. 5). It is understood that the capsids can be all the same, all different, or some being the same and some different.

In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is a rational polyploid.

In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is independently selected from the group consisting of: AAV2G9, AAV2.5, AAVDJ, and AAV2.

In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is AAV2G9. In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is AAV2.5. In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is AAVDJ. In some embodiments, the capsid of the first rAAV, second rAAV, third rAAV, fourth rAAV, fifth rAAV, sixth rAAV, seventh rAAV, eighth rAAV, ninth rAAV, tenth rAAV, or more, is AAV2.

In some embodiments, the first and/or second (and/or third and/or fourth and/or fifth and/or sixth and/or seventh and/or eighth and/or ninth and/or tenth, etc.) rAAV is at a concentration of $10^{8}$ viral genomes per mL (vg/mL) to $10^{15}$ vg/mL, $10^{9}$ vg/mL to $10^{15}$ vg/mL, $10^{10}$ vg/mL to $10^{15}$ vg/mL, $10^{11}$ vg/mL to $10^{15}$ vg/mL, $10^{12}$ vg/mL to $10^{15}$ vg/mL, $10^{13}$ vg/mL to $10^{15}$ vg/mL, $10^{11}$ vg/mL to $10^{12}$ vg/mL, $10^{12}$ vg/mL to $10^{13}$ vg/mL, $10^{13}$ vg/mL to $10^{14}$ vg/mL, $10^{14}$ vg/mL to $10^{15}$ vg/mL, $10^{8}$ vg/mL to $10^{14}$ vg/mL, $10^{8}$ vg/mL to $10^{13}$ vg/mL, $10^{8}$ vg/mL to $10^{12}$ vg/mL, $10^{8}$ vg/mL to $10^{11}$ vg/mL, $10^{8}$ vg/mL to $10^{10}$ vg/mL, or $10^{8}$ vg/mL to $10^{9}$ vg/mL. In some embodiments, the first and/or second (and/or third and/or fourth and/or fifth and/or sixth and/or seventh and/or eighth and/or ninth and/or tenth, etc.) rAAV is at a concentration of $10^{8}$ vg/mL to $10^{13}$ vg/mL. In some embodiments, the first and/or second (and/or third and/or fourth and/or fifth and/or sixth and/or seventh and/or eighth and/or ninth and/or tenth, etc.) rAAV is at a concentration of at least $10^{8}$ vg/mL, at least $10^{9}$ vg/mL, at least $10^{10}$ vg/mL, at least $10^{11}$ vg/mL, at least $10^{12}$ vg/mL, at least $10^{13}$ vg/mL, at least $10^{14}$ vg/mL, at least $10^{15}$ vg/mL, or more. In some embodiments, the first and/or second (and/or third and/or fourth and/or fifth and/or sixth and/or seventh and/or eighth and/or ninth and/or tenth, etc.) rAAV is at a concentration of at most $10^{9}$ vg/mL, at most $10^{10}$ vg/mL, at most $10^{11}$ vg/mL, at most $10^{12}$ vg/mL, at most $10^{13}$ vg/mL, at most $10^{14}$ vg/mL, or at most $10^{15}$ vg/mL. It is understood that each of the individual rAAV concentrations described herein can be used to define lower and upper values of a rAAV concentration range.

In some embodiments, the first and/or second (and/or third and/or fourth and/or fifth and/or sixth and/or seventh and/or eighth and/or ninth and/or tenth, etc.) solution comprises $1\times10^{13}$ to $2\times10^{13}$ of the first and/or second (and/or third and/or fourth and/or fifth and/or sixth and/or seventh and/or eighth and/or ninth and/or tenth, etc.) rAAV viral genomes total. In some embodiments, the first and/or second solution (and/or third and/or fourth and/or fifth and/or sixth and/or seventh and/or eighth and/or ninth and/or tenth, etc.) comprises $5\times10^{13}$ to $6\times10^{13}$ of first and/or second (and/or third and/or fourth and/or fifth and/or sixth and/or seventh and/or eighth and/or ninth and/or tenth, etc.) rAAV viral genomes total. In some embodiments, the first and/or second (and/or third and/or fourth and/or fifth and/or sixth and/or seventh and/or eighth and/or ninth and/or tenth, etc.) solution comprises at least $1\times10^{13}$, at least $2\times10^{13}$, at least $3\times10^{13}$, at least $4\times10^{13}$, at least $5\times10^{13}$, at least $6\times10^{13}$, at least $7\times10^{13}$, at least $8\times10^{13}$, at least $9\times10^{13}$, or more of the first and/or second (and/or third and/or fourth and/or fifth and/or sixth and/or seventh and/or eighth and/or ninth and/or tenth, etc.) rAAV viral genomes total. In some embodiments, the first and/or second (and/or third and/or fourth and/or fifth and/or sixth and/or seventh and/or eighth and/or ninth and/or tenth, etc.) solution comprises at most $1\times10^{13}$, at most $2\times10^{13}$, at most $3\times10^{13}$, at most $4\times10^{13}$, at most $5\times10^{13}$, at most $6\times10^{13}$, at most $7\times10^{13}$, at most $8\times10^{13}$, at most $9\times10^{13}$, $1\times10^{11}$ to $1\times10^{14}$ vg total, $1\times10^{11}$ to $1\times10^{13}$ vg total, $1\times10^{11}$ to $1\times10^{12}$ vg total, $1\times10^{12}$ to $1\times10^{13}$ vg total, $1\times10^{12}$ to $1\times10^{14}$ vg total, $1\times10^{13}$ to $1\times10^{14}$ vg total, $1\times10^{13}$ to $6\times10^{13}$ vg total, $2\times10^{13}$ to $5\times10^{13}$ vg total, or $1\times10^{13}$ to $2\times10^{13}$, or more of the first and/or second (and/or third and/or fourth and/or fifth and/or sixth and/or seventh and/or eighth and/or ninth and/or tenth, etc.) rAAV viral genomes total. It is understood that each of the individual rAAV amounts described herein can be used to define lower and upper values of an rAAV amount range.

In some embodiments, the first and/or second (and/or third and/or fourth and/or fifth and/or sixth and/or seventh and/or eighth and/or ninth and/or tenth, etc.) solution comprises $1\times10^{10}$ viral genomes total (e.g., $4\times10^{8}$ vg/mL to $1\times10^{9}$ vg/mL).

In some embodiments, the transgene(s) of the first rAAV are the same transgene(s) as the second (and/or third and/or fourth and/or fifth and/or sixth and/or seventh and/or eighth and/or ninth and/or tenth, etc.) rAAV. In some embodiments, the transgene(s) of the first rAAV are different transgene(s) than the second (and/or third and/or fourth and/or fifth and/or sixth and/or seventh and/or eighth and/or ninth and/or tenth, etc.) rAAV. In some embodiments, the transgene(s) of the first rAAV, second rAAV, third rAAV, fourth rAAV, fifth rAAV, sixth rAAV, seventh rAAV, eighth rAAV, ninth rAAV, tenth rAAV, or more, is selected from the group consisting of: (a) a reporter gene, (b) a gene that when expressed in the subject is effective to treat a kidney-associated disorder, (c) an inhibitor of a gene or protein such that inhibition is effective to treat a kidney-associated disorder, or any combination thereof.

In some embodiments, the transgene(s) of the first rAAV is activated by at least one kidney-specific promoter that is the same as at least one kidney-specific promoter activating the transgene(s) of the second (and/or third and/or fourth and/or fifth and/or sixth and/or seventh and/or eighth and/or ninth and/or tenth, etc.) rAAV. In some embodiments, the transgene(s) of the first rAAV is activated by at least one kidney-specific promoter that is different than the at least one kidney-specific promoter activating the transgene(s) of the second (and/or third and/or fourth and/or fifth and/or sixth and/or seventh and/or eighth and/or ninth and/or tenth, etc.) rAAV.

In some embodiments, the time period for subsequent administration of the second solution is at least one day. In some embodiments, the time period for subsequent administration between administering the first solution and the second solution (or between the second solution and the third solution, or between the third solution and the fourth solution, or between the fourth solution and the fifth solution, or between the fifth solution and a sixth solution, or between the sixth solution and the seventh solution, or between the seventh solution and the eighth solution, or between the eighth solution and the ninth solution, or between the ninth solution and the tenth solution) is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 1 year, or more.

In some embodiments, the time period for subsequent administration of the second solution is determined based on the efficacy or longevity of the administration of the first solution comparing an rAAV. In some embodiments, the time period for subsequent administration in between administering the first solution and the second solution (or between the second solution and the third solution, or between the third solution and the fourth solution, or between the fourth solution and the fifth solution, or between the fifth solution and a sixth solution, or between the sixth solution and the seventh solution, or between the seventh solution and the eighth solution, or between the eighth solution and the ninth solution, or between the ninth solution and the tenth solution) is determined based on the efficacy or longevity of the administration of at least one of the previous solutions comparing an rAAV.

The efficacy or longevity can be determined, for example, by tests of rAAV transduction of the kidney (e.g., sequencing for rAAV genomes (or a bar code therein); expression of an rAAV-delivered reporter gene or transgene (e.g., RNA or protein-based assays such as RT-qPCR, ELISA, histological staining, or flow cytometry)), anti-rAAV serology (e.g., in the urine or blood), or occurrence of symptoms related to a kidney-associated disorder (for which the rAAV was administered to treat). If the efficacy or longevity falls below a certain level, then a solution comprising a subsequent rAAV (comprising a capsid that is the same or different than previous rAAV(s); comprising transgene(s) that are the same or different than previous rAAV(s)) is administered to the subject.

In various embodiments, the first solution is administered to a first kidney and the second, i.e., contralateral, kidney of the subject is not simultaneously treated. Rather, retrograde administration of a solution to the contralateral kidney is delayed relative to retrograde rAAV administration of the first kidney to confirm that the retrograde rAAV administration to the first kidney is effective and does not result in substantial adverse effects that would suggest to a treating medical professional not treating the contralateral kidney in the same or similar manner. Accordingly, retrograde rAAV administration to the contralateral kidney can be delayed relative to retrograde rAAV administration of the first kidney at least 1 day, at least 2 days, at least 3 days, at least 4 days, at least 5 days, at least 6 days, at least 1 week, at least 2 weeks, at least 3 weeks, at least 4 weeks, or at least 5 weeks. In other embodiments, the contralateral kidney is treated by retrograde administration of rAAV on the same day as the first kidney.

In some embodiments, the first solution is administered to a first kidney of the subject, and the second solution is administered to a second kidney of the subject. In some embodiments, the first solution (or second solution, third solution, fourth solution, fifth solution, sixth solution, seventh solution, eighth solution, ninth solution, tenth solution, or more) is administered to a first kidney of the subject, and the second solution (or first solution, third solution, fourth solution, fifth solution, sixth solution, seventh solution, eighth solution, ninth solution, tenth solution, or more) is administered to a second kidney of the subject.

In some embodiments, a solution comprising the first rAAV is administered to a first kidney of the subject, and a solution comprising the second rAAV is administered to the first kidney of the subject. In some embodiments, at least one solution comprising the first rAAV, second rAAV, third rAAV, fourth rAAV, fifth rAAV, sixth rAAV, seventh rAAV, eighth rAAV, ninth rAAV, tenth rAAV, or more, are each administered to the same kidney of the subject. In some embodiments, at least one solution comprising the first rAAV, second rAAV, third rAAV, fourth rAAV, fifth rAAV, sixth rAAV, seventh rAAV, eighth rAAV, ninth rAAV, tenth rAAV, or more, are each administered to the same or different kidney of the subject, or combinations thereof.

In some embodiments, a solution comprising the first rAAV is administered to both kidneys of the subject, and a solution comprising the second rAAV is administered to both kidneys of the subject. In some embodiments, at least one solution comprising the first rAAV, second rAAV, third rAAV, fourth rAAV, fifth rAAV, sixth rAAV, seventh rAAV, eighth rAAV, ninth rAAV, tenth rAAV, or more, are each administered to both kidneys of the subject. In some embodiments, at least one solution comprising the first rAAV, second rAAV, third rAAV, fourth rAAV, fifth rAAV, sixth rAAV, seventh rAAV, eighth rAAV, ninth rAAV, tenth rAAV, or more, are each administered to a single kidney or to both kidneys of the subject, or combinations thereof.

In some embodiments, at least one solution comprising the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is from about 0.13 mL/kg to about 0.33 mL/kg, from about 0.20 mL/kg to about 0.27 mL/kg, from about 0.27 mL/kg to about 0.33 mL/kg, from about 0.13 mL/kg to about 0.35 mL/kg, about 0.15 mL/kg to about 0.35 mL/kg, about 0.2 mL/kg to about 0.35 mL/kg, from about 0.25 mL/kg to about 0.35 mL/kg, from about 0.3 mL/kg to about 0.35 mL/kg, from about 0.13 mL/kg to about 0.30 mL/kg, from about 0.13 mL/kg to about 0.25 mL/kg, or from about 0.13 mL/kg to about 0.2 mL/kg. In some embodiments, the volume of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is at least 0.13 mL/kg, at least 0.20 mL/kg, or at least 0.27 mL/kg. In some embodiments, the volume of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is at most 0.33 mL/kg.

In some embodiments, the volume of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is 0.13 mL/kg, 0.14 mL/kg, 0.15 mL/kg, 0.16 mL/kg, 0.17 mL/kg, 0.18 mL/kg, 0.19 mL/kg, 0.2 mL/kg, 0.21 mL/kg, 0.22 mL/kg, 0.23 mL/kg, 0.24 mL/kg, 0.25 mL/kg, 0.26 mL/kg, 0.27 mL/kg, 0.28 mL/kg, 0.29 mL/kg, 0.3 mL/kg, 0.31 mL/kg, 0.32 mL/kg, 0.33 mL/kg, 0.34 mL/kg, 0.35 mL/kg, 0.05-0.15 mL/kg, 0.10-0.20 mL/kg, 0.15-0.25 mL/kg, 0.20-0.30 mL/kg, 0.25-0.35 mL/kg, 0.05-0.10 mL/kg, 0.10-0.15 mL/kg, 0.15-0.20 mL/kg, 0.20-0.25 mL/kg, 0.25-0.30 mL/kg, 0.30-0.35 mL/kg, 0.05-0.35 mL/kg, 0.10-0.35 mL/kg, 0.15-0.35 mL/kg, 0.20-0.35 mL/kg, 0.05-0.20 mL/kg, 0.05-0.25 mL/kg, or 0.05-0.30 mL/kg. It is understood that each of the individual volumes described herein can be used to define lower and upper values of a volume range.

In some embodiments, the volume of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is selected from the group consisting of at least 0.05 mL/kg, at least 0.1 mL/kg, at least 0.13 mL/kg, at least 0.14 mL/kg, at least 0.15 mL/kg, at least 0.16 mL/kg, at least 0.17 mL/kg, at least 0.18 mL/kg, at least 0.19 mL/kg, at least 0.20 mL/kg, at least 0.21 mL/kg, at least 0.22 mL/kg, at least 0.23 mL/kg, at least 0.24 mL/kg, at least 0.25 mL/kg, at least 0.26 mL/kg, at least 0.27 mL/kg, at least 0.28 mL/kg, at least 0.29 mL/kg, at least 0.30 mL/kg, at least 0.31 mL/kg, at least 0.32 mL/kg, at least 0.33 mL/kg, at least 0.34 mL/kg, at least 0.35 mL/kg, 0.05-0.15 mL/kg, 0.10-0.20 mL/kg, 0.15-0.25 mL/kg, 0.20-0.30 mL/kg, 0.25-0.35 mL/kg, 0.05-0.10 mL/kg, 0.10-0.15 mL/kg, 0.15-0.20 mL/kg, 0.20-0.25 mL/kg, 0.25-0.30 mL/kg, 0.30-0.35 mL/kg, 0.05-0.35 mL/kg, 0.10-0.35 mL/kg, 0.15-0.35 mL/kg, 0.20-0.35 mL/kg, 0.05-0.20 mL/kg, 0.05-0.25 mL/kg, or 0.05-0.30 mL/kg. In some embodiments, the volume of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is selected from the group consisting of at most 0.30 mL/kg, at most 0.31 mL/kg, at most 0.32 mL/kg, at most 0.33 mL/kg, at most 0.34 mL/kg, or at most 0.35 mL/kg, of the subject. the volume of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is about 0.24 mL/kg. It is understood that each of the individual volumes described herein can be used to define lower and upper values of a volume range.

In some embodiments, the volume of the first and/or second (and/or third and/or fourth and/or fifth and/or sixth and/or seventh and/or eighth and/or ninth and/or tenth, etc.) solution is the same as the volume of the first and/or second (and/or third and/or fourth and/or fifth and/or sixth and/or seventh and/or eighth and/or ninth and/or tenth, etc.) solution. In some embodiments, the volume of the first and/or second (and/or third and/or fourth and/or fifth and/or sixth and/or seventh and/or eighth and/or ninth and/or tenth, etc.) solution is different than the volume of the first and/or second (and/or third and/or fourth and/or fifth and/or sixth and/or seventh and/or eighth and/or ninth and/or tenth, etc.) solution. In some embodiments, the volume of the first and/or second (and/or third and/or fourth and/or fifth and/or sixth and/or seventh and/or eighth and/or ninth and/or tenth, etc.) solution can be adjusted by a person of skill in the art, such as a physician or other medical professional.

In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is such that the kidney does not undergo ischemic damage. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is about 15 minutes subsequent to the isolating or blocking. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is 10-60 minutes subsequent to the isolating or blocking. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is 15-45 minutes subsequent to the isolating or blocking. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is 20-40 minutes subsequent to the isolating or blocking. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is 30-60 minutes subsequent to the isolating or blocking. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is about 15-30 minutes subsequent to the isolating or blocking. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is about 30 minutes subsequent to the isolating or blocking. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is no more than 45 minutes (min) subsequent to the isolating or blocking.

In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is at least 10 min, at least 11 min, at least 12 min, at least 13 min, at least 14 min, at least 15 min, at least 16 min, at least 17 min, at least 18 min, at least 19 min, at least 20 min, at least 21 min, at least 22 min, at least 23 min, at least 24 min, at least 25 min, at least 26 min, at least 27 min, at least 28 min, at least 29 min, at least 30 min, at least 31 min, at least 32 min, at least 33 min, at least 34 min, at least 35 min, at least 36 min, at least 37 min, at least 38 min, at least 39 min, at least 40 min, at least 41 min, at least 42 min, at least 43 min, at least 44 min, at least 45 min, at least 46 min, at least 47 min, at least 48 min, at least 49 min, at least 50 min, at least 51 min, at least 52 min, at least 53 min, at least 54 min, at least 55 min, at least 56 min, at least 57 min, at least 58 min, or at least 59 min subsequent to the isolating or blocking. It is understood that each of the individual times described herein can be used to define lower and upper values of a time range.

In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is at most 10 min, at most 11 min, at most 12 min, at most 13 min, at most 14 min, at most 15 min, at most 16 min, at most 17 min, at most 18 min, at most 19 min, at most 20 min, at most 21 min, at most 22 min, at most 23 min, at most 24 min, at most 25 min, at most 26 min, at most 27 min, at most 28 min, at most 29 min, at most 30 min, at most 31 min, at most 32 min, at most 33 min, at most 34 min, at most 35 min, at most 36 min, at most 37 min, at most 38 min, at most 39 min, at most 40 min, at most 41 min, at most 42 min, at most 43 min, at most 44 min, at most 45 min, at most 46 min, at most 47 min, at most 48 min, at most 49 min, at most 50 min, at most 51 min, at most 52 min, at most 53 min, at most 54 min, at most 55 min, at most 56 min, at most 57 min, at most 58 min, at most 59 min, or at most 60 min subsequent to the isolating or blocking. It is understood that each of the individual times described herein can be used to define lower and upper values of a time range.

In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is the same as the first and/or second (and/or third and/or fourth and/or fifth and/or sixth and/or seventh and/or eighth and/or ninth and/or tenth, etc.) isolating or blocking time period. In some embodiments, the first and/or second (and/or third and/or fourth and/or fifth and/or sixth and/or seventh and/or eighth and/or ninth and/or tenth, etc.) kidney isolating time period or blocking time period of the at least one renal blood vessel is different than the first and/or second (and/or third and/or fourth and/or fifth and/or sixth and/or seventh and/or eighth and/or ninth and/or tenth, etc.) isolating or blocking time period. In some embodiments, the first and/or second (and/or third and/or fourth and/or fifth and/or sixth and/or seventh and/or eighth and/or ninth and/or tenth, etc.) isolating or blocking time period can be adjusted by a person of skill in the art, such as a physician or other medical professional.

In aspects comprising at least one subsequent administration of an rAAV, each administration of the rAAV can be performed as described herein. In some embodiments, at least one solution comprising the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is administered in the retrograde route to the ureter using a catheter. In some embodiments, the catheter used to administer the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV is a balloon catheter. In some embodiments, the balloon catheter is inflated to block the ureter after administration of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV. In some embodiments, the balloon catheter is un-inflated to unblock the ureter after the first or second (and/or third and/or fourth and/or fifth and/or sixth and/or seventh and/or eighth and/or ninth and/or tenth, etc.) blocking time period.

In some embodiments, the at least one renal blood vessel is isolated or blocked using a catheter, e.g., during at least one of the subsequent administrations of an rAAV through a retrograde ureter route. In some embodiments, the catheter used to isolate or block the at least one renal blood vessel is a balloon catheter. In some embodiments, the balloon catheter is inflated to isolate or block the at least one renal blood vessel and occlude blood supply to the kidney prior to administration of the first and/or second (and/or third and/or fourth and/or fifth and/or sixth and/or seventh and/or eighth and/or ninth and/or tenth, etc.) solution comprising the first and/or second (and/or third and/or fourth and/or fifth and/or sixth and/or seventh and/or eighth and/or ninth and/or tenth, etc.) rAAV. In some embodiments, the at least one renal blood vessel is isolated or blocked using a clamp, e.g., during at least one of the subsequent administrations of an rAAV through a retrograde ureter route.

Pharmaceutical Compositions

Described herein are pharmaceutical compositions comprising at least one rAAV as described herein, and optionally a pharmaceutically acceptable carrier. In some embodiments, the pharmaceutical composition comprising at least one rAAV comprises one or more AAV capsid protein selected from Table 1. In other embodiments, the pharmaceutical composition comprising at least one rAAV comprises one or more AAV capsid protein selected from serotype AAV1, AAV2, AAV3, AAV4, AAV5, AAV6, AAV7, AAV8, AAV9, AAV10, AAV11, AAV12, AAV13, AAVrh74, AAVrh10, pol, AAV9-PHP.B, AAV9-PHP.eB, AAVLK03, AAVAnc80L65, AAVDJ, AAV1A6ii, AAV1P5ii, AAV4A1ii, AAV7P4i, AAV9A1i, AAV9A2i, AAV9A6i, AAV9P1i, AAV9P2i, AAV9P5i, AAVrh10A1i, AAVrh10A2i, AAVrh10P1i, AAV12P2ii, AAVS10P1i, AAV JEA, AAV2 3xA P2i, AAVDJ P2i, AAV2i8, AAV2G9, AAV2.5, AAV4E, and AAV4A.

In some embodiments, the pharmaceutical composition comprising at least one rAAV comprises one or more AAV capsid protein selected from AAV2, AAV6, AAVLK03, AAVDJ, AAV9A2i, AAV9A6i, AAVrh10A2i, AAV2g9, or AAV2.5 (see e.g., FIG. 4). In some embodiments, the pharmaceutical composition comprising at least one rAAV comprises one or more AAV capsid protein selected from AAV2, AAVDJ, AAVJEA (minimal), AAV2g9, or AAV2.5 (see e.g., FIG. 5). In some embodiments, the pharmaceutical composition comprising at least one rAAV is a rational polyploid.

In some embodiments, the pharmaceutical composition comprising at least one rAAV comprises one or more AAV capsid protein selected from serotype AAV1, AAV2, AAV3a, AAV3b, AAV4, AAV5, AAV6, AAV7, AAV8, AAV9, AAV2G9, AAV2.5G9, AAV2.5, AAVrh8, AAVrh10, AAVrh74, AAV10, AAV11, and AAVDJ.

In some embodiments, the pharmaceutical composition comprising at least one rAAV comprises a capsid selected from the group consisting of: AAV2G9, AAV2.5, AAVDJ, and AAV2. In some embodiments, the pharmaceutical composition comprising at least one rAAV comprises a capsid from AAV2G9. In some embodiments, the pharmaceutical composition comprising at least one rAAV comprises a capsid from AAV2.5. In some embodiments, the pharmaceutical composition comprising at least one rAAV comprises a capsid from AAVDJ. In some embodiments, the pharmaceutical composition comprising at least one rAAV comprises a capsid from AAV2.

In some embodiments, the pharmaceutical composition comprising at least one rAAV does not comprise a capsid protein from serotype AAV9. In some embodiments, the rAAV is not rAAV9.

In one aspect, described herein is a pharmaceutical composition comprising a recombinant adeno-associated virus (rAAV) comprising: (a) an AAV2G9 capsid protein; (b) a transgene comprising: a gene selected from the group consisting of AGXT (type I), BSND (type IV), CLCN5 (type I), CLCNKA (type IV), CLCNKB, CLCNKB (type III and IV), COL4A3, COL4A4, COL4A5, GANAB, GRHPR (type II), HNF1B, HOGA1 (type III), KCNJ1 (type II), MAGED2 (type V), MUC1 (type I), NPHP1, NPHS1, NPHS2, OCRL (type II), PKD1, PKD2, PKHD1, SEC61A1, SLC12A1, SLC12A3, SLC3A1, SLC7A9, VHL, and combinations thereof; and (c) a pharmaceutically acceptable carrier.

In one aspect, described herein is a pharmaceutical composition comprising a recombinant adeno-associated virus (rAAV) comprising: (a) an AAV2G9 capsid protein; (b) Aquaporin 2 (AQP2); ATPase Na+/K+ Transporting Subunit Alpha 1 (ATP1A1); ATPase H+ Transporting V0 Subunit A4 (ATP6V0A4); ATPase H+ Transporting V1 Subunit B1 (ATP6V1B1); Arginine Vasopressin Receptor 2 (AVPR2); Barttin CLCNK (chloride channel K) Type Accessory Subunit Beta (BSND); Carbonic Anhydrase 2 (CA2); Calcium Sensing Receptor (CaSR); Chloride Voltage-Gated Channel 5 (CLCN5); CLCNKA (Chloride Voltage-Gated Channel Ka); Chloride Voltage-Gated Channel Kb (CLCNKB); Claudin 16 (CLDN16); Claudin 19 (CLDN19); Cyclin And CBS Domain Divalent Metal Cation Transport Mediator 2 (CNNM2); Cullin 3 (CUL3); Cytochrome P450 Family 11 Subfamily B Member 1 (CYP11B1); Cytochrome P450 Family 11 Subfamily B Member 2 (CYP11B2); Cytochrome P450 Family 17 Subfamily A Member 1 (CYP17A1); Cytochrome P450 Family 21 Subfamily A Member 2 (CYP21A2); Epidermal Growth Factor (EGF); Epidermal Growth Factor Receptor (EGFR); Enoyl-CoA Hydratase And 3-Hydroxyacyl CoA Dehydrogenase (EHHADH); FAM111 (family 111) Trypsin Like Peptidase A (FAM111A); Forkhead Box I1 (FOXI1); FXYD Domain/Motif Containing Ion Transport Regulator 2 (FXYD2); Glycine Amidinotransferase (GATM); guanine nucleotide binding protein; alpha stimulating (GNAS); hepatocyte nuclear factor 1 (HNF1) Homeobox B (HNF1B); Hepatocyte Nuclear Factor 4 Alpha (HNF4A); Hydroxysteroid 11-Beta Dehydrogenase 2 (HSD11B2); Hydroxy-Delta-5-Steroid Dehydrogenase, 3 Beta- And Steroid Delta-Isomerase 2 (HSD3B2); Potassium Voltage-Gated Channel Subfamily A Member 1 (KCNA1); Potassium Inwardly Rectifying Channel Subfamily J Member 1 (KCNJ1); Potassium Inwardly Rectifying Channel Subfamily J Member 10 (KCNJ10); Kelch Like Family Member 3 (KLHL3); Melanoma Antigen Gene Family Member D2 (MAGED2); Nuclear Receptor Subfamily 3 Group C Member 2 (NR3C2); Oculocerebrorenal Syndrome Of Lowe (OCRL) Inositol Polyphosphate-5-Phosphatase; Pterin-4 Alpha-Carbinolamine Dehydratase 1 (PCBD1); Phosphate Regulating Endopeptidase X-Linked (PHEX); Sodium Channel Epithelial 1 Subunit Alpha (SCNN1A); Sodium Channel Epithelial 1 Subunit Beta (SCNN1B); Sodium Channel Epithelial 1 Subunit Gamma (SCNN1G); Solute Carrier Family 12 Member 1 (SLC12A1); Solute Carrier Family 12 Member 3 (SLC12A3); Solute Carrier Family 1 Member 1 (SLC1A1); Solute Carrier Family 2 Member 2 (SLC2A2); Solute Carrier Family 34 Member 1 (SLC34A1); Solute Carrier Family 34 Member 3 (SLC34A3); Solute Carrier Family 36 Member 2 (SLC36A2); Solute Carrier Family 3 Member 1 (SLC3A1); Solute Carrier Family 4 Member 1 (SLC4A1); Solute Carrier Family 6 Member 19 (SLC6A19); Solute Carrier Family 6 Member 20 (SLC6A20); Solute Carrier Family 7 Member 7 (SLC7A7); Solute Carrier Family 7

Member 9 (SLC7A9); Transient Receptor Potential Cation Channel Subfamily M Member 6 (TRPM6); WD Repeat Domain 72 (WDR72); With-no-lysine (WNK, Lysine Deficient) Protein Kinase 1 (WNK1); With-no-lysine (WNK, Lysine Deficient) Protein Kinase 4 (WNK4); and combinations thereof; and (c) a pharmaceutically acceptable carrier.

In one aspect, described herein is a pharmaceutical composition comprising a recombinant adeno-associated virus (rAAV) comprising: (a) an AAV2G9 capsid protein; (b) a transgene comprising: an inhibitor of a gene or protein selected from the group consisting of: REN, SCNN1A, SCNN1B, and UMOD; and (c) a pharmaceutically acceptable carrier.

In some embodiments, the active ingredients of the pharmaceutical composition comprise the rAAV as described herein. In some embodiments, the active ingredients of the pharmaceutical composition consist essentially of the rAAV as described herein. In some embodiments, the active ingredients of the pharmaceutical composition consist of the rAAV as described herein.

In some embodiments, the pharmaceutical composition comprises $1\times10^{13}$ to $2\times10^{13}$ rAAV viral genomes total. In some embodiments, the pharmaceutical composition comprises $5\times10^{13}$ to $6\times10^{13}$ rAAV viral genomes total. In some embodiments, the pharmaceutical composition comprises at least $1\times10^{13}$, at least $2\times10^{13}$, at least $3\times10^{13}$, at least $4\times10^{13}$, at least $5\times10^{13}$, at least $6\times10^{13}$, at least $7\times10^{13}$, at least $8\times10^{13}$, at least $9\times10^{13}$, or more rAAV viral genomes total. In some embodiments, the pharmaceutical composition comprises at most $1\times10^{13}$, at most $2\times10^{13}$, at most $3\times10^{13}$, at most $4\times10^{13}$, at most $5\times10^{13}$, at most $6\times10^{13}$, at most $7\times10^{13}$, at most $8\times10^{13}$, at most $9\times10^{13}$, or more rAAV viral genomes total. In some embodiments, the pharmaceutical composition comprises $10^{8}$ viral genomes per mL (vg/mL) to $10^{15}$ vg/mL, $10^{9}$ vg/mL to $10^{11}$ vg/mL, $10^{10}$ vg/mL to $10^{11}$ vg/mL, $10^{11}$ vg/mL to $10^{15}$ vg/mL, $10^{12}$ vg/mL to $10^{11}$ vg/mL, $10^{13}$ vg/mL to $10^{11}$ vg/mL, $10^{11}$ vg/mL to $10^{12}$ vg/mL, $10^{12}$ vg/mL to $10^{13}$ vg/mL, $10^{13}$ vg/mL to $10^{14}$ vg/mL, $10^{14}$ vg/mL to $10^{11}$ vg/mL, $10^{8}$ vg/mL to $10^{14}$ vg/mL, $10^{8}$ vg/mL to $10^{13}$ vg/mL, $10^{8}$ vg/mL to $10^{12}$ vg/mL, $10^{8}$ vg/mL to $10^{11}$ vg/mL, $10^{8}$ vg/mL to $10^{10}$ vg/mL, or $10^{8}$ vg/mL to $10^{9}$ vg/mL rAAV. It is understood that each of the individual rAAV concentrations described herein can be used to define lower and upper values of an rAAV concentration range.

In some embodiments, the pharmaceutical composition comprises $1\times10^{10}$ rAAV viral genomes total (e.g., $4\times10^{8}$ vg/mL to $1\times10^{9}$ vg/mL).

In some embodiments, the pharmaceutical composition (e.g., the pharmaceutically acceptable carrier; e.g., the solution as described herein) is in a unit dose of about 0.13 mL/kg to 0.33 mL/kg, from about 0.20 mL/kg to about 0.27 mL/kg, from about 0.27 mL/kg to about 0.33 mL/kg, from about 0.13 mL/kg to about 0.35 mL/kg, about 0.15 mL/kg to about 0.35 mL/kg, about 0.2 mL/kg to about 0.35 mL/kg, from about 0.25 mL/kg to about 0.35 mL/kg, from about 0.3 mL/kg to about 0.35 mL/kg, from about 0.13 mL/kg to about 0.30 mL/kg, from about 0.13 mL/kg to about 0.25 mL/kg, or from about 0.13 mL/kg to about 0.2 mL/kg (the kg being the weight of the subject). In some embodiments, the pharmaceutical composition is in a unit dose of at least 0.13 mL/kg. In some embodiments, the pharmaceutical composition is in a unit dose of at least 0.20 mL/kg. In some embodiments, the pharmaceutical composition is in a unit dose of at least 0.27 mL/kg. In some embodiments, the pharmaceutical composition is in a unit dose of about 0.24 mL/kg. In some embodiments, the pharmaceutical composition is in a unit dose of at most 0.33 mL/kg. In some embodiments, the pharmaceutical composition is in a unit dose of at least 0.05 mL/kg, at least 0.1 mL/kg, at least 0.13 mL/kg, at least 0.14 mL/kg, at least 0.15 mL/kg, at least 0.16 mL/kg, at least 0.17 mL/kg, at least 0.18 mL/kg, at least 0.19 mL/kg, at least 0.20 mL/kg, at least 0.21 mL/kg, at least 0.22 mL/kg, at least 0.23 mL/kg, at least 0.24 mL/kg, at least 0.25 mL/kg, at least 0.26 mL/kg, at least 0.27 mL/kg, at least 0.28 mL/kg, at least 0.29 mL/kg, at least 0.30 mL/kg, at least 0.31 mL/kg, at least 0.32 mL/kg, at least 0.33 mL/kg, at least 0.34 mL/kg, or at least 0.35 mL/kg. In some embodiments, the pharmaceutical composition is in a unit dose of at most 0.30 mL/kg, at most 0.31 mL/kg, at most 0.32 mL/kg, at most 0.33 mL/kg, at most 0.34 mL/kg, or at most 0.35 mL/kg.

In some embodiments, the pharmaceutical composition is in a unit dose selected from the group consisting of 0.13 mL/kg, 0.14 mL/kg, 0.15 mL/kg, 0.16 mL/kg, 0.17 mL/kg, 0.18 mL/kg, 0.19 mL/kg, 0.2 mL/kg, 0.21 mL/kg, 0.22 mL/kg, 0.23 mL/kg, 0.24 mL/kg, 0.25 mL/kg, 0.26 mL/kg, 0.27 mL/kg, 0.28 mL/kg, 0.29 mL/kg, 0.3 mL/kg, 0.31 mL/kg, 0.32 mL/kg, 0.33 mL/kg, 0.34 mL/kg, 0.35 mL/kg, 0.35 mL/kg, 0.05-0.15 mL/kg, 0.10-0.20 mL/kg, 0.15-0.25 mL/kg, 0.20-0.30 mL/kg, 0.25-0.35 mL/kg, 0.05-0.10 mL/kg, 0.10-0.15 mL/kg, 0.15-0.20 mL/kg, 0.20-0.25 mL/kg, 0.25-0.30 mL/kg, 0.30-0.35 mL/kg, 0.05-0.35 mL/kg, 0.10-0.35 mL/kg, 0.15-0.35 mL/kg, 0.20-0.35 mL/kg, 0.05-0.20 mL/kg, 0.05-0.25 mL/kg, or 0.05-0.30 mL/kg. It is understood that each of the individual volumes described herein can be used to define lower and upper values of a volume range.

The dosage ranges, for the administration of the pharmaceutical composition comprising the rAAV, according to the methods described herein, depend upon, for example, the form of the pharmaceutical composition, its potency (e.g., transduction efficiency of the rAAV, such as measured using the efficiency index, see e.g., FIG. 4-5), and the extent to which symptoms, markers, or indicators of a kidney-associated disorder described herein are desired to be reduced. The dosage should not be so large as to cause adverse side effects, such as immunogenicity (e.g., immune responses against the AAV capsid antigens or the transgene products). Generally, the dosage can vary with the age, condition, and sex of the patient and can be determined by one of skill in the art. The dosage can also be adjusted by the individual physician in the event of any complication.

The efficacy of the pharmaceutical composition, in, e.g., the treatment of a kidney-associated disorder as described herein can be determined by the skilled clinician. However, a treatment is considered "effective treatment," as the term is used herein, if one or more of the signs or symptoms of a kidney-associated disorder described herein are altered in a beneficial manner, other clinically accepted symptoms are improved, or even ameliorated, or a desired response is induced, e.g., by at least 10% following treatment according to the methods described herein. Efficacy can be assessed, for example, by measuring a marker, indicator, symptom, and/or the incidence of a kidney-associated disorder treated according to the methods described herein. Efficacy can also be measured by a failure of an individual to worsen as assessed by hospitalization, or need for medical interventions (i.e., progression of the kidney-associated disorder is halted). Methods of measuring these indicators are known to those of skill in the art and/or are described herein. Treatment includes any treatment of a disorder in an individual or an animal and includes: (1) inhibiting the kidney-associated disorder, e.g., preventing a worsening of symptoms; or (2) relieving the severity of the kidney-associated disorder, e.g., causing regression of symptoms. An effective amount for the treatment of a disorder means that amount which, when administered to a subject in need thereof, is sufficient to result in effective treatment as that term is defined herein, for that disorder. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of a specific kidney-associated disorder.

For example, a mouse model for Cystinuria A is described in Livrozet et al. "An animal model of type A cystinuria due to spontaneous mutation in 129S2/SvPasCrl mice." PLoS One. 2014 Jul. 21, 9(7):e102700, the contents of which are incorporated herein by reference in their entirety. This Cystinuria A mouse model was identified by comparing the Slc3a1 gene sequence of 129S2/SvPasCrl (high occurrence of symptoms related to Cystinuria, including crystalluria and aminoaciduria) and C57BL/6J (low occurrence of such symptoms). An 1232G>A missense mutation was identified in the 129S2/SvPasCrl Slc3a1 gene; this corresponds to an E383K mutation in the expressed rBAT polypeptide. In some embodiments, the Cystinuria A mouse model comprises an 1232G>A missense mutation in the Slc3a1 gene, corresponding to an E383K mutation in the expressed rBAT polypeptide. The 1232G>A mutation in mouse Slc3a1/rBAT (see e.g., SEQ ID NO: 17) corresponds to an 1150G>A mutation in human Slc3a1/rBAT CDS (see e.g., SEQ ID NO: 5). The E383K mutation in mouse Slc3a1/rBAT (see e.g., SEQ ID NO: 18) corresponds to an E384K mutation in human Slc3a1/rBAT (see e.g., SEQ ID NO: 7). Other animal models of Cystinuria A or Cystinuria B known to the skilled person can also be used.

*Mus musculus* solute carrier family 3, member 1 (Slc3a1), mRNA, NCBI Reference Sequence: NM_009205.2, 2307 nt, CDS corresponds to nt 86-2143 of SEQ ID NO: 17; the 1232G nucleotide in SEQ ID NO: 17 (bolded, double-underlined) can be mutated to 1232A in a mouse model of Cystinuria A,

SEQ ID NO: 17

CATTAACAAAGCACAGCGCTCAGCAAGACACCTTTCTACCTCTGTCCCTGCTGGAAAGCA

CCAGGAAGAGCTACACAGGGTAGACATGGATGAGGACAAAGGCAAGAGAGACCCCATC

CAAATGAGTTTGAAGGGATGCCGAACCAATAACGGGTTTGTCCAAAATGAAGACATTCC

GGAGCAGGACCCAGACCCAGGCTCCAGGGACACCCCACAGCCCAACGCCGTGAGTATCC

CTGCTCCAGAGGAGCCTCACCTAAAGGCGGTGCGGCCCTATGCAGGGATGCCCAAGGAA

GTACTCTTCCAGTTCTCCGGCCAGGCTCGCTACCGGGTGCCCCGAGAGATCCTCTTCTGG

CTCACCGTGGTTTCCGTGTTCCTGCTCATTGGAGCCACCATAGCCATCATCGTCATCTCTC

CAAAATGCCTTGACTGGTGGCAAGCAGGTCCCATATACCAGATCTACCCGAGGTCTTTTA

AGGACAGTGACAAGGATGGGAATGGAGACCTGAAAGGTATCCAGGAGAAGCTGGACTA

TATCACTGCTTTAAACATAAAGACTCTTTGGATCACTTCCTTTTATAAATCATCTTTGAAA

GACTTCAGATACGCTGTTGAGGATTTCAAAGAAATTGACCCTATTTTTGGAACAATGAAA

GATTTTGAGAATTTGGTTGCTGCCATCCATGACAAAGGTTTAAAATTAATAATTGATTTC

ATACCAAACCACACTAGTGACAAACATCCTTGGTTCCAATCGAGTAGGACACGGAGCGG

AAAATACACCGATTACTACATCTGGCACAACTGTACCCATGTCAACGGTGTAACCACCCC

TCCCAACAACTGGCTGAGTGTGTATGGAAACTCCAGCTGGCACTTTGATGAAGTACGAA

AGCAATGTTATTTTCACCAGTTTTTGAAAGAGCAACCAGATTTAAATTTCCGAAATCCTG

CTGTTCAAGAGGAAATAAAGGAAATAATAACGTTCTGGCTCTCGAAGGGTGTTGATGGG

TTTAGTTTTGATGCAGTTAAATTTCTTCTGGAAGCGAAGGATCTGAGAAATGAAATCCAA

GTGAATACATCCCAAATTCCGGACACGGTCACCCACTACTCAGAGCTGTACCATGACTTC

ACCACAACTCAGGTGGGAATGCATGACATCGTCCGAGACTTCCGGCAGACCATGAACCA

GTACAGCAGGGAGCCTGGCAGATACCGGTTCATGGGGGCCGAAGCCTCAGCTGAGAGCA

TCGAGAGGACCATGATGTACTATGGCTTGCCATTTATCCAGGAAGCCGACTTTCCTTTCA

ACAAGTACTTCACCACAATAGGCACTCTCTCTGGGCATACTGTCTATGAAGTTATCACAT

CCTGGATGGAAAACATGCCTGAAGGAAAATGGCCCAATTGGATGACTGGCGGACCGGAG

ACTCCTCGGCTGACTTCTCGAGTAGGGAGTGAGTATGTCAACGCCATGCACATGCTCCTG

TTCACACTCCCGGGAACGCCCATCACTTACTATGGAGAGGAAATCGGGATGGGAGACAT

TTCCGTTACAAATTTCAACGAGAGCTATGATAGTACTACCCTTGTCTCCAAGTCACCGAT

-continued

GCAGTGGGACAATAGTTCCAATGCTGGGTTTACTGAGGCCAACCACACCTGGCTACCCAC

AAACTCTGACTACCACACCGTCAATGTGGATGTCCAAAAGACCCAGCCGAGCTCAGCAC

TGAGGCTGTATCAGGATCTGAGTCTACTCCATGCCACAGAGCTGGTCCTCAGCCGGGGCT

GGTTTTGCCTCTTGAGAGACGACAGTCACTCTGTGGTGTACACAAGAGAGCTGGACGGC

ATAGATAACGTCTTCCTCGTGGTTCTGAATTTTGGAGAATCATCAACTGTGCTAAATCTA

CAGGGGATCATTTCAGATCTTCCTCCAGAGCTGAGAATAAGGTTAAGTACCAACTCAGCC

TCCAAAGGCAGTGCTGTTGACACCCGTGCCATTTCTCTGGAGAAGGGAGAGGGCCTGGT

CTTGGAGCACAGCACGAAGGCTCCCCTCCATCAGCAGGCCGCTTTCAGAGACAGATGCTT

TGTTTCCAGTCGGGCGTGCTACTCCAGTGCACTGGACATCCTCTATAGCTCGTGTTAGGA

AGGAAGCTCCCTAAGAGATGGCCACCCAGAACATCACGTACGCACAGGGCTGAGCAGAC

TCATGAATGGCATCAATTCTTAGATATTTCTGTAGCACGAATGCACTGTTTTTAAAGTGTT

TAAAAGATTATGCCAAAATACTAAAGCATTTAAATATGAAAA

*Mus musculus* solute carrier family 3, member 1 (Slc3a1), NCBI ref NP_033231.2, 685 aa; the E384 residue in SEQ ID NO: 18 (bolded, double-underlined) can be mutated to K384 in a mouse model of Cystinuria A,

SEQ ID NO: 18

MDEDKGKRDPIQMSLKGCRTNNGFVQNEDIPEQDPDPGSRDTPQPNAVSIPAPEEPHLKAVR

PYAGMPKEVLFQFSGQARYRVPREILFWLTVVSVFLLIGATIAIIVISPKCLDWWQAGPIYQIY

PRSFKDSDKDGNGDLKGIQEKLDYITALNIKTLWITSFYKSSLKDFRYAVEDFKEIDPIFGTMK

DFENLVAAIHDKGLKLIIDFIPNHTSDKHPWFQSSRTRSGKYTDYYIWHNCTHVNGVTTPPNN

WLSVYGNSSWHFDEVRKQCYFHQFLKEQPDLNFRNPAVQEEIKEIITFWLSKGVDGFSFDAV

KFLLEAKDLRNEIQVNTSQIPDTVTHYSELYHDFTTTQVGMHDIVRDFRQTMNQYSREPGRY

RFMGAEASAESIERTMMYYGLPFIQEADFPFNKYFTTIGTLSGHTVYEVITSWMENMPEGKW

PNWMTGGPETPRLTSRVGSEYVNAMHMLLFTLPGTPITYYGEEIGMGDISVTNFNESYDSTTL

VSKSPMQWDNSSNAGFTEANHTWLPTNSDYHTVNVDVQKTQPSSALRLYQDLSLLHATELV

LSRGWFCLLRDDSHSVVYTRELDGIDNVFLVVLNFGESSTVLNLQGIISDLPPELRIRLSTNSA

SKGSAVDTRAISLEKGEGLVLEHSTKAPLHQQAAFRDRCFVSSRACYSSALDILYSSC

When using an experimental animal model, efficacy of treatment is evidenced when a statistically significant change in a marker is observed. For example, in an animal model of cystinuria the marker showing efficacious treatment following rAAV administration can be a decreased level of crystalluria and/or aminoaciduria. In vitro and animal model assays allow the assessment of a given dose of the pharmaceutical composition.

As described herein, the solution or pharmaceutical composition can comprise at least one pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids; (23) serum component, such as serum albumin, HDL and LDL; (24) $C_2$-$C_{12}$ alcohols; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g., the rAAV as described herein.

Additional non-limiting examples of the pharmaceutically acceptable carrier include sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments, the pharmaceutically acceptable carrier comprises mannitol. In some embodiments, the pharmaceutical composition comprises 25% mannitol. In some embodiments, the pharmaceutical composition comprises at least 5%, at least 10%, at least 15%, at least 20%, at least 25%, at least 30%, at least 35%, or at least 40% mannitol. In some embodiments, the pharmaceutical composition comprises at most 5%, at most 10%, at most 15%, at most 20%, at most 25%, at most 30%, at most 35%, or at most 40% mannitol. In some embodiments, the effect of a specific pharmaceutically acceptable carrier, such as mannitol, can be tested in an animal model (e.g., rat, pig). In some embodiments, the pharmaceutically acceptable carrier does not significantly decrease the efficacy of the rAAV. In some embodiments, the pharmaceutically acceptable carrier significantly increases the efficacy of the rAAV.

Delivery vehicles such as liposomes, nanocapsules, microparticles, microspheres, lipid particles, lipid nanoparticles, vesicles, and the like, can be used for the introduction of the rAAV of the present disclosure into suitable host cells (e.g., kidney tubule cells). In particular, the rAAV vector delivered transgenes can be formulated for delivery either encapsulated in a lipid particle, a liposome, a vesicle, a nanosphere, or a nanoparticle or the like.

Such formulations can be preferred for the introduction of pharmaceutically acceptable formulations of the nucleic acids or the rAAV constructs disclosed herein. The formation and use of liposomes is generally known to those of skill in the art. Liposomes have been developed with improved serum stability and circulation half-times (U.S. Pat. No. 5,741,516). Further, various methods of liposome and liposome-like preparations as drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 m. Sonication of MLVs results in the formation of small unilamellar vesicles (SUVs) with diameters in the range of 200 to 500 A, containing an aqueous solution in the core.

Alternatively, nanocapsule formulations of the rAAV can be used. Nanocapsules can generally entrap substances in a stable and reproducible way. To avoid side effects due to intracellular polymeric overloading, such ultrafine particles (sized around 0.1 m) should be designed using polymers able to be degraded in vivo. Biodegradable polyalkyl-cyanoacrylate nanoparticles that meet these requirements are contemplated for use.

In one embodiment, one can use a nanoparticle, e.g., a lipid nanoparticle (LPN), instead of an AAV capsid to deliver the viral AAV cargo. The term "nanoparticles" also encompasses liposomes and lipid particles having the size of a nanoparticle. Exemplary liposomes can comprise, e.g., DSPC, DPPC, DSPG, Cholesterol, hydrogenated soy phosphatidylcholine, soy phosphatidyl choline, methoxypolyethylene glycol (mPEG-DSPE) phosphatidyl choline (PC), phosphatidyl glycerol (PG), distearoylphosphatidylcholine, and combinations thereof. In some embodiments of any of the aspects, the carrier is, comprises, or consists of a lipid nanoparticle (LNP). Lipid nanoparticles can comprise multiple components, including, e.g., ionizable lipids (such as MC3, DLin-MC3-DMA, ALC-0315, or SM-102), pegylated lipids (such as PEG2000-C-DMG, PEG2000-DMG, ALC-0159), phospholipids (such as DSPC), and cholesterol.

In some embodiments, the LNP comprises (4-hydroxybutyl)azanediyl bis(hexane-6,1-diyl)bis(2-hexyldecanoate), an ionizable cationic lipid (ALC-0315, Chemical Abstracts Service (CAS) Registry Number 2036272-55-4; (2-hexyldecanoate), 2-[(polyethylene glycol)-2000]-N,N-ditetradecylacetamide, a PEG-lipid (ALC-0159, CAS 1849616-42-7); 1,2-distearoyl-sn-glycero-3-phosphocholine, a helper lipid (DSPC, CAS 816-94-4); and/or cholesterol, a helper lipid (Chol, CAS 57-88-5). In some embodiments, the LNP comprises heptadecan-9-yl 8-((2-hydroxyethyl)(6-oxo-6-(undecyloxy)hexyl)amino)octanoate, an ionizable cationic lipid (SM-102, CAS 2089251-47-6); 1,2-dimyristoyl-rac-glycero-3-methoxypolyethylene glycol-2000, a PEG-lipid (PEG2000-DMG, CAS 160743-62-4); 1,2-distearoyl-sn-glycero-3-phosphocholine, a helper lipid (DSPC, CAS 816-94-4); and/or cholesterol, a helper lipid (Chol, CAS 57-88-5). In some embodiments, the LNP comprises ALC-0315, ALC-0159, SM-102, PEG2000-DMG, DSPC, cholesterol, or any combination thereof. See e.g., Alshrari et al., Journal of Infection and Public Health 15 (2022) 123-131; Tenchov et al., ACS Nano 2021, 15, 16982-17015; Schoenmaker et al., International Journal of Pharmaceutics 601 (2021) 120586; Suzuki et al., Drug Metabolism and Pharma-cokinetics 41 (2021) 100424; the contents of each of which are incorporated herein by reference in their entireties.

Generally, the lipid nanoparticles have a mean diameter selected to provide an intended therapeutic effect. Accordingly, in some aspects, the lipid nanoparticle has a mean diameter from about 30 nm to about 150 nm, more typically from about 50 nm to about 150 nm, more typically about 60 nm to about 130 nm, more typically about 70 nm to about 110 nm, most typically about 85 nm to about 105 nm, and preferably about 100 nm. In some aspects, the disclosure provides for lipid particles that are larger in relative size to common nanoparticles and about 150 to 250 nm in size. Lipid nanoparticle particle size can be determined by quasi-elastic light scattering using, for example, a MALVERN ZETASIZER NANO ZS (Malvern, UK) system.

Depending on the intended use of the lipid particles, the proportions of the components can be varied, and the delivery efficiency of a particular formulation can be measured using, for example, an endosomal release parameter (ERP) assay.

The nucleic acid can be complexed with the lipid portion of the particle or encapsulated in the lipid position of the lipid nanoparticle. In some embodiments, the nucleic acid can be fully encapsulated in the lipid position of the lipid nanoparticle, thereby protecting it from degradation by a nuclease, e.g., in an aqueous solution. In some embodiments, the nucleic acid in the lipid nanoparticle is not substantially degraded after exposure of the lipid nanoparticle to a nuclease at 37 °C, e.g., for at least about 20, 30, 45, or 60 minutes. In some embodiments, the nucleic acid in the lipid nanoparticle is not substantially degraded after incubation of the particle in serum at 37 °C, e.g., for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours.

In certain embodiments, the lipid nanoparticles are substantially non-toxic to mammals such as humans.

In some embodiments, lipid nanoparticles are solid core particles that possess at least one lipid bilayer. In other embodiments, the lipid nanoparticles have a non-bilayer structure, i.e., a non-lamellar (i.e., non-bilayer) morphology. Without limitations, the non-bilayer morphology can include, for example, three dimensional tubes, rods, cubic symmetries, etc. The non-lamellar morphology (i.e., non-bilayer structure) of the lipid particles can be determined using analytical techniques known to and used by those of skill in the art. Such techniques include, but are not limited to, Cryo-Transmission Electron Microscopy ("Cryo-TEM"), Differential Scanning calorimetry ("DSC"), X-Ray Diffraction, etc. For example, the morphology of the lipid nanoparticles (lamellar vs. non-lamellar) can readily be assessed and characterized using, e.g., Cryo-TEM analysis as described in US2010/0130588, content of which is incorporated herein by reference in its entirety.

In some further embodiments, the lipid nanoparticles having a non-lamellar morphology are electron dense. In embodiments, the lipid nanoparticle is either unilamellar or multilamellar in structure. In some aspects, the disclosure provides for a lipid nanoparticle formulation that comprises multi-vesicular particles and/or foam-based particles.

Lipid nanoparticles can form spontaneously upon mixing of mRNA and the lipid(s). Depending on the desired particle size distribution, the resultant nanoparticle mixture can be extruded through a membrane (e.g., 100 nm cut-off) using, for example, a thermobarrel extruder, such as LIPEX Extruder (NORTHERN LIPIDS, INC). In some cases, the extrusion step can be omitted. Ethanol removal and simultaneous buffer exchange can be accomplished by, for example, dialysis or tangential flow filtration.

Generally, lipid nanoparticles can be formed by any method known in the art including. For example, the lipid nanoparticles can be prepared by the methods described, for example, in US2013/0037977, US2010/0015218, US2013/0156845, US2013/0164400, US2012/0225129, and US2010/0130588, content of each of which is incorporated herein by reference in its entirety. In some embodiments, lipid nanoparticles can be prepared using a continuous mixing method, a direct dilution process, or an in-line dilution process. The processes and apparatuses for apparatuses for preparing lipid nanoparticles using direct dilution and in-line dilution processes are described in US2007/0042031, content of which is incorporated herein reference in its entirety. The processes and apparatuses for preparing lipid nanoparticles using step-wise dilution processes are described in US2004/0142025, content of which is incorporated herein reference in its entirety.

DEFINITIONS

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal, e.g., for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal, or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a kidney-associated disorder. A subject can be male or female.

A subject can be one who has been previously diagnosed with or identified as suffering from or having a condition in need of treatment (e.g., a kidney-associated disorder) or one or more complications related to such a condition, and optionally, have already undergone treatment for a kidney-associated disorder or the one or more complications related to a kidney-associated disorder. Alternatively, a subject can also be one who has not been previously diagnosed as having a kidney-associated disorder or one or more complications related to a kidney-associated disorder. For example, a subject can be one who exhibits one or more risk factors for a kidney-associated disorder or one or more complications related to a kidney-associated disorder or a subject who does not exhibit risk factors.

A "subject in need" of treatment for a particular condition can be a subject having that condition, diagnosed as having that condition, or at risk of developing that condition.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (e.g., mRNA) or antisense RNA derived from a nucleic acid fragment or fragments and/or to the translation of mRNA into a polypeptide.

"Expression products" include RNA transcribed from a gene, and polypeptides obtained by translation of mRNA transcribed from a gene. The term "gene" refers to the nucleic acid sequence which is transcribed (DNA) to RNA in vitro or in vivo when operably linked to appropriate regulatory sequences. The gene may or may not include regions preceding and following a coding region, e.g. 5' untranslated (5'UTR) or "leader" sequences and 3' UTR or "trailer" sequences, as well as intervening sequences (introns) between individual coding segments (exons).

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments, the methods described herein are performed sequentially, i.e., step (a) followed by step (b) followed by step (c), etc. for any additional steps.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments, a nucleic acid encoding a polypeptide as described herein (e.g., at least one transgene) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. Further, as used herein, the term "vector" refers to a polynucleotide sequence suitable for transferring transgenes into a host cell. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disorder, e.g., a kidney-associated disorder. The term "treating" includes reducing or alleviating at least one adverse effect or symptom of a kidney-associated disorder. Treatment is generally "effective" if one or more symptoms or clinical markers are reduced. Alternatively, treatment is "effective" if the progression of a disorder is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disorder, stabilized (i.e., not worsening) state of disorder, delay or slowing of disorder progression, amelioration or palliation of the disorder state, remission (whether partial or total), and/or decreased mortality, whether detectable or undetectable. The term "treatment" of a disorder also includes providing relief from the symptoms or side-effects of the disorder (including palliative treatment).

As used herein, the term "pharmaceutical composition" refers to the active agent in combination with a pharmaceutically acceptable carrier e.g., a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in or within nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by the retrograde ureter route. Such activity can be performed, e.g., by a medical professional and/or the subject being treated.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

It is understood that each of the individual values described herein can be used to define lower and upper values of a range.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in cell biology, immunology, and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A method of transducing nephrons in a kidney of a subject with a recombinant adeno-associated virus (rAAV), the method comprising:
   guiding a catheter through the subject's urethra, bladder, and ureter; and
   administering a solution comprising the rAAV to the renal pelvis of the kidney through the catheter at a volume of from about 0.13 mL/kg to about 0.33 mL/kg, the kg being the weight of the subject, wherein nephrons of the kidney are transduced with the rAAV at a high efficiency.
2. The method of paragraph 1, wherein the solution comprising the rAAV is administered to the kidney for about 0.5 minutes to about 60 minutes.
3. The method of paragraph 1, wherein the solution comprising the rAAV is administered to the kidney for about 1 minute to about 2 minutes.
4. The method of paragraph 1, wherein the solution comprising the rAAV is administered at an intra-renal pressure of from about 25 cm $H_2O$ to about 55 cm $H_2O$.
5. The method of paragraph 1, wherein the method results in the transduction of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or more of the nephrons in the kidney with the rAAV.
6. The method of paragraph 1, wherein the transduction efficiency of the rAAV of the nephrons in the kidney is at least 2-fold, at least 5-fold, at least 10-fold, at least 50-fold, at least 100-fold, at least 400-fold, at least 1000-fold, or at least 3500-fold increased compared to a corresponding transduction efficiency of corresponding nephrons in another kidney treated by intravenous administration of the solution comprising the rAAV.
7. The method of paragraph 1, wherein the rAAV does not comprise an AAV9 capsid, and the transduction efficiency of the rAAV of the nephrons in the kidney is at least 2-fold, at least 5-fold, at least 10-fold, at least 50-fold, at least 100-fold, at least 400-fold, at least 1000-fold, or at least 3500-fold increased compared to a corresponding transduction efficiency achieved by administering rAAV comprising an AAV9 capsid to another kidney by the same method.
8. The method of paragraph 1, wherein the rAAV does not comprise an AAV9 capsid, and the transduction efficiency of the rAAV in proximal tubule cells of the nephrons in the kidney is at least 2-fold, at least 5-fold, at least 10-fold, at least 50-fold, at least 100-fold, at least 400-fold, at least 1000-fold, or at least 3500-fold increased compared to a corresponding transduction efficiency in proximal tubule cells achieved by administering rAAV comprising an AAV9 capsid to another kidney by the same method.
9. The method of paragraph 1, further comprising a step of blocking a renal blood vessel of the kidney selected from the group consisting of a renal artery, a renal vein, and a combination thereof, prior to administering the solution comprising the rAAV.
10. The method of paragraph 9, further comprising a step of unblocking the renal blood vessel after a period of time of from about 10 minutes to about 60 minutes after administering the solution comprising the rAAV.

11. The method of paragraph 1, wherein the kidney is not isolated from systemic circulation.

12. The method of paragraph 1, wherein a renal blood vessel selected from the group consisting of a renal artery, a renal vein, and a combination thereof of the kidney is not blocked during performance of the method.

13. The method of paragraph 1, wherein the solution comprising the rAAV is administered to the kidney at an intra-renal pressure of from about 27 cm $H_2O$ to about 80 cm $H_2O$.

14. The method of paragraph 1, wherein the subject is a human, a non-human primate, a horse, a dog, or a pig.

15. The method of paragraph 1, wherein at least about 30% of the nephrons of the kidney are transduced with the rAAV.

16. The method of paragraph 1, wherein the volume of the solution comprising the rAAV administered to the subject is from about 0.13 mL/kg to about 0.33 mL/kg.

17. The method of paragraph 1, wherein the volume of the solution comprising the rAAV administered to the subject is from about 0.27 mL/kg to about 0.33 mL/mg.

18. The method of paragraph 1, wherein the solution comprising the rAAV is administered using a balloon catheter.

19. The method of paragraph 9, wherein the renal blood vessel is blocked using a balloon catheter.

20. The method of paragraph 9, wherein the renal blood vessel is blocked using a clamp.

21. The method of paragraph 9, wherein only one of the renal artery or renal vein is blocked.

22. The method of paragraph 1, wherein the renal vein of the kidney is not blocked.

23. The method of paragraph 1, wherein the method does not comprise a continuous perfusion of an isolated kidney.

24. The method of paragraph 1, wherein the method does not comprise a closed circuit comprising the kidney.

25. The method of paragraph 1, wherein the method does not comprise a substantially closed system comprising the kidney.

26. The method of paragraph 1, wherein the method does not comprise diverting circulation from the kidney.

27. The method of paragraph 1, wherein the method does not comprise bypassing the kidney.

28. The method of paragraph 1, wherein the method is performed in vivo.

29. The method of paragraph 1, wherein the method is not performed ex vivo.

30. The method of paragraph 10, wherein the period of time for blocking the at least one renal blood vessel is 15-45 minutes subsequent to the blocking.

31. The method of paragraph 10, wherein the period of time for blocking the at least one renal blood vessel is 20-40 minutes subsequent to the blocking.

32. The method of paragraph 10, wherein the period of time for blocking the at least one renal blood vessel is about 15-30 minutes subsequent to the blocking.

33. The method of paragraph 10, wherein the volume of the solution comprising the rAAV is from about 0.13 mL/kg to about 0.33 mL/kg, and wherein the period of time for blocking the renal blood vessel is about 15-30 minutes subsequent to the blocking.

34. The method of paragraph 1, wherein the rAAV comprises an AAV capsid protein selected from Table 1.

35. The method of paragraph 1, wherein the rAAV comprises a capsid protein selected from the group consisting of AAV2G9, AAV2.5, AAVDJ, and AAV2.

36. The method of paragraph 35, wherein the capsid protein is AAV2G9.

37. The method of paragraph 1, wherein the rAAV comprises a rational polyploid.

38. The method of paragraph 1, wherein the solution comprises the rAAV at a concentration of $10^8$ viral genomes per mL (vg/mL) to $10^{15}$ vg/mL.

39. The method of paragraph 1, wherein the solution comprises the rAAV at a concentration of $10^8$ vg/mL to $10^{13}$ vg/mL.

40. The method of paragraph 1, wherein the solution comprises $1\times10^{13}$ to $2\times10^{13}$ rAAV viral genomes total.

41. The method of paragraph 1, wherein the solution comprises $5\times10^{13}$ to $6\times10^{13}$ rAAV viral genomes total.

42. The method of paragraph 1, wherein the solution comprises $1\times10^{10}$ viral genomes total.

43. The method of paragraph 1, wherein the rAAV comprises a transgene.

44. The method of paragraph 43, wherein the transgene is selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof.

45. The method of paragraph 43, wherein the transgene is selected from the group consisting of Aquaporin 2 (AQP2); ATPase Na+/K+ Transporting Subunit Alpha 1 (ATP1A1); ATPase H+ Transporting V0 Subunit A4 (ATP6V0A4); ATPase H+ Transporting V1 Subunit B1 (ATP6V1B1); Arginine Vasopressin Receptor 2 (AVPR2); Barttin CLCNK (chloride channel K) Type Accessory Subunit Beta (BSND); Carbonic Anhydrase 2 (CA2); Calcium Sensing Receptor (CaSR); Chloride Voltage-Gated Channel 5 (CLCN5); CLCNKA (Chloride Voltage-Gated Channel Ka); Chloride Voltage-Gated Channel Kb (CLCNKB); Claudin 16 (CLDN16); Claudin 19 (CLDN19); Cyclin And CBS Domain Divalent Metal Cation Transport Mediator 2 (CNNM2); Cullin 3 (CUL3); Cytochrome P450 Family 11 Subfamily B Member 1 (CYP11B1); Cytochrome P450 Family 11 Subfamily B Member 2 (CYP11B2); Cytochrome P450 Family 17 Subfamily A Member 1 (CYP17A1); Cytochrome P450 Family 21 Subfamily A Member 2 (CYP21A2); Epidermal Growth Factor (EGF); Epidermal Growth Factor Receptor (EGFR); Enoyl-CoA Hydratase And 3-Hydroxyacyl CoA Dehydrogenase (EHHADH); FAM111 (family 111) Trypsin Like Peptidase A (FAM111A); Forkhead Box I1 (FOXI1); FXYD Domain/Motif Containing Ion Transport Regulator 2 (FXYD2); Glycine Amidinotransferase (GATM); guanine nucleotide binding protein; alpha stimulating (GNAS); hepatocyte nuclear factor 1 (HNF1) Homeobox B (HNF1B); Hepatocyte Nuclear Factor 4 Alpha (HNF4A); Hydroxysteroid 11-Beta Dehydrogenase 2 (HSD11B2); Hydroxy-Delta-5-Steroid Dehydrogenase, 3 Beta- And Steroid Delta-Isomerase 2 (HSD3B2); Potassium Voltage-Gated Channel Subfamily A Member 1 (KCNA1); Potassium Inwardly Rectifying Channel Subfamily J Member 1 (KCNJ1); Potassium Inwardly Rectifying Channel Subfamily J Member 10 (KCNJ10); Kelch Like Family Member 3 (KLHL3); Melanoma Antigen Gene Family Member D2 (MAGED2); Nuclear Receptor Subfamily 3 Group C Member 2 (NR3C2); Oculocerebrorenal Syndrome Of Lowe (OCRL) Inositol Polyphosphate-5-Phosphatase; Pterin-4 Alpha-Carbinolamine Dehydratase 1 (PCBD1); Phosphate Regulating Endopeptidase X-Linked (PHEX); Sodium Channel Epithelial 1 Subunit Alpha (SCNN1A); Sodium Channel Epithelial 1 Subunit Beta (SCNN1B); Sodium Channel Epithelial 1 Subunit Gamma (SCNN1G); Solute Carrier Family 12 Member 1 (SLC12A1); Solute Carrier Family 12 Member 3 (SLC12A3); Solute Carrier Family 1 Member 1 (SLC1A1); Solute Carrier Family 2 Member 2 (SLC2A2); Solute Carrier Family 34 Member 1 (SLC34A1); Solute Carrier Family 34 Member 3 (SLC34A3); Solute Carrier Family 36 Member 2 (SLC36A2); Solute Carrier Family 3 Member 1 (SLC3A1); Solute Carrier Family 4 Member 1 (SLC4A1); Solute Carrier Family 6 Member 19 (SLC6A19); Solute Carrier Family 6 Member 20 (SLC6A20); Solute Carrier Family 7 Member 7 (SLC7A7); Solute Carrier Family 7 Member 9 (SLC7A9); Transient Receptor Potential Cation Channel Subfamily M Member 6 (TRPM6); WD Repeat Domain 72 (WDR72); With-no-lysine (WNK, Lysine Deficient) Protein Kinase 1 (WNK1); With-no-lysine (WNK, Lysine Deficient) Protein Kinase 4 (WNK4); and combinations thereof.

46. The method of paragraph 43, wherein the transgene comprises an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD).

47. The method of paragraph 1, wherein circulating serum of the subject does not neutralize the rAAV upon administration.

48. The method of paragraph 1, wherein the subject has antibodies that neutralize the rAAV to be administered in the circulating serum, and the antibodies do not neutralize the rAAV in the kidney upon administration.

49. The method of paragraph 1, wherein a subsequent administration of the rAAV of paragraph 1 is performed without resulting in a substantial inflammatory response in the kidney.

50. The method of paragraph 49, wherein the subsequent administration is at least one day later.

51. The method of paragraph 49, wherein the subsequent administration is at least one month later.

52. The method of paragraph 1, wherein the method transduces proximal tubules of the kidney with the rAAV.

53. The method of paragraph 1, wherein the method transduces at least one cell population of a glomerulus, a glomerular capsule, a proximal convoluted tubule, the loop of Henle, a distal convoluted tubule, or a collecting duct of the kidney with the rAAV.

54. The method of paragraph 1, wherein the rAAV comprises a kidney-specific promoter.

55. The method of paragraph 54, wherein the kidney-specific promoter is selected from the group consisting of kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.

56. The method of paragraph 54, wherein the kidney-specific promoter is a synthetic promoter.

57. The method of paragraph 1, wherein the rAAV has a genome comprising a promoter specific to proximal convoluted tubules and/or collecting ducts.

58. A method of treating a kidney-associated disorder in a subject in need thereof, the method comprising administering a recombinant adeno-associated virus (rAAV) to the subject by performing the method according to paragraph 1.

59. The method of paragraph 58, wherein the kidney-associated disorder is selected from the group consisting of autosomal dominant polycystic kidney disease (ADPKD); Alport syndrome; autosomal dominant tubulointerstitial kidney disease (ADTKD); medullary cystic kidney disease; nephronophthisis; Bartter Syndrome; Von Hippel-Lindau syndrome; Gitelman syndrome; congenital nephrotic syndrome; primary hyperoxaluria; Dent disease; Thin Basement Membrane Nephropathy; cystinuria; Liddle syndrome; Papillorenal syndrome; and cystinosis.

60. The method of paragraph 58, wherein the kidney-associated disorder is selected from the group consisting of Apparent mineralocorticoid excess, Autosomal dominant hypocalcemia, Autosomal dominant hypomagnesemia, Bartter type 1, Bartter type 2, Bartter type 3, Bartter type 4a, Bartter type 4b, Bartter type 5, Congenital adrenal hyperplasia type 1, Congenital adrenal hyperplasia type 2, Congenital adrenal hyperplasia type 4, Congenital adrenal hyperplasia type 5, Cystinuria A, Cystinuria B, Dent disease type 1, Dent disease type 2/Lowe syndrome, Dicarboxylic aminoaciduria, Distal RTA, EAST/SeSAME syndrome, Fanconi Bickel syndrome, Fanconi renotubular syndrome 1, Fanconi renotubular syndrome 2, Fanconi renotubular syndrome 3, Fanconi renotubular syndrome 4, Gitelman syndrome, Glucocorticoid remediable aldosteronism, Hartnup disorder, Hereditary hypophosphatemic rickets with hypercalciuria, HNF1B-related kidney disease, Hyperphenylalaninemia BH4-deficient, Hypomagnesemia type 1/hypomagnesemia with secondary hypocalcemia, Hypomagnesemia type 2, Hypomagnesemia type 3/familial hypomagnesemia with hypercalciuria and nephrocalcinosis, Hypomagnesemia type 4, Hypomagnesemia type 5/familial hypomagnesemia with hypercalciuria and nephrocalcinosis, Hypomagnesemia, seizures, and mental retardation type 1, Hypomagnesemia, seizures, and mental retardation type 2, Iminoglycinuria, Kenny-Caffey syndrome type 2, Liddle syndrome, Lysinuric protein intolerance, Neonatal inflammatory skin and bowel disease type 2, Nephrogenic diabetes insipidus, Nephrogenic syndrome of inappropriate antidiuresis, Pseudohypoaldosteronism type 1, Pseudohypoaldosteronism type 1A, Pseudohypoaldosteronism type 2b, Pseudohypoaldosteronism type 2c, Pseudohypoaldosteronism type 2d, Pseudohypoaldosteronism type 2e, Renal tubular acidosis type 3, and X-linked hypophosphatemic rickets.

61. The method of paragraph 58, wherein the kidney-associated disorder is Cystinuria, and the transgene is SLC3A1 and/or SLC7A9.

62. The method of paragraph 58, wherein the kidney-associated disorder is autosomal dominant polycystic kidney disease (ADPKD), and the transgene is PKD1, PKD2, and/or GANAB.

63. A method of transducing at least about 10% of the nephrons in a kidney of a subject with a recombinant adeno-associated virus (rAAV), the method comprising:

a) blocking a renal blood vessel of the kidney selected from the group consisting of a renal artery, a renal vein, and a combination thereof;

b) guiding a catheter through the subject's urethra, bladder, and ureter;

c) administering a solution comprising the rAAV to the renal pelvis of the kidney through the catheter at a volume of from about 0.13 mL/kg to about 0.33 mL/kg, the kg being the weight of the subject; and d) unblocking the renal blood vessel after a period of time of from about 10 minutes to about 60 minutes after administering the solution comprising the rAAV, wherein the method results in the transduction of at least about 10% of the nephrons in the kidney with the rAAV.

64. A method of transducing at least about 25% of the nephrons in a kidney of a subject with a recombinant adeno-associated virus (rAAV), the method comprising:

a) blocking a renal blood vessel of the kidney selected from the group consisting of a renal artery, a renal vein, and a combination thereof;

b) guiding a catheter through the subject's urethra, bladder, and ureter;

c) administering a solution comprising the rAAV to the renal pelvis of the kidney through the catheter at a volume of from about 0.13 mL/kg to about 0.33 mL/kg, the kg being the weight of the subject; and d) unblocking the renal blood vessel after a period of time of from about 10 minutes to about 60 minutes after administering the solution comprising the rAAV, wherein the method results in the transduction of at least about 25% of the nephrons in the kidney with the rAAV.

65. A method of transducing at least about 25% of the nephrons in a kidney of a subject with a recombinant adeno-associated virus (rAAV), the method comprising:

a) blocking a renal artery of the kidney and not blocking a renal vein of the kidney;

b) guiding a catheter through the subject's urethra, bladder, and ureter;

c) administering a volume of a solution comprising the rAAV to the renal pelvis of the kidney through the catheter; and d) unblocking the renal artery after a period of time of from about 10 minutes to about 60 minutes after administering the solution comprising the rAAV, wherein the method results in the transduction of at least about 25% of the nephrons in the kidney with the rAAV.

66. A method of transducing nephrons in a kidney of a subject, the method comprising:

a) blocking a renal blood vessel selected from the group consisting of a renal artery, a renal vein, and a combination thereof of the kidney;

b) guiding a catheter through the subject's urethra, bladder, and ureter;

c) administering a volume of a solution comprising rAAV to the renal pelvis of the kidney through the catheter, the rAAV not being rAAV9; and d) unblocking the renal blood vessel after a period of time of from about 10 minutes to about 60 minutes after administering the solution comprising the rAAV, wherein the method results in a transduction efficiency that is at least 2-fold higher compared to a corresponding transduction efficiency achieved by administering rAAV comprising an AAV9 capsid to another kidney by the same method.

67. The method of paragraph 66, wherein the rAAV comprises a capsid protein selected from Table 1.

68. The method of paragraph 66, wherein the rAAV has at least 2-fold higher transduction efficiency in the kidney compared to a corresponding transduction efficiency achieved by administering rAAV comprising an AAV9 capsid to another kidney by the same method.

69. The method of paragraph 66, wherein the rAAV has 400-fold higher transduction efficiency in the kidney compared to a corresponding transduction efficiency achieved by administering rAAV comprising an AAV9 capsid to another kidney by the same method.

70. A method of transducing at least about 25% of the nephrons in a kidney of a subject with a recombinant adeno-associated virus (rAAV), the method comprising:

a) isolating the kidney from systemic circulation;

b) guiding a catheter through the subject's urethra, bladder, and ureter;

c) administering a solution comprising the rAAV to the renal pelvis of the kidney through the catheter at a volume of from about 0.13 mL/kg to about 0.33 mL/kg, the kg being the weight of the subject; and d) re-establishing the kidney into systemic circulation after a period of time of from about 10 minutes to about 60 minutes after administering the solution comprising the rAAV, wherein the method results in the transduction of at least about 25% of the nephrons in the kidney with the rAAV.

71. A method of treating a kidney disorder in a subject in need thereof, the method comprising:

administering to a kidney of the subject a first recombinant adeno-associated virus (rAAV) encoding a transgene that is therapeutic toward the kidney disorder; and subsequent to administering the first rAAV, administering to the kidney or a different kidney of the subject a second rAAV encoding the transgene or a different transgene that is therapeutic toward to the kidney disorder, wherein the first rAAV and the second rAAV are cross seroreactive, and wherein the subject does not elicit a significant immune response to the second rAAV in the kidney.

72. The method of paragraph 71, wherein at least one solution comprising the first and/or second rAAV is administered to the kidney at an intra-renal pressure of from about 25 cm $H_2O$ to about 55 cm $H_2O$.
73. The method of paragraph 71, wherein a solution comprising the second rAAV is administered after about a week.
74. The method of paragraph 71, wherein the first and/or second rAAVs are administered by an administration method comprising:
guiding a catheter through the subject's urethra, bladder, and ureter; and
administering a solution comprising the first or second rAAV through the catheter to the renal pelvis of the kidney at a volume of from about 0.13 mL/kg to about 0.33 mL/kg, the kg being the weight of the subject.
75. The method of paragraph 71, wherein the first and/or second rAAVs are administered by an administration method comprising:
a) blocking a renal blood vessel of the kidney selected from the group consisting of a renal artery, a renal vein, and a combination thereof;
b) guiding a catheter through the subject's urethra, bladder, and ureter;
c) administering a volume of a solution comprising the first or second rAAV through the catheter to the renal pelvis of the kidney or a different kidney at a volume of volume is from about 0.13 mL/kg to about 0.33 mL/kg, the kg being the weight of the subject; and
d) unblocking renal blood vessel after a period of time of from about 10 minutes to about 60 minutes administering the solution comprising the first or second rAAV.
76. The method of paragraph 71, wherein the administration method results in at least about 25% of the nephrons in the kidney being transduced with the rAAV.
77. The method of paragraph 71, wherein the subject has neutralizing antibodies toward the first rAAV therapeutic prior to the administering.
78. The method of paragraph 71, wherein the capsid protein of the first rAAV is the same serotype as the capsid protein of the second rAAV.
79. The method of paragraph 71, wherein the capsid protein of the first rAAV is a different serotype as the capsid protein of the second rAAV.
80. The method of paragraph 71, wherein the time period for subsequent administration of the second rAAV is determined based on the efficacy or longevity of the administration of the first rAAV.
81. The method of paragraph 71, wherein the first rAAV is administered to a first kidney of the subject, and the second rAAV is administered to a second kidney of the subject.
82. The method of paragraph 71, wherein the first rAAV is administered to a first kidney of the subject, and the second rAAV is administered to the first kidney of the subject.
83. The method of paragraph 71, wherein the first rAAV is administered to both kidneys of the subject, and the second rAAV is administered to both kidneys of the subject.
84. A method of treating a kidney disorder in a subject in need thereof, the subject being seropositive for a recombinant adeno-associated virus (rAAV) therapeutic, the method comprising:
administering to a kidney of the subject the rAAV therapeutic encoding a transgene that is therapeutic toward the kidney disorder,
wherein the subject does not elicit a significant immune response to the rAAV therapeutic in the kidney.
85. The method of paragraph 84, wherein the subject has neutralizing antibodies toward the rAAV therapeutic prior to the administering.
86. The method of paragraph 84, wherein the rAAV is administered by an administration method comprising:
guiding a catheter through the subject's urethra, bladder, and ureter; and
administering a solution comprising the first or second rAAV through the catheter to the renal pelvis of the kidney at a volume of from about 0.13 mL/kg to about 0.33 mL/kg, the kg being the weight of the subject.
87. The method of paragraph 84, wherein the rAAV is administered by an administration method comprising:
a) blocking a renal blood vessel of the kidney selected from the group consisting of a renal artery, a renal vein, and a combination thereof;
b) guiding a catheter through the subject's urethra, bladder, and ureter;
c) administering a solution comprising the rAAV to the renal pelvis of the kidney at a volume of from about 0.13 mL/kg to about 0.33 mL/kg, the kg being the weight of the subject; and
d) unblocking renal blood vessel after a period of time of from about 10 minutes to about 60 minutes after administering the solution comprising the rAAV, wherein the administration method results in at least about 25% of the nephrons in the kidney being transduced with the rAAV.
88. A method of transducing at least about 25% of the nephrons in a kidney of a subject with a recombinant adeno-associated virus (rAAV), the method comprising:
a) blocking a renal blood vessel selected from the group consisting of a renal artery, a renal vein, and a combination thereof of the kidney;
b) guiding a catheter through the subject's urethra, bladder, and ureter;
c) administering a solution comprising the rAAV to the renal pelvis of the kidney through the catheter at a volume of from about 0.13 mL/kg to about 0.33 mL/kg, the kg being the weight of the subject, wherein the rAAV comprises a capsid protein selected from Table 1; and
d) unblocking the renal blood vessel after a period of time of from about 10 minutes to about 60 minutes after administering the solution comprising the rAAV,
wherein the method results in the transduction of at least about 25% of the nephrons in the kidney with the rAAV.
89. A method of treating a kidney-associated disorder in a subject in need thereof, the method comprising administering the rAAV to the subject by performing the method according to paragraph 88.
90. The method of paragraph 89, wherein the rAAV is administered to the kidney at an intra-renal pressure of from about 25 cm $H_2O$ to about 55 cm $H_2O$.
91. The method of paragraph 89, wherein the volume of the solution is 0.27 mL/kg to 0.33 mL/kg.

92. The method of paragraph 89, wherein the period of time is 30-60 minutes after administering the solution comprising the rAAV.
93. The method of paragraph 89, wherein the subject is seropositive for the rAAV prior to the administration of the solution comprising the rAAV.
94. The method of any one of paragraphs 1, 58, 63-66, 70, 71, 84, 88, or 89, wherein the rAAV is administered in liposomes, nanocapsules, microparticles, microspheres, lipid particles, lipid nanoparticles, or vesicles.
95. The method of any one of paragraphs 1, 58, 63-66, 70, 71, 84, 88, or 89, wherein the subject the rAAV is administered in lipid nanoparticles (LNPs).
96. A pharmaceutical composition comprising a recombinant adeno-associated virus (rAAV) comprising:
   a) an AAV capsid protein selected from Table 1;
   b) a transgene comprising:
      i) a gene selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof; or
      ii) an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD); and
   c) a pharmaceutically acceptable carrier.
97. A pharmaceutical composition comprising a recombinant adeno-associated virus (rAAV) comprising:
   a) an AAV capsid protein selected from Table 1;
   b) a transgene comprising a gene selected from the group consisting of Aquaporin 2 (AQP2); ATPase Na+/K+ Transporting Subunit Alpha 1 (ATP1A1); ATPase H+ Transporting V0 Subunit A4 (ATP6VOA4); ATPase H+ Transporting V1 Subunit B1 (ATP6V1B1); Arginine Vasopressin Receptor 2 (AVPR2); Barttin CLCNK (chloride channel K) Type Accessory Subunit Beta (BSND); Carbonic Anhydrase 2 (CA2); Calcium Sensing Receptor (CaSR); Chloride Voltage-Gated Channel 5 (CLCN5); CLCNKA (Chloride Voltage-Gated Channel Ka); Chloride Voltage-Gated Channel Kb (CLCNKB); Claudin 16 (CLDN16); Claudin 19 (CLDN19); Cyclin And CBS Domain Divalent Metal Cation Transport Mediator 2 (CNNM2); Cullin 3 (CUL3); Cytochrome P450 Family 11 Subfamily B Member 1 (CYP11B1); Cytochrome P450 Family 11 Subfamily B Member 2 (CYP11B2); Cytochrome P450 Family 17 Subfamily A Member 1 (CYP17A1); Cytochrome P450 Family 21 Subfamily A Member 2 (CYP21A2); Epidermal Growth Factor (EGF); Epidermal Growth Factor Receptor (EGFR); Enoyl-CoA Hydratase And 3-Hydroxyacyl CoA Dehydrogenase (EHHADH); FAM111 (family 111) Trypsin Like Peptidase A (FAM111A); Forkhead Box I1 (FOXI1); FXYD Domain/Motif Containing Ion Transport Regulator 2 (FXYD2); Glycine Amidinotransferase (GATM); guanine nucleotide binding protein; alpha stimulating (GNAS); hepatocyte nuclear factor 1 (HNF1) Homeobox B (HNF1B); Hepatocyte Nuclear Factor 4 Alpha (HNF4A); Hydroxysteroid 11-Beta Dehydrogenase 2 (HSD11B2); Hydroxy-Delta-5-Steroid Dehydrogenase, 3 Beta- And Steroid Delta-Isomerase 2 (HSD3B2); Potassium Voltage-Gated Channel Subfamily A Member 1 (KCNA1); Potassium Inwardly Rectifying Channel Subfamily J Member 1 (KCNJ1); Potassium Inwardly Rectifying Channel Subfamily J Member 10 (KCNJ10); Kelch Like Family Member 3 (KLHL3); Melanoma Antigen Gene Family Member D2 (MAGED2); Nuclear Receptor Subfamily 3 Group C Member 2 (NR3C2); Oculocerebrorenal Syndrome Of Lowe (OCRL) Inositol Polyphosphate-5-Phosphatase; Pterin-4 Alpha-Carbinolamine Dehydratase 1 (PCBD1); Phosphate Regulating Endopeptidase X-Linked (PHEX); Sodium Channel Epithelial 1 Subunit Alpha (SCNN1A); Sodium Channel Epithelial 1 Subunit Beta (SCNN1B); Sodium Channel Epithelial 1 Subunit Gamma (SCNN1G); Solute Carrier Family 12 Member 1 (SLC12A1); Solute Carrier Family 12 Member 3 (SLC12A3); Solute Carrier Family 1 Member 1 (SLC1A1); Solute Carrier Family 2 Member 2 (SLC2A2); Solute Carrier Family 34 Member 1 (SLC34A1); Solute Carrier Family 34 Member 3 (SLC34A3); Solute Carrier Family 36 Member 2 (SLC36A2); Solute Carrier Family 3 Member 1 (SLC3A1); Solute Carrier Family 4 Member 1 (SLC4A1); Solute Carrier Family 6 Member 19 (SLC6A19); Solute Carrier Family 6 Member 20 (SLC6A20); Solute Carrier Family 7 Member 7 (SLC7A7); Solute Carrier Family 7 Member 9 (SLC7A9); Transient Receptor Potential Cation Channel Subfamily M Member 6 (TRPM6); WD Repeat Domain 72 (WDR72); With-no-lysine (WNK, Lysine Deficient) Protein Kinase 1 (WNK1); With-no-lysine (WNK, Lysine Deficient) Protein Kinase 4 (WNK4); and combinations thereof; and
   c) a pharmaceutically acceptable carrier.
98. The pharmaceutical composition of paragraph 96 or 97, wherein the pharmaceutically acceptable carrier comprises mannitol.
99. The pharmaceutical composition of paragraph 96 or 97, wherein the AAV comprises a capsid protein of AAV2G9.
100. The pharmaceutical composition of paragraph 96 or 97, wherein the solution that comprises the rAAV is at a concentration of $10^8$ viral genomes per mL (vg/mL) to $10^{15}$ vg/mL.

101. The pharmaceutical composition of paragraph 96 or 97, wherein solution that comprises the rAAV is at a concentration of $10^8$ vg/mL to $10^{13}$ vg/mL.
102. The pharmaceutical composition of paragraph 96 or 97, wherein the pharmaceutical composition comprises $1\times10^{13}$ to $2\times10^{13}$ rAAV viral genomes total.
103. The pharmaceutical composition of paragraph 96 or 97, wherein the pharmaceutical composition comprises $5\times10^{13}$ to $6\times10^{13}$ rAAV viral genomes total.
104. The pharmaceutical composition of paragraph 96 or 97, wherein the pharmaceutical composition is in a unit dose of from about 0.13 mL/kg to about 0.33 mL/kg, the kg being the weight of the subject.
105. The pharmaceutical composition of paragraph 96 or 97, wherein the pharmaceutical composition is in a unit dose of from about 0.27 mL/kg to about 0.33 mL/kg.
106. The pharmaceutical composition of paragraph 96 or 97, wherein the transgene comprises a reporter protein.
107. The pharmaceutical composition of paragraph 96 or 97, wherein the genome of the rAAV comprises a kidney-specific promoter.
108. The pharmaceutical composition of paragraph 107, wherein the kidney-specific promoter is selected from the group consisting of: kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.
109. The pharmaceutical composition of paragraph 107, wherein the kidney-specific promoter is a synthetic promoter.
110. The pharmaceutical composition of paragraph 96 or 97, wherein the genome of the rAAV comprises a promoter specific to proximal convoluted tubules and/or collecting ducts.
111. The pharmaceutical composition of paragraph 96 or 97, wherein the rAAV is formulated for delivery in liposomes, nanocapsules, microparticles, microspheres, lipid particles, lipid nanoparticles, or vesicles.
112. The pharmaceutical composition of paragraph 96 or 97, wherein the rAAV is formulated for delivery in lipid nanoparticles (LNPs).
113. A method of transducing nephrons in a kidney of a subject with a recombinant adeno-associated virus (rAAV), the method comprising: guiding a catheter through the subject's urethra, bladder, and ureter; and administering a solution comprising the rAAV to the renal pelvis of the kidney at a volume of from about 0.13 mL/kg to about 0.33 mL/kg, the kg being the weight of the subject, wherein the rAAV comprises AAV2G9, and wherein nephrons of the kidney are transduced with the rAAV at a high efficiency.

Some embodiments of the technology described herein can be defined according to any of the following numbered paragraphs:

1. A method of transducing at least about 25% of the nephrons in a kidney of a subject with a recombinant adeno-associated virus (rAAV), the method comprising:
   a) blocking a renal blood vessel of the kidney selected from the group consisting of a renal artery, a renal vein, and a combination thereof;
   b) administering a volume of a solution comprising the rAAV into a ureter of the kidney in a retrograde route, wherein the volume is from about 0.13 mL/kg to about 0.33 mL/kg, the kg being the weight of the subject; and
   c) unblocking the renal blood vessel after a period of time of from about 10 minutes to about 60 minutes subsequent to the blocking,
   wherein the method results in the transduction of at least about 25% of the nephrons in the kidney with the rAAV.
2. The method of paragraph 1, wherein the rAAV is administered to the kidney at an intra-renal pressure of from about 27 cm $H_2O$ to about 80 cm $H_2O$.
3. The method of paragraph 1, wherein the subject is a human, non-human primate, horse, dog, or pig.
4. The method of paragraph 1, wherein at least about 30% of the nephrons of the kidney are transduced with the rAAV.
5. The method of paragraph 1, wherein the volume of the solution comprising the rAAV is from about 0.2 mL/kg to about 0.27 mL/kg.
6. The method of paragraph 1, wherein the volume of the solution comprising the rAAV is from about 0.27 mL/kg to about 0.33 mL/mg.
7. The method of paragraph 1, wherein the solution comprising the rAAV is administered in the retrograde route to the ureter using a balloon catheter.
8. The method of paragraph 1, wherein the renal blood vessel is blocked using a balloon catheter.
9. The method of paragraph 1, wherein the renal blood vessel is blocked using a clamp.
10. The method of paragraph 1, wherein only one of the renal artery or renal vein is blocked.
11. The method of paragraph 1, wherein the renal vein is not blocked.
12. The method of paragraph 1, wherein the method does not comprise a continuous perfusion of the kidney.
13. The method of paragraph 1, wherein the method does not comprise a closed circuit comprising the kidney.
14. The method of paragraph 1, wherein the method does not comprise a substantially closed system comprising the kidney.
15. The method of paragraph 1, wherein the method does not comprise diverting circulation from the kidney.
16. The method of paragraph 1, wherein the method does not comprise bypassing the kidney.
17. The method of paragraph 1, wherein the method is performed in vivo.
18. The method of paragraph 1, wherein the method is not performed ex vivo.
19. The method of paragraph 1, wherein the period of time for blocking the at renal blood vessel is 15-45 minutes subsequent to the blocking.
20. The method of paragraph 1, wherein the period of time for blocking the at renal blood vessel is 20-40 minutes subsequent to the blocking.
21. The method of paragraph 1, wherein the period of time for blocking the at renal blood vessel is about 30 minutes subsequent to the blocking.
22. The method of paragraph 1, wherein the volume of the solution comprising the rAAV is from about 0.2 mL/kg to about 0.27 mL/kg, and wherein the period of time for blocking the renal blood vessel is about 30 minutes subsequent to the blocking.
23. The method of paragraph 1, wherein the rAAV comprises an AAV capsid protein selected from Table 1.
24. The method of paragraph 1, wherein the rAAV is selected from the group consisting of AAV2G9, AAV2.5, AAVDJ, and AAV2.
25. The method of paragraph 1, wherein the rAAV comprises a capsid protein from serotype AAV2G9.

26. The method of paragraph 1, wherein the rAAV is a rational polyploid.
27. The method of paragraph 1, wherein the rAAV is at a concentration of $10^8$ viral genomes per mL (vg/mL) to $10^{15}$ vg/mL.
28. The method of paragraph 1, wherein the rAAV is at a concentration of $10^8$ vg/mL to $10^{13}$ vg/mL.
29. The method of paragraph 1, wherein the solution comprises $1\times10^{13}$ to $2\times10^{13}$ rAAV viral genomes total.
30. The method of paragraph 1, wherein the solution comprises $5\times10^{13}$ to $6\times10^{13}$ rAAV viral genomes total.
31. The method of paragraph 1, wherein the solution comprises $1\times10^{10}$ viral genomes total.
32. The method of paragraph 1, wherein the rAAV comprises a transgene.
33. The method of paragraph 32, wherein the transgene is selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof.
34. The method of paragraph 32, wherein the transgene comprises an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD).
35. The method of paragraph 1, wherein circulating serum of the subject does not neutralize the rAAV upon administration.
36. The method of paragraph 1, wherein the subject has antibodies that neutralize the rAAV to be administered in the circulating serum and the antibodies do not neutralize the rAAV in the kidney upon administration.
37. The method of paragraph 1, wherein a subsequent administration of the rAAV of paragraph 1 is performed without resulting in a substantial inflammatory response in the kidney.
38. The method of paragraph 37, wherein the subsequent administration is at least one month later.
39. The method of paragraph 1, wherein the method transduces proximal tubules of the kidney with the rAAV.
40. The method of paragraph 1, wherein the method transduces at least one of a glomerulus, a glomerular capsule, a proximal convoluted tubule, the loop of Henle, or a distal convoluted tubule of the kidney with the rAAV.
41. The method of paragraph 1, wherein the rAAV comprises a kidney-specific promoter.
42. The method of paragraph 41, wherein the kidney-specific promoter is selected from the group consisting of kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.
43. The method of paragraph 41, wherein the kidney-specific promoter is a synthetic promoter.
44. The method of paragraph 1, wherein the rAAV has a genome comprising a promoter specific to proximal convoluted tubules and/or collecting ducts.
45. A method of treating a kidney-associated disorder in a subject in need thereof, the method comprising administering a recombinant adeno-associated virus (rAAV) to the subject by performing the method according to paragraph 1.
46. The method of paragraph 45, wherein the kidney-associated disorder is selected from the group consisting of autosomal dominant polycystic kidney disease (ADPKD); Alport syndrome; autosomal dominant tubulointerstitial kidney disease (ADTKD); medullary cystic kidney disease; nephronophthisis; Bartter Syndrome; Von Hippel-Lindau syndrome; Gitelman syndrome; congenital nephrotic syndrome; primary hyperoxaluria; Dent disease; Thin Basement Membrane Nephropathy; cystinuria; Liddle syndrome; Papillorenal syndrome; and cystinosis.
47. A method of transducing at least about 25% of the nephrons in a kidney of a subject with a recombinant adeno-associated virus (rAAV), the method comprising:
   a) blocking a renal artery of the kidney and not blocking a renal vein of the kidney;
   b) administering a volume of a solution comprising the rAAV into a ureter of the kidney in a retrograde route; and
   c) unblocking the renal artery after a period of time of from about 10 minutes to about 60 minutes subsequent to the blocking, wherein the method results in the transduction of at least about 25% of the nephrons in the kidney with the rAAV.
48. A method of transducing nephrons in a kidney of a subject, the method comprising:
   a) blocking a renal blood vessel selected from the group consisting of a renal artery, a renal vein, and a combination thereof of the kidney;
   b) administering a volume of a solution comprising rAAV into a ureter of the kidney in a retrograde route, the rAAV not being rAAV9; and
   c) unblocking the renal blood vessel after a period of time of from about 10 minutes to about 60 minutes subsequent to the blocking, wherein the method results in a transduction efficiency that is at least 2-fold higher than a corresponding administration using rAAV9 instead of the rAAV.
49. The method of paragraph 48, wherein the rAAV is selected from the capsids of Table 1.
50. The method of paragraph 48, wherein the rAAV has 400-fold higher transduction efficiency in the kidney compared to AAV9.

51. A method of transducing at least about 25% of the nephrons in a kidney of a subject with a recombinant adeno-associated virus (rAAV), the method comprising:
  a) isolating the kidney from systemic circulation;
  b) administering a volume of a solution comprising the rAAV into a ureter of the kidney in a retrograde route, wherein the volume is from about 0.13 mL/kg to about 0.33 mL/kg, the kg being the weight of the subject; and
  c) re-establishing the kidney into systemic circulation after a period of time of from about 10 minutes to about 60 minutes after the isolating, wherein the method results in the transduction of at least about 25% of the nephrons in the kidney with the rAAV.

52. A method of treating a kidney disorder in a subject in need thereof, the method comprising:
  administering to a kidney of the subject a first recombinant adeno-associated virus (rAAV) encoding a transgene that is therapeutic toward the kidney disorder; and
  subsequent to administering the first rAAV, administering to the kidney or a different kidney of the subject a second rAAV encoding the transgene or a different transgene that is therapeutic toward to the kidney disorder,
  wherein the first rAAV and the second rAAV are cross seroreactive, and
  wherein the subject does not elicit a significant immune response to the second rAAV in the kidney.

53. The method of paragraph 52, wherein the first and/or second rAAV is administered to the kidney at an intra-renal pressure of from about 27 cm $H_2O$ to about 80 cm $H_2O$.

54. The method of paragraph 52, wherein the second rAAV is administered after about a week.

55. The method of paragraph 52, wherein the first and second rAAVs are administered by an administration method comprising:
  a) blocking a renal blood vessel of the kidney selected from the group consisting of a renal artery, a renal vein, and a combination thereof;
  b) administering a volume of a solution comprising the first or second rAAV into a ureter of the kidney or a second ureter to the different kidney in a retrograde route, wherein the volume is from about 0.13 mL/kg to about 0.33 mL/kg, the kg being the weight of the subject; and
  c) unblocking renal blood vessel after a period of time of from about 10 minutes to about 60 minutes subsequent to the blocking.

56. The method of paragraph 55, wherein the administration method results in at least about 25% of the nephrons in the kidney being transduced with the rAAV.

57. The method of paragraph 52, wherein the subject has neutralizing antibodies toward the first rAAV therapeutic prior to the administering.

58. The method of paragraph 52, wherein the capsid of the first rAAV is the same serotype as the capsid of the second rAAV.

59. The method of paragraph 52, wherein the capsid of the first rAAV is a different serotype as the capsid of the second rAAV.

60. The method of paragraph 52, wherein the time period for subsequent administration of the second rAAV is determined based on the efficacy or longevity of the administration of the first rAAV.

61. The method of paragraph 52, wherein the first rAAV is administered to a first kidney of the subject, and the second rAAV is administered to a second kidney of the subject.

62. The method of paragraph 52, wherein the first rAAV is administered to a first kidney of the subject, and the second rAAV is administered to the first kidney of the subject.

63. The method of paragraph 52, wherein the first rAAV is administered to both kidneys of the subject, and the second rAAV is administered to both kidneys of the subject.

64. A method of treating a kidney disorder in a subject in need thereof, the subject being seropositive for a recombinant adeno-associated virus (rAAV) therapeutic, the method comprising:
  administering to a kidney of the subject the rAAV therapeutic encoding a transgene that is therapeutic toward the kidney disorder,
  wherein the subject does not elicit a significant immune response to the rAAV therapeutic in the kidney.

65. The method of paragraph 64, wherein the subject has neutralizing antibodies toward the rAAV therapeutic prior to the administering.

66. The method of paragraph 64, wherein the rAAV is administered by an administration method comprising:
  a) blocking a renal blood vessel of the kidney selected from the group consisting of a renal artery, a renal vein, and a combination thereof;
  b) administering a volume of a solution comprising the rAAV into a ureter of the kidney in a retrograde route, wherein the volume is from about 0.13 mL/kg to about 0.33 mL/kg, the kg being the weight of the subject; and
  c) unblocking renal blood vessel after a period of time of from about 10 minutes to about 60 minutes subsequent to the blocking,
    wherein the administration method results in at least about 25% of the nephrons in the kidney being transduced with the rAAV.

67. A method of transducing at least about 25% of the nephrons in a kidney of a subject with a recombinant adeno-associated virus (rAAV), the method comprising:
  a) blocking a renal blood vessel selected from the group consisting of a renal artery, a renal vein, and a combination thereof of the kidney;
  b) administering a volume of a solution comprising the rAAV into a ureter of the kidney in a retrograde route, wherein the volume is from about 0.13 mL/kg to about 0.33 mL/kg, the kg being the weight of the subject, wherein the rAAV comprises a capsid protein from Table 1; and
  c) unblocking the renal blood vessel after a period of time of from about 10 minutes to about 60 minutes subsequent to the blocking,
    wherein the method results in the transduction of at least about 25% of the nephrons in the kidney with the rAAV.

68. A method of treating a kidney-associated disorder in a subject in need thereof, the method comprising administering the rAAV to the subject by performing the method according to paragraph 67.

69. The method of paragraph 67, wherein the rAAV is administered to the kidney at an intra-renal pressure of from about 27 cm $H_2O$ to about 80 cm $H_2O$.
70. The method of paragraph 67, wherein the volume of the solution is 0.13 mL/kg to 0.33 mL/kg.
71. The method of paragraph 67, wherein the period of time is 30-60 minutes subsequent to the blocking.
72. The method of paragraph 67, wherein the subject is seropositive for the rAAV prior to the administration of the solution comprising the rAAV.
73. A pharmaceutical composition comprising a recombinant adeno-associated virus (rAAV) comprising:
    a) an AAV capsid selected from Table 1;
    b) a transgene comprising:
        i) a gene selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof; or
        ii) an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD); and
    c) a pharmaceutically acceptable carrier.
74. The pharmaceutical composition of paragraph 73, wherein the pharmaceutically acceptable carrier comprises mannitol.
75. The pharmaceutical composition of paragraph 73, wherein the AAV capsid is AAV2G9.
76. The pharmaceutical composition of paragraph 73, wherein the rAAV is at a concentration of $10^8$ viral genomes per mL (vg/mL) to $10^{15}$ vg/mL.
77. The pharmaceutical composition of paragraph 73, wherein the rAAV is at a concentration of $10^8$ vg/mL to $10^{13}$ vg/mL.
78. The pharmaceutical composition of paragraph 73, wherein the pharmaceutical composition comprises $1\times10^{13}$ to $2\times10^{13}$ rAAV viral genomes total.
79. The pharmaceutical composition of paragraph 73, wherein the pharmaceutical composition comprises $5\times10^{13}$ to $6\times10^{13}$ rAAV viral genomes total.
80. The pharmaceutical composition of paragraph 73, wherein the pharmaceutical composition is in a unit dose of from about 0.13 mL/kg to about 0.33 mL/kg, the kg being the weight of the subject.
81. The pharmaceutical composition of paragraph 73, wherein the pharmaceutical composition is in a unit dose of from about 0.27 mL/kg to about 0.33 mL/kg.
82. The pharmaceutical composition of paragraph 73, wherein the transgene comprises a reporter protein.
83. The pharmaceutical composition of paragraph 73, wherein the genome of the rAAV comprises a kidney-specific promoter.
84. The pharmaceutical composition of paragraph 83, wherein the kidney-specific promoter is selected from the group consisting of: kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.
85. The pharmaceutical composition of paragraph 83, wherein the kidney-specific promoter is a synthetic promoter.
86. The pharmaceutical composition of paragraph 73, wherein the genome of the rAAV comprises a promoter specific to proximal convoluted tubules and/or collecting ducts.

Some embodiments of the technology described herein can be defined according to any of the following numbered paragraphs:

1. A method of transducing at least about 25% of the proximal tubules in a kidney of a subject with a recombinant adeno-associated virus (rAAV), the method comprising:
    a) blocking a renal blood vessel of the kidney selected from the group consisting of a renal artery, a renal vein, and a combination thereof;
    b) administering a volume of a solution comprising the rAAV into a ureter of the kidney in a retrograde route, wherein the volume is from about 0.13 mL/kg to about 0.33 mL/kg, the kg being the weight of the subject; and
    c) unblocking the renal blood vessel after a period of time of from about 10 minutes to about 60 minutes, wherein the method results in the transduction of at least about 25% of the proximal tubules in the kidney with the rAAV.
2. The method of paragraph 1, wherein the rAAV is administered to the kidney at an intra-renal pressure of from about 27 cm $H_2O$ to about 80 cm $H_2O$.
3. The method of paragraph 1, wherein the subject is a human, non-human primate, horse, dog, or pig.
4. The method of paragraph 1, wherein at least about 30% of the proximal tubules of the kidney are transduced with the rAAV.
5. The method of paragraph 1, wherein the volume of the solution comprising the rAAV is from about 0.2 mL/kg to about 0.27 mL/kg.
6. The method of paragraph 1, wherein the volume of the solution comprising the rAAV is from about 0.27 mL/kg to about 0.33 mL/mg.
7. The method of paragraph 1, wherein the solution comprising the rAAV is administered in the retrograde route to the ureter using a balloon catheter.
8. The method of paragraph 1, wherein the renal blood vessel is blocked using a balloon catheter.
9. The method of paragraph 1, wherein the renal blood vessel is blocked using a clamp.

10. The method of paragraph 1, wherein the period of time for blocking the at renal blood vessel is 15-45 minutes.
11. The method of paragraph 1, wherein the period of time for blocking the at renal blood vessel is 20-40 minutes.
12. The method of paragraph 1, wherein the period of time for blocking the at renal blood vessel is about 30 minutes.
13. The method of paragraph 1, wherein the volume of the solution comprising the rAAV is from about 0.2 mL/kg to about 0.27 mL/kg, and wherein the period of time for blocking the renal blood vessel is about 30 minutes.
14. The method of paragraph 1, wherein the rAAV comprises an AAV capsid protein from serotype AAV1, AAV2, AAV3a, AAV3b, AAV4, AAV5, AAV6, AAV7, AAV8, AAV9, AAV2G9, AAV2.5G9, AAV2.5, AAVrh8, AAVrh10, AAVrh74, AAV10, AAV11, and AAVDJ.
15. The method of paragraph 1, wherein the rAAV is selected from the group consisting of AAV2G9, AAV2.5, AAVDJ, and AAV2.
16. The method of paragraph 1, wherein the rAAV comprises a capsid protein from serotype AAV2G9.
17. The method of paragraph 1, wherein the rAAV is a rational polyploid.
18. The method of paragraph 1, wherein the rAAV is at a concentration of $10^8$ viral genomes per mL (vg/mL) to $10^{15}$ vg/mL.
19. The method of paragraph 1, wherein the rAAV is at a concentration of $10^8$ vg/mL to $10^{13}$ vg/mL.
20. The method of paragraph 1, wherein the solution comprises $1\times10^{13}$ to $2\times10^{13}$ rAAV viral genomes total.
21. The method of paragraph 1, wherein the solution comprises $5\times10^{13}$ to $6\times10^{13}$ rAAV viral genomes total.
22. The method of paragraph 1, wherein the solution comprises $1\times10^{10}$ viral genomes total.
23. The method of paragraph 1, wherein the rAAV comprises a transgene.
24. The method of paragraph 23, wherein the transgene is selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof.
25. The method of paragraph 23, wherein the transgene comprises an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD).
26. The method of paragraph 1, wherein circulating serum of the subject does not neutralize the rAAV upon administration.
27. The method of paragraph 1, wherein the subject has antibodies that neutralize the rAAV to be administered in the circulating serum and the antibodies do not neutralize the rAAV in the kidney upon administration.
28. The method of paragraph 1, wherein a subsequent administration of the rAAV of paragraph 1 is performed without resulting in a substantial inflammatory response in the kidney.
29. The method of paragraph 28, wherein the subsequent administration is at least one month later.
30. The method of paragraph 1, wherein the rAAV transduces nephrons of the kidney.
31. The method of paragraph 1, wherein the rAAV transduces a glomerulus, a glomerular capsule, a proximal convoluted tubule, the loop of Henle, or a distal convoluted tubule of a nephron of the kidney.
32. The method of paragraph 1, wherein the rAAV comprises a kidney-specific promoter.
33. The method of paragraph 33, wherein the kidney-specific promoter is selected from the group consisting of: kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.
34. The method of paragraph 33, wherein the kidney-specific promoter is a synthetic promoter.
35. The method of paragraph 1, wherein the genome of the rAAV comprises a promoter specific to the proximal convoluted tubule and/or the collecting duct.
36. A method of treating a kidney-associated disorder in a subject in need thereof, the method comprising administering a recombinant adeno-associated virus (rAAV) to the subject by performing the method according to paragraph 1.
37. The method of paragraph 36, wherein the kidney-associated disorder is selected from the group consisting of: autosomal dominant polycystic kidney disease (ADPKD); Alport syndrome; autosomal dominant tubulointerstitial kidney disease (ADTKD); medullary cystic kidney disease; nephronophthisis; Bartter Syndrome; Von Hippel-Lindau syndrome; Gitelman syndrome; congenital nephrotic syndrome; primary hyperoxaluria; Dent disease; Thin Basement Membrane Nephropathy; cystinuria; Liddle syndrome; Papillorenal syndrome; and cystinosis.
38. A method of treating a kidney disorder in a subject in need thereof, the method comprising:
administering to a kidney of the subject a first recombinant adeno-associated virus (rAAV) encoding a transgene that is therapeutic toward the kidney disorder; and
subsequent to administering the first rAAV, administering to the kidney or a different kidney of the subject a second rAAV encoding the transgene or a different transgene that is therapeutic toward to the kidney disorder,
wherein the first rAAV and the second rAAV are cross seroreactive, and
wherein the subject does not elicit a significant immune response to the second rAAV in the kidney.

39. The method of paragraph 38, wherein the first and/or second rAAV is administered to the kidney at an intra-renal pressure of from about 27 cm $H_2O$ to about 80 cm $H_2O$.
40. The method of paragraph 38, wherein the second rAAV is administered after about a week.
41. The method of paragraph 38, wherein the first and second rAAVs are administered by an administration method comprising:
   a) blocking a renal blood vessel of the kidney selected from the group consisting of a renal artery, a renal vein, and a combination thereof;
   b) administering a volume of a solution comprising the first or second rAAV into a ureter of the kidney or a second ureter to the different kidney in a retrograde route, wherein the volume is from about 0.13 mL/kg to about 0.33 mL/kg, the kg being the weight of the subject; and
   c) unblocking renal blood vessel after a period of time of from about 10 minutes to about 60 minutes,
   wherein the administration method results in at least about 25% of the proximal tubules in the kidney being transduced with the rAAV.
42. The method of paragraph 38, wherein the subject has neutralizing antibodies toward the first rAAV therapeutic prior to the administering.
43. The method of paragraph 38, wherein the capsid of the first rAAV is the same serotype as the capsid of the second rAAV.
44. The method of paragraph 38, wherein the capsid of the first rAAV is a different serotype as the capsid of the second rAAV.
45. The method of paragraph 38, wherein the time period for subsequent administration of the second rAAV is determined based on the efficacy or longevity of the administration of the first rAAV.
46. The method of paragraph 38, wherein the first rAAV is administered to a first kidney of the subject, and the second rAAV is administered to a second kidney of the subject.
47. The method of paragraph 38, wherein the first rAAV is administered to a first kidney of the subject, and the second rAAV is administered to the first kidney of the subject.
48. The method of paragraph 38, wherein the first rAAV is administered to both kidneys of the subject, and the second rAAV is administered to both kidneys of the subject.
49. A method of treating a kidney disorder in a subject in need thereof, the subject being seropositive for a recombinant adeno-associated virus (rAAV) therapeutic, the method comprising:
   administering to a kidney of the subject the rAAV therapeutic encoding a transgene that is therapeutic toward the kidney disorder,
   wherein the subject does not elicit a significant immune response to the rAAV therapeutic in the kidney.
50. The method of paragraph 49, wherein the subject has neutralizing antibodies toward the rAAV therapeutic prior to the administering.
51. The method of paragraph 49, wherein the rAAV is administered by an administration method comprising:
   a) blocking a renal blood vessel of the kidney selected from the group consisting of a renal artery, a renal vein, and a combination thereof;
   b) administering a volume of a solution comprising the rAAV into a ureter of the kidney in a retrograde route, wherein the volume is from about 0.13 mL/kg to about 0.33 mL/kg, the kg being the weight of the subject; and
   c) unblocking renal blood vessel after a period of time of from about 10 minutes to about 60 minutes,
   wherein the administration method results in at least about 25% of the proximal tubules in the kidney being transduced with the rAAV.
52. A method of transducing at least about 25% of the proximal tubules in a kidney of a subject with a recombinant adeno-associated virus (rAAV), the method comprising:
   a) blocking a renal blood vessel selected from the group consisting of a renal artery, a renal vein, and a combination thereof of the kidney;
   b) administering a volume of a solution comprising the rAAV into a ureter of the kidney in a retrograde route, wherein the volume is from about 0.13 mL/kg to about 0.33 mL/kg, the kg being the weight of the subject, wherein the rAAV comprises a capsid protein from serotype AAV2G9; and
   c) unblocking the renal blood vessel after a period of time of from about 10 minutes to about 60 minutes,
   wherein the method results in the transduction of at least about 25% of the proximal tubules in the kidney with the rAAV.
53. A method of treating a kidney-associated disorder in a subject in need thereof, the method comprising administering the rAAV to the subject by performing the method according to paragraph 52.
54. The method of paragraph 52, wherein the rAAV is administered to the kidney at an intra-renal pressure of from about 27 cm $H_2O$ to about 80 cm $H_2O$.
55. The method of paragraph 52, wherein the volume of the solution is 0.13 mL/kg to 0.33 mL/kg.
56. The method of paragraph 52, wherein the period of time is 30-60 minutes.
57. The method of paragraph 52, wherein the subject is seropositive for the rAAV prior to the administration of the solution comprising the rAAV.
58. A pharmaceutical composition comprising a recombinant adeno-associated virus (rAAV) comprising:
   a) AAV2G9;
   b) a transgene comprising:
      i) a gene selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof; or ii) an inhibitor of a gene or protein selected from the group consisting of: Renin (REN), Sodium Channel Epithelial 1 Subunit Alpha (SCNN1A), Sodium Channel Epithelial 1 Subunit Beta (SCNN1B), and Uromodulin (UMOD); and c) a pharmaceutically acceptable carrier.

59. The pharmaceutical composition of paragraph 58, wherein the pharmaceutically acceptable carrier comprises mannitol.

60. The pharmaceutical composition of paragraph 58, wherein the rAAV is at a concentration of $10^8$ viral genomes per mL (vg/mL) to $10^{15}$ vg/mL.

61. The pharmaceutical composition of paragraph 58, wherein the rAAV is at a concentration of $10^8$ vg/mL to $10^{13}$ vg/mL.

62. The pharmaceutical composition of paragraph 58, wherein the pharmaceutical composition comprises $1\times10^{13}$ to $2\times10^{13}$ rAAV viral genomes total.

63. The pharmaceutical composition of paragraph 58, wherein the pharmaceutical composition comprises $5\times10^{13}$ to $6\times10^{13}$ rAAV viral genomes total.

64. The pharmaceutical composition of paragraph 58, wherein the pharmaceutical composition is in a unit dose of from about 0.13 mL/kg to about 0.33 mL/kg, the kg being the weight of the subject.

65. The pharmaceutical composition of paragraph 58, wherein the pharmaceutical composition is in a unit dose of from about 0.27 mL/kg to about 0.33 mL/kg.

66. The pharmaceutical composition of paragraph 58, wherein the transgene comprises a reporter protein.

67. The pharmaceutical composition of paragraph 58, wherein the genome of the rAAV comprises a kidney-specific promoter.

68. The pharmaceutical composition of paragraph 67, wherein the kidney-specific promoter is selected from the group consisting of: kidney-specific cadherin (KSPC) gene promoter; Na+/glucose co-transporter (SGLT2) gene promoter; sodium potassium, 2 chloride co-transporter (NKCC2) gene promoter; and E-cadherin (ECAD) gene promoter.

69. The pharmaceutical composition of paragraph 67, wherein the kidney-specific promoter is a synthetic promoter.

70. The pharmaceutical composition of paragraph 58, wherein the genome of the rAAV comprises a promoter specific to the proximal convoluted tubule and/or the collecting duct.

The technology described herein is further illustrated by the following examples which in no way should be construed as being further limiting.

EXAMPLES

Example 1: Retrograde Administration of rAAV to Rat Kidneys

Retrograde ureter administration of rAAV to a kidney can be performed according to the methods described herein. Here, a library of rAAV comprising a yellow fluorescent protein (YFP) transgene driven by the CMV promoter was administered to rat kidneys by such a retrograde administration. The library included, among others, the following capsids: AAV1, AAV2, AAV3, AAV4, AAV5, AAV6, AAV7, AAV8, AAV9, AAV10, AAV11, AAV12, AAV13, AAVrh74, AAVrh10, pol, AAV9-PHP.B, AAV9-PHP.eB, AAVLK03, AAVAnc80L65, AAVDJ, AAV1A6ii, AAV1P5ii, AAV4A1ii, AAV7P4i, AAV9A1i, AAV9A2i, AAV9A6i, AAV9P1i, AAV9P2i, AAV9P5i, AAVrh10A1i, AAVrh10A2i, AAVrh10P1i, AAV12P2ii, AAVS10P1i, AAV JEA, AAV2 3xA P2i, AAVDJ P2i, AAV2i8, AAV2G9, AAV2.5, AAV4E, and AAV4A.

More particularly, in each rat, the left renal artery was clamped, and a catheter was inserted into the urethra, pushed through the bladder, and then guided up the left ureter to the entry of the renal pelvis. A balloon of the catheter was then inflated (to occlude the ureter), and from 260 μL/kg to 300 μL/kg of a solution comprising the rAAV library was injected toward the left kidney. The solution further included a formulation buffer, 25% mannitol, and from $1\times10^{13}$ to $2\times10^{13}$ rAAV viral genomes. The right kidney of each rat was not treated with the library. The ureteral catheter was removed between 15 minutes to 45 minutes after the administration and the renal arteries were then de-clamped. After isolation of the kidneys, histological analyses, including YFP staining, were performed to determine levels of transduction in the exposed and unexposed kidneys.

Figure 1:
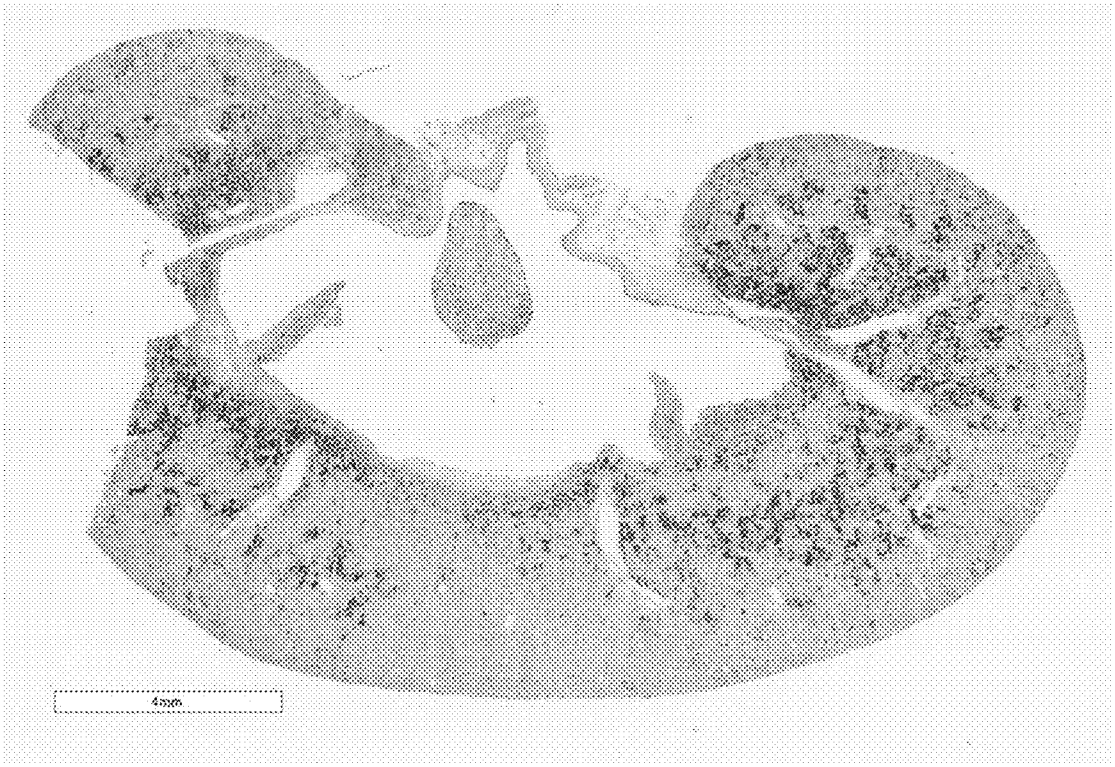
FIG. 1 shows histological sections of rat kidneys following retrograde ureter administration of a rAAV library. The top panel shows YFP expression (stained brown) in the library exposed left kidney and the bottom panel shows no detectable YFP expression in the unexposed right kidney.
Figure 1:
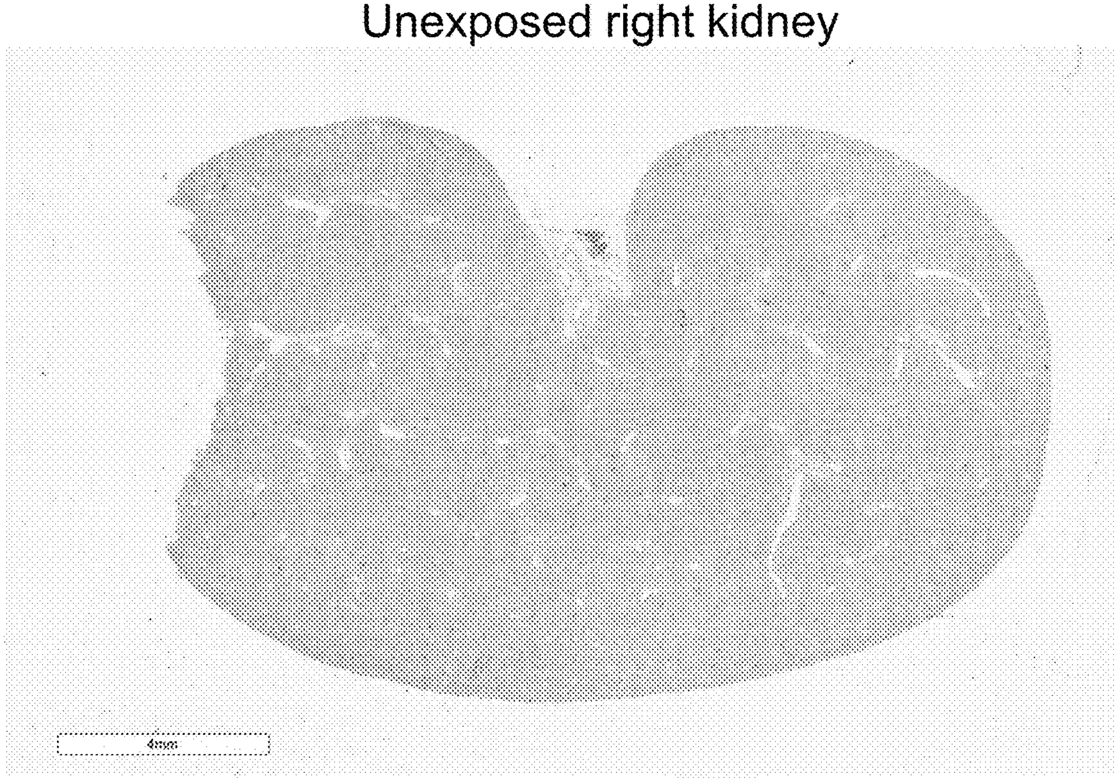

FIG. 1 shows histological sections of an exposed, i.e., treated, left kidney and unexposed right kidney following the retrograde ureter administration of the rAAV library to the left kidney. The top panel shows YFP expression (stained brown) in the library exposed left kidney and the bottom panel shows no detectable YFP expression in the unexposed right kidney. These results demonstrate that the exposed kidney was heavily transduced by the rAAV library, with about 30% of the nephrons being transduced.

Figure 2:
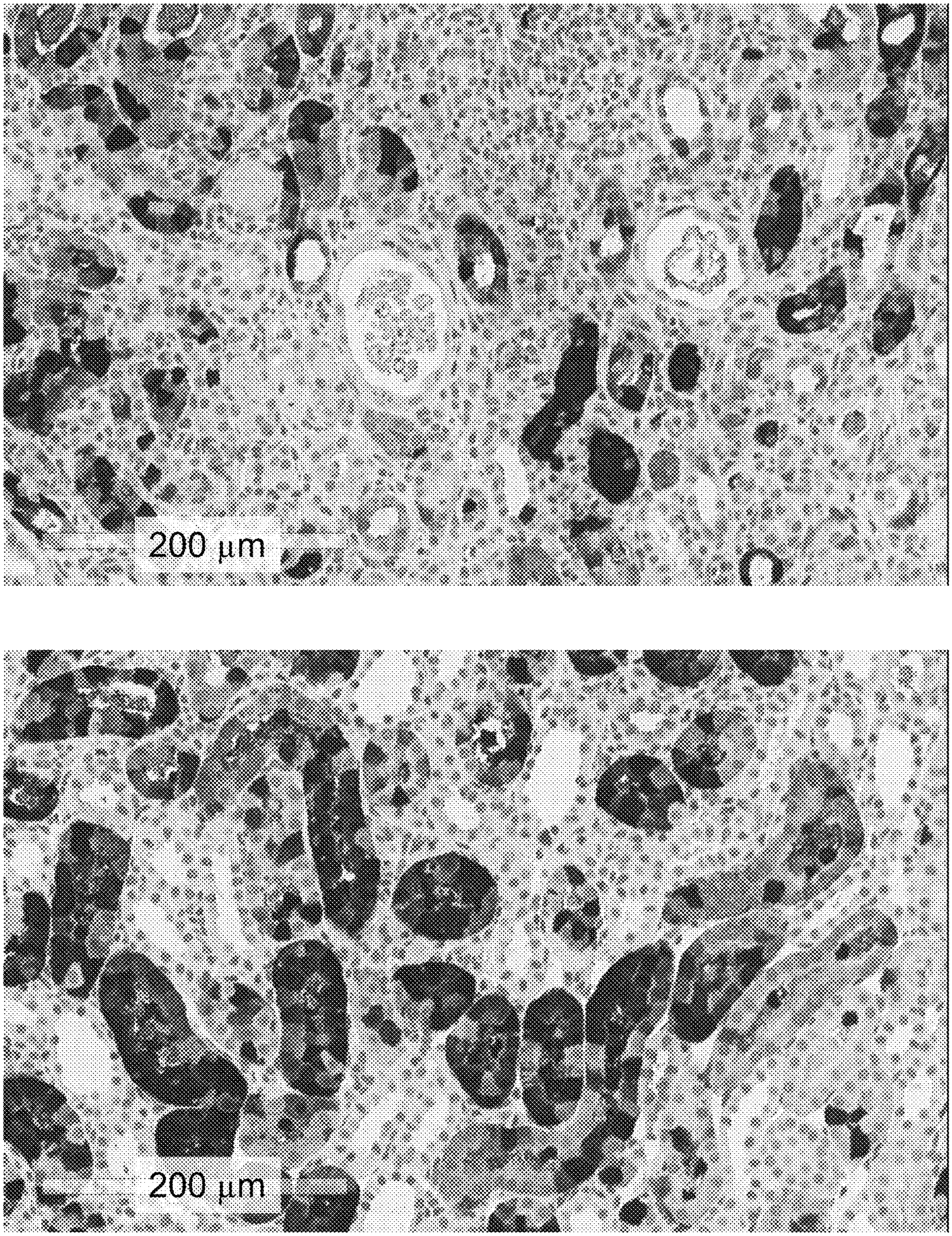
FIG. 2 shows magnified images from FIG. 1. These images show that the kidney tubules were heavily transduced by the library compared to the negative control.

FIG. 2 shows magnified images from the histological section of the exposed kidney of FIG. 1, top panel. This figure shows that the kidney tubules were highly transduced following administration of the rAAV library to rat kidneys.

Figure 3:
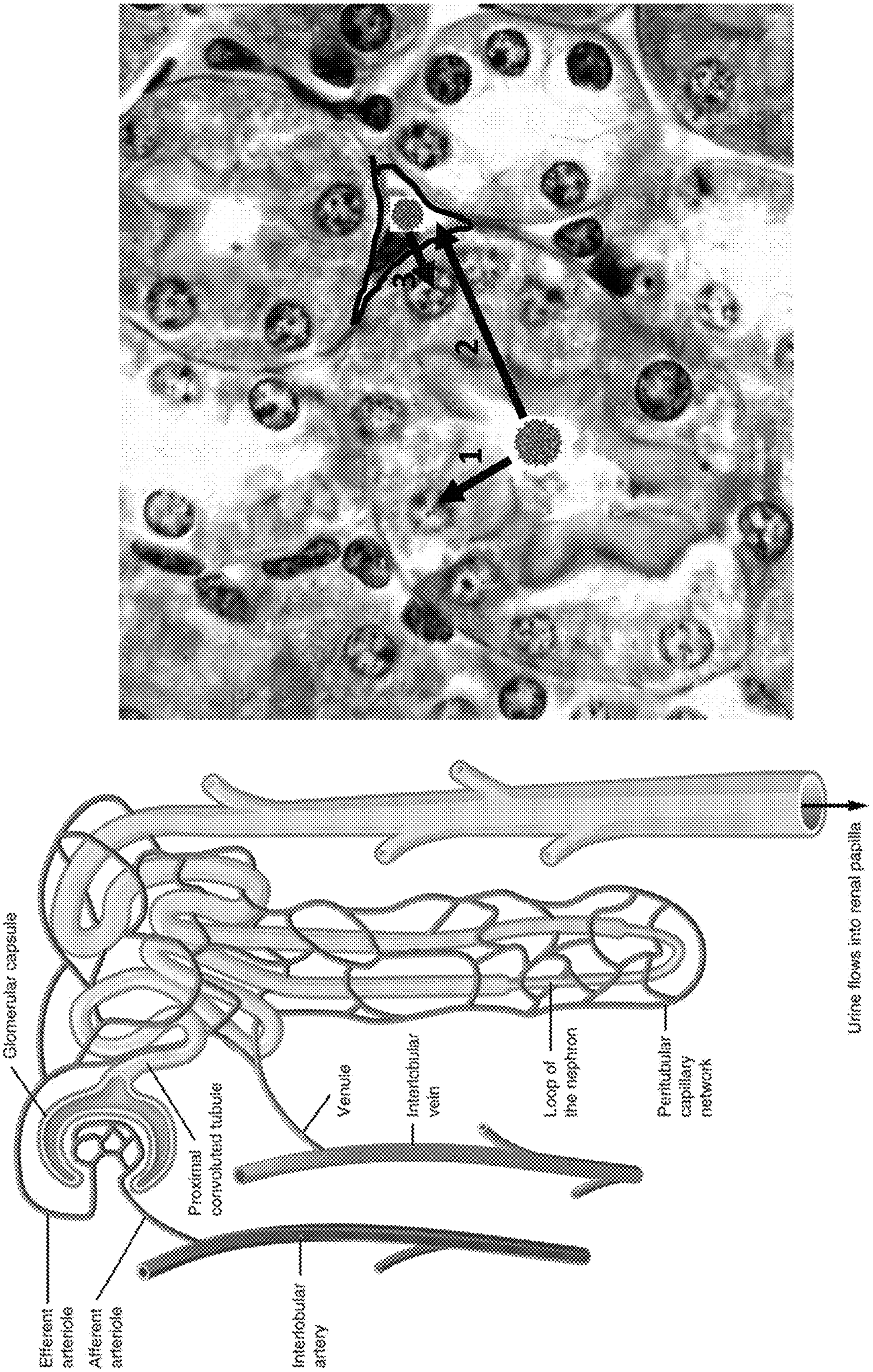
FIG. 3 shows a nephron schematic and an image illustrating the multiple paths for transduction.

After retrograde administration through the ureter, the rAAV enters the lumen of microscopic structures of the nephron, including: the collecting duct, distal convoluted tubule, nephron loop, proximal convoluted tubule (also known as the proximal tubule), and glomerular capsule. rAAV can reach systemic circulation via capillaries on opposing side of tubules (e.g., the glomerulus and/or the peritubular capillary network). FIG. 3 shows three paths for rAAV transduction. Path 1 shows rAAV in the lumen of the proximal tubule entering and transducing a nucleus of an adjacent proximal tubule cell. Path 2 shows rAAV transported from the lumen of the proximal tubule, across an adjacent proximal tubule cell, and into the renal interstitial space (i.e., secretion, where transport to circulation may be possible). Path 3 shows rAAV transported from the renal interstitial space, as in Path 2, and back into an adjacent proximal tubule cell, where the nucleus is transduced (i.e., reabsorption). Thus, the rAAV can transduce proximal tubule cells using multiple combinations of secretion and/or reabsorption mechanisms.

FIG. 4 is a bar graph showing the efficiency index of library rAAVs normalized to AAV9 in the kidney medulla (e.g., substantially comprising loops of Henle and collecting ducts) or kidney cortex (e.g., substantially comprising glomeruli, proximal tubules, and distal tubules). The efficiency index of each tested rAAV normalized to AAV9 was calculated as follows in Formula I: (cDNA reads [%]/input [%])/(cDNA AAV9 reads [%]/input AAV9 [%]). FIG. 5 is a dot plot showing the efficiency index of selected rAAVs from FIG. 4 normalized to AAV9 in the kidney medulla or kidney cortex. Table 3 provides values for each of the capsids shown in FIG. 5. Relative to AAV9, AAV2g9 exhibits about 3500-fold higher combined efficiency, AAV2.5 exhibits over 800-fold higher combined efficiency, AAVDJ exhibits over 200-fold higher combined efficiency, and AAV2 exhibits over 100-fold higher combined efficiency.

TABLE 3

Raw fold values of efficiency index for each rAAV replicate compared to AAV9.

| rAAV | Cortex | Medulla | Average Cortex | Average Medulla | Combined Average |
|---|---|---|---|---|---|
| AAV2 | 322.38 | 7.14 | 192 | 62 | 127 |
| | 129.4 | 141.6 | | | |
| | 125.68 | 37.71 | | | |
| AAV9 | 1 | 1 | 1 | 1 | 1 |
| | 1 | 1 | | | |
| | 1 | 1 | | | |
| AAVDJ | 394.57 | 54.83 | 263 | 166 | 215 |
| | 216.07 | 277.06 | | | |
| | 177.45 | 166.3 | | | |
| AAVJEA | 1.68 | 2.59 | 1.7 | 2.2 | 1.95 |
| | 1.6 | 1.97 | | | |
| | 1.82 | 2.23 | | | |
| AAV2i8 | 0.12 | 0.07 | 0.08 | 0.08 | 0.08 |
| | 0.14 | 0.07 | | | |
| | 0.09 | 0.1 | | | |
| AAV2g9 | 8144.02 | 425.9 | 5025 | 1964 | 3495 |
| | 3712.28 | 3965.81 | | | |
| | 3218.97 | 1500.3 | | | |
| AAV2.5 | 2082.65 | 61.3 | 1194 | 441 | 818 |
| | 779.6 | 959.05 | | | |
| | 721.04 | 301.57 | | | |

These results indicate that a wide array of AAV capsids can be administered to kidneys by the retrograde route and result in higher levels of transduction with a lower administration volume relative to what is known in the art.

Example 2: Retrograde Administration of rAAV to Pig Kidneys rAAV was administered to 75 kg pigs via retrograde administration. The rAAV comprised AAV2g9 and a viral genome comprising a GFP and luciferase transgenes driven by the CMV promoter. During the retrograde administrations, the renal arteries were occluded, the rAAV was administered by way of the ureter and maintained in the kidneys for less than 1 hour. As a result, about 30% or more of the nephrons in the kidneys can be transduced with no significant immune response detected in the kidneys.

Figure 6A:
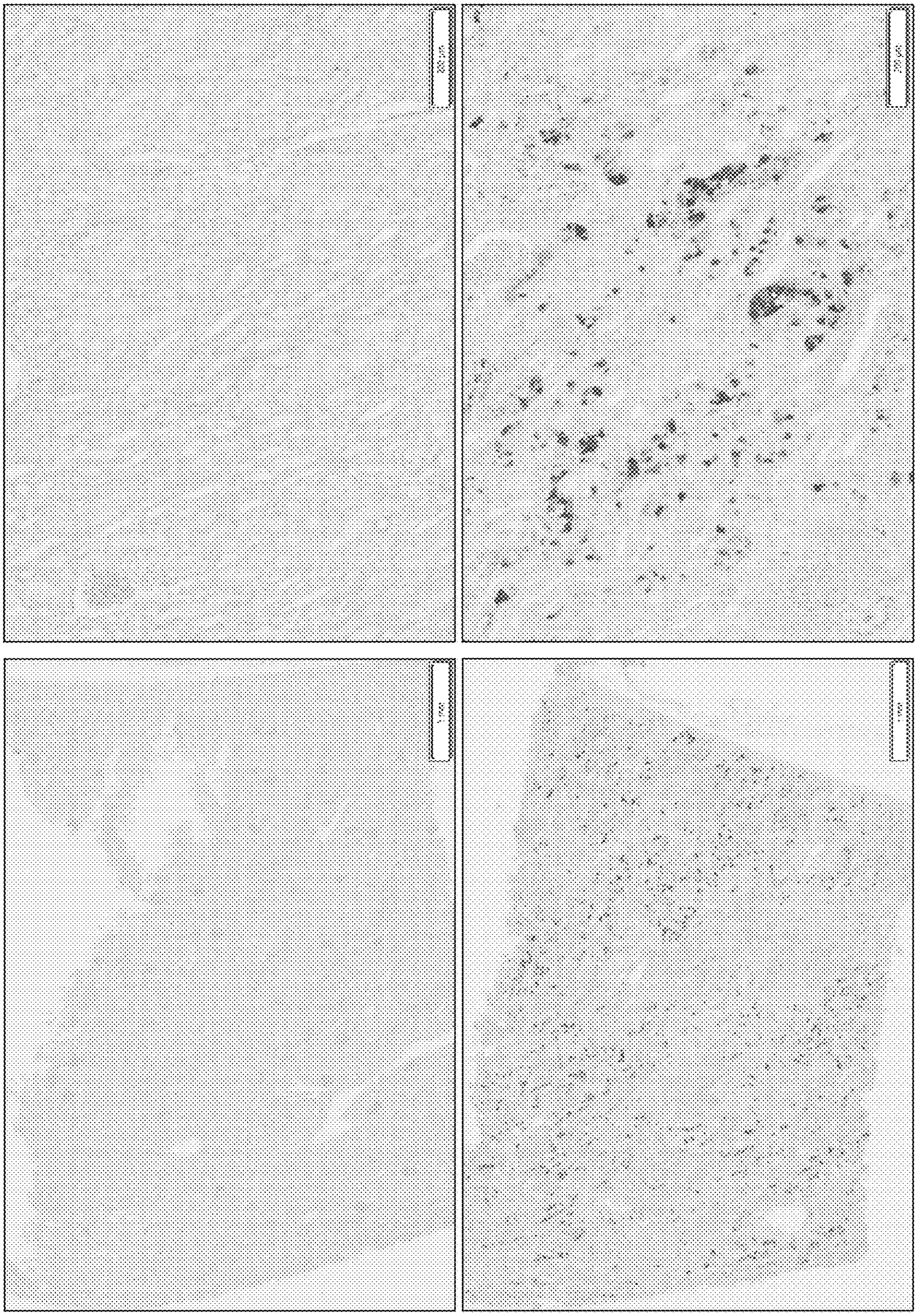
FIG. 6A-6X is a series of images and graphs showing the results of retrograde ureter administration of AAV2G9 in pigs (see e.g., Example 2).
Figure 6B:
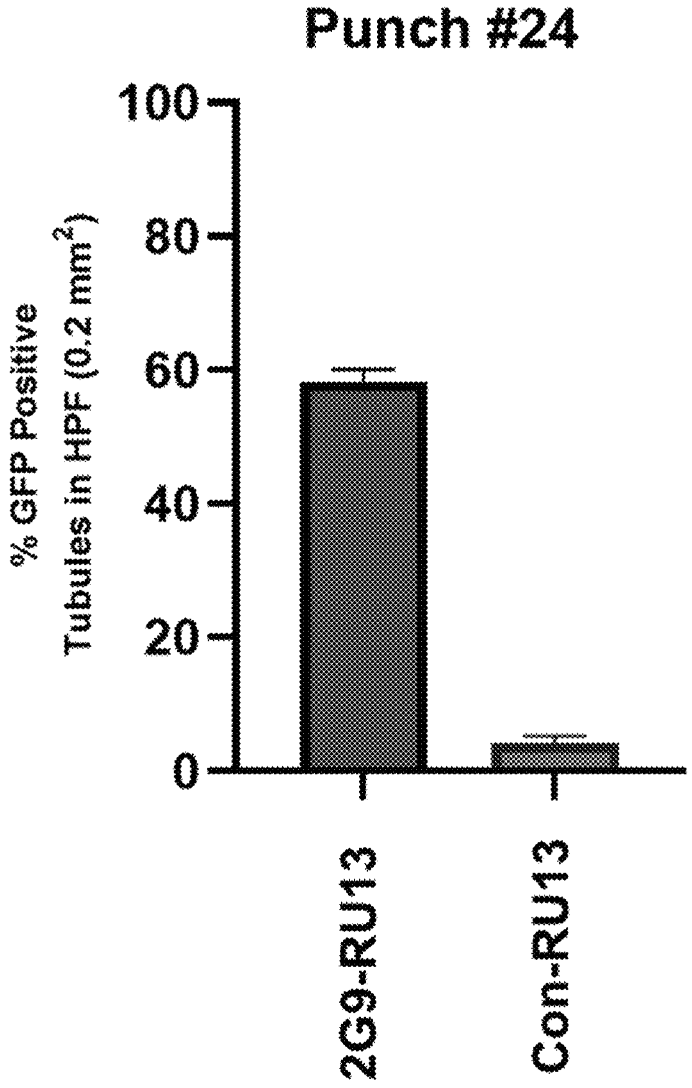
FIG. 6B is a bar graph showing quantification of the sample shown in FIG. 6A, indicating the percentage of positive tubules.
Figure 6C:
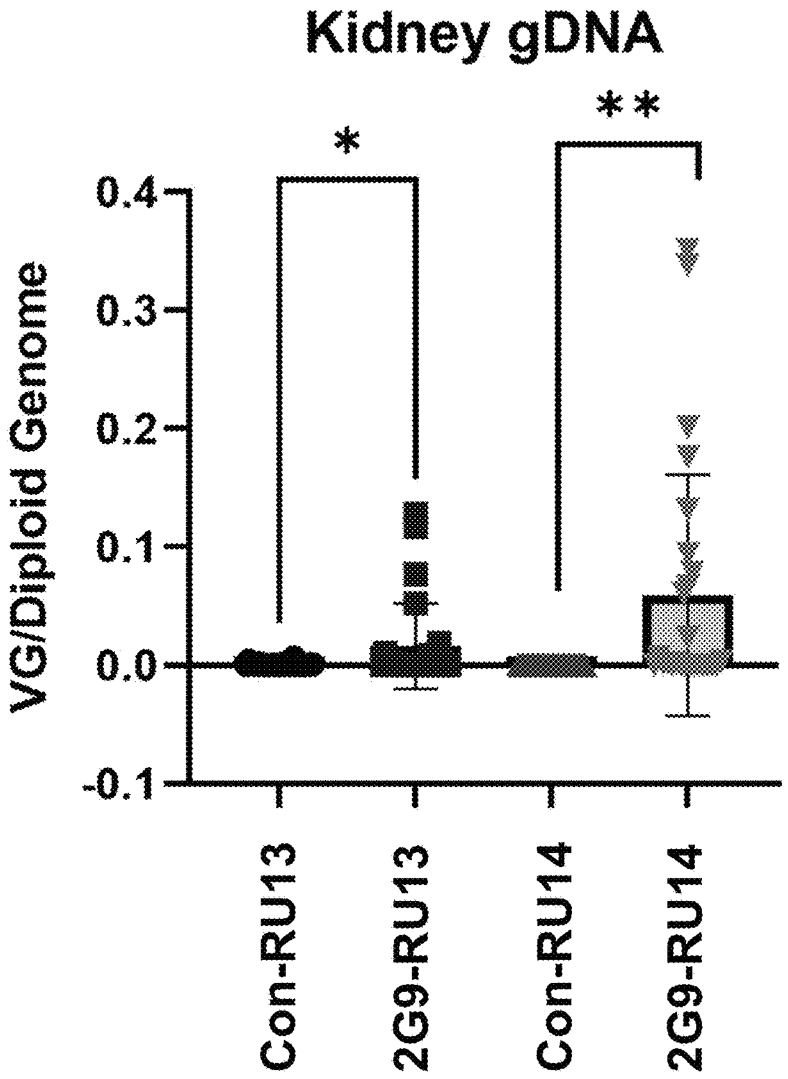
FIG. 6C-6H are bar graphs and quantitative tables showing kidney AAV gDNA (FIG. 6C), kidney AAV protein (FIG. 6D), kidney AAV cDNA (FIG. 6E), liver AAV gDNA (FIG. 6F), liver AAV protein (FIG. 6G), and liver AAV cDNA (FIG. 6H) following retrograde ureter administration of AAV2G9 to the treated kidney ("2G9") or contralateral kidney ("con") in pig subjects RU13 and RU14. "NoRT" is a RT-PCR negative control indicating no reverse transcriptase.
Figure 6D:
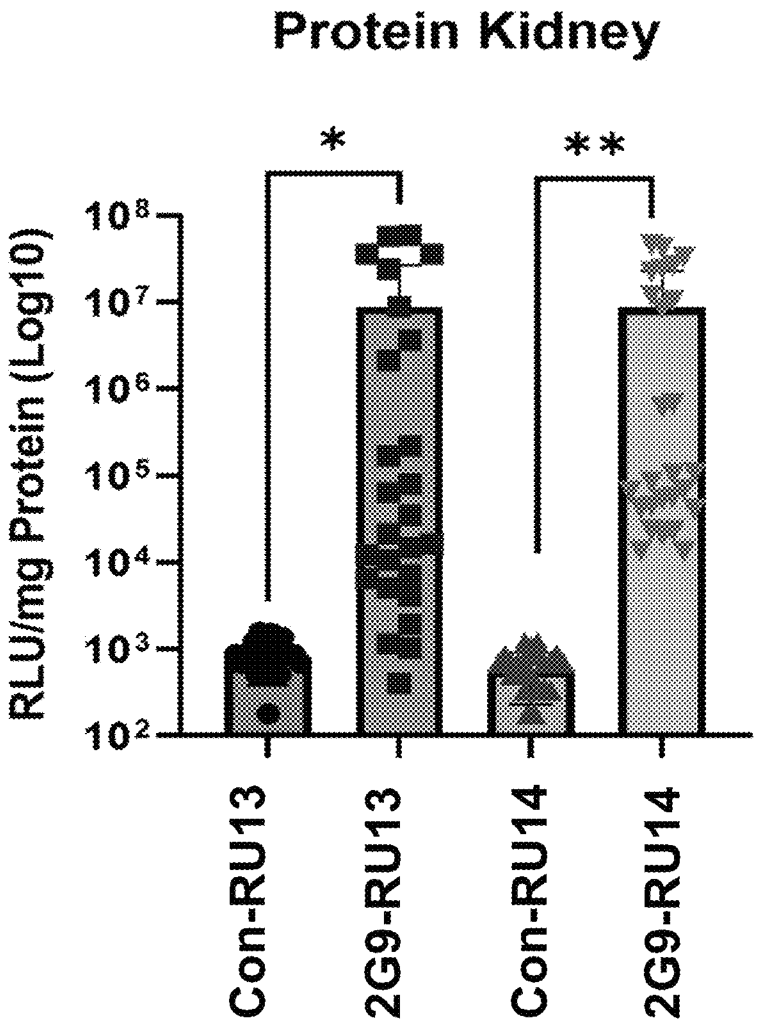
Figure 6E:
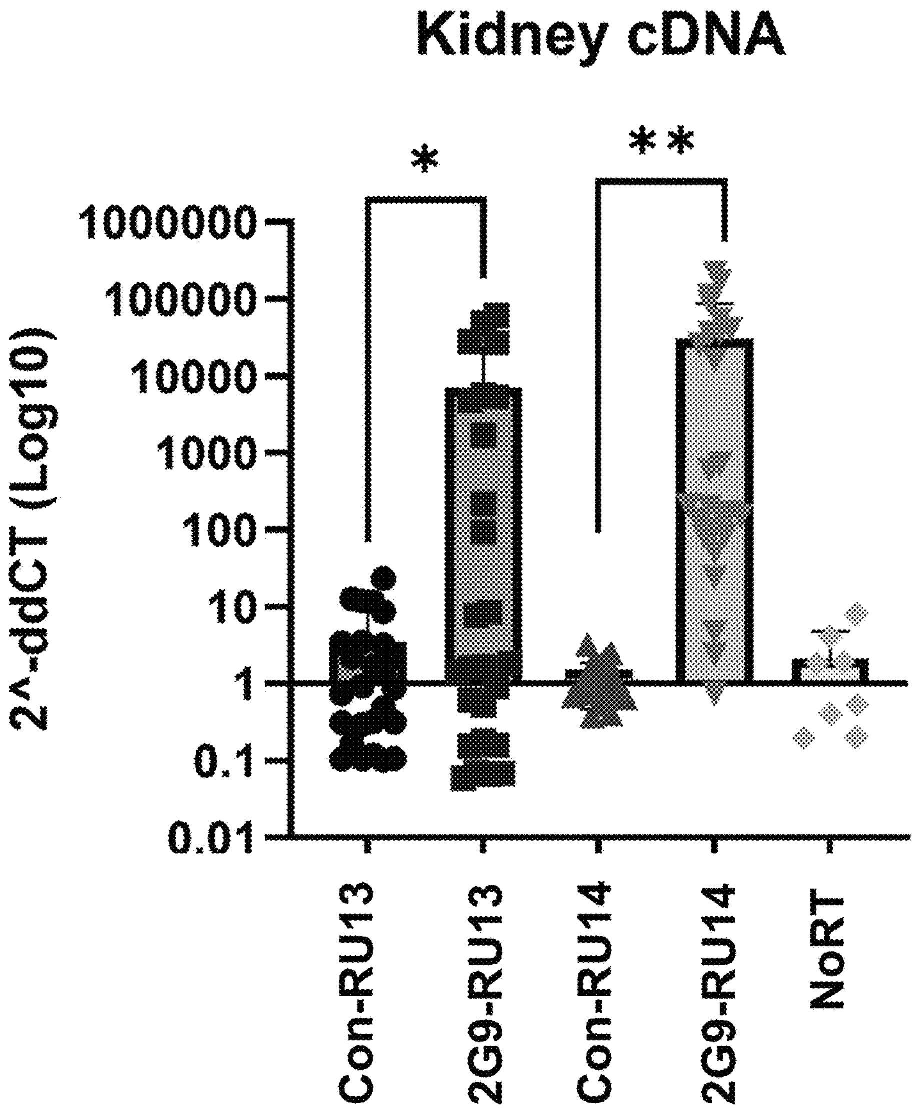
Figure 6F:
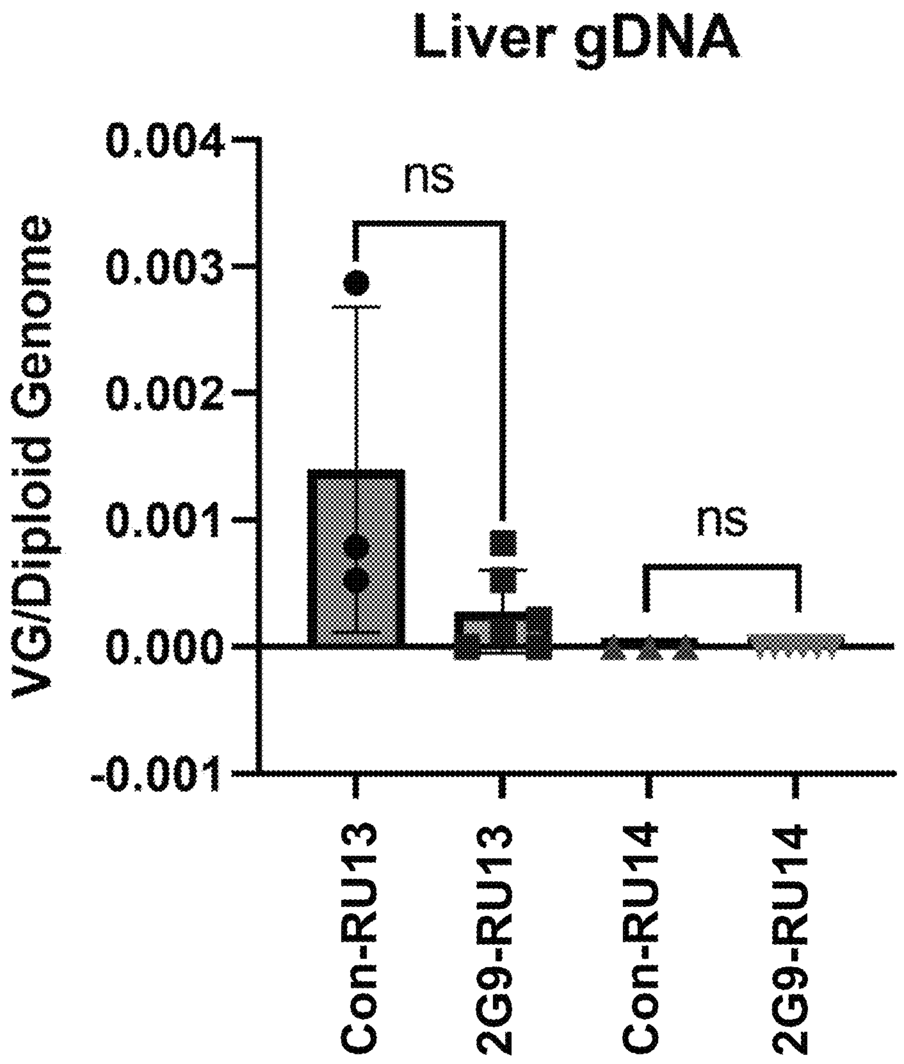
Figure 6G:
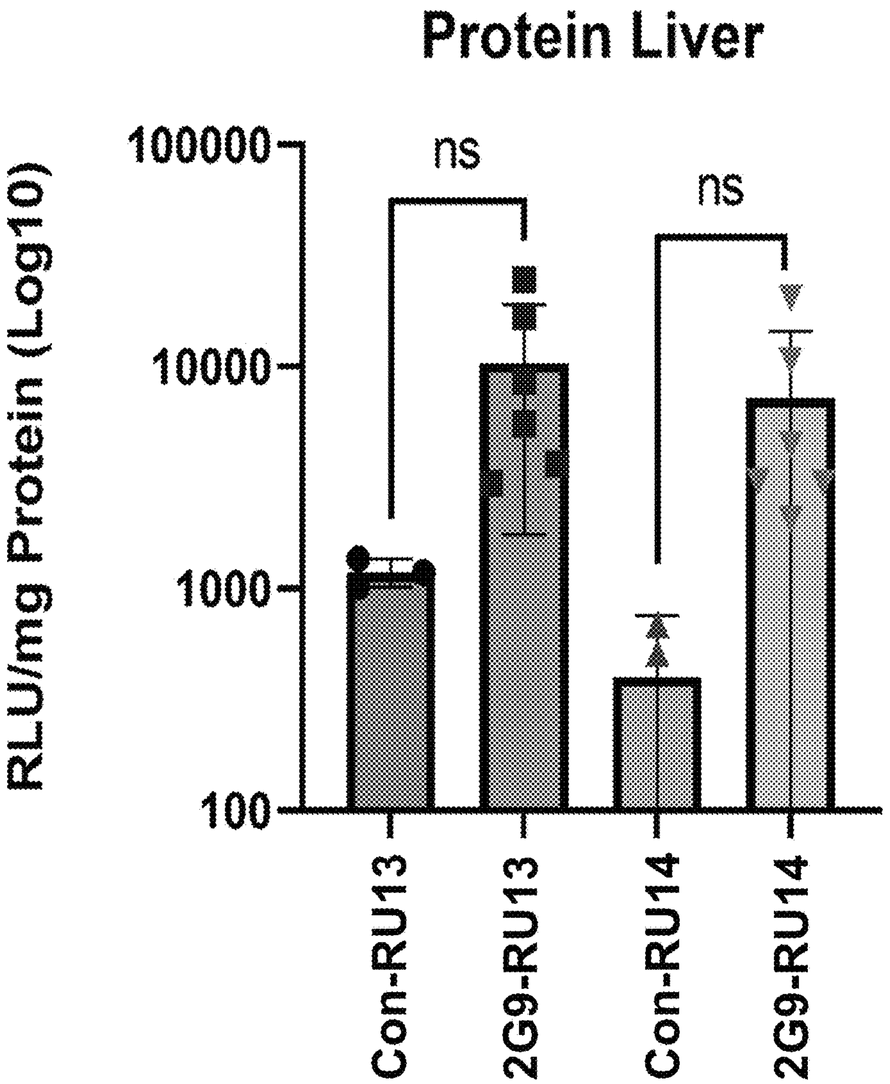
Figure 6H:
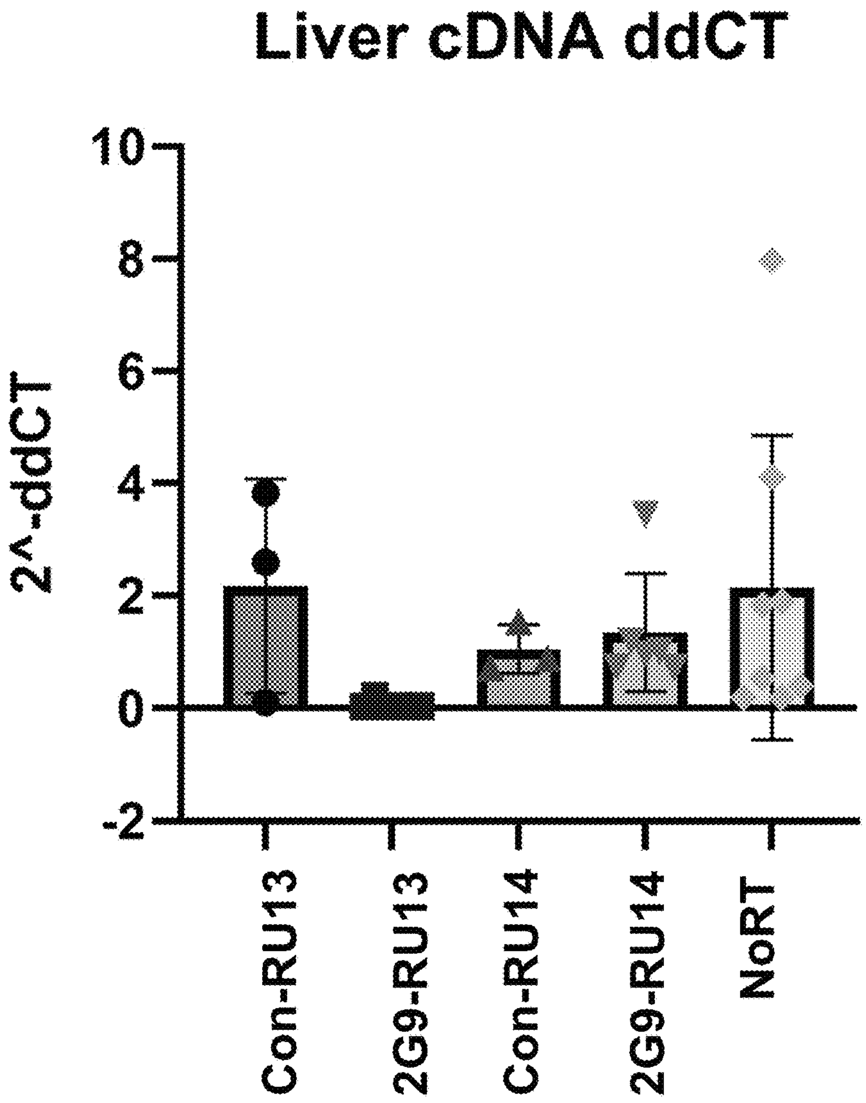

More particularly, RU13 and RU14 were replicate experiments, each performed in a separate pig subject with the same experimental parameters. In RU13 and RU14, 1.41×$10^{13}$ viral genomes (vg) total of AAV2g9 were injected at 0.24 mL/kg (the mL being the volume of the administered AAV2G9 solution, and the kg being the weight of the subject; 18 mL total; 7.8×$10^{11}$ vg/mL). The surgery was performed by occluding the renal artery only, injecting the virus by way of the corresponding ureter, and incubating for 15 minutes with warm ischemia (i.e., the subject's body temperature was maintained). After 15 minutes of incubation, the artery clamp was removed, and then the contralateral kidney was removed. The subjects were sacrificed two weeks later for harvest. The contralateral kidneys were removed to show the safety of the procedure and that the vector was not damaging the exposed kidneys to such an extent that would impact the subjects' health. Removing the contralateral kidneys immediately after the administration ensures that if there were deleterious effects from the retrograde administration or from the vector that the unexposed contralateral kidneys would not compensate for any damage to the exposed kidneys. Data from the contralateral kidneys thus provides a safety check, as well as an internal control. FIGS. 6A-6X show results from the rAAV retrograde kidney administration to the pigs.

Downstream analysis showed a heterogeneous transduction in the kidney with some areas being highly transduced (see e.g., FIG. 6C-6E, FIG. 6M-6O, FIG. 6S-6U). The highest transduction events were observed at the cortex of the kidney, and the lowest transduction events were observed in the renal pelvis region of the kidney (see e.g., FIG. 6I-6L). IHC staining demonstrated that AAV2G9 targeted kidney tubule cells (see e.g., FIG. 6A-64). Genomic DNA ddPCR showed no presence of the vector genome in the liver (see e.g., FIG. 6F-6H, FIG. 6P-6R, FIG. 6V-6X).

Tables 4-7 show quantification of the samples taken at the locations shown in FIGS. 6I-6L. In Tables 4-7, unformatted text indicates that the AAV protein level was less than 1×$10^4$ RLU/mg protein, italicized text indicates that the AAV protein level was between 1×$10^4$ and 1×$10^4$ RLU/mg protein, bolded text indicates that the AAV protein level was between 1×$10^5$ and 1×$10^6$ RLU/mg protein, and italicized bolded text indicates that the AAV protein level was greater than 1×$10^6$ RLU/mg protein.

TABLE 4

Figure 6I:
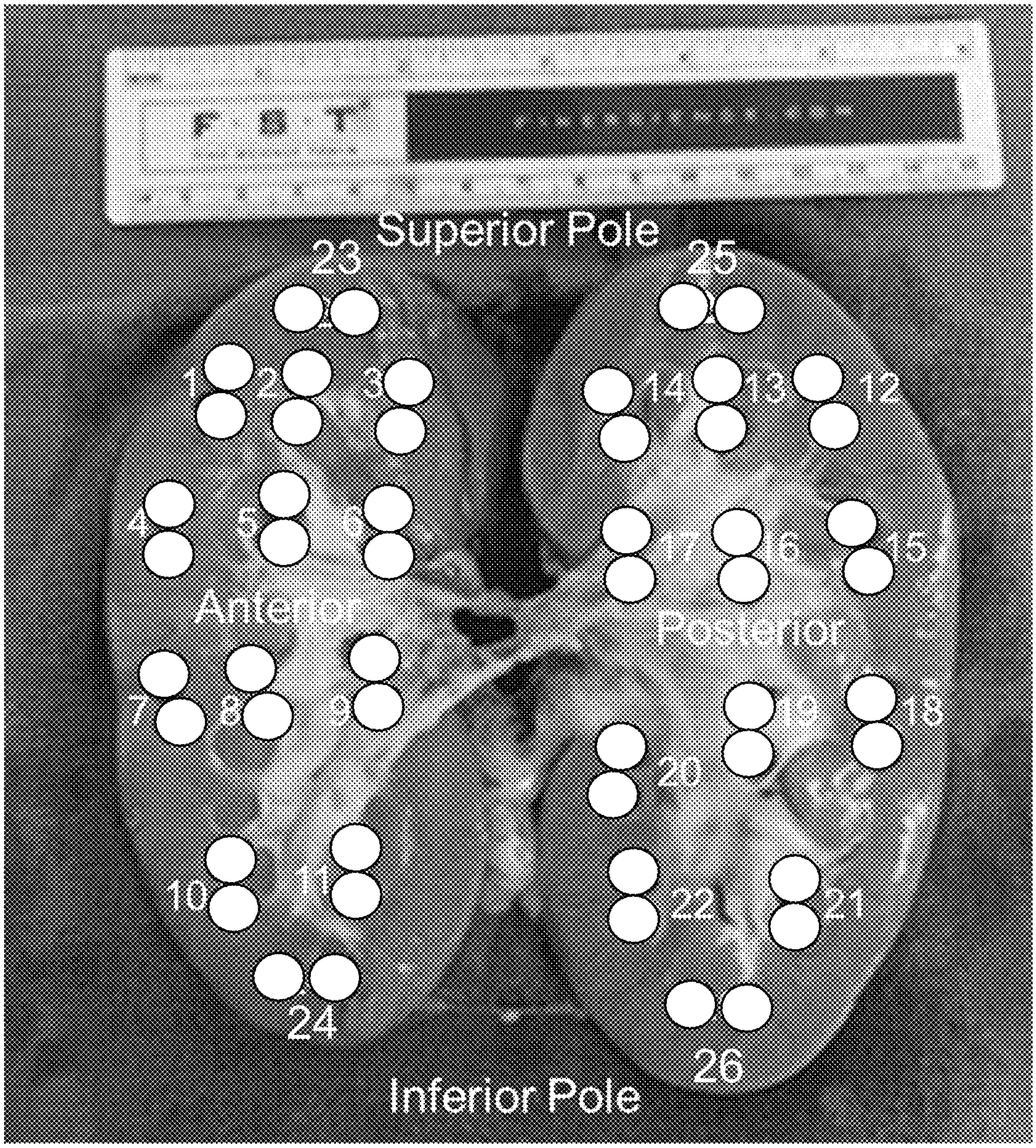
FIG. 6I-6L are images showing the punch locations for kidney samples 1-26 in contralateral control kidney of subject RU13 (FIG. 6I), AAV2G9-administered kidney of subject RU13 (FIG. 6J), contralateral control kidney of subject RU14 (FIG. 6K), and AAV2G9-administered kidney of subject RU14 (FIG. 6L); white circles indicate that the AAV protein level was less than 1.00E+04 RLU/mg protein, light gray circles indicate that the AAV protein level was between 1.00E+04 and 1.00E+05 RLU/mg protein, dark gray circles indicate that the AAV protein level was between 1.00E+05 and 1.00E+06 RLU/mg protein, and black circles indicate that the AAV protein level was greater than 1.00E+06 RLU/mg protein. See also Tables 4-7 in Example 2, which correspond to FIG. 6I-6L, respectively.
Figure 6J:
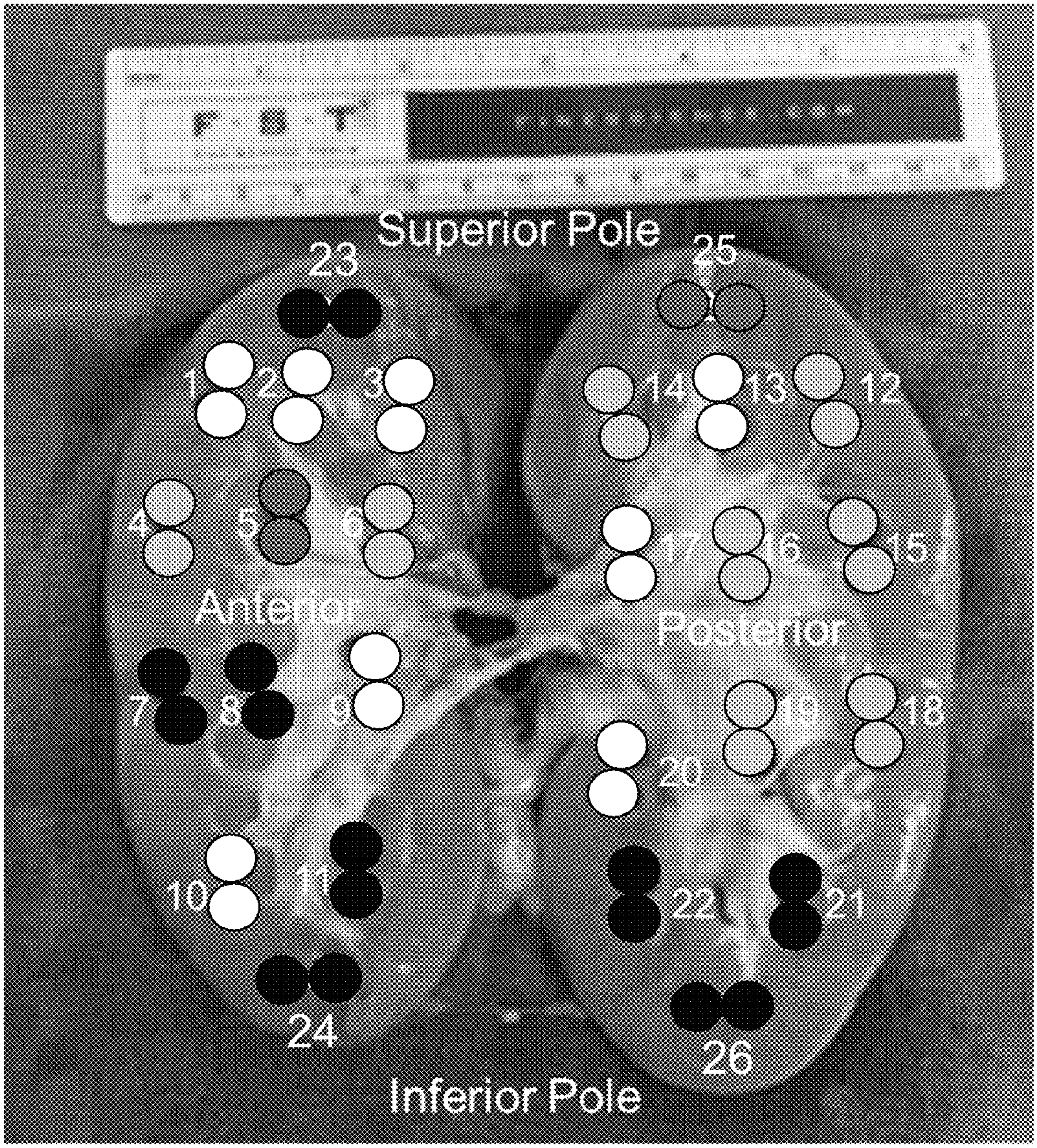
Figure 6K:
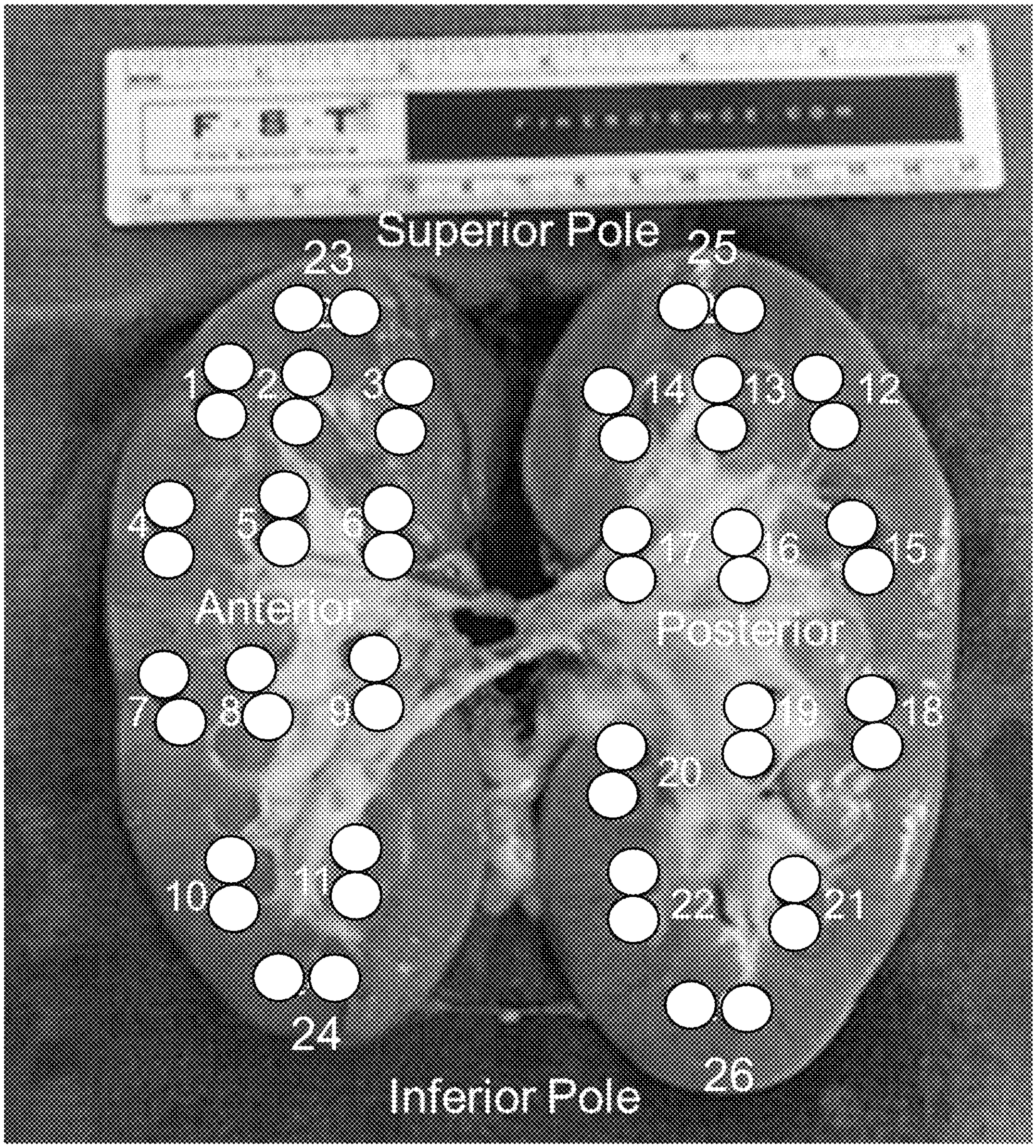
Figure 6L:
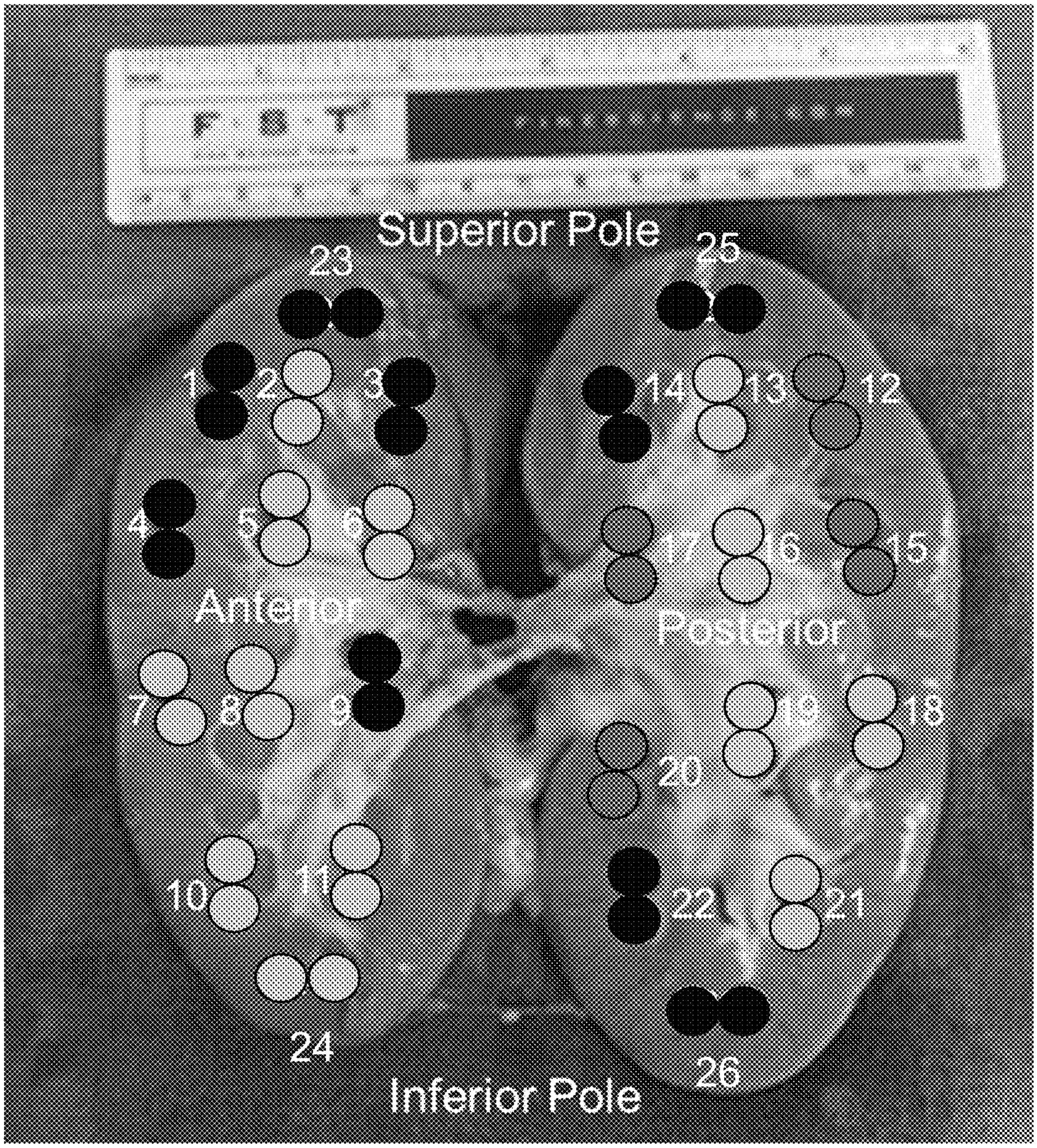
Figure 6N:
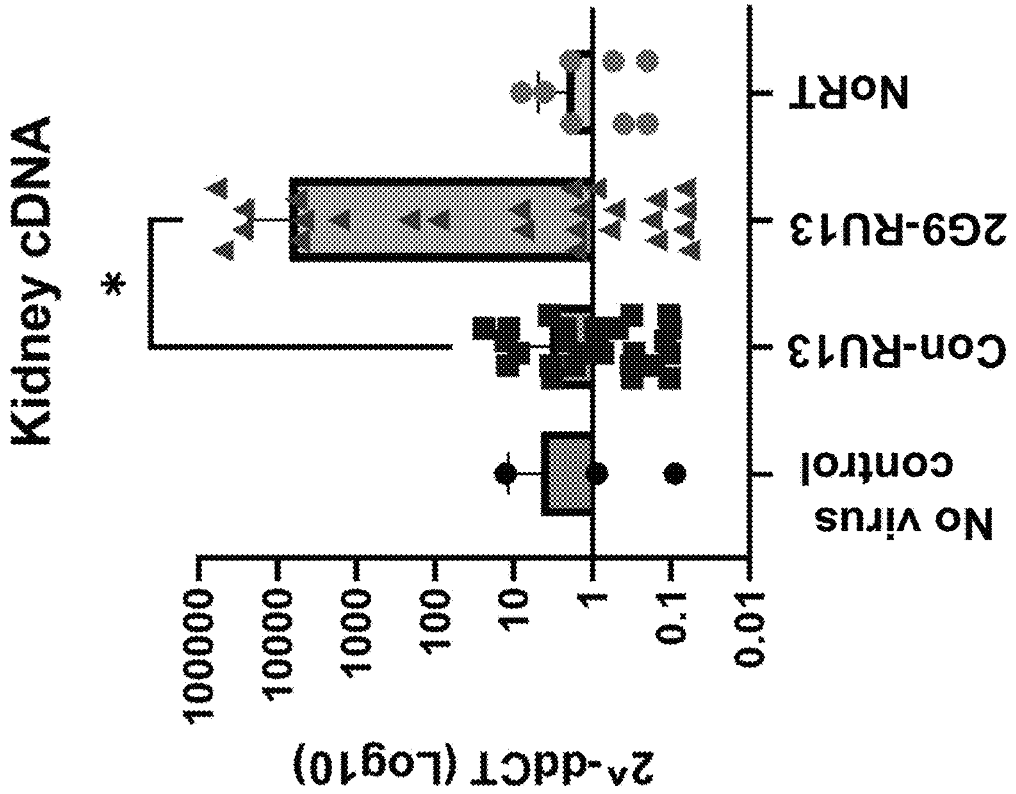
FIG. 6M-6R are bar graphs showing viral quantification following retrograde ureter administration of AAV2G9 to the treated kidney ("2G9") or contralateral kidney ("con") in pig subject RU13: kidney AAV viral copy number (VCN) (FIG. 6M), kidney AAV cDNA (FIG. 6N), kidney AAV protein (FIG. 6O), liver AAV VCN (FIG. 6P), liver AAV cDNA (FIG. 6Q), and liver AAV protein (FIG. 6R).
Figure 6M:
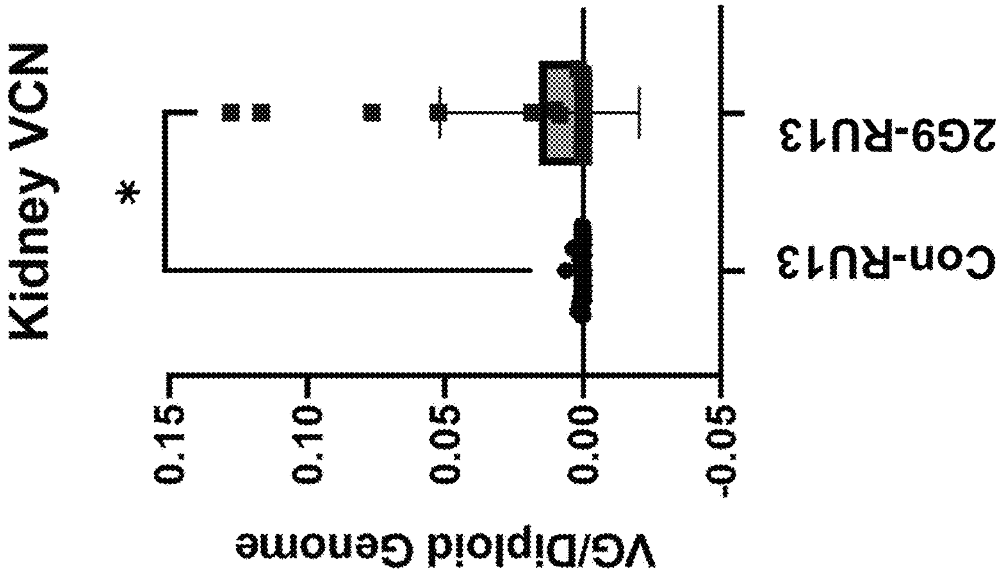
Figure 6O:
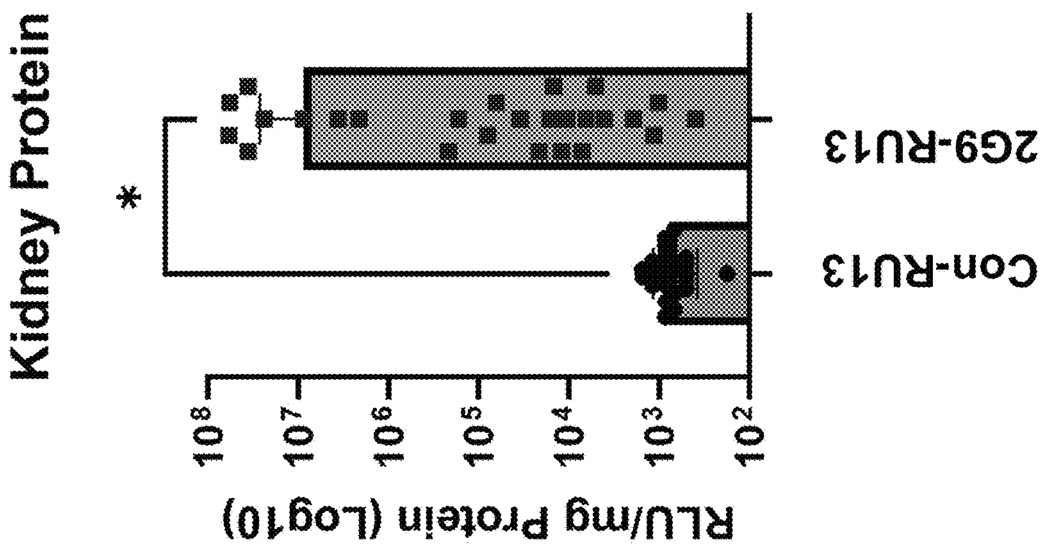
Figure 6P:
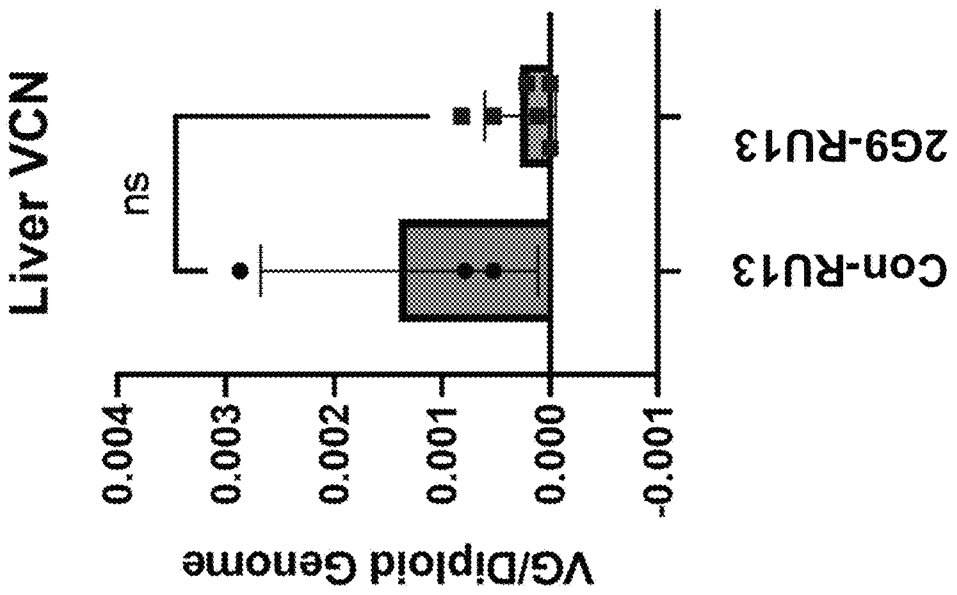
Figure 6R:
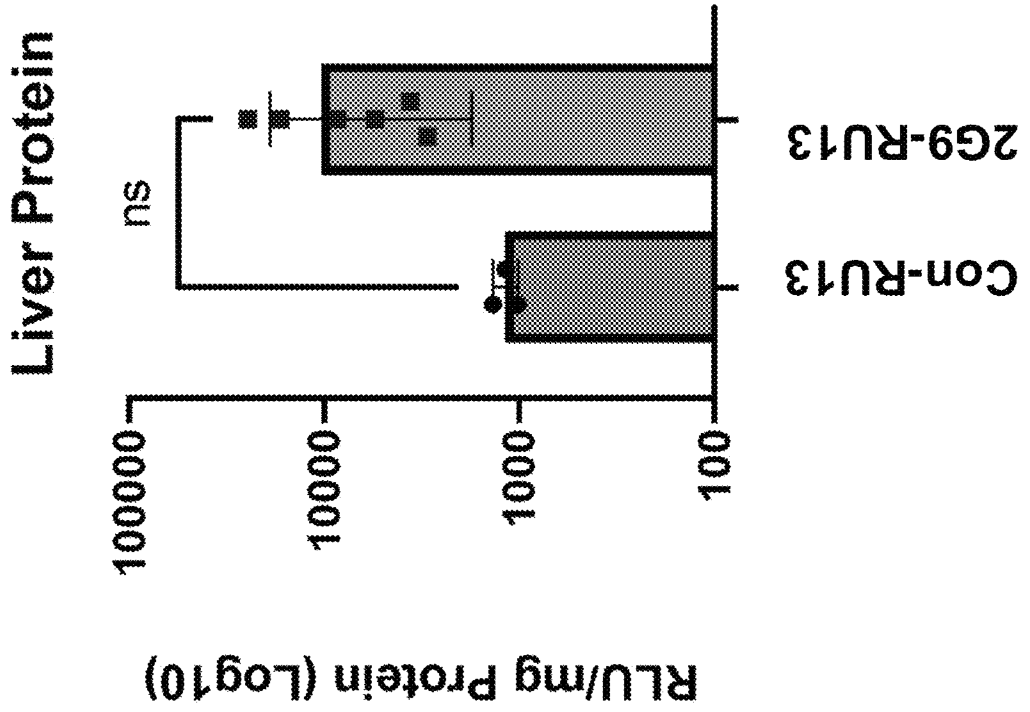
Figure 6Q:
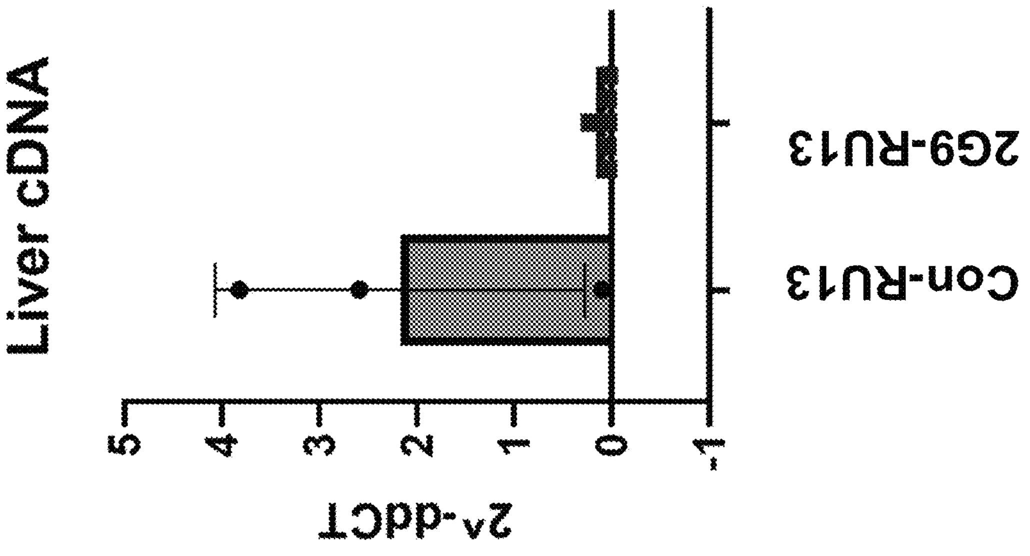
Figure 6S:
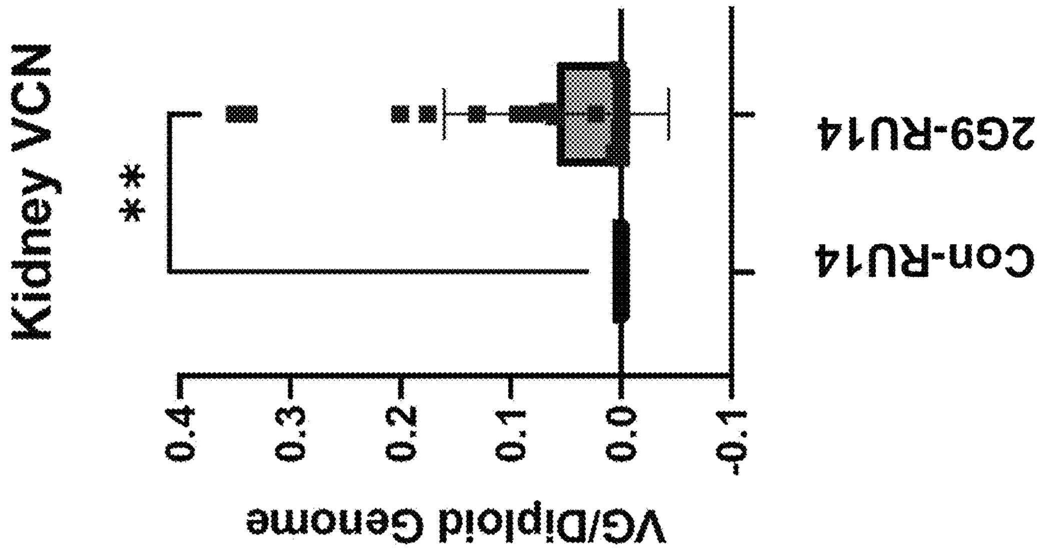
Figure 6T:
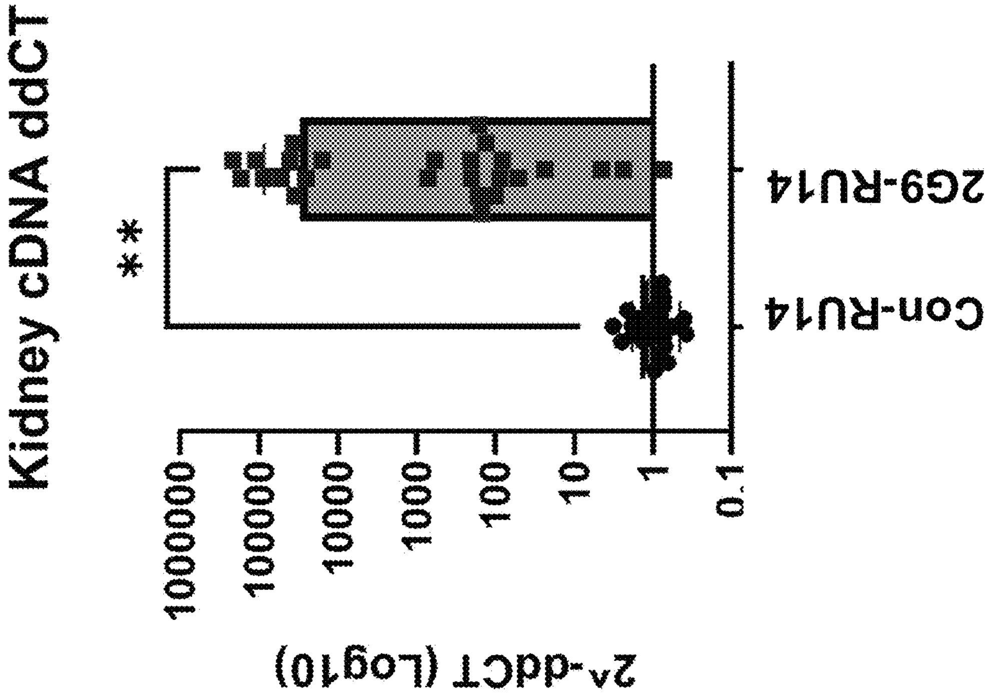
Figure 6V:
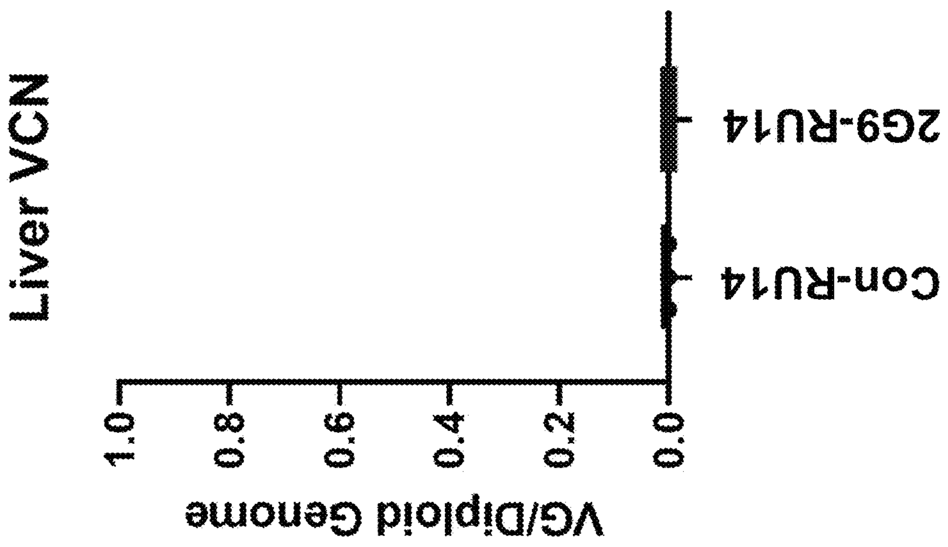
Figure 6U:
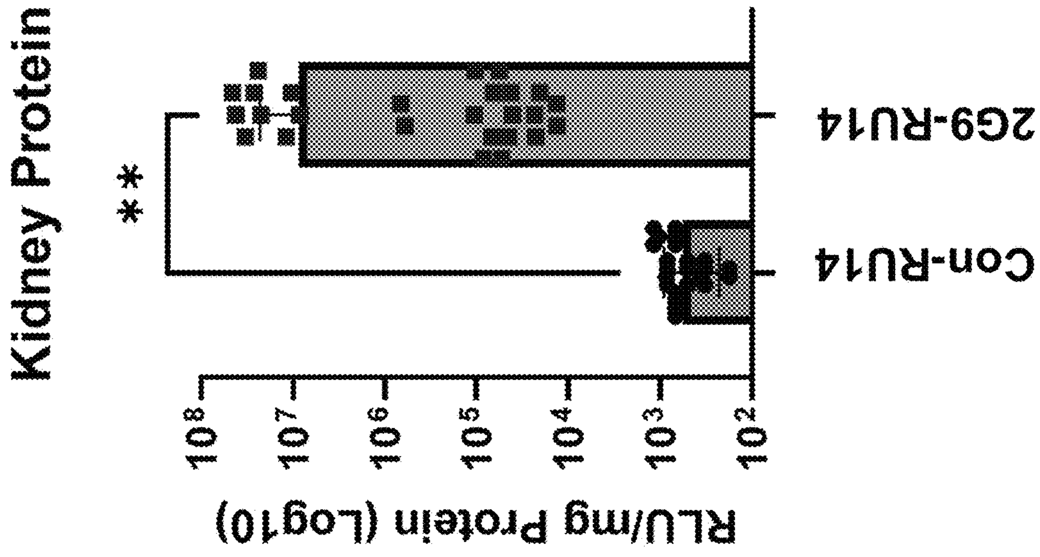
Figure 6W:
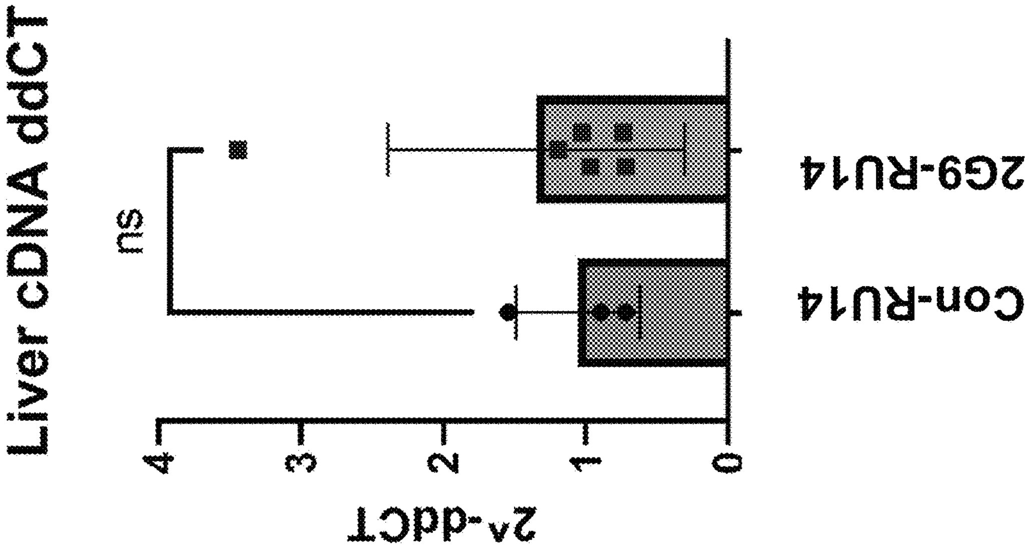
Figure 6X:
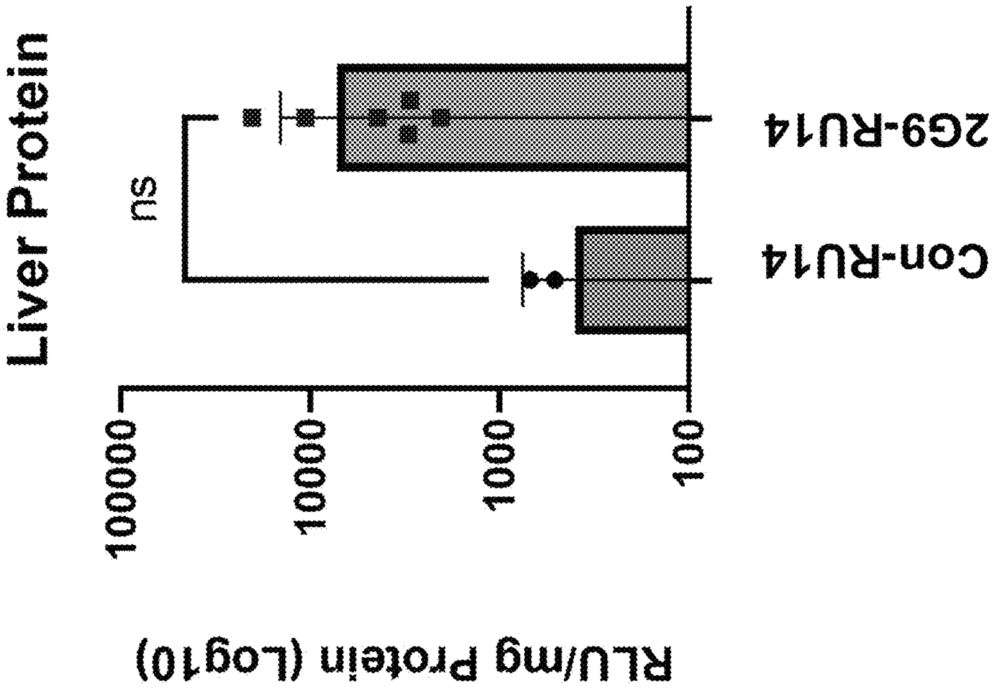

RD-Control-RU13 (see e.g., FIG. 6I)

| Sample | Protein RLU/mg Protein | CT (eGFP) | CT (GAPDH) | RNA dCT | RNA 2^-ddCT | DNA (ddPCR) GFP/ug gDNA | VG/DG |
|---|---|---|---|---|---|---|---|
| Kidney 1 | 6.89E+02 | 40.000 | 18.969 | 21.031 | 0.105 | 6.65E+01 | 0.000399 |
| Kidney 2 | 1.36E+03 | 39.235 | 18.845 | 20.391 | 0.164 | 1.44E+02 | 0.000866 |
| Kidney 3 | 0.00E+00 | 40.000 | 19.004 | 20.996 | 0.108 | 1.89E+01 | 0.000113 |
| Kidney 4 | 8.67E+02 | 35.765 | 19.123 | 16.642 | 2.198 | 2.44E+02 | 0.001466 |
| Kidney 5 | 8.44E+02 | 37.026 | 19.049 | 17.977 | 0.871 | 1.09E+03 | 0.006530 |
| Kidney 6 | 8.67E+02 | 34.987 | 19.023 | 15.963 | 3.519 | 7.52E+01 | 0.000451 |
| Kidney 7 | 6.89E+02 | 36.397 | 19.110 | 17.286 | 1.406 | 4.56E+01 | 0.000273 |
| Kidney 8 | 1.04E+03 | 38.604 | 19.150 | 19.454 | 0.313 | 7.64E+01 | 0.000458 |
| Kidney 9 | 5.11E+02 | 38.646 | 19.115 | 19.531 | 0.297 | 4.22E+01 | 0.000253 |
| Kidney 10 | 1.53E+03 | 35.719 | 19.059 | 16.660 | 2.172 | 0.00E+00 | 0.000000 |
| Kidney 11 | 1.20E+03 | 37.928 | 19.102 | 18.826 | 0.484 | 1.11E+02 | 0.000667 |

TABLE 4-continued

| RD-Control-RU13 (see e.g., FIG. 6I) | | | | | | | |
|---|---|---|---|---|---|---|---|
| | Protein | | | RNA | | DNA (ddPCR) | |
| | RLU/mg | | CT | | | GFP/ug | |
| Sample | Protein | CT (eGFP) | (GAPDH) | dCT | 2^-ddCT | gDNA | VG/DG |
| Kidney 12 | 6.89E+02 | 40.000 | 18.976 | 21.024 | 0.105 | 5.29E+01 | 0.000318 |
| Kidney 13 | 5.11E+02 | 38.377 | 18.941 | 19.436 | 0.317 | 5.14E+01 | 0.000308 |
| Kidney 14 | 8.44E+02 | 37.335 | 19.121 | 18.214 | 0.740 | 3.53E+02 | 0.002119 |
| Kidney 15 | 1.20E+03 | 38.469 | 19.054 | 19.415 | 0.322 | 5.31E+01 | 0.000319 |
| Kidney 16 | 5.11E+02 | 40.000 | 19.150 | 20.850 | 0.119 | 4.55E+01 | 0.000273 |
| Kidney 17 | 8.44E+02 | 33.787 | 19.580 | 14.207 | 11.886 | 1.77E+01 | 0.000106 |
| Kidney 18 | 8.67E+02 | 33.070 | 18.949 | 14.121 | 12.615 | 2.16E+01 | 0.000130 |
| Kidney 19 | 6.89E+02 | 32.099 | 18.879 | 13.219 | 23.571 | 2.18E+01 | 0.000131 |
| Kidney 20 | 5.11E+02 | 40.000 | 18.931 | 21.069 | 0.102 | 2.45E+01 | 0.000147 |
| Kidney 21 | 8.44E+02 | 33.498 | 18.826 | 14.672 | 8.612 | 3.81E+01 | 0.000229 |
| Kidney 22 | 5.11E+02 | 35.906 | 18.891 | 17.015 | 1.698 | 7.30E+01 | 0.000438 |
| Kidney 23 | 1.78E+02 | 33.289 | 19.039 | 14.250 | 11.536 | 2.33E+02 | 0.001399 |
| Kidney 24 | 0.00E+00 | 35.007 | 18.982 | 16.026 | 3.370 | 0.00E+00 | 0.000000 |
| Kidney 25 | 8.67E+02 | 35.093 | 19.013 | 16.080 | 3.246 | 6.64E+02 | 0.003986 |
| Kidney 26 | 1.56E+03 | 36.863 | 18.979 | 17.884 | 0.929 | 1.84E+01 | 0.000110 |
| Liver 1 | 1.18E+03 | 33.755 | 20.181 | 13.574 | 3.825 | 4.79E+02 | 0.0028726 |
| Liver 2 | 1.36E+03 | 34.017 | 19.883 | 14.134 | 2.594 | 1.32E+02 | 0.0007911 |
| Liver 3 | 1.02E+03 | 38.748 | 19.928 | 18.820 | 0.101 | 8.81E+01 | 0.0005287 |

TABLE 5

| RD-AAV2G9-RU13 (see e.g., FIG. 6J) | | | | | | | |
|---|---|---|---|---|---|---|---|
| | Protein | | | RNA | | DNA (ddPCR) | |
| | RLU/mg | | CT | | | GFP/ug | |
| Sample | Protein | CT (eGFP) | (GAPDH) | dCT | 2^-ddCT | gDNA | VG/DG |
| Kidney 1 | 4.00E+02 | 35.74 | 18.48 | 17.26 | 1.437 | 0.00E+00 | 0.000 |
| Kidney 2 | 1.15E+03 | 36.34 | 18.43 | 17.90 | 0.916 | 0.00E+00 | 0.000 |
| Kidney 3 | 1.03E+03 | 40.00 | 18.36 | 21.64 | 0.069 | 2.31E+01 | 0.000 |
| Kidney 4 | *1.23E+04* | 37.02 | 18.33 | 18.69 | 0.531 | 0.00E+00 | 0.000 |
| Kidney 5 | **1.69E+05** | 28.48 | 18.46 | 10.02 | **216.710** | 1.07E+02 | 0.001 |
| Kidney 6 | *1.07E+04* | 35.39 | 18.32 | 17.07 | 1.631 | 5.39E+01 | 0.000 |
| Kidney 7 | ***3.65E+06*** | 24.05 | 18.52 | 5.53 | ***4,860.323*** | 3.12E+03 | 0.019 |
| Kidney 8 | ***8.83E+06*** | 23.64 | 18.37 | 5.27 | ***5,827.723*** | 1.69E+03 | 0.010 |
| Kidney 9 | 7.20E+03 | 35.05 | 18.18 | 16.87 | 1.874 | 0.00E+00 | 0.000 |
| Kidney 10 | 5.10E+03 | 36.77 | 18.29 | 18.48 | 0.615 | 5.06E+01 | 0.000 |
| Kidney 11 | ***2.42E+07*** | 24.21 | 18.82 | 5.38 | ***5,381.236*** | 1.42E+03 | 0.009 |
| Kidney 12 | *2.14E+04* | 35.44 | 18.38 | 17.07 | 1.636 | 2.18E+01 | 0.000 |
| Kidney 13 | 4.12E+03 | 38.63 | 18.39 | 20.25 | 0.181 | 0.00E+00 | 0.000 |
| Kidney 14 | *6.42E+04* | 33.09 | 18.40 | 14.69 | 8.521 | 3.11E+01 | 0.000 |
| Kidney 15 | *1.63E+04* | 40.00 | 18.16 | 21.84 | 0.060 | 4.66E+01 | 0.000 |
| Kidney 16 | *3.49E+04* | 40.00 | 18.33 | 21.67 | 0.067 | 4.34E+01 | 0.000 |
| Kidney 17 | 1.93E+03 | 40.00 | 18.41 | 21.59 | 0.071 | 0.00E+00 | 0.000 |
| Kidney 18 | *7.98E+04* | 33.04 | 18.21 | 14.83 | 7.717 | 6.72E+01 | 0.000 |
| Kidney 19 | *1.48E+04* | 38.66 | 18.20 | 20.46 | 0.156 | 3.38E+01 | 0.000 |
| Kidney 20 | 6.50E+03 | 38.53 | 18.10 | 20.43 | 0.159 | 5.58E+01 | 0.000 |
| Kidney 21 | ***5.82E+07*** | 20.71 | 18.53 | 2.17 | ***49,815.328*** | 1.95E+04 | 0.117 |
| Kidney 22 | ***3.62E+07*** | 21.72 | 18.71 | 3.01 | ***27,970.995*** | 8.75E+03 | 0.052 |
| Kidney 23 | ***2.16E+06*** | 25.33 | 18.28 | 7.06 | ***1,689.853*** | 3.08E+02 | 0.002 |
| Kidney 24 | ***5.93E+07*** | 20.26 | 18.39 | 1.87 | ***61,362.569*** | 2.14E+04 | 0.128 |
| Kidney 25 | **2.21E+05** | 29.44 | 18.21 | 11.23 | **93.434** | 1.05E+02 | 0.000 |
| Kidney 26 | ***3.59E+07*** | 21.53 | 18.50 | 3.03 | ***27,452.802*** | 1.28E+04 | 0.077 |
| Liver 1 | *2.46E+04* | 40.00 | 19.68 | 20.32 | 0.036 | 1.88E+01 | 0.000 |
| Liver 2 | 3.65E+03 | 40.00 | 19.60 | 20.40 | 0.034 | 0.00E+00 | 0.000 |
| Liver 3 | *1.68E+04* | 37.37 | 19.74 | 17.63 | 0.230 | 0.00E+00 | 0.000 |
| Liver 4 | 5.52E+03 | 40.00 | 20.09 | 19.91 | 0.047 | 1.36E+02 | 0.000 |
| Liver 5 | 8.58E+03 | 40.00 | 19.85 | 20.15 | 0.040 | 8.78E+01 | 0.000 |
| Liver 6 | 2.98E+03 | 40.00 | 19.81 | 20.19 | 0.039 | 3.66E+01 | 0.000 |
| Nodule | *5.65E+04* | 38.98 | 18.97 | 20.01 | | 0.00E+00 | 0.000 |

TABLE 6

| RD-Control-RU14 (see e.g., FIG. 6K) | | | | | | | |
|---|---|---|---|---|---|---|---|
| | | Protein | | | | DNA (ddPCR) | |
| | RLU/mg | | CT | RNA | | GFP/ug | |
| Sample | Protein | CT (eGFP) | (GAPDH) | dCT | 2^-ddCT | gDNA | VG/DG |
| Kidney 1 | 8.67E+02 | 40.000 | 19.516 | 20.484 | 1.101 | 0.000E+00 | 0.000 |
| Kidney 2 | 0.00E+00 | 40.000 | 18.955 | 21.045 | 0.746 | 0.000E+00 | 0.000 |
| Kidney 3 | 1.20E+03 | 40.000 | 19.157 | 20.843 | 0.858 | 4.467E+01 | 0.000 |
| Kidney 4 | 5.11E+02 | 40.000 | 19.315 | 20.685 | 0.958 | 3.796E+01 | 0.000 |
| Kidney 5 | 8.44E+02 | 40.000 | 19.015 | 20.985 | 0.778 | 0.000E+00 | 0.000 |
| Kidney 6 | 8.44E+02 | 40.000 | 18.495 | 21.505 | 0.543 | 0.000E+00 | 0.000 |
| Kidney 7 | 3.56E+02 | 40.000 | 19.082 | 20.918 | 0.815 | 0.000E+00 | 0.000 |
| Kidney 8 | 3.33E+02 | 38.813 | 19.074 | 19.739 | 1.845 | 0.000E+00 | 0.000 |
| Kidney 9 | 1.20E+03 | 40.000 | 18.786 | 21.214 | 0.664 | 0.000E+00 | 0.000 |
| Kidney 10 | 1.78E+02 | 38.729 | 18.917 | 19.812 | 1.754 | 0.000E+00 | 0.000 |
| Kidney 11 | 6.89E+02 | 40.000 | 18.072 | 21.928 | 0.405 | 7.229E+01 | 0.000 |
| Kidney 12 | 6.89E+02 | 40.000 | 19.707 | 20.293 | 1.256 | 0.000E+00 | 0.000 |
| Kidney 13 | 8.44E+02 | 40.000 | 17.985 | 22.015 | 0.381 | 0.000E+00 | 0.000 |
| Kidney 14 | 0.00E+00 | 40.000 | 18.946 | 21.054 | 0.741 | 0.000E+00 | 0.000 |
| Kidney 15 | 6.89E+02 | 40.000 | 18.888 | 21.112 | 0.712 | 0.000E+00 | 0.000 |
| Kidney 16 | 3.33E+02 | 40.000 | 19.416 | 20.584 | 1.027 | 0.000E+00 | 0.000 |
| Kidney 17 | 1.78E+02 | 40.000 | 19.009 | 20.991 | 0.774 | 0.000E+00 | 0.000 |
| Kidney 18 | 6.89E+02 | 38.690 | 18.636 | 20.054 | 1.484 | 0.000E+00 | 0.000 |
| Kidney 19 | 6.89E+02 | 40.000 | 18.990 | 21.010 | 0.764 | 0.000E+00 | 0.000 |
| Kidney 20 | 5.11E+02 | 38.996 | 18.817 | 20.179 | 1.360 | 0.000E+00 | 0.000 |
| Kidney 21 | 0.00E+00 | 40.000 | 20.187 | 19.813 | 1.753 | 0.000E+00 | 0.000 |
| Kidney 22 | 3.33E+02 | 37.976 | 19.050 | 18.926 | 3.241 | 0.000E+00 | 0.000 |
| Kidney 23 | 6.89E+02 | 38.822 | 19.542 | 19.279 | 2.537 | 0.000E+00 | 0.000 |
| Kidney 24 | 1.04E+03 | 40.000 | 18.957 | 21.043 | 0.747 | 0.000E+00 | 0.000 |
| Kidney 25 | 6.89E+02 | 40.000 | 18.853 | 21.147 | 0.695 | 0.000E+00 | 0.000 |
| Kidney 26 | 5.11E+02 | 38.690 | 19.160 | 19.530 | 2.133 | 0.000E+00 | 0.000 |
| Liver 1 | 6.89E+02 | 39.056 | 20.218 | 18.838 | 1.544 | 0.000E+00 | 0.000 |
| Liver 2 | 5.11E+02 | 40.000 | 20.064 | 19.936 | 0.722 | 0.000E+00 | 0.000 |
| Liver 3 | 0.00E+00 | 40.000 | 20.379 | 19.621 | 0.897 | 0.000E+00 | 0.000 |

TABLE 7

| RD-AAV2G9-RU14 (see e.g., FIG. 6L) | | | | | | | |
|---|---|---|---|---|---|---|---|
| | | Protein | | | | DNA (ddPCR) | |
| | RLU/mg | | CT | RNA | | GFP/ug | |
| Sample | Protein | CT (eGFP) | (GAPDH) | dCT | 2^-ddCT | gDNA | VG/DG |
| Kidney 1 | ***2.25E+07*** | ***25.077*** | 19.576 | 5.501 | ***35642.069*** | 1.567E+04 | ***0.094*** |
| Kidney 2 | *4.23E+04* | *32.989* | 19.029 | 13.960 | *101.325* | 0.000E+00 | *0.000* |
| Kidney 3 | ***2.67E+07*** | ***22.879*** | 19.011 | 3.868 | ***110567.818*** | 3.352E+04 | ***0.201*** |
| Kidney 4 | ***8.60E+06*** | ***25.418*** | 19.455 | 5.964 | ***25870.589*** | 1.111E+04 | ***0.067*** |
| Kidney 5 | *2.05E+04* | *33.504* | 18.551 | 14.953 | *50.899* | 0.000E+00 | *0.000* |
| Kidney 6 | *4.08E+04* | *35.147* | 19.095 | 16.052 | *23.758* | 0.000E+00 | *0.000* |
| Kidney 7 | *2.34E+04* | *33.111* | 18.942 | 14.169 | *87.676* | 2.940E+02 | *0.002* |
| Kidney 8 | *1.35E+04* | *37.425* | 19.001 | 18.424 | *4.590* | 0.000E+00 | *0.000* |
| Kidney 9 | ***3.34E+07*** | ***22.187*** | 18.946 | 3.241 | ***170760.276*** | 5.856E+04 | ***0.351*** |
| Kidney 10 | *6.56E+04* | *29.870* | 18.720 | 11.149 | *710.825* | 5.130E+02 | *0.003* |
| Kidney 11 | *8.42E+04* | *32.112* | 18.549 | 13.564 | *133.318* | 0.000E+00 | *0.000* |
| Kidney 12 | **1.04E+05** | **30.155** | 18.730 | 11.425 | **587.099** | 1.938E+02 | **0.001** |
| Kidney 13 | *5.64E+04* | *31.432* | 18.466 | 12.967 | *201.702* | 1.154E+03 | *0.007* |
| Kidney 14 | ***4.58E+07*** | ***21.541*** | 18.654 | 2.887 | ***218228.802*** | 5.642E+04 | ***0.338*** |
| Kidney 15 | **1.07E+05** | **32.288** | 19.025 | 13.264 | **164.165** | 0.000E+00 | **0.000** |
| Kidney 16 | *6.80E+04* | *32.063* | 18.796 | 13.267 | *163.781* | 0.000E+00 | 0.000 |
| Kidney 17 | **6.16E+05** | **25.347** | 18.694 | 6.653 | **16046.002** | 3.850E+03 | **0.023** |
| Kidney 18 | *2.28E+04* | *37.955* | 18.587 | 19.368 | *2.387* | 0.000E+00 | *0.000* |
| Kidney 19 | *1.34E+04* | *40.000* | 18.926 | 21.074 | *0.731* | 0.000E+00 | *0.000* |
| Kidney 20 | **6.78E+05** | **33.081** | 19.686 | 13.395 | **149.850** | 4.869E+01 | **0.000** |
| Kidney 21 | *4.49E+04* | *31.433* | 18.489 | 12.945 | *204.800* | 2.936E+02 | *0.002* |
| Kidney 22 | ***4.25E+07*** | ***22.830*** | 18.641 | 4.189 | ***88489.700*** | 2.930E+04 | ***0.176*** |
| Kidney 23 | ***1.20E+07*** | ***24.428*** | 19.507 | 4.920 | ***53325.229*** | 1.295E+04 | ***0.078*** |
| Kidney 24 | *5.35E+04* | *33.538* | 19.276 | 14.262 | *82.170* | 0.000E+00 | *0.000* |
| Kidney 25 | ***1.05E+07*** | ***24.595*** | 19.282 | 5.313 | ***40609.484*** | 1.013E+04 | ***0.061*** |
| Kidney 26 | ***2.42E+07*** | ***24.947*** | 19.495 | 5.452 | ***36869.365*** | 2.177E+04 | ***0.131*** |
| Liver 1 | *2.04E+04* | *40.000* | 20.065 | 19.935 | *0.722* | 0.000E+00 | *0.000* |
| Liver 2 | 2.97E+03 | 40.000 | 20.792 | 19.208 | 1.195 | 0.000E+00 | 0.000 |

TABLE 7-continued

| RD-AAV2G9-RU14 (see e.g., FIG. 6L) | | | | | | | |
|---|---|---|---|---|---|---|---|
| | Protein | | | | | DNA (ddPCR) | |
| | RLU/mg | | CT | RNA | | GFP/ug | |
| Sample | Protein | CT (eGFP) | (GAPDH) | dCT | 2^-ddCT | gDNA | VG/DG |
| Liver 3 | 3.02E+03 | 40.000 | 20.490 | 19.510 | 0.970 | 0.000E+00 | 0.000 |
| Liver 4 | 2.05E+03 | 37.667 | 19.987 | 17.680 | 3.447 | 0.000E+00 | 0.000 |
| Liver 5 | *1.06E+04* | *40.000* | 20.575 | 19.425 | *1.028* | 0.000E+00 | *0.000* |
| Liver 6 | 4.42E+03 | 40.000 | 20.096 | 19.904 | 0.738 | 0.000E+00 | 0.000 |

In contrast to what is known in the art, described herein is the development of a method of administering rAAV to kidneys by a retrograde route that uses a lower volume of viral vector and results in higher levels of nephron and kidney cell transduction and decreased immune response. This method is clinically relevant and useful for the treatment of many kidney disorders.

Example 3: Retrograde Administration of rAAV to the Kidneys of Non-Human Primates (NHP)

AAV2G9 vector was administered to 2 male non-human primates (Rhesus macaque subjects NHP_RU1 and NHP_RU2) via retrograde ureter administration. AAV2G9 was modified to express GFP and luciferase transgenes driven by the CMV promoter.

The NHPs received an immune suppression regimen since the GFP and luciferase transgenes can be immunogenic in fully immunocompetent animals; immune suppression need not be used when non-immunogenic transgenes are used. The NHP immune suppression regimen was as follows: Day −1: DEPO-MEDROL® (methylprednisolone acetate) 40 mg/kg intramuscular (IM)+Tacrolimus (calcineurin-inhibitor) 0.1 mg/kg IM. Day 0: Surgery/Virus delivery via Ureter (Blood and urine collection; pressure testing and removal of contralateral kidney; liver sample). Day 6: DEPO-MEDROL® 40 mg/kg IM+Tacrolimus 0.1 mg/kg IM. Day 14: Sacrifice (Blood and urine collection; removal of kidney and liver sample).

NHP_RU1: On the day of administration, subject NHP_RU1 was 12 kg in total body weight, and its contralateral (untreated) kidney weighed 19.2 g. The contralateral kidney (i.e., the untreated kidney) was tested for intra-renal pressure and was removed before vector injection. Intrarenal pressure was tested using a 3-way valve system injecting increasing volumes of saline. The intrarenal pressure was approximately 46 cm $H_2O$. Prior to vector injection, the liver was biopsied, and urine and serum were sampled. The renal artery and ureter of the remaining kidney was clamped, and 2.5 mL of vector solution ($2.30\times10^{13}$ vg/mL AAV2g9-Lux2a_GFP; $5.75\times10^{13}$ VG Total injected; $4.8\times10^{12}$ vg/kg; 0.2083 mL/kg) was injected via the ureter using a catheter above the ureteral clamp to administer the vector solution into the renal pelvis, i.e., by retro-ureteral injection. Time for rAAV administration was about 30 seconds. There were then 15 minutes of warm ischemia after vector injection, a blood sample was drawn, and then the renal artery and the ureter were unclamped.

Fourteen days later, subject NHP_RU1 was sacrificed. On the day of sacrifice, subject NHP_RU1 was 12.1 kg in total body weight, and its 2G9-administered kidney weighed 22.52 g. Urine and blood samples were taken prior to sacrifice. After sacrifice, the kidney and liver were removed and kept on ice prior to sampling, and the removed kidney was flushed with cold saline in the surgical suite.

NHP_RU2: On the day of administration, subject NHP_RU2 was 9.7 kg in total body weight, and its contralateral (untreated) kidney weighed 23.3 g. The contralateral kidney (i.e., the untreated kidney) was tested for intra-renal pressure and was removed before vector injection; the intrarenal pressure was approximately 46 cm $H_2O$. Prior to vector injection, the liver was biopsied, and urine and serum were sampled. The renal artery and ureter of the remaining kidney were clamped, and 2.4 mL of vector solution ($2.30\times10^{13}$ vg/mL AAV2g9_Lux2a_GFP; $5.52\times10^{13}$ VG Total injected; $5.69\times10^{12}$ vg/kg; 0.2474 mL/kg) was injected neat via the ureter using a catheter above the ureteral clamp to administer the vector solution into the renal pelvis, i.e., by retro-ureteral injection. The time for administration of the rAAV was about 30 seconds. There were then 15 minutes of warm ischemia after vector injection, a blood sample was drawn, and then the renal artery and the ureter were unclamped. Samples were stored on ice prior to sampling.

Fourteen days later, subject NHP_RU2 was sacrificed. On the day of sacrifice, subject NHP_RU2 was 8.95 kg in total body weight, and its 2G9-administered kidney weighed 21.72g. Urine and blood samples were taken prior to sacrifice. After sacrifice, the kidney and liver were removed and kept on ice prior to sampling, and the removed kidney was flushed with cold saline in the surgical suite.

Samples and/or histological sections of the NHP kidneys and/or livers were analyzed for GFP staining, rAAV DNA levels, eGFP cDNA levels, and luciferase protein levels (see e.g., FIG. 7A-7M and Tables 8-10, below).

TABLE 8

| NHP DNA (see e.g., FIG. 7G) | |
|---|---|
| Sample: | Average VCN (vg/dg) |
| NHP_Con_RU1 Kidney | 7.018E−05 |
| NHP_Con_RU1 Liver | 1.133E−05 |
| NHP_2G9_RU1 Kidney | 1.51E+01 |
| NHP_2G9_RU1 Liver | 8.608E−05 |
| NHP_Con_RU2 Kidney | 4.00E−03 |
| NHP_Con_RU2 Liver | 4.00E−03 |
| NHP_2G9_RU2 Kidney | 1.49E+01 |
| NHP_2G9_RU2 Liver | 2.00E+00 |

TABLE 9

| NHP eGFP cDNA (see e.g., FIG. 7H) | |
|---|---|
| Sample: | Average Relative Fold-Change |
| NHP_Con_RU1 Kidney | 1.59E+00 |
| NHP_Con_RU1 Liver | 1.03E+00 |
| NHP_2G9_RU1 Kidney | 9.18E+06 |
| NHP_2G9_RU1 Liver | 9.67E-01 |
| NHP_Con_RU2 Kidney | 1.10E+00 |
| NHP_Con_RU2 Liver | 1.02E+00 |
| NHP_2G9_RU2 Kidney | 3.40E+06 |
| NHP_2G9_RU2 Liver | 1.60E+03 |

TABLE 10

| NHP Luciferase Protein (see e.g., FIG. 7J) | |
|---|---|
| Sample: | Average RLU/mg Protein |
| NHP_Con_RU1 Kidney | 2.22E+02 |
| NHP_Con_RU1 Liver | 3.93E+02 |
| NHP_2G9_RU1 Kidney | 1.31E+08 |
| NHP_2G9_RU1 Liver | 1.37E+03 |
| NHP_Con_RU2 Kidney | 3.30E+02 |
| NHP_Con_RU2 Liver | 8.56E+02 |
| NHP_2G9_RU2 Kidney | 1.00E+08 |
| NHP_2G9_RU2 Liver | 2.34E+05 |

Figure 7A:
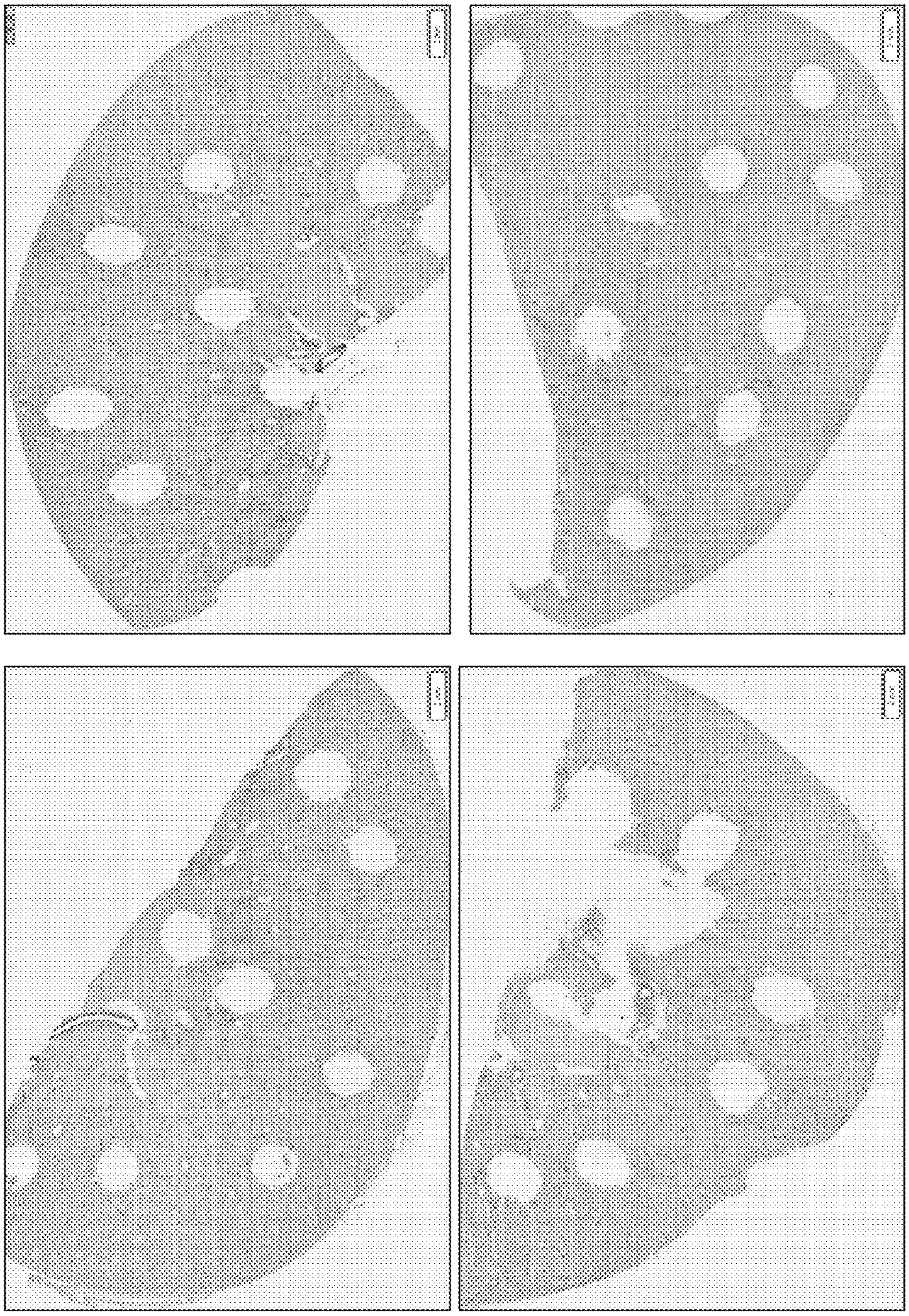
Figure 7B:
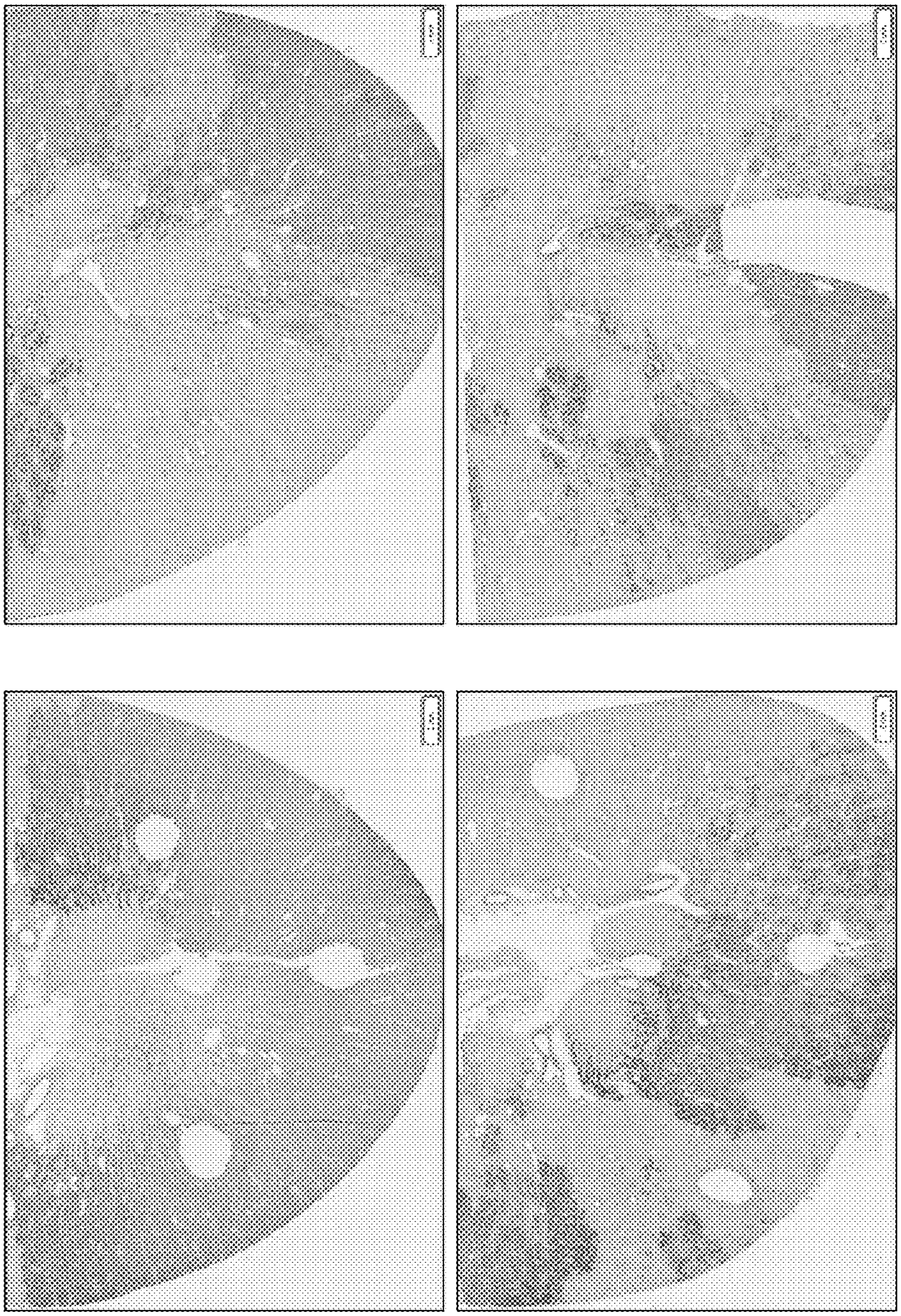
Figure 7C:
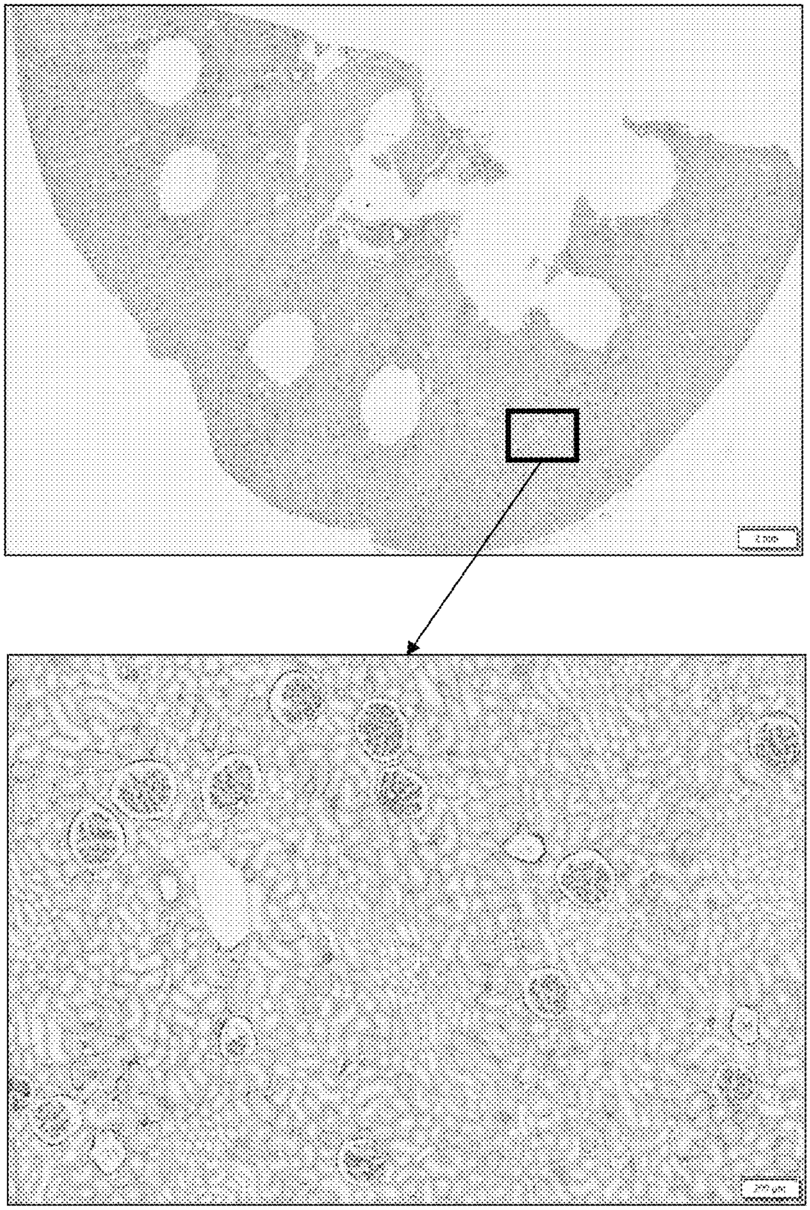
Figure 7D:
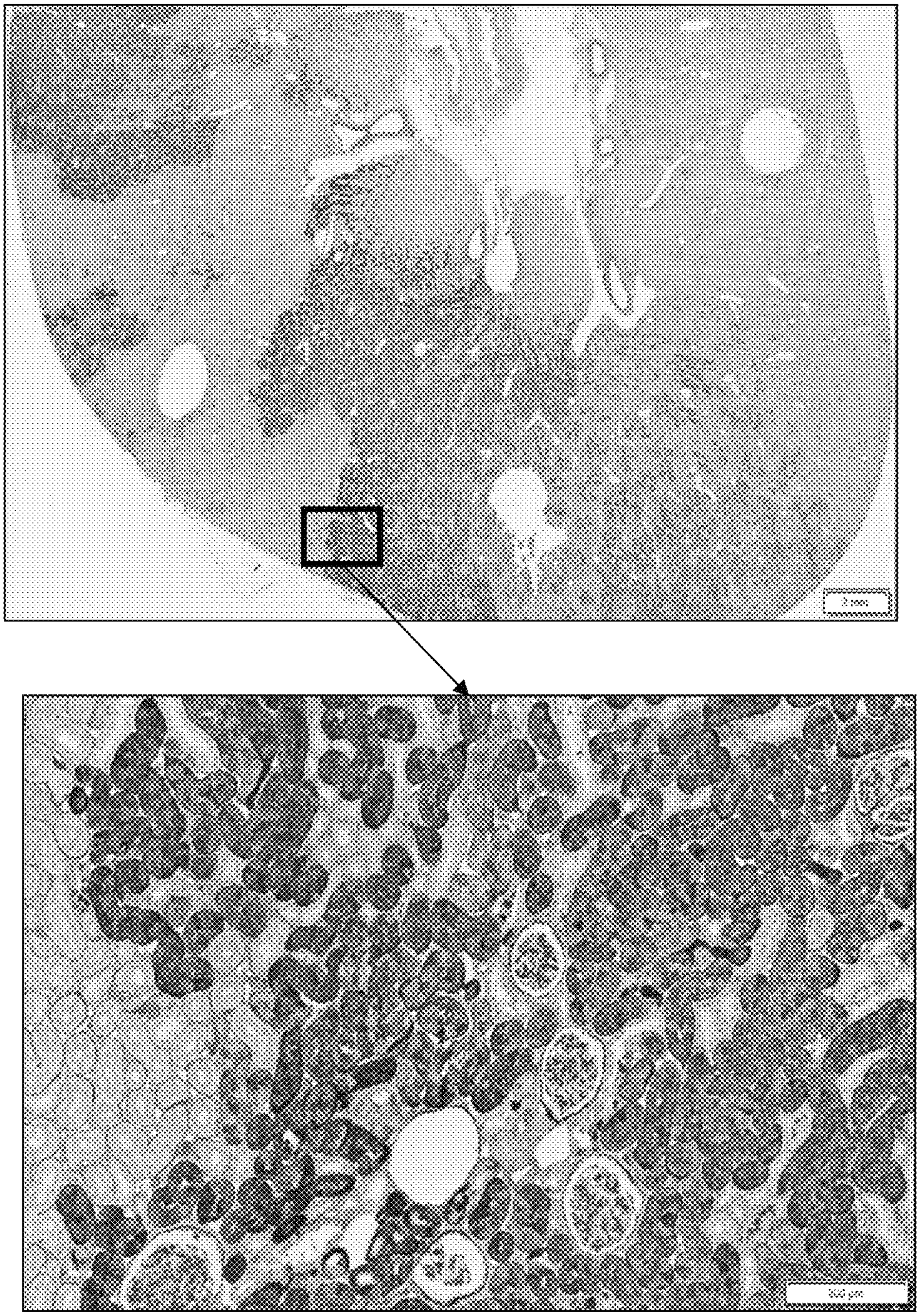
Figure 7E:
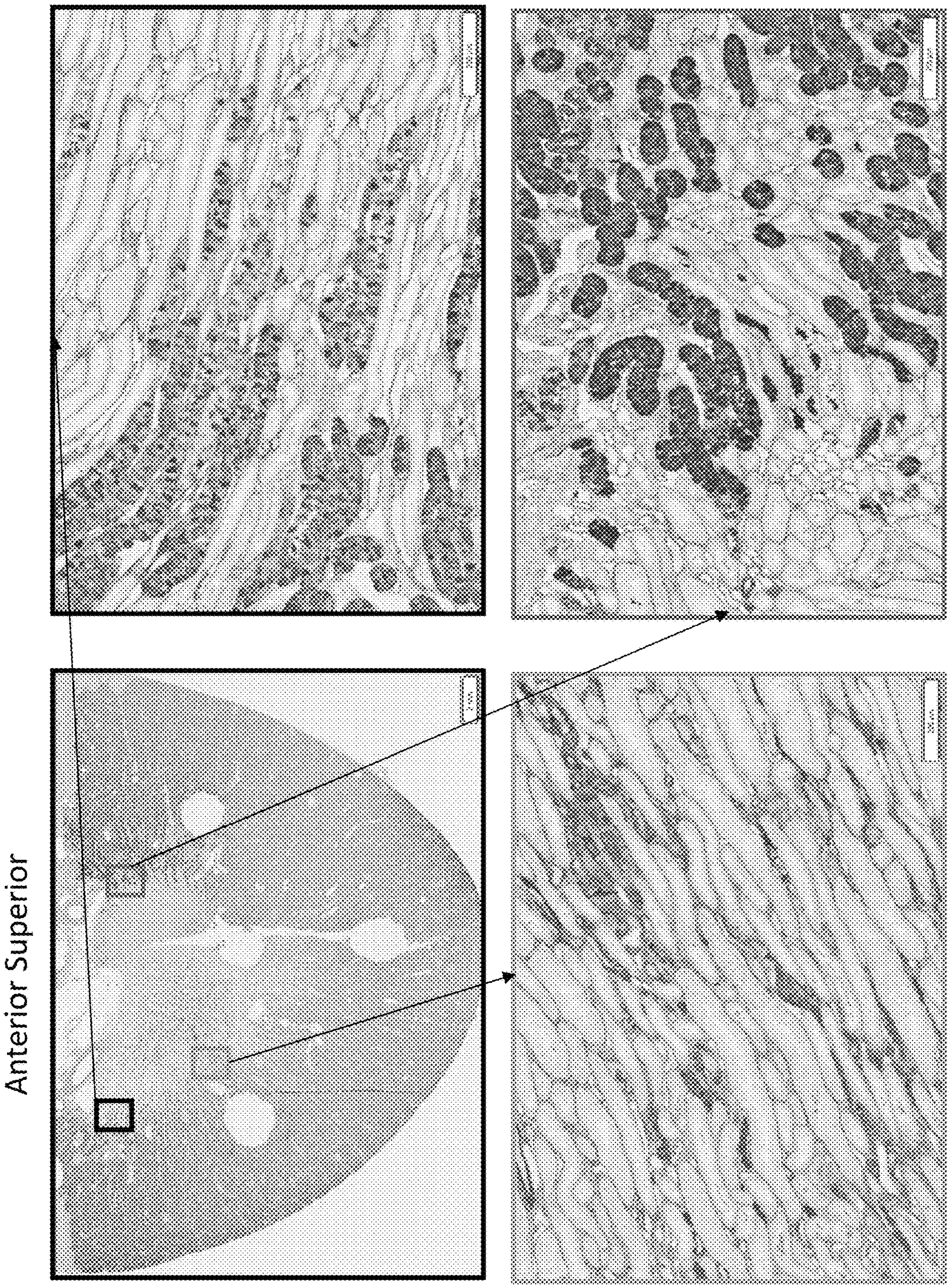
Figure 7F:
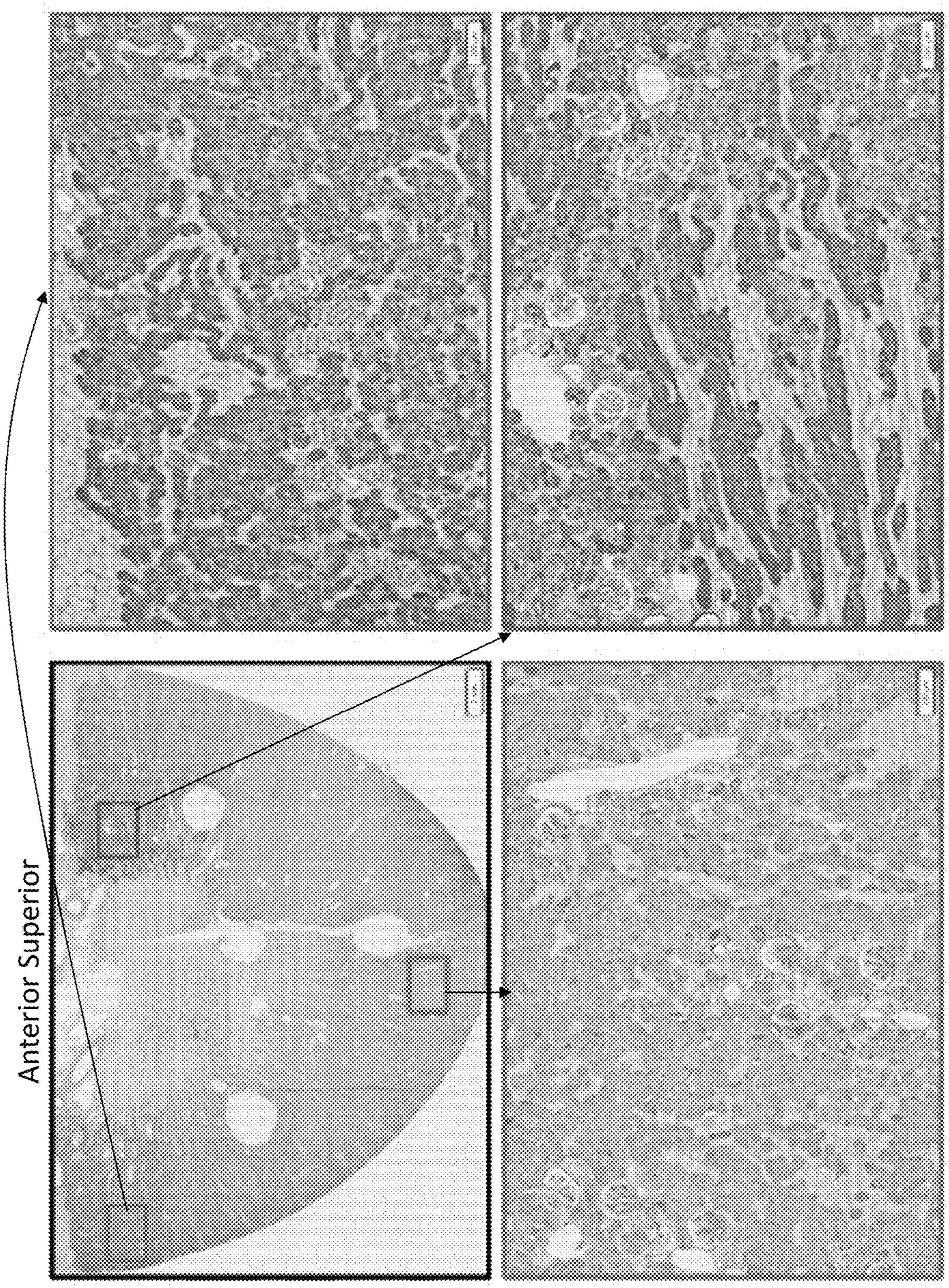
Figure 7G:
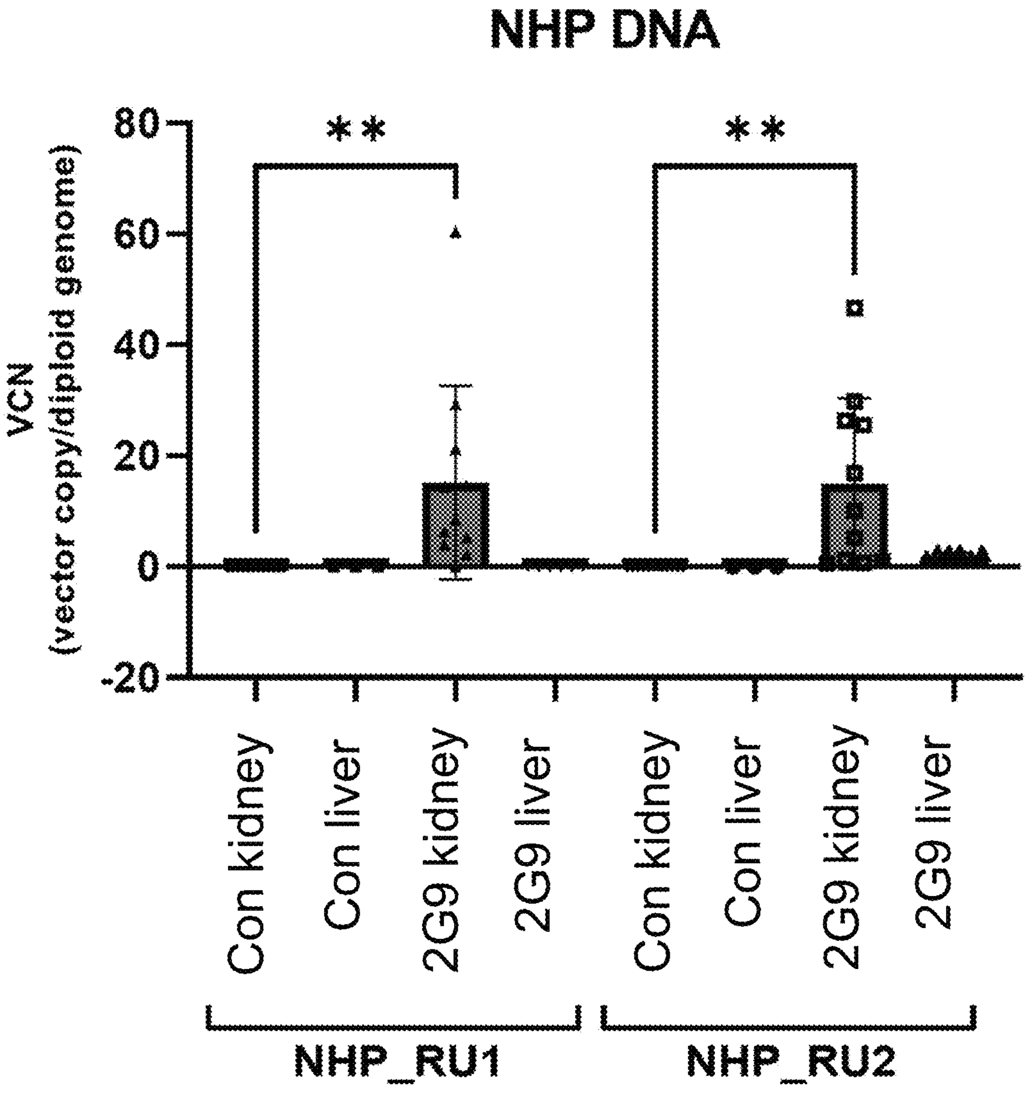
Figure 7H:
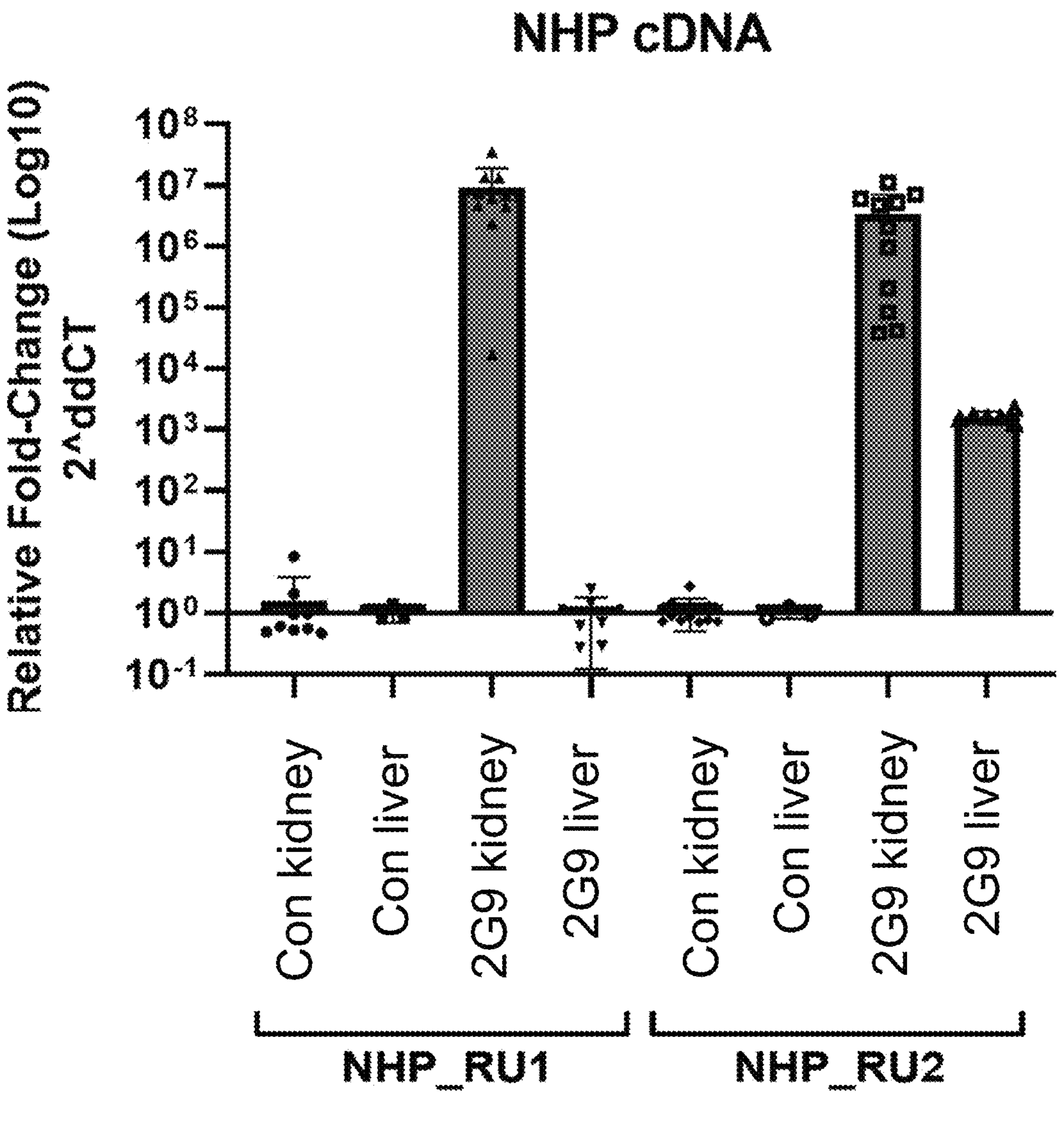
Figure 7I:
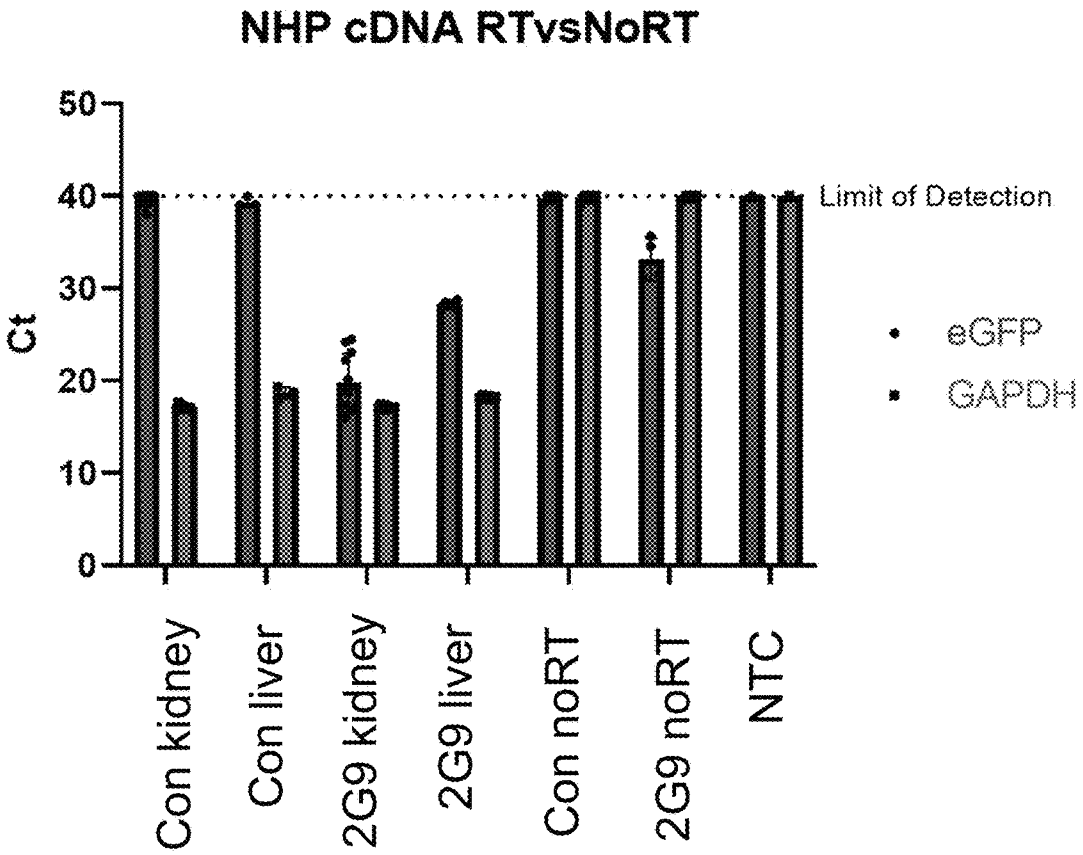
Figure 7J:
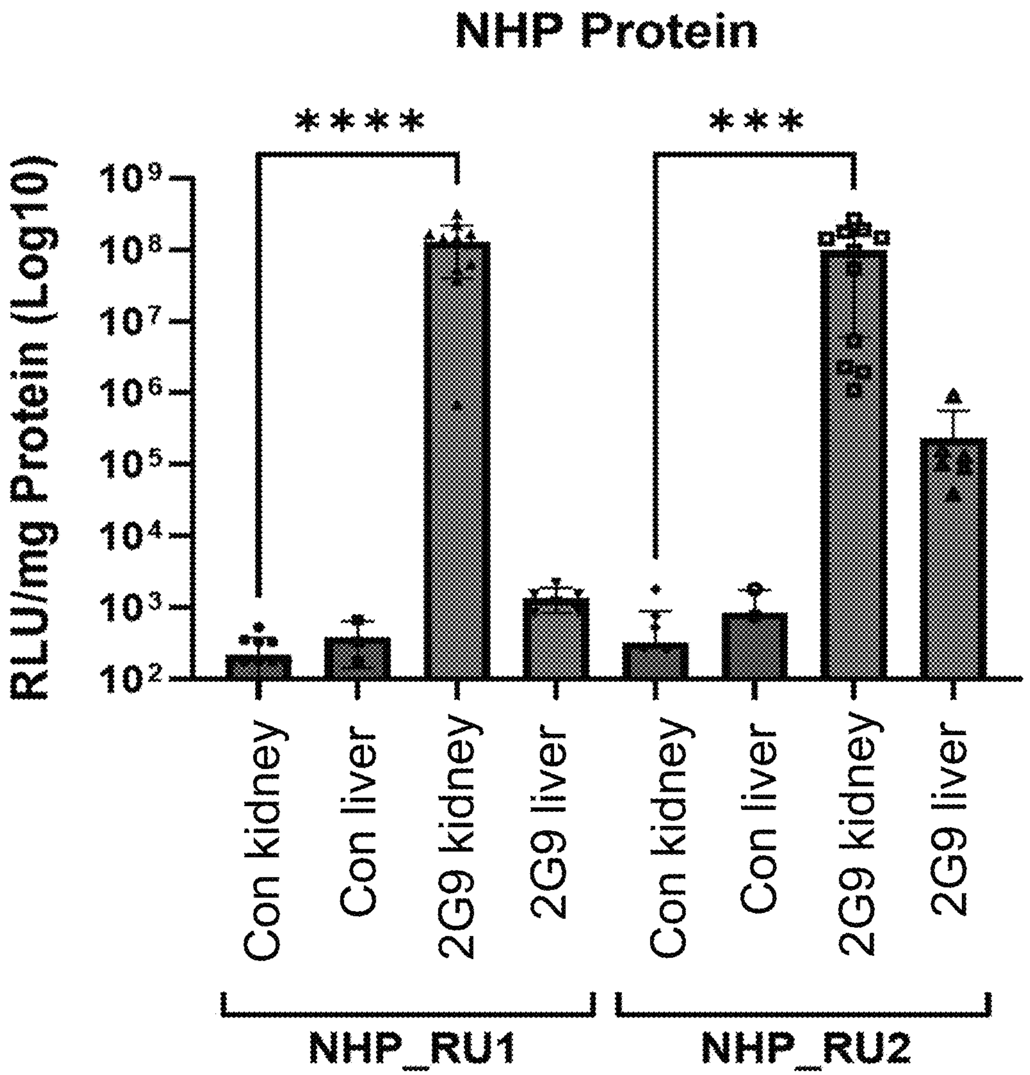

The vg/dg:RLU correlation coefficient (r) was 0.9229 (see e.g., FIG. 7G and FIG. 7I).

Co-Staining for Cells of the PCT and DCT CD

Figure 8A:
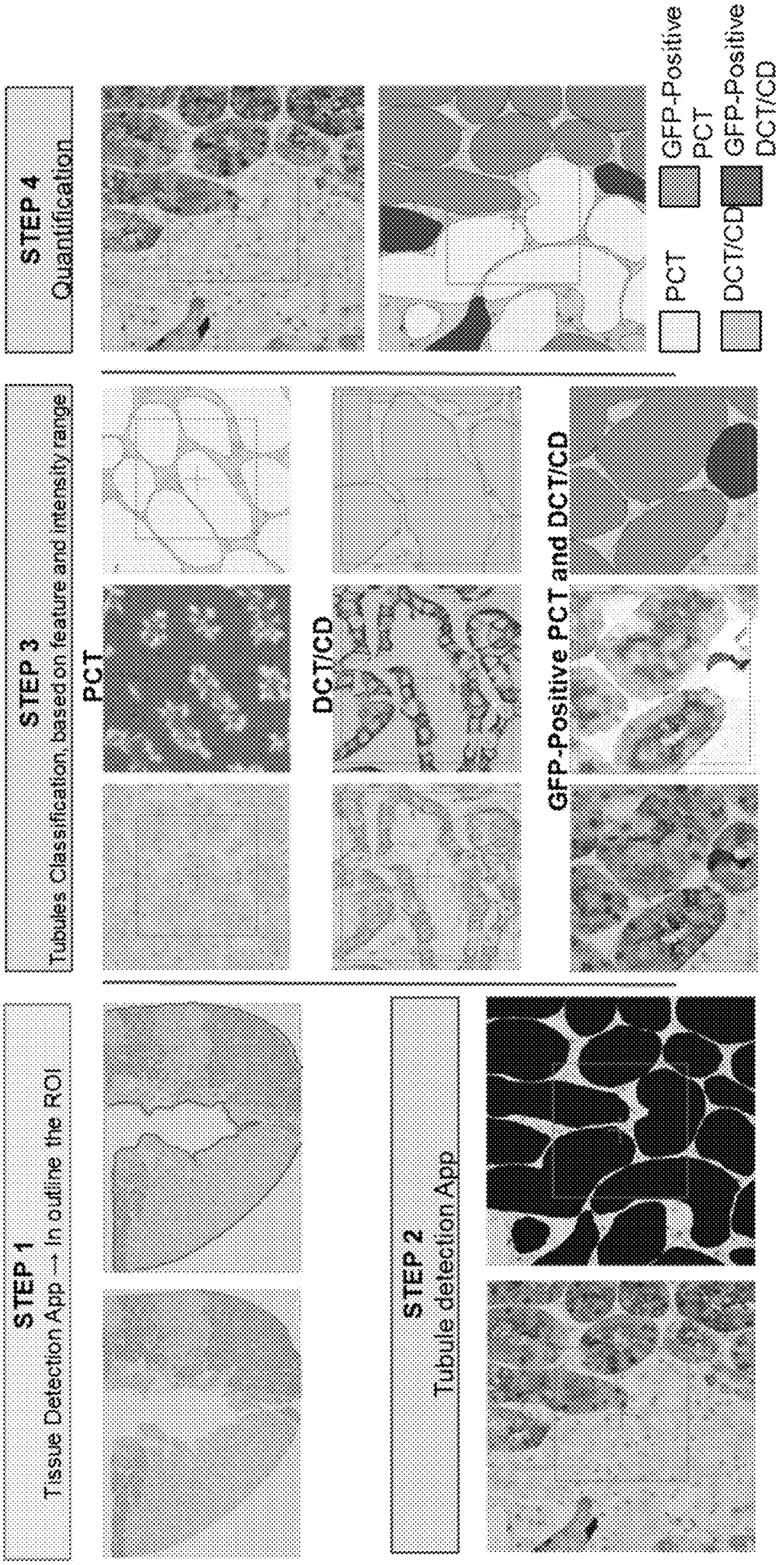
FIG. 8A-8E is a series of images showing co-staining of kidneys from non-human primates administered AAV2G9 using the retrograde ureter route (see e.g., Example 3).
Figure 8B:
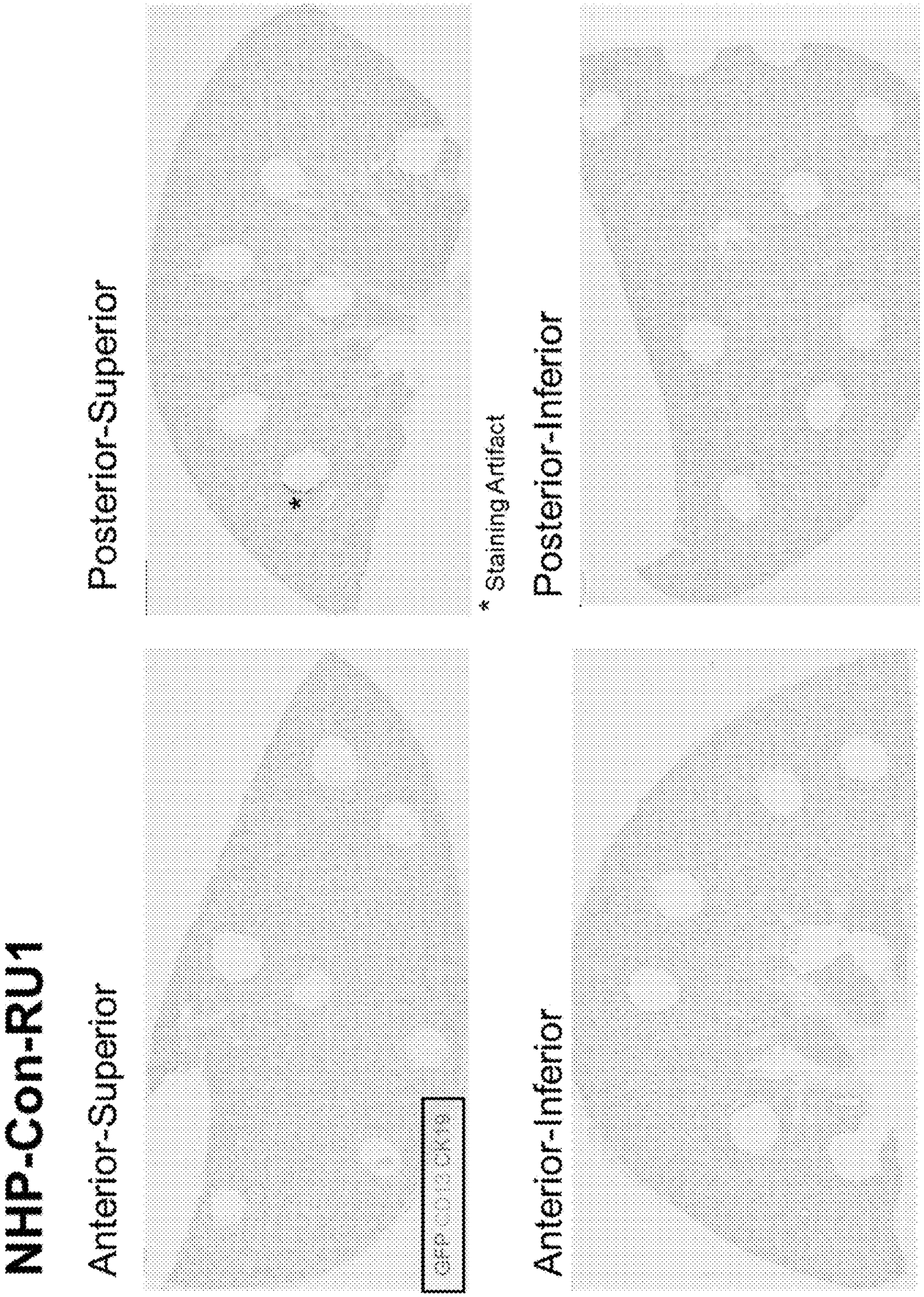
Figure 8C:
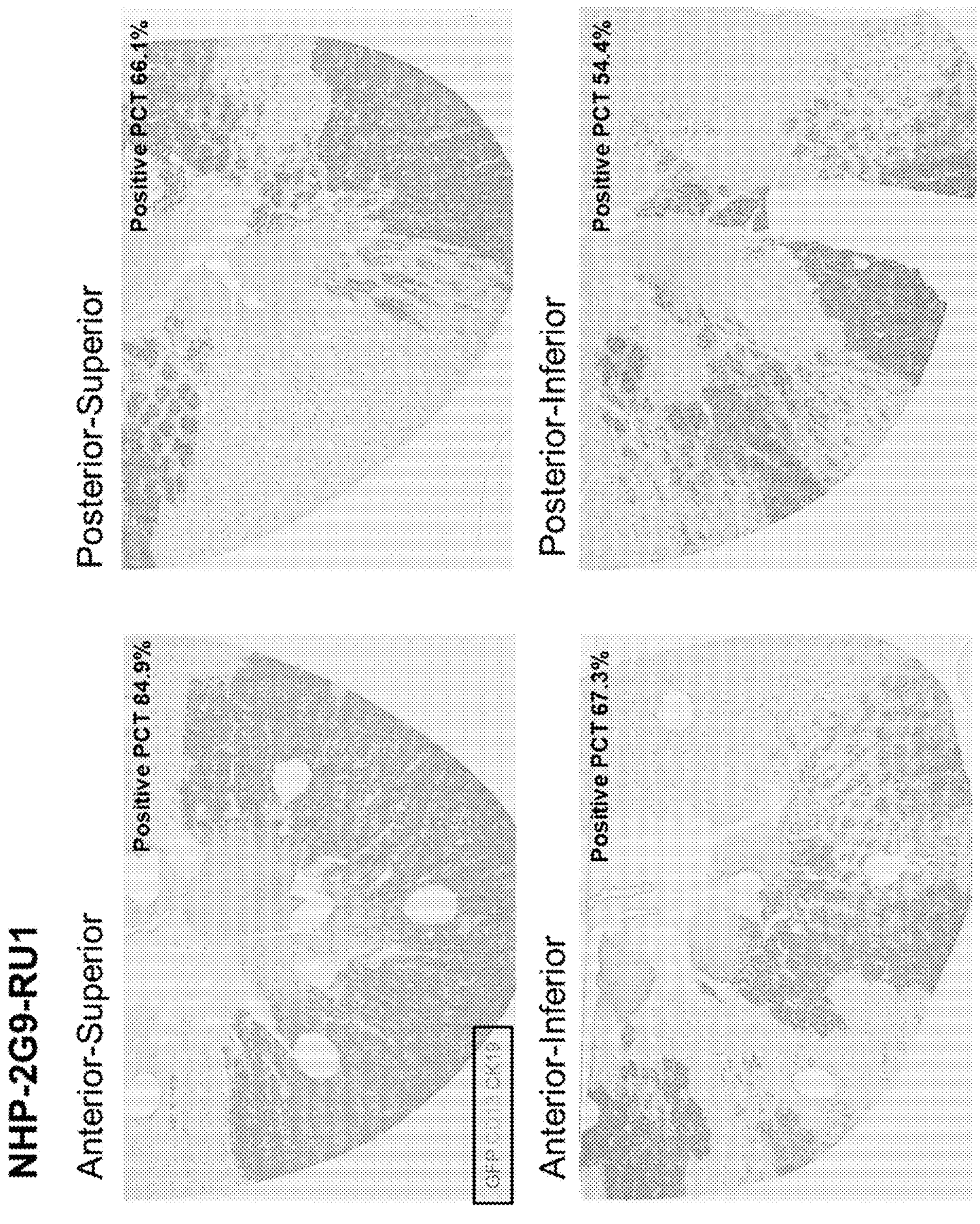
Figure 8D:
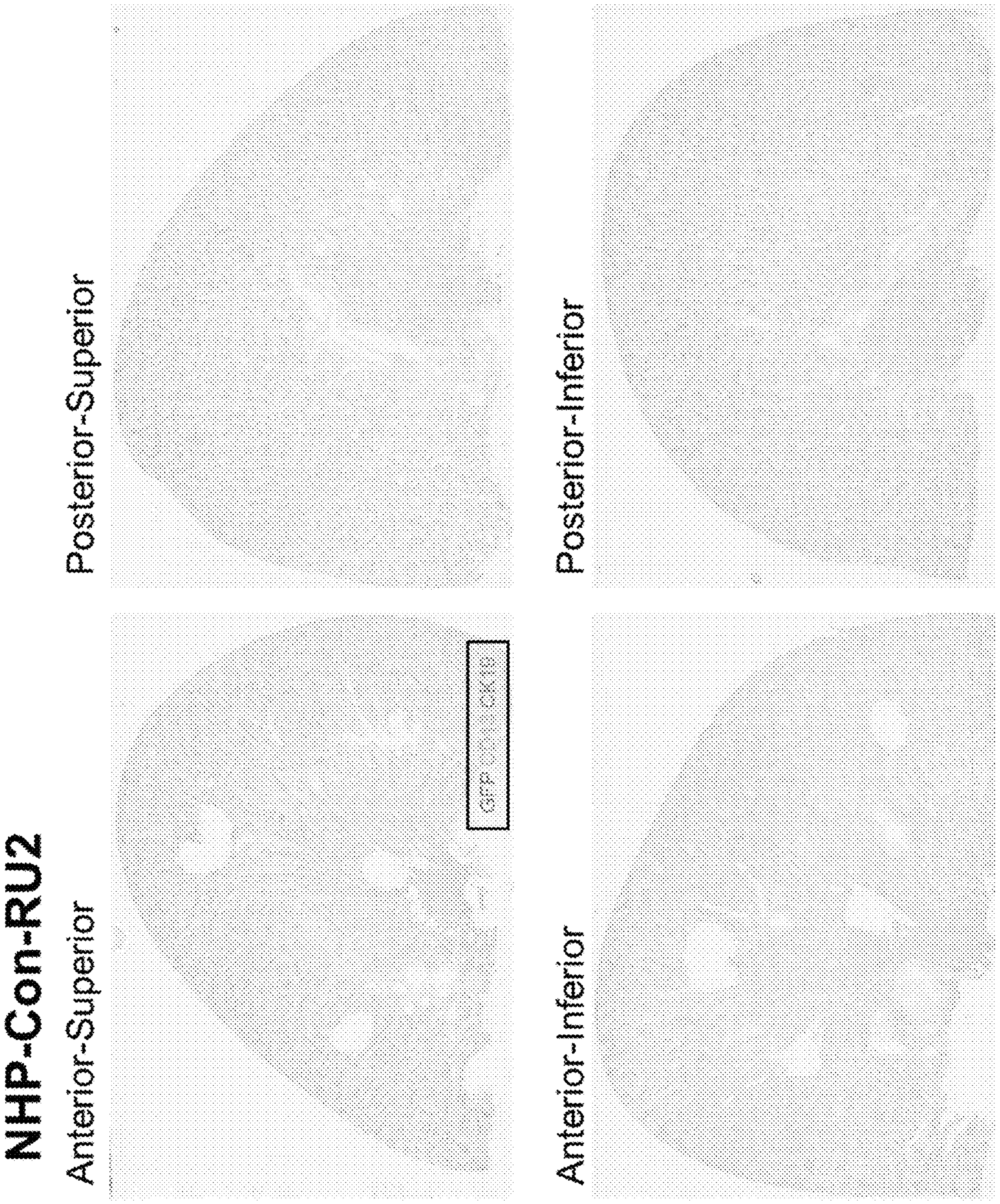
Figure 8E:
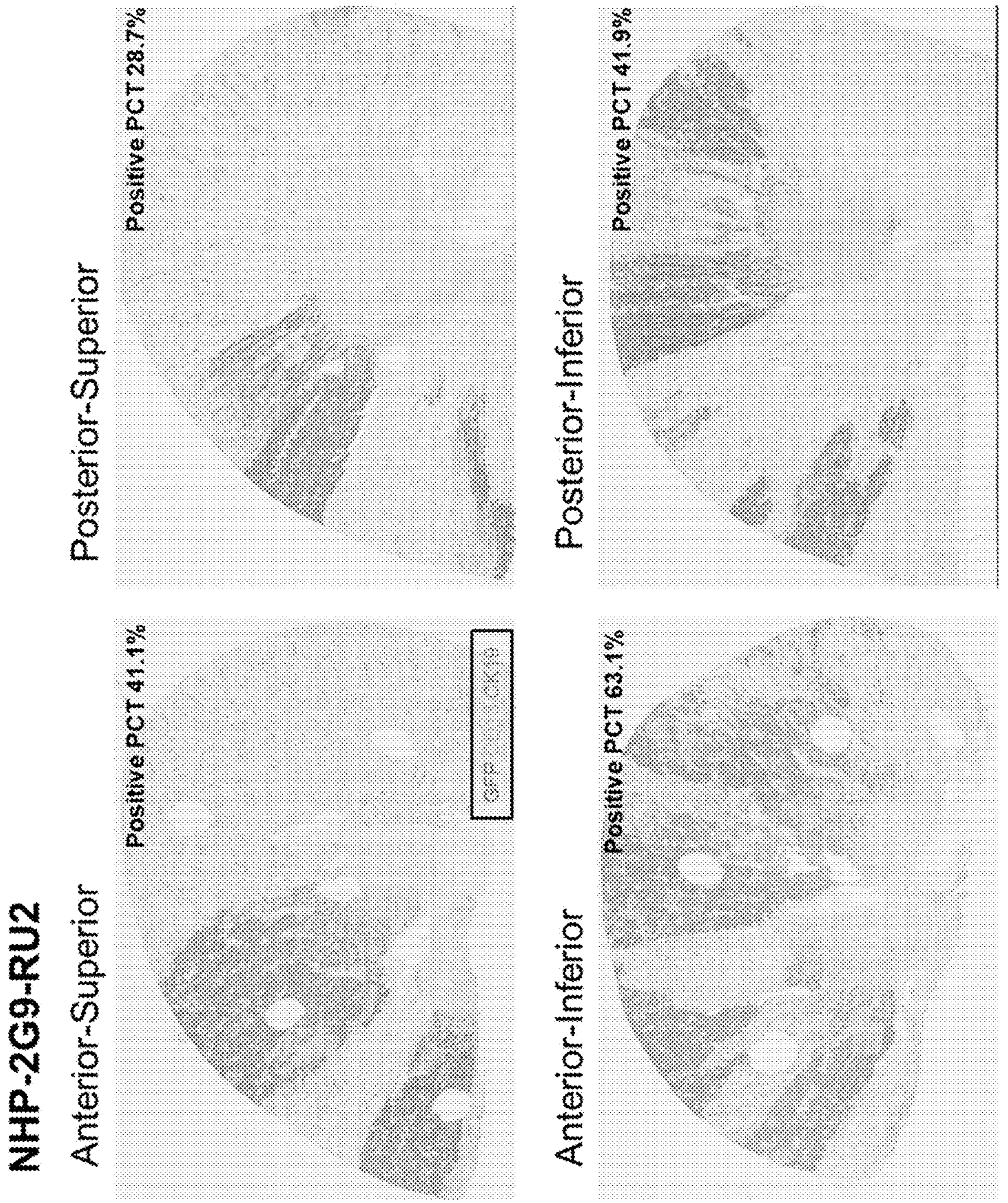

Histology sections from the contralateral and AAV2G9-administered kidneys from NHP-Con-RU1 and NHP-Con-RU2 were co-stained for AAV2G9 (GFP—purple staining; ABCAM® Ab6673), proximal convoluted tubules (CD13—yellow staining; ABCAM® Ab108382), and distal convoluted tubules and collecting ducts (CK19—blue staining; ABCAM® Ab52625). The sections were analyzed with VISIOPHARM®, a Pathology Image Analysis Software, which includes Artificial Intelligence (AI)/Deep Learning Application Protocol Packages (APPs). As detailed in FIG. 8A, image analysis was performed across the entirety of each section. In step 1, a tissue detection application detected the tissue, and a region of interest (ROI) was outlined. In step 2, a tubule detection application detected the tubules. In step 3, the tubules were classified based on feature and staining intensity range for GFP, CD13, and CK19. After discriminating proximal convoluted tubules (PCT; CD13+) and distal convoluted tubules and collecting ducts (DCT/CD; CK19+) independently, the AI system recognized GFP-positive PCT (CD13+, GFP+) and GFP-positive DCT/CD (CK19+, GFP+) for analysis. In step 4, the following regions were quantified: total PCT (CD13+), GFP-positive PCT (CD13+, GFP+), total DCT/CD (CK19+), and GFP-positive DCT/CD (CK19+, GFP+). The results of this analysis are shown in FIG. 8B-8E and Tables 11-12. The last column in Table 11, "% GFP Positive PCT" was calculated by dividing the number of "GFP-Positive PCT" by the number of "Total PCT" to determine the percentage. The last column in Table 12, "% GFP Positive DCT/CD" was calculated by dividing the number of "GFP-Positive DCT/CD" by the number of "Total DCT/CD" to determine the percentage.

TABLE 11

Proximal convoluted tubule (PCT) co-staining (see e.g., FIG. 8A-8E)

| | | Total PCT | GFP-Positive PCT | % GFP Positive PCT |
|---|---|---|---|---|
| NHP-Con-RU1 (see e.g., FIG. 8B) | Anterior-Superior | 13403 | 0 | 0 |
| | Anterior-Inferior | 14662 | 0 | 0 |
| | Posterior-Superior | 12957 | 0 | 0 |
| | Posterior-Inferior | 19952 | 0 | 0 |
| | Total | 60974 | 0 | 0 |
| NHP_2G9_RU1 (see e.g., FIG. 8C) | Anterior-Superior | 48837 | 41467 | 84.90898 |
| | Anterior-Inferior | 40070 | 26957 | 67.27477 |
| | Posterior-Superior | 43976 | 29051 | 66.06103 |
| | Posterior-Inferior | 35436 | 19270 | 54.37973 |
| | Total | 168319 | 116745 | 69.35937 |
| NHP-Con-RU2 (see e.g., FIG. 8D) | Anterior-Superior | 23703 | 0 | 0 |
| | Anterior-Inferior | 28630 | 0 | 0 |
| | Posterior-Superior | 25019 | 0 | 0 |
| | Posterior-Inferior | 26495 | 0 | 0 |
| | Total | 103847 | 0 | 0 |
| NHP_2G9_RU2 (see e.g., FIG. 8E) | Anterior-Superior | 37938 | 15612 | 41.15135 |
| | Anterior-Inferior | 40837 | 25784 | 63.13882 |
| | Posterior-Superior | 33356 | 9589 | 28.74745 |
| | Posterior-Inferior | 40502 | 16983 | 41.93126 |
| | Total | 152633 | 67968 | 44.53034 |

TABLE 12

Distal convoluted tubule (DCT) and collecting duct (CD) co-staining

| | | Total DCT/CD | GFP-Positive DCT/CD | % GFP Positive DCT/CD |
|---|---|---|---|---|
| NHP-Con-RU1 (see e.g., FIG. 8B) | Anterior-Superior | 20671 | 0 | 0 |
| | Anterior-Inferior | 23595 | 0 | 0 |
| | Posterior-Superior | 22382 | 0 | 0 |
| | Posterior-Inferior | 28740 | 0 | 0 |
| | Total | 95388 | 0 | 0 |
| NHP_2G9_RU1 (see e.g., FIG. 8C) | Anterior-Superior | 35025 | 8872 | 25.33048 |
| | Anterior-Inferior | 31231 | 6972 | 22.32397 |
| | Posterior-Superior | 36234 | 7632 | 21.06309 |
| | Posterior-Inferior | 32368 | 8852 | 27.34800 |
| | Total | 134858 | 32328 | 23.97188 |

TABLE 12-continued

| Distal convoluted tubule (DCT) and collecting duct (CD) co-staining | | | | |
|---|---|---|---|---|
| | | Total DCT/CD | GFP-Positive DCT/CD | % GFP Positive DCT/CD |
| NHP-Con-RU2 (see e.g., FIG. 8D) | Anterior-Superior | 27344 | 0 | 0 |
| | Anterior-Inferior | 32413 | 0 | 0 |
| | Posterior-Superior | 22200 | 0 | 0 |
| | Posterior-Inferior | 28562 | 0 | 0 |
| | Total | 110519 | 0 | 0 |
| NHP_2G9_RU2 (see e.g., FIG. 8E) | Anterior-Superior | 22827 | 6945 | 30.42450 |
| | Anterior-Inferior | 26198 | 6007 | 22.92923 |
| | Posterior-Superior | 39255 | 5488 | 13.98038 |
| | Posterior-Inferior | 34791 | 5533 | 15.90354 |
| | Total | 123071 | 23973 | 19.47899 |

As shown in FIG. 8B-8E and Table 11, over 25% (e.g., 54.38% to 84.91%, 69.36% mean for NHP_2G9_RU1; 28.75% to 63.14%, 41.93% mean for NHP_2G9_RU2) of proximal convoluted tubules in four representative sections of each of the AAV-administered kidneys were positive for AAV2G9, and there was no AAV2G9 staining in the contralateral kidneys (see NHP-Con-RU1 and NHP-Con-RU2). As shown in FIG. 8B-8E and Table 12, over 10% (e.g., 21.06% to 27.35%, 23.97% mean for NHP_2G9_RU1; 13.98% to 30.42%, 19.48% mean for NHP_2G9_RU2) of distal convoluted tubule and collecting ducts in four representative sections of each of the kidneys were positive for AAV2G9, and there was no AAV2G9 staining in the contralateral kidneys (see NHP-Con-RU1 and NHP-Con-RU2).

Neutralizing Antibody Levels

Figure 9A:
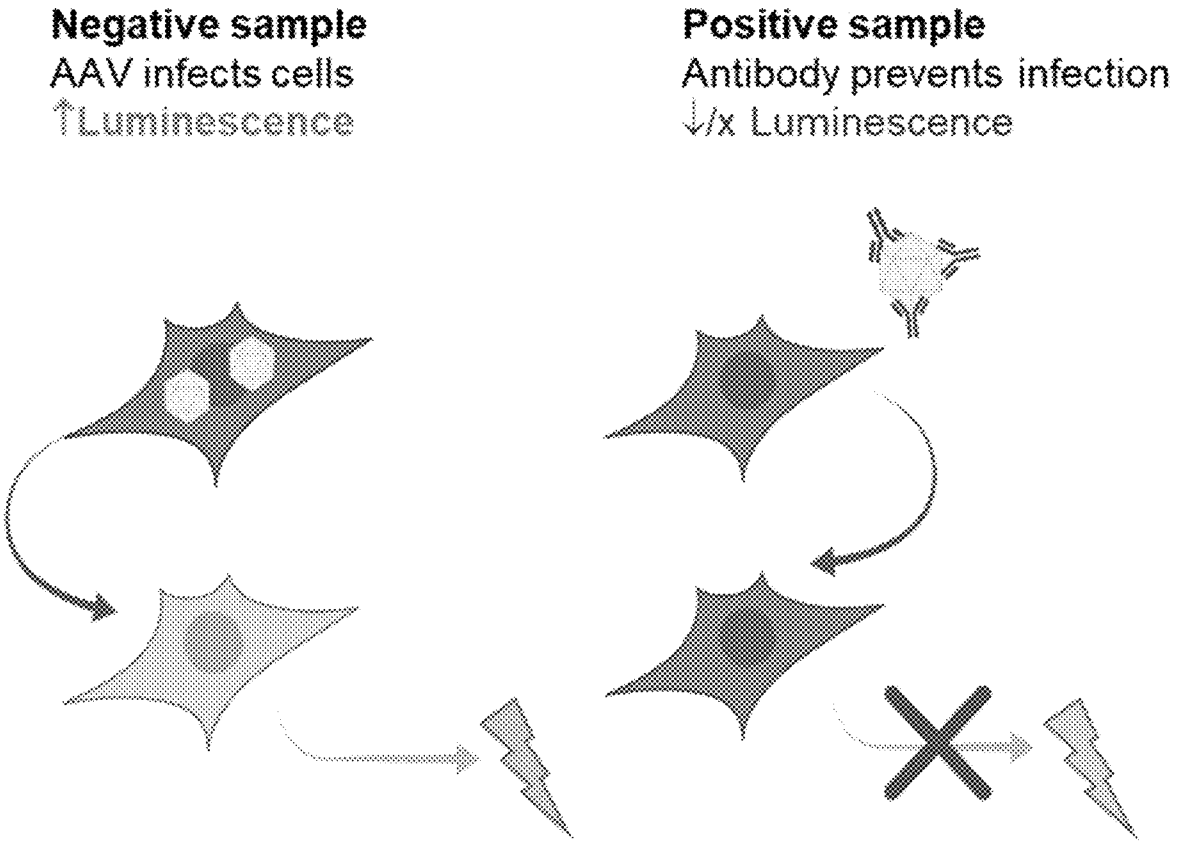
FIG. 9A-9D are a series of graphs and tables showing the quantification of AAV2G9-neutralizing antibody levels in the serum of non-human primates NHP-RU1 and NHP-RU2.

The levels of AAV neutralizing antibodies (NAbs) were quantified using a transduction inhibition assay. The assay uses human embryonic kidney (HEK) cells and an AAV reporter vector containing secreted nanoluciferase (AAV2G9_SecNLuc). In a NAb-negative sample, AAV infects cells, leading to an increase in luminescence. In a NAb-positive sample, NAbs reduce or prevent AAV infection, leading to reduced or no luminescence (see e.g., FIG. 9A). A Multiplicity of Infection (MOI) of 100 was used for AAV2G9_SecNLuc. Serum samples were serially diluted (1:1 to 1:1,000,000). AAV2G9 and the serum dilutions were added to wells plated with HEK cells. The luminescence signal was measured 48 hours later. An AAV2 Antibody A20 was used as a positive control. The Nab assay used a collection of NHP negative serum samples (BIOIVT®) to standardize the assay and as negative controls. For more details about transduction inhibition assays to detect AAV NAbs, see e.g., Baatartsogt et al. "A sensitive and reproducible cell-based assay via secNanoLuc to detect neutralizing antibody against adeno-associated virus vector capsid," Mol Ther Methods Clin Dev 22: 162-171 (2021); Meliani et al. "Determination of Anti-Adeno-Associated Virus Vector Neutralizing Antibody Titer with an In Vitro Reporter System," Hum Gene Ther Methods 26(2): 45-53 (2015); Schulz et al. "Binding and neutralizing anti-AAV antibodies: Detection and implications for rAAV-mediated gene therapy," Mol Ther 31(3): 616-630 (2023-03-01) the contents of each of which are incorporated herein by reference in their entireties.

"Norm RLU" (see e.g., FIG. 9B-9D) refers to "Test Sample RLU" divided by the "Mean RLU of Negative Control". A lower Norm RLU indicates a higher level of NAbs. Negative samples had Norm RLU values between 0.5 and 2.5; positive samples typically had Norm RLU values less than 0.1 The antibody titer of positive samples was determined using the half-maximal inhibitory concentration (IC50) by interpolating from the dilution when the curve crossed 0.5 Norm RLU (see e.g., the dotted lines in FIG. 9B-9D). Descriptive statistics, such as standard deviations, precision (% CV), and normalized values (NormRLU) were determined using MICROSOFT EXCEL.

Figure 9B:
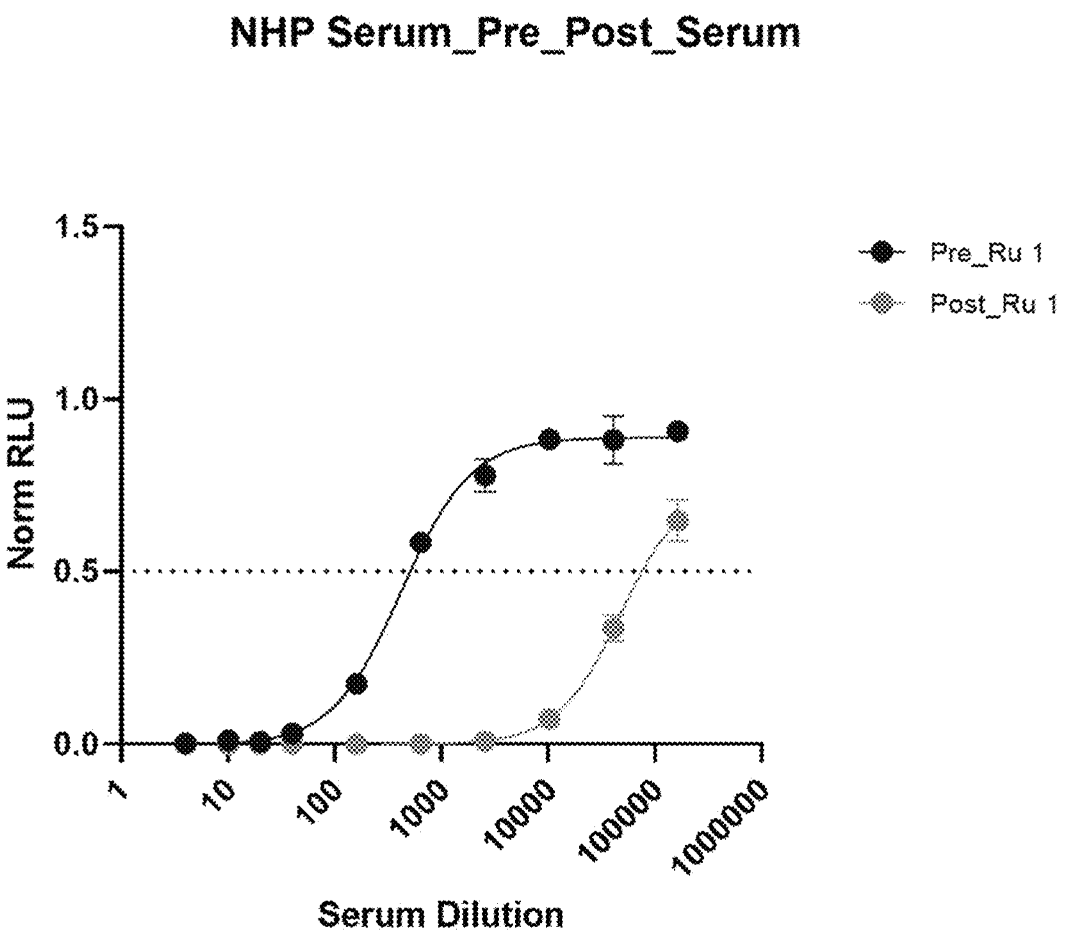
Figure 9C:
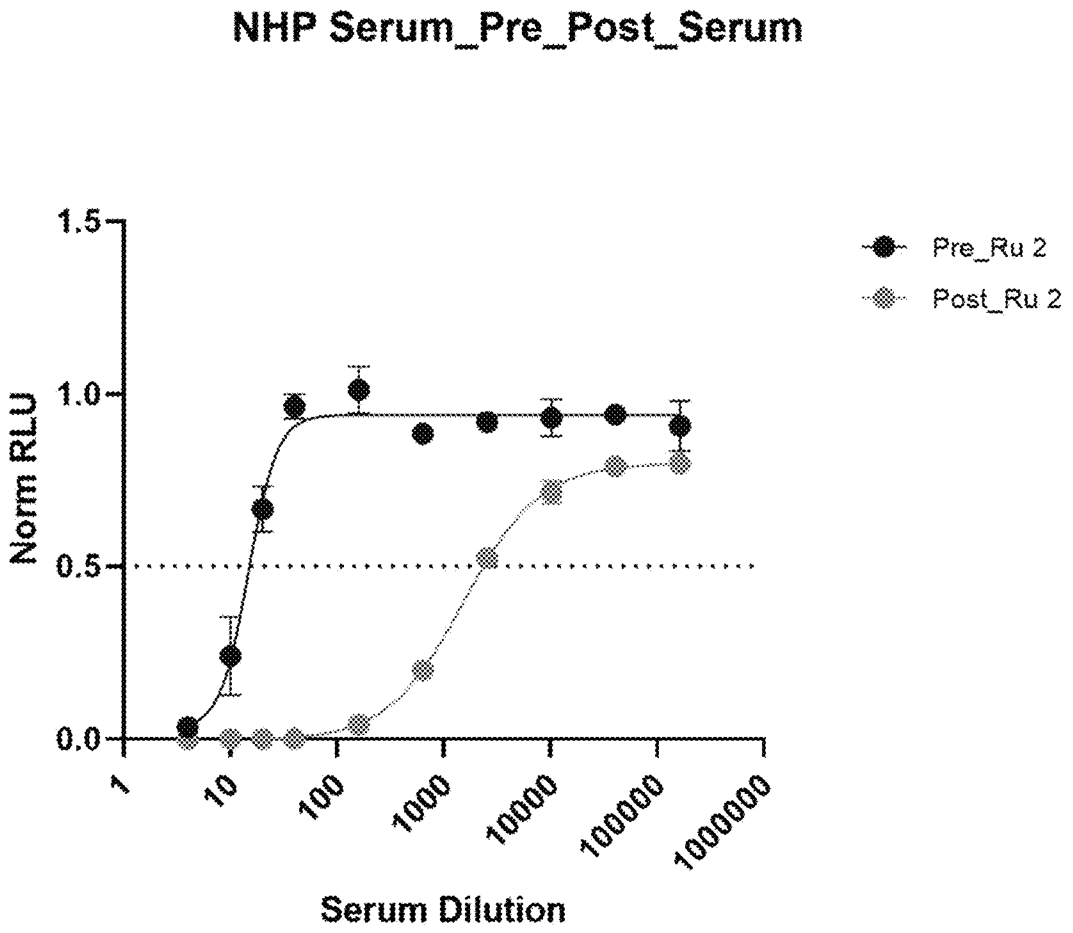
Figure 9D:
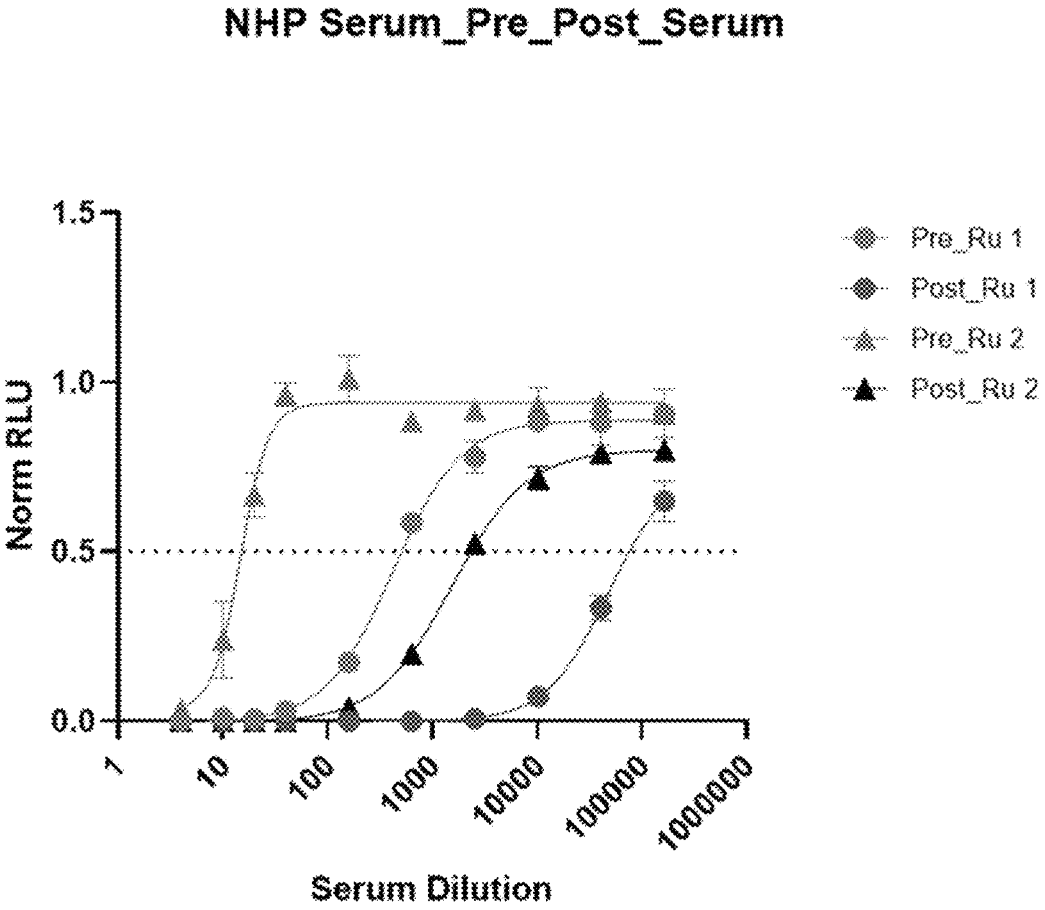

Both NHP-RU1 and NHP-RU2 had pre-existing AAV neutralizing antibodies (see e.g., FIG. 9B-9D). NHP-RU2 had lower levels of pre-existing NAbs (titer of about 1:15) compared to NHP-RU1 (titer of about 1:512) prior to AAV administration. Post AAV retrograde administration, there was a marked increase in the titer of AAV antibodies in serum. NHP-RU1, which had higher levels of pre-existing NAbs, also developed a higher titer of NAbs post-AAV compared to NHP-RU2.

The minimal detection of rAAV in the liver of NHP-RU1 compared to NHP-RU2 (see e.g., FIG. 7G-7I) further supports that NHP-RU1 had higher levels of pre-existing neutralizing antibodies against AAV2G9 compared to NHP-RU2. Such neutralizing antibodies did not inhibit rAAV transduction in the kidneys of NHP-RU1 and NHP-RU2 (see e.g., FIG. 7G-71). Thus, retrograde kidney administration of an rAAV can be performed in individuals regardless of their pre-existing immune status, including those seropositive for the specific rAAV. Furthermore, retrograde kidney administration can be used for repeated dosing of the same individual, despite the development of neutralizing antibodies.

Example 4: Retrograde Administration of rAAV to the Kidneys of Humans

In this Example, rAAV is administered to the kidneys of humans using retrograde administration to induce transduction of a transgene in the nephrons of the human kidneys.

A vector as described herein, encoding a transgene, is packaged into rAAV. The rAAV is selected from Table 1. For example, the rAAV is AAV2G9, AAV2.5, AAVDJ, or AAV2. As another example, the rAAV is AAV2G9. The kidney-associated disorder of interest and the associated transgene is selected from Table 2A or Table 2B. The transgene can be under the control of a kidney-specific promoter, non-limiting examples of which are provided herein. AAV9 expressing the same transgene can be used as a comparative control. Male and/or female subjects are pre-screened for neutralizing antibodies against the selected rAAV (e.g., AAV2G9, AAV2.5, AAVDJ, AAV2, AAV9).

The rAAV is administered to humans (e.g., 20-90 kg) via retrograde administration. The details of the administration is determined using the results of testing in mammals, such as pigs and/or non-human primates. For example, the rAAV is administered (e.g., at a concentration of about $1\times10^{11}$ vg/mL, about $1\times10^{12}$ vg/mL, about $1\times10^{13}$ vg/mL, about $2\times10^{13}$ vg/mL, about $3\times10^{13}$ vg/mL, about $4\times10^{13}$ vg/mL, about $5\times10^{13}$ vg/mL, or more) in a total volume that can range from about 0.13 mL/kg to about 0.33 mL/kg, the kg being the weight of the human subject. Exemplary total volumes include about 2.6 mL (e.g., 0.13 mL/kg for a 20 kg human subject), about 6.6 mL (0.33 mL/kg for a 20 kg human subject), about 7.8 mL (e.g., 0.13 mL/kg for a 60 kg human subject), about 10.4 mL (0.13 mL/kg for a 80 kg human subject), about 11.7 mL (e.g., 0.13 mL/kg for a 90 kg human subject), about 19.8 mL (e.g., 0.33 mL/kg for a 60 kg human subject), about 26.4 mL (0.33 mL/kg for a 80 kg human subject), about 29.7 mL (0.33 mL/kg for a 90 kg human subject), or from about 2.5 mL to about 30.0 mL.

In some groups, the renal artery and/or vein are not clamped or otherwise occluded. In other groups, the renal artery and/or renal vein can be occluded (e.g., starting immediately before rAAV administration and ending about 10 minutes to 60 minutes after the rAAV administration) using a balloon catheter, e.g., inserted through the femoral artery, femoral vein, internal jugular vein, and the like, as determined by a medical professional.

The rAAV is administered by guiding a catheter through the urethra, bladder, and ureter into the renal pelvis of the kidney. The urethral catheter can be used to occlude outflow from the urethra during rAAV administration, for example, by inflation of a balloon catheter. The rAAV is administered to the kidney at an intra-renal pressure of from about 25 cm $H_2O$ to about 55 cm $H_2O$, at a volume range of from about 2.5 mL to about 30.0 mL, and/or at a viral capsid concentration of about $1\times10^{11}$ vg/mL to about $5\times10^{13}$ vg/mL. The rAAV is administered over a period of 0.5 to 2 minutes.

After a sufficient amount of time (e.g., 1 day, 1 week, 1 month, 2 months, 3 months, 4 months, 5 months, 6 months, 1 year, or more), the human subjects are evaluated for kidney health, which can be specific to the kidney-associated disease and administered rAAV and transgene. The rAAV-administered subjects are compared to a negative control (e.g., no rAAV) and/or to a comparative control (e.g., rAAV9).

Example 5: Retrograde Administration of rAAV to the Kidneys of Seropositive Pigs rAAV was administered to a 90 kg pig subject RU26 via ureter retrograde administration. The rAAV comprised AAV2G9 and a viral genome comprising a GFP and luciferase transgenes driven by the CMV promoter. RU26 was seropositive for AAV2G9 due to previous administration via intravenous (IV) administration with $1.00\times10^{13}$ VG of AAV2G9 to provoke immunity against the AAV2G9 capsid, 15 days prior to the retrograde ureter administration described below.

Two weeks (14 days) after the IV administration of AAV2G9, pig subject RU26 received an immune suppression regimen since the GFP and luciferase transgenes can be immunogenic in fully immunocompetent animals; immune suppression need not be used when non-immunogenic transgenes are used. The pig immune suppression regimen was as follows: Day −1: DEPO-MEDROL® (methylprednisolone acetate) 40 mg/kg intramuscular (IM)+Tacrolimus (calcineurin-inhibitor) 0.1 mg/kg IM. Day 0: Surgery/Virus delivery via Ureter (Blood and urine collection; pressure testing and removal of contralateral kidney; liver sample). Day 6: DEPO-MEDROL® 40 mg/kg IM+Tacrolimus 0.1 mg/kg IM. Day 14: Sacrifice (Blood and urine collection; removal of kidney and liver sample).

On Day 0, $1.00\times10^{14}$ viral genomes (vg) total of AAV2G9 were injected at 0.25 mL/kg (the mL being the volume of the administered AAV2G9 solution, and the kg being the weight of the subject; 22 mL total; $4.55\times10^{12}$ vg/mL).

Figure 10A:
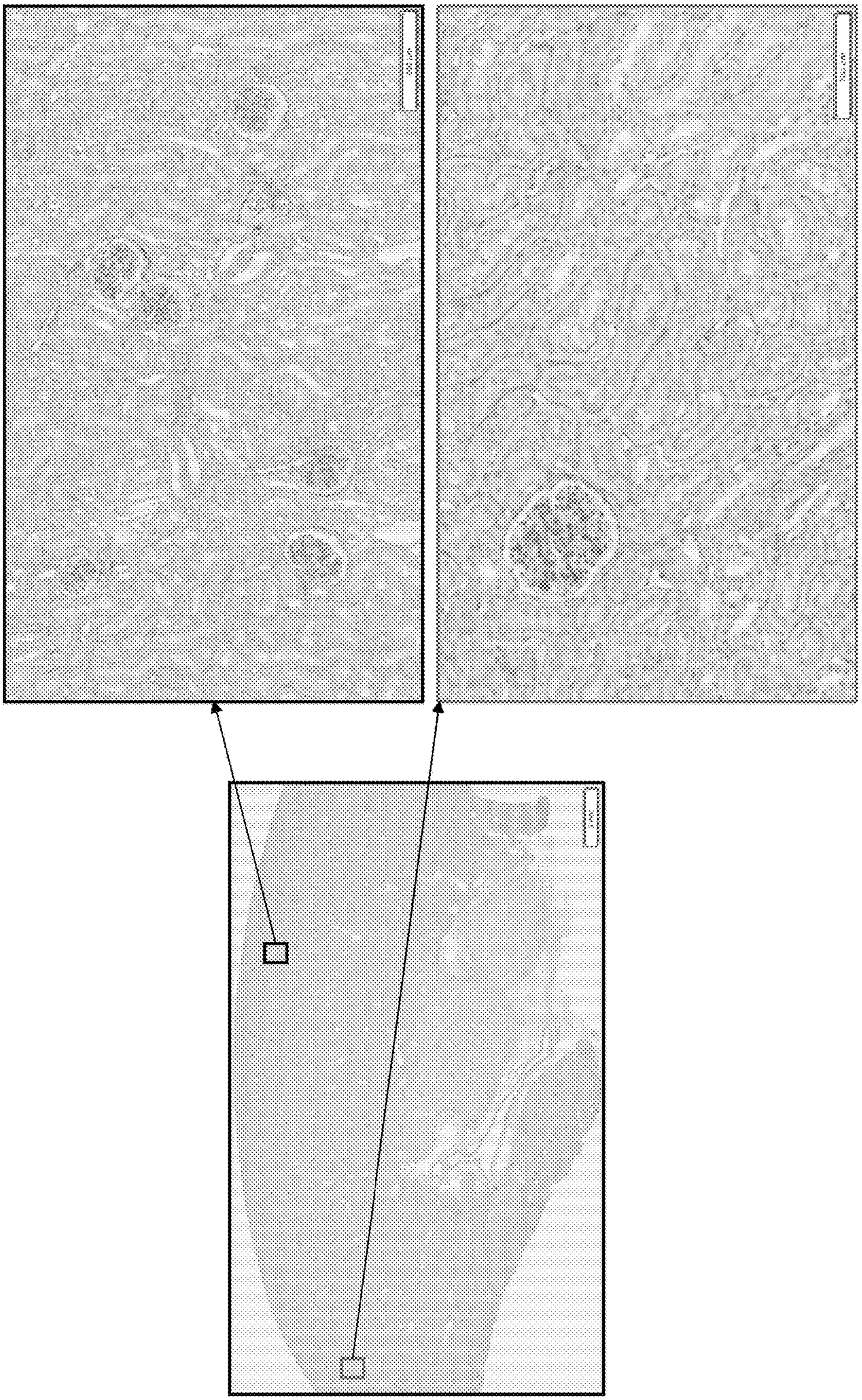
FIG. 10A-10E are a series of images and graphs showing AAV2G9 retrograde ureter administration to seropositive pig subject RU26 (see e.g., Example 5).
Figure 10B:
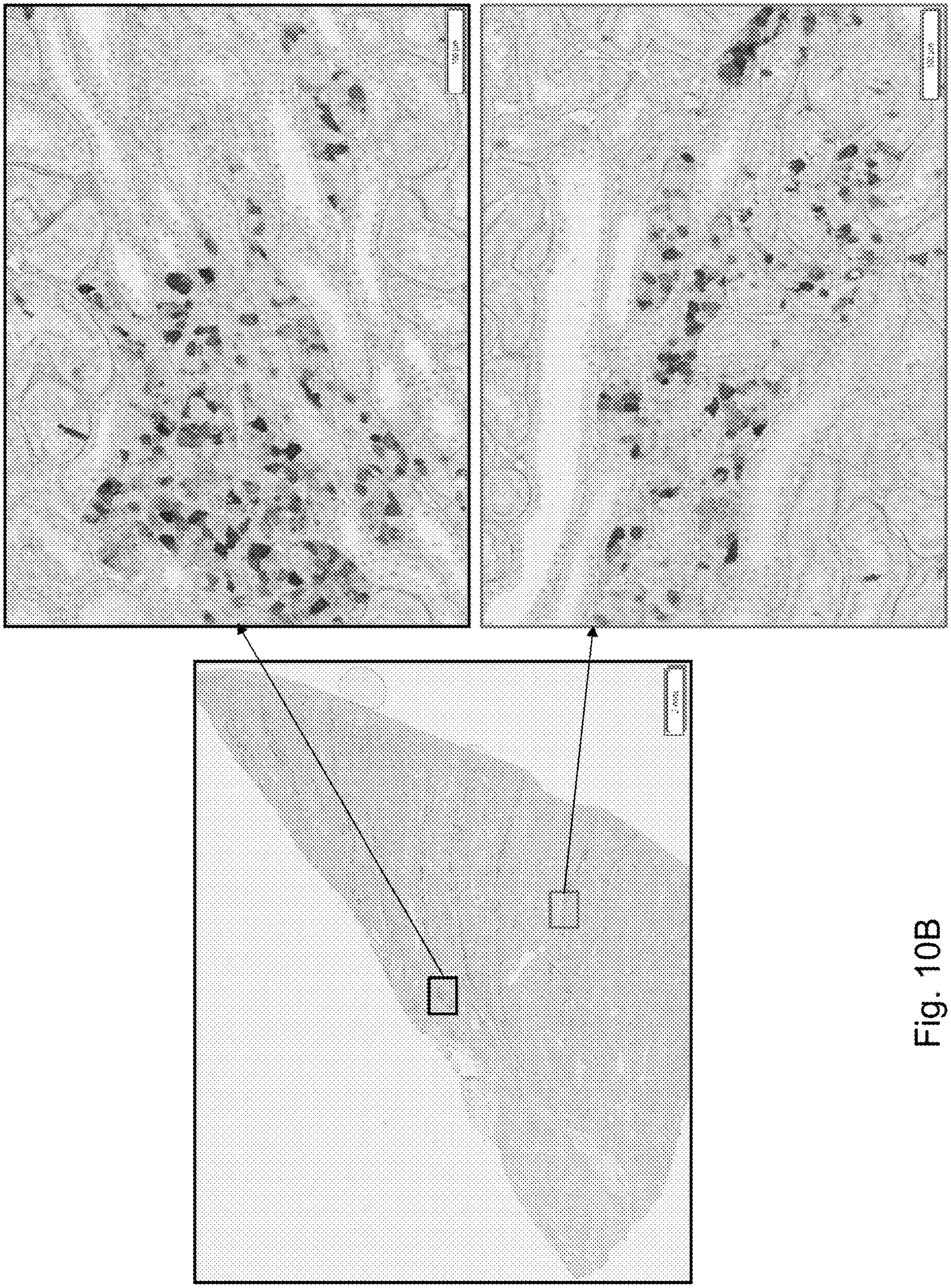
Figure 10C:
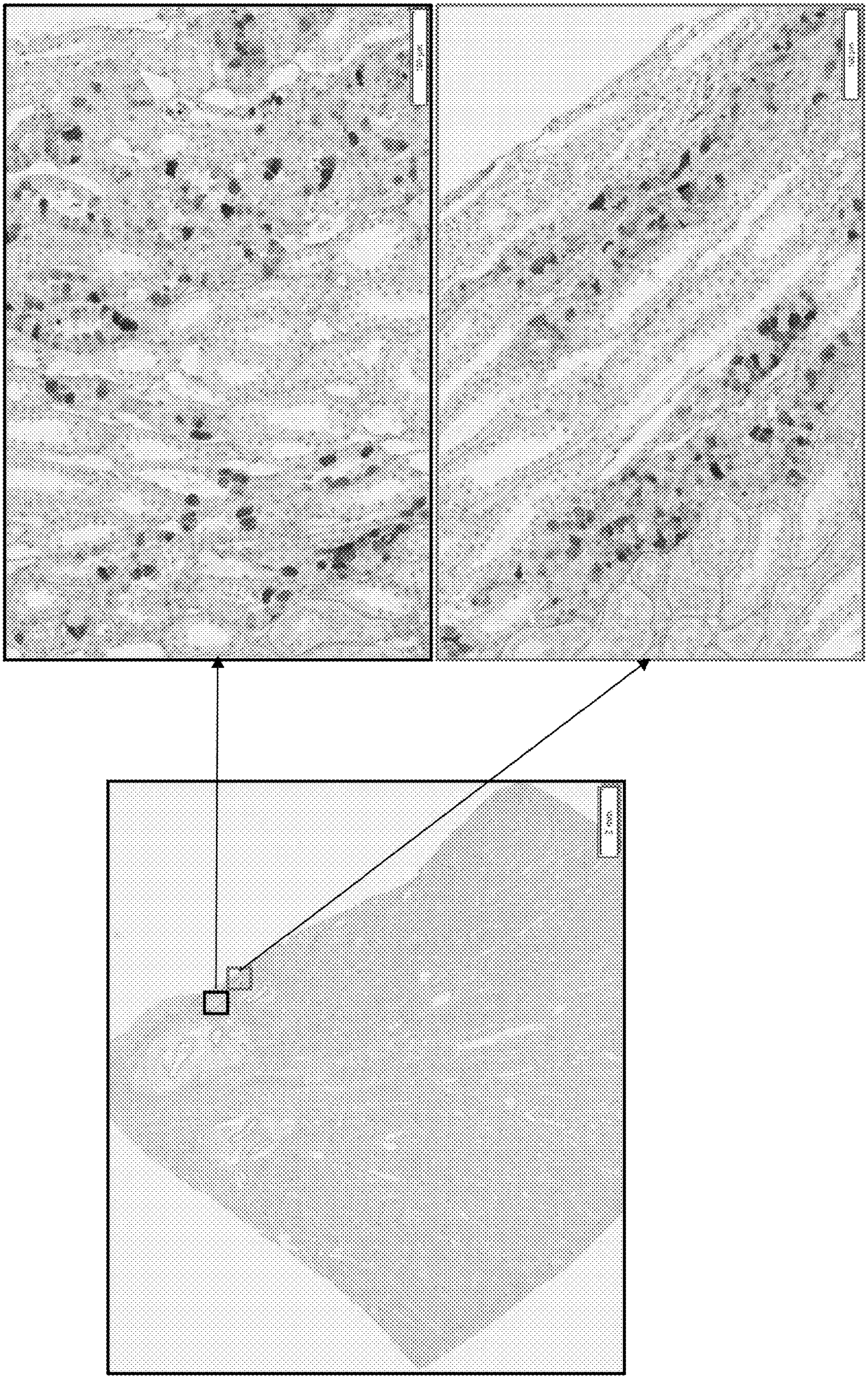
Figure 10D:
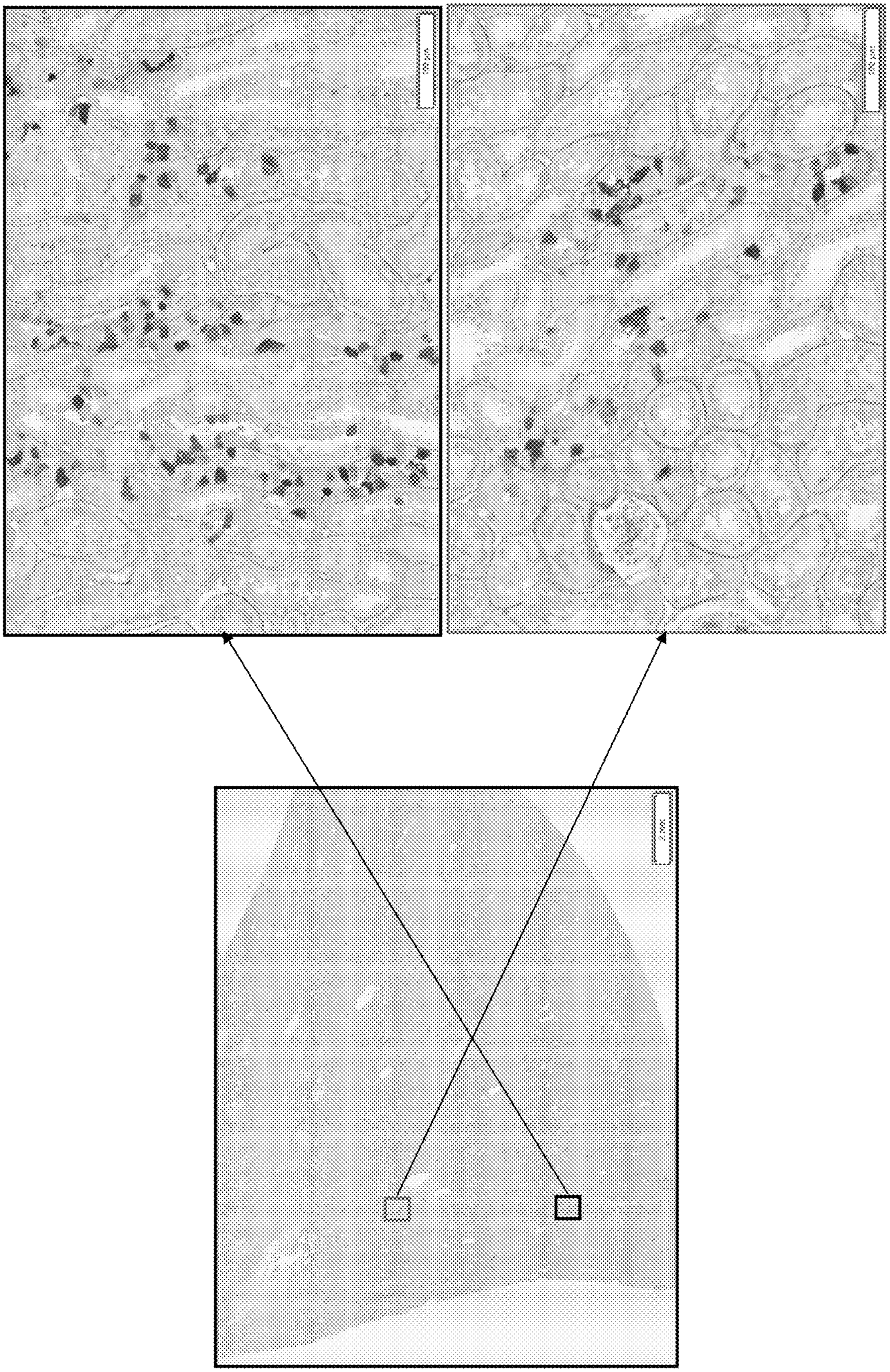
Figure 10E:
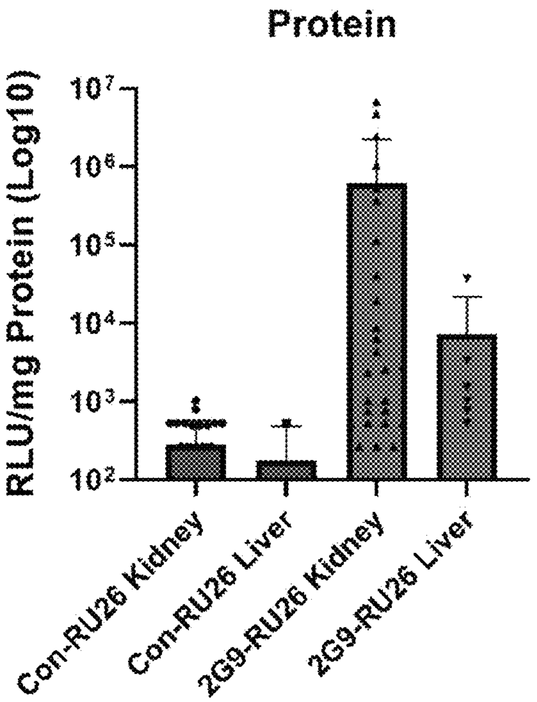

The contralateral kidney, a liver biopsy, urine, and a serum sample were taken prior to the 2G9 injection. The surgery was performed by occluding the renal artery and ureter, and the virus was injected by way of the corresponding ureter over 1 minute and 30 seconds, and incubating for 15 minutes with warm ischemia (i.e., the subject's body temperature was maintained). The intrarenal pressure during the 2G9 injection was approximately 46 cm $H_2O$. After 15 minutes of incubation, the artery clamp was removed. The subject was sacrificed two weeks later for harvest of the 2G9-injected kidney, the liver, urine, and serum. Kidney histology sections were analyzed for GFP staining (see e.g., FIG. 10A-10D). Kidney and liver samples were analyzed for luciferase activity (see e.g., FIG. 10E). Serum samples are analyzed for AAV neutralizing antibodies.

As demonstrated in FIG. 10A-10E, retrograde administration of AAV2G9 in a seropositive pig resulted in robust transduction in the injected kidney. Thus, retrograde kidney administration of an rAAV can be performed in individuals regardless of their pre-existing immune status, including those seropositive for the specific rAAV.

What is claimed herein is:

1. A method of administering a recombinant adeno-associated virus (rAAV) to a kidney of a subject, comprising:

a) blocking a renal artery of the kidney such that flow of blood is stopped for a period of time of about 10 minutes to about 15 minutes; while b) administering a solution comprising the rAAV into a ureter to a renal pelvis of the kidney by a retrograde route, at a volume of about 0.13 mL/kg to about 0.33 mL/kg, the kg being the weight of the subject, wherein the rAAV comprises an AAV2G9 capsid protein; wherein the solution comprises the rAAV at a concentration of $1\times10^{11}$ viral genomes per mL (vg/mL) to $1\times10^{14}$ vg/mL rAAV; and wherein the solution comprising the rAAV is administered at an intra-renal pressure of 27 cm $H_2O$ to 68 cm $H_2O$;

wherein the subject is a pig, a non-human primate, or a human;

wherein the method results in the transduction of at least about 25% of proximal tubules in the kidney with the rAAV.

2. The method of claim 1, wherein administering the solution comprising the rAAV is by a balloon catheter which is guided up the ureter to an entry of the renal pelvis and the balloon is then inflated to block the ureter to substantially or completely stop the flow of urine for the period of time.

3. The method of claim 2, further comprising blocking a renal vein of the kidney such that flow of blood is substantially or completely stopped for the period of time.

4. The method of claim 1, wherein blocking is with a balloon catheter or a clamp.

5. The method of claim 1, wherein the solution comprising the rAAV is maintained in the kidney for less than 1 hour.

6. The method of claim 1, wherein the method does not comprise a continuous perfusion of an isolated kidney by an external circuit.

7. The method of claim 1, wherein administering is by manually delivering the solution to the renal pelvis using a plunger associated with a catheter or cannula or an automatic injection with a pump.

8. The method of claim 1, wherein a renal vein of the kidney is not blocked.

9. The method of claim 1, wherein the intra-renal pressure results in pyelotubular reflux or pyelovenous backflow with no fornix rupture.

10. The method of claim 1, wherein the intra-renal pressure is 27 cm $H_2O$ to 41 cm $H_2O$ and results in pyelotubular reflux.

11. The method of claim 1, wherein the intra-renal pressure is 41 cm $H_2O$ to 68 cm $H_2O$ and results in pyelovenous backflow with no fornix rupture.

12. The method of claim 1, wherein the volume is about 0.13 mL/kg to about 0.25 mL/kg, the kg being the weight of the subject.

13. The method of claim 1, wherein the method results in transduction of at least 40% of nephrons in the kidney by the rAAV, as determined in an experimental animal subject.

14. The method of claim 1, wherein the rAAV comprises a transgene.

15. The method of claim 14, wherein the transgene is selected from the group consisting of Alanine-Glyoxylate Aminotransferase (AGXT); Bartter Syndrome, Infantile, With Sensorineural Deafness (BSND); Chloride Voltage-Gated Channel 5 (CLCN5); Chloride Voltage-Gated Channel Ka (CLCNKA); Chloride Voltage-Gated Channel Kb (CLCNKB); Collagen Type IV Alpha 3 Chain (COL4A3); Collagen Type IV Alpha 4 Chain (COL4A4); Collagen Type IV Alpha 5 Chain (COL4A5); Glucosidase II Alpha Subunit (GANAB); Glyoxylate And Hydroxypyruvate Reductase (GRHPR); Hepatic Nuclear Factor 1 (HNF1) Homeobox B (HNF1B); 4-Hydroxy-2-Oxoglutarate Aldolase 1 (HOGA1); Potassium Inwardly Rectifying Channel Subfamily J Member 1 (KCNJ1); MAGED2 (type V); Mucin 1 (MUC1); Nephrocystin 1 (NPHP1); Nephrin (NPHS1); Nephrosis 2 (NPHS2; Podocin); Inositol Polyphosphate-5-Phosphatase (OCRL); Polycystin 1 (PKD1); Polycystin 2 (PKD2); Polycystic Kidney And Hepatic Disease 1 (PKHD1); Protein transport protein Sec61 subunit alpha isoform 1 (SEC61A1); Solute Carrier Family 12 Member 1 (SLC12A1); Solute Carrier Family 12 Member 3 (SLC12A3); Solute Carrier Family 3 Member 1 (SLC3A1); Solute Carrier Family 7 Member 9 (SLC7A9); Von Hippel-Lindau Tumor Suppressor (VHL); and combinations thereof; or wherein the transgene comprises an inhibitor of a gene or protein selected from the group consisting of Renin (REN), Sodium Channel Epithelial 1 Subunit Alpha (SCNN1A), Sodium Channel Epithelial 1 Subunit Beta (SCNN1B), and Uromodulin (UMOD).

16. The method of claim 14, wherein the transgene is operably linked to a ubiquitous promoter or a kidney-specific promoter.

17. The method of claim 16, wherein the ubiquitous promoter is selected from the group consisting of: cytomegalovirus (CMV), beta actin (B-Act), chicken beta-actin promoter (CAG), elongation factor-1 alpha (EF1), Early Growth Response 1 (EGR1), Eukaryotic Initiation Factor 4A1 (eIF4A1), Ferritin Heavy Chain (FerH), Ferritin Light Chain (FerL), Glyceraldehyde 3-Phosphate Dehydrogenase (GAPDH), Glucose-Regulated Protein 78 (GRP78), Glucose-Regulated Protein 94 (GRP94), Heat Shock Protein 70 (HSP70), Beta-Kinesin (B-Kin), Phosphoglycerate Kinase 1 (PGK-1), Rosa26, or Ubiquitin B promoters, or composites or combinations thereof; or wherein the kidney-specific promoter is a synthetic promoter or is selected from the group consisting of a kidney-specific cadherin (KSPC) gene promoter; a Na+/glucose co-transporter (SGLT2) gene promoter; a sodium potassium, a 2 chloride co-transporter (NKCC2) gene promoter; and an E-cadherin (ECAD) gene promoter.

18. The method of claim 16, wherein the promoter is specific to proximal tubules.

19. The method of claim 14, wherein the transgene is selected from Solute Carrier Family 3 Member 1 (SLC3A1), Solute Carrier Family 7 Member 9 (SLC7A9), Polycystin 1 (PKD1), Polycystin 2 (PKD2), and/or Glucosidase II Alpha Subunit (GANAB).

20. The method of claim 1, wherein the transduction of the proximal tubules is determined by co-staining cells of the proximal tubules in a pig kidney sample or in a non-human primate kidney sample.

21. The method of claim 20, wherein the wherein the transduction of the proximal tubules is determined by (a) quantifying the number of transgene-positive cells and thick brush border-positive cells in the kidney sample, and (b) determining a transduction percentage by dividing the number of transgene-positive and thick brush border-positive cells by the number of thick brush border-positive cells.

22. A method of administering a recombinant adeno-associated virus (rAAV) to a kidney of a pig or primate, comprising:

a) blocking a renal artery of the kidney to stop blood flow;

b) administering a solution comprising the rAAV into a renal pelvis of the kidney by retrograde ureter administration at a volume of about 0.13 to about 0.33 mL/kg subject weight, wherein the rAAV comprises an AAV2G9 capsid protein; wherein the solution comprises the rAAV at a concentration of $1\times10^{11}$ viral genomes per mL (vg/mL) to $1\times10^{14}$ vg/mL rAAV; and wherein the solution comprising the rAAV is administered at an intra-renal pressure of 27 cm $H_2O$ to 68 cm $H_2O$; and c) unblocking the renal artery after a period of about 15 minutes;

to thereby transduce at least about 25% of proximal tubules in the kidney.

23. A method of transducing at least about 25% of proximal tubules in a kidney of a pig or primate with a recombinant adeno-associated virus (rAAV), comprising:

a) inserting a catheter through the subject's ureter into a renal pelvis of the kidney;

b) blocking a renal artery to stop the flow of blood;

c) administering a solution comprising the rAAV to the renal pelvis of the kidney through the catheter at a volume of about 0.13 to about 0.33 mL/kg weight of the pig or primate, wherein the rAAV comprises an AAV2G9 capsid protein; wherein the solution comprises the rAAV at a concentration of $1\times10^{11}$ viral genomes per mL (vg/mL) to $1\times10^{14}$ vg/mL rAAV; and wherein the solution comprising the rAAV is administered at an intra-renal pressure of 27 cm $H_2O$ to 68 cm $H_2O$; and d) unblocking the renal artery after a period of about 15 minutes;

to thereby transduce at least about 25% of the proximal tubules-nephrons.

* * * * *

SEQUENCE LISTING

```
Sequence total quantity: 18
SEQ ID NO: 1           moltype = AA  length = 735
FEATURE                Location/Qualifiers
source                 1..735
                       mol_type = protein
                       organism = adeno-associated virus 2
SEQUENCE: 1
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                   735

SEQ ID NO: 2           moltype = AA  length = 736
FEATURE                Location/Qualifiers
```

```
source                  1..736
                        mol_type = protein
                        organism = Adeno-associated vius 9
SEQUENCE: 2
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 3            moltype = AA  length = 735
FEATURE                 Location/Qualifiers
source                  1..735
                        mol_type = protein
                        organism = synthetic construct
SEQUENCE: 3
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGGSSNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSVAGPSNM AVQGRNWLPG  480
PCYRQQRVSK TSADNNNSEF AWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 4            moltype = AA  length = 735
FEATURE                 Location/Qualifiers
source                  1..735
                        mol_type = protein
                        organism = synthetic construct
SEQUENCE: 4
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSVAGPSNM AVQGRNWLPG  480
PCYRQQRVSK TSADNNNSEF AWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 5            moltype = DNA  length = 2058
FEATURE                 Location/Qualifiers
source                  1..2058
                        mol_type = unassigned DNA
                        organism = Homo sapiens
SEQUENCE: 5
atggctgaag ataaaagcaa gagagactcc atcgagatga gtatgaaggg atgccagaca  60
aacaacgggt ttgtccataa tgaagacatt ctggagcaga ccccggatcc aggaagctca  120
acagacaacc tgaagcacag caccaggggc atccttggct cccaggagcc cgacttcaag  180
ggcgtccagc cctatgcggg gatgcccaag gaggtgctgt tccagttctc tggccaggcc  240
cgctaccgca tacctcggga gatcctcttc tggctcacag tggcttctgt gctggtgctc  300
atcgcggcca ccatagccat cattgccctc tctccaaagt gcctagactg gtggcaggag  360
gggcccatgt accagatcta cccaaggtct ttcaaggaca gtaacaagga tgggaacgga  420
gatctgaaag gtattcaaga taaactggac tacatcacag ctttaaatat aaaaactgtt  480
tggattactt cattttataa atcgtccctt aaagatttca gatatggtgt tgaagatttc  540
cgggaagttg atcccatttt tggaacgatg gaagattttg agaatctggt tgcagccata  600
catgataaag gtttaaaatt aatcatcgat ttcataccaa accacacgag tgataaacat  660
atttggtttc aattgagtcg gacacggaca ggaaaatata ctgattatta tatctggcat  720
gactgtaccc atgaaaatgg caaaaccatt ccacccaaca actggttaag tgtgtatgga  780
aactccagtt ggcactttga cgaagtgcga aaccaatgtt attttcatca gtttatgaaa  840
gagcaacctg atttaaattt ccgcaatcct gatgttcaag aagaaataaa agaaatttta  900
```

```
cggttctggc tcacaaaggg tgttgatggt tttagtttgg atgctgttaa attcctccta  960
gaagcaaagc acctgagaga tgagatccaa gtaaataaga cccaaatccc ggacacggtc  1020
acacaatact cggagctgta ccatgacttc accaccacgc aggtgggaat gcacgacatt  1080
gtccgcagct tccggcagac catggaccaa tacagcacgg agcccggcag atacaggttc  1140
atggggactg aagcctatgc agagagtatt gacaggaccg tgatgtacta tggattgcca  1200
tttatccaag aagctgattt tcccttcaac aattacctca gcatgctaga cactgtttct  1260
gggaacagcg tgtatgaggt tatcacatcc tggatggaaa acatgccaga aggaaaatgg  1320
cctaactgga tgattggtgg accagacagt tcacggctga cttcgcgttt ggggaatcag  1380
tatgtcaacg tgatgaacat gcttctttc acactccctg gaactcctat aacttactat  1440
ggagaagaaa ttggaatggg aaatattgta gccgcaaatc tcaatgaaag ctatgatatt  1500
aataccccttc gctcaaagtc accaatgcag tgggacaata gttcaaatgc tggtttttct  1560
gaagctagta acacctggtt acctaccaat tcagattacc acactgtgaa tgttgatgtc  1620
caaaagactc agcccagatc ggctttgaag ttatatcaag atttaagtct acttcatgcc  1680
aatgagctac tcctcaacag gggctggttt tgccatttga ggaatgacag ccactatgtt  1740
gtgtacacaa gagagctgga tggcatcgac agaatcttta tcgtggttct gaattttgga  1800
gaatcaacac tgttaaatct acataatatg atttcgggcc ttcccgctaa aatgagaata  1860
aggttaagta ccaattctgc cgacaaaggc agtaaagttg atacaagtgg catttttctg  1920
gacaagggag agggactcat ctttgaacac aacacgaaga atctccttca tcgccaaaca  1980
gctttcagag atagatgctt tgtttccaat cgagcatgct attccagtgt actgaacata  2040
ctgtatacct cgtgttag                                                2058

SEQ ID NO: 6            moltype = DNA  length = 1464
FEATURE                 Location/Qualifiers
source                  1..1464
                        mol_type = unassigned DNA
                        organism = Homo sapiens
SEQUENCE: 6
atgggggata ctggcctgag aaagcggaga gaggatgaga agtcgatcca gagccaagag  60
cctaagacca ccagtctcca aaaggagctg ggcctcatca gtggcatctc catcatcgtg  120
ggcaccatca ttggctctgg gatcttcgtt tcccccaagt ctgtgctcag caacacggaa  180
gctgtggggc cctgcctcat catatgggcg gcttgcgggg tcctcgcgac gctgggtgcc  240
ctgtgctttg cggagcttgg cacaatgatc accaagtcag ggggagagta tccctacctg  300
atggaggcct acgggcccat ccccgcctac ctcttctcct gggccagcct gatcgtcatt  360
aagcccacgt ccttcgccat catctgcctc agcttctccg agtatgtgtg tgcgcccttc  420
tatgtgggct gcaagcctcc tcaaatcgtt gtgaaatgcc tggccgccgc cgccatcttg  480
ttcatctcga cagtgaactc actgagcgtg cggctgggaa gctacgtcca gaacatcttc  540
accgcggcca agctggtgat cgtggccatc atcatcatca gcgggctggt gctcctggcc  600
caaggaaaca caaagaattt tgataattct ttcgagggcg cccagctgtc tgtgggagcc  660
atcagcctgg cgttttacaa tggactctgg gcctatgatg gatggaatca actcaattac  720
atcacagaag aacttagaaa cccttacaga aacctgcctt tggccattat catcgggatc  780
cccctggtga cggcgtgcta catcctcatg aacgtgtcct acttcaccgt gatgactgcc  840
accgaactcc tgcagtccca ggcggtggct gtgacatttg gtgaccgtgt tctctatcct  900
gcttcttgga tcgttccact ttttgtggca ttttcaacca tcggtgctgc taacgggacc  960
tgcttcacag cgggcagact catttacgtg gcgggccggg agggtcacat gctcaaagtg  1020
ctttcttaca tcagcgtcag gcgcctcact ccagcccccg ccatcatctt ttatggtatc  1080
atagcaacga tttatatcat ccctggtgac ataaactcgt tagtcaatta tttcagcttt  1140
gccgcatggc tgttttatgg cctgacgatt ctaggactca tcgtgatgag atttacaagg  1200
aaagagctgg aaaggcctat caaggtgccc gtagtcattc ccgtcttgat gacactcatc  1260
tctgtgtttt tggttctggc tccaatcatc agcaagccca cctgggagta cctctactgt  1320
gtgctgttta tattaagcgg ccttttattt tacttcctgt ttgtccacta caagtttgga  1380
tgggctcaga aaatctcaaa gccgattacc atgcaccttc agatgctaat ggaagtggtc  1440
ccaccggagg aagaccctga gtaa                                         1464

SEQ ID NO: 7            moltype = AA  length = 685
FEATURE                 Location/Qualifiers
source                  1..685
                        mol_type = protein
                        organism = Homo sapiens
SEQUENCE: 7
MAEDKSKRDS IEMSMKGCQT NNGFVHNEDI LEQTPDPGSS TDNLKHSTRG ILGSQEPDFK  60
GVQPYAGMPK EVLFQFSGQA RYRIPREILF WLTVASVLVL IAATIAIIAL SPKCLDWWQE  120
GPMYQIYPRS FKDSNKDGNG DLKGIQDKLD YITALNIKTV WITSFYKSSL KDFRYGVEDF  180
REVDPIFGTM EDFENLVAAI HDKGLKLIID FIPNHTSDKH IWFQLSRTRT GKYTDYYIWH  240
DCTHENGKTI PPNNWLSVYG NSSWHFDEVR NQCYFHQFMK EQPDLNFRNP DVQEEIKEIL  300
RFWLTKGVDG FSLDAVKFLL EAKHLRDEIQ VNKTQIPDTV TQYSELYHDF TTTQVGMHDI  360
VRSFRQTMDQ YSTEPGRYRF MGTEAYAESI DRTVMYYGLP FIQEADFPFN NYLSMLDTVS  420
GNSVYEVITS WMENMPEGKW PNWMIGGPDS SRLTSRLGNQ YVNVMNMLLF TLPGTPITYY  480
GEEIGMGNIV AANLNESYDI NTLRSKSPMQ WDNSSNAGFS EASNTWLPTN SDYHTVNVDV  540
QKTQPRSALK LYQDLSLLHA NELLLNRGWF CHLRNDSHYV VYTRELDGID RIFIVVLNFG  600
ESTLLNLHNM ISGLPAKMRI RLSTNSADKG SKVDTSGIFL DKGEGLIFEH NTKNLLHRQT  660
AFRDRCFVSN RACYSSVLNI LYTSC                                        685

SEQ ID NO: 8            moltype = AA  length = 487
FEATURE                 Location/Qualifiers
source                  1..487
                        mol_type = protein
                        organism = Homo sapiens
SEQUENCE: 8
MGDTGLRKRR EDEKSIQSQE PKTTSLQKEL GLISGISIIV GTIIGSGIFV SPKSVLSNTE  60
```

```
AVGPCLIIWA ACGVLATLGA LCFAELGTMI TKSGGEYPYL MEAYGPIPAY LFSWASLIVI  120
KPTSFAIICL SFSEYVCAPF YVGCKPPQIV VKCLAAAAIL FISTVNSLSV RLGSYVQNIF  180
TAAKLVIVAI IIISGLVLLA QGNTKNFDNS FEGAQLSVGA ISLAFYNGLW AYDGWNQLNY  240
ITEELRNPYR NLPLAIIIGI PLVTACYILM NVSYFTVMTA TELLQSQAVA VTFGDRVLYP  300
ASWIVPLFVA FSTIGAANGT CFTAGRLIYV AGREGHMLKV LSYISVRRLT PAPAIIFYGI  360
IATIYIIPGD INSLVNYFSF AAWLFYGLTI LGLIVMRFTR KELERPIKVP VVIPVLMTLI  420
SVFLVLAPII SKPTWEYLYC VLFILSGLLF YFLFVHYKFG WAQKISKPIT MHLQMLMEVV  480
PPEEDPE                                                          487

SEQ ID NO: 9           moltype = DNA  length = 12909
FEATURE                Location/Qualifiers
source                 1..12909
                       mol_type = unassigned DNA
                       organism = Homo sapiens
SEQUENCE: 9
atgccgcccg ccgcgcccgc ccgcctggcg ctggccctgg gcctgggcct gtggctcggg  60
gcgctggcgg ggggccccgg gcgcggctgc gggccctgcg agcccccctg cctctgcggc  120
ccagcgcccg gcgccgcctg ccgcgtcaac tgctcgggcc gcgggctgcg gacgctcggt  180
cccgcgctgc gcatccccgc ggacgccaca gcgctagacg tctcccacaa cctgctccgg  240
gcgctggacg ttgggctcct ggcgaacctc tcggcgctgg cagagctgga tataagcaac  300
aacaagattt ctacgttaga agaaggaata tttgctaatt tatttaattt aagtgaaata  360
aacctgagtg ggaacccgtt tgagtgtgac tgtggcctgg cgtggctgcc gcgatgggcg  420
gaggagcagc aggtgcgggt ggtgcagccc gaggcagcca cgtgtgctgg gcctggctcc  480
ctggctggcc agcctctgct tggcatcccc ttgctggaca gtggctgtgg tgaggagtat  540
gtcgcctgcc tccctgacaa cagctcaggc accgtggcag cagtgtcctt ttcagctgcc  600
cacgaaggcc tgcttcagcc agaggcctgc agcgccttct gcttctccac cggccagggc  660
ctcgcagccc tctcggagca gggctggtgc ctgtgtgggg cggcccagcc ctccagtgcc  720
tcctttgcct gcctgtccct ctgctccggc cccccgccac ctcctgcccc cacctgtagg  780
ggccccaccc tcctccagca cgtcttccct gcctccccag gggccaccct ggtggggccc  840
cacggacctc tggcctctgg ccagctagca gccttccaca tcgctgcccc gctccctgtc  900
actgccacac gctgggactt cggagacggc tccgccgagg tggatgccgc tgggccggct  960
gcctcgcatc gctatgtgct gcctgggcgc tatcacgtga cggccgtgct ggccctgggg  1020
gccggctcag ccctgctggg gacagacgtg caggtggaag cggcacctgc cgccctggag  1080
ctcgtgtgcc cgtcctcggt gcagagtgac gagagcctcg acctcagcat ccagaaccgc  1140
ggtggttcag gcctggaggc cgcctacagc atcgtggccc tgggcgagga gccggcccga  1200
gcggtgcacc cgctctgccc ctcggacacg gagatcttcc ctggcaacgg gcactgctac  1260
cgcctggtgg tggagaaggc ggcctggctg caggcgcagg agcagtgtca ggcctgggcc  1320
ggggccgccc tggcaatggt ggacagtccc gccgtgcagc gcttcctggt ctcccgggtc  1380
accaggagcc tagacgtgtg gatcggcttc tcgactgtgc agggggtgga ggtgggccca  1440
gcgccgcagg gcgaggcctt cagcctggag agctgccaga actggctgcc cggggagcca  1500
cacccagcca cagccgagca ctgcgtccgg ctcgggccca ccgggtggtg taacaccgac  1560
ctgtgctcag cgccgcacag ctacgtctgc gagctgcagc ccggaggccc agtgcaggat  1620
gccgagaacc tcctcgtggg agcgcccagt ggggacctgc aggaccccct gacgcctctg  1680
gcacagcagg acggcctctc agccccgcac gagcccgtgg aggtcatggt attcccgggc  1740
ctgcgtctga gccgtgaagc cttcctcacc acggccgaat ttgggaccca ggagctccgg  1800
cggcccgccc agctgcggct gcaggtgtac cggctcctca gcacagcagg gaccccggag  1860
aacggcagcg agcctgagag caggtccccg gacaacagga cccagctggc ccccgcgtgc  1920
atgccagggg gacgctggtg ccctggagcc aacatctgct tgccgctgga cgcctcctgc  1980
cacccccagg cctgcgccaa tggctgcacg tcagggccag ggctacccgg ggcccccctat  2040
gcgctatgga gagagttcct cttctccgtt cccgcggggc cccccgcgca gtactcggtc  2100
accctccacg gccaggatgt cctcatgctc cctggtgacc tcgttggctt gcagcacgac  2160
gctggccctg gcgccctcct gcactgctcg ccggctcccg gccaccctgg tccccgggcc  2220
ccgtacctct ccgccaacgc ctcgtcatgg ctgccccact tgccagccca gctggagggc  2280
acttgggcct gccctgcctg tgccctgcgg ctgcttgcag ccacggaaca gctcaccgtg  2340
ctgctgggct tgaggcccaa ccctggactg cggctgcctg ggcgctatga ggtccgggca  2400
gaggtgggca atggcgtgtc caggcacaac ctctcctgca gctttgacgt ggtctcccca  2460
gtggctgggc tgcgggtcat ctaccctgcc ccccgcgacg gccgcctcta cgtgcccacc  2520
aacggctcag ccttggtgct ccaggtggac tctggtgcca acgccacggc cacggctcgc  2580
tggcctgggg gcagtgtcag cgcccgcttt gagaatgtct gccctgccct ggtggccacc  2640
ttcgtgcccg gctgcccctg ggagaccaac gataccctgt tctcagtggt agcactgccg  2700
tggctcagtg agggggagca cgtggtggac gtggtggtgg aaaacagcgc cagccgggcc  2760
aacctcagcc tgcgggtgac ggcggaggag cccatctgtg gcctccgcgc cacgcccagc  2820
cccgaggccc gtgtactgca gggagtccta gtgaggtaca gccccgtggt ggaggccggc  2880
tcggacatgg tcttccggtg gaccatcaac gacaagcagt ccctgacctt ccagaacgtg  2940
gtcttcaatg tcatttatca gagcgcggcg gtcttcaagc tctcactgac ggcctccaac  3000
cacgtgagca acgtcaccgt gaactacaac gtaaccgtgg agcggatgaa caggatgcag  3060
ggtctgcagg tctccacagt gccggccgtg ctgtccccca atgccacgct agcactgacg  3120
gcgggcgtgc tggtggactc ggccgtggag gtggccttcc tgtggacctt tggggatggg  3180
gagcaggccc tccaccagtt ccagcctccg tacaacgagt ccttccccgt tccagacccc  3240
tcggtggccc aggtgctggt ggagcacaat gtcatgcaca cctacgctgc cccaggtgag  3300
tacctcctga ccgtgctggc atctaatgcc ttcgagaacc tgacgcagca ggtgcctgtg  3360
agcgtgcgcg cctccctgcc ctccgtggct gtgggtgtga gtgacggcgt cctggtggcc  3420
ggccggcccg tcaccttcta cccgcacccg ctgccctcgc ctgggggtgt tctttacacg  3480
tgggacttcg gggacggctc ccctgtcctg acccagagcc agccggctgc caaccacacc  3540
tatgcctcga ggggcaccta ccacgtgcgc ctggaggtca acaacacggt gagcggtgcg  3600
gcggcccagg cggatgtgcg cgtctttgag gagctccgcg gactcagcgt ggacatgagc  3660
ctggccgtgg agcagggcgc ccccgtggtg gtcagcgccg cggtgcagac gggcgacaac  3720
atcacgtgga ccttcgacat gggggacggc accgtgctgt cgggcccgga ggcaacagtg  3780
gagcatgtgt acctgcgggc acagaactgc acagtgaccg tgggtgcggc cagccccgcc  3840
```

```
ggccacctgg cccggagcct gcacgtgctg gtcttcgtcc tggaggtgct gcgcgttgaa  3900
cccgccgcct gcatccccac gcagcctgac gcgcggctca cggcctacgt caccgggaac  3960
ccggcccact acctcttcga ctggaccttc ggggatggct cctccaacac gaccgtgcgg  4020
gggtgcccga cggtgacaca caacttcacg cggagcggca cgttccccct ggcgctggtg  4080
ctgtccagcc gcgtgaacag ggcgcattac ttcaccagca tctgcgtgga gccagaggtg  4140
ggcaacgtca ccctgcagcc agagaggcag tttgtgcagc tcggggacga ggcctggctg  4200
gtggcatgtg cctggccccc gttcccctac cgctacacct gggactttgg caccgaggaa  4260
gccgcccccca cccgtgccag gggccctgag gtgacgttca tctaccgaga cccaggctcc  4320
tatcttgtga cagtcaccgc gtccaacaac atctctgctg ccaatgactc agccctggtg  4380
gaggtgcagg agcccgtgct ggtcaccagc atcaaggtca atggctccct tgggctggag  4440
ctgcagcagc cgtacctgtt ctctgctgtg ggccgtgggc gccccgccag ctacctgtgg  4500
gatctggggg acggtgggtg gctcgagggt ccggaggtca cccacgctta caacagcaca  4560
ggtgacttca ccgttagggt ggccggctgg aatgaggtga gccgcagcga ggcctggctc  4620
aatgtgacgg tgaagcggcg cgtgcggggg ctcgtcgtca atgcaagccg cacggtggtg  4680
cccctgaatg ggagcgtgag cttcagcacg tcgctggagg ccggcagtga tgtgcgctat  4740
tcctgggtgc tctgtgaccg ctgcacgccc atccctgggg gtcctaccat ctcttacacc  4800
ttccgctccg tgggcacctt caatatcatc gtcacggctg agaacgaggt gggctccgcc  4860
caggacagca tcttcgtcta tgtcctgcag ctcatagagg ggctgcaggt ggtgggcggt  4920
ggccgctact tccccaccaa ccacacggta cagctgcagg ccgtggttag ggatggcacc  4980
aacgtctcct acagctggac tgcctggagg gacaggggcc cggccctggc cggcagcggc  5040
aaaggcttct cgctcaccgt gctcgaggcc ggcacctacc atgtgcagct gcgggccacc  5100
aacatgctgg gcagcgcctg ggccgactgc accatggact tcgtggagcc tgtggggtgg  5160
ctgatggtgg ccgcctcccc gaacccagct gccgtcaaca caagcgtcac cctcagtgcc  5220
gagctggctg gtggcagtgg tgtcgtatac acttggtcct tggaggaggg gctgagctgg  5280
gagacctccg agccatttac cacccatagc ttccccacac ccggcctgca cttggtcacc  5340
atgacggcag ggaacccgct gggctcagcc aacgccaccg tggaagtgga tgtgcaggtg  5400
cctgtgagtg gcctcagcat cagggccagc gagcccggag gcagcttcgt ggcggccggg  5460
tcctctgtgc ccttttgggg gcagctggcc acgggcacca atgtgagctg gtgctgggct  5520
gtgcccggcg gcagcagcaa gcgtggccct catgtcacca tggtcttccc ggatgctggc  5580
accttctcca tccggctcaa tgcctccaac gcagtcagct gggtctcagc cacgtacaac  5640
ctcacggcgg aggagcccat cgtgggcctg gtgctgtggg ccagcagcaa ggtggtggcg  5700
cccgggcagc tggtccattt tcagatcctg ctggctgccg gctcagctgt caccttccgc  5760
ctgcaggtcg gcggggccaa ccccgaggtg ctcccccggc cccgtttctc ccacagcttc  5820
ccccgcgtcg gagaccacgt ggtgagcgtg cggggcaaaa accacgtgag ctgggcccag  5880
gcgcaggtgc gcatcgtggt gctggaggcc gtgagtgggc tgcaggtgcc caactgctgc  5940
gagcctggca tcgccacggg cactgagagg aacttcacag cccgcgtgca gcgcggctct  6000
cgggtcgcct acgcctggta cttctcgctg cagaaggtcc agggcgactc gctggtcatc  6060
ctgtcgggcc gcgacgtcac ctacacgccc gtggccgcgg ggctgttgga gatccaggtg  6120
cgcgccttca acgccctggg cagtgagaac cgcacgctgg tgctggaggt tcaggacgcc  6180
gtccagtatg tggccctgca gagcggcccc tgcttcacca accgctcggc gcagtttgag  6240
gccgccacca gccccagccc ccggcgtgtg gcctaccact gggactttgg ggatgggtcg  6300
ccagggcagg acacagatga gcccagggcc gagcactcct acctgaggcc tggggactac  6360
cgcgtgcagg tgaacgcctc caacctggtg agcttcttcg tggcgcaggc cacggtgacc  6420
gtccaggtgc tggcctgccg ggagccggag gtggacgtgg tcctgcccct gcaggtgctg  6480
atgcggcgat cacagcgcaa ctacttggag gcccacgttg acctgcgcga ctgcgtcacc  6540
taccagactg agtaccgctg ggaggtgtat cgcaccgcca gctgccagcg gccggggcgc  6600
ccagcgcgtg tggccctgcc cggcgtggac gtgagccggc ctcggctggt gctgccgcgg  6660
ctggcgctgc ctgtggggca ctactgcttt gtgtttgtcg tgtcatttgg ggacacgcca  6720
ctgacacaga gcatccaggc caatgtgacg gtggccccccg agcgcctggt gcccatcatt  6780
gagggtggct cataccgcgt gtggtcagac acacgggacc tggtgctgga tgggagcgag  6840
tcctacgacc ccaacctgga ggacggcgac cagacgccgc tcagtttcca ctgggcctgt  6900
gtggcttcga cacagaggga ggctggcggg tgtgcgctga actttgggcc ccgcgggagc  6960
agcacggtca ccattccacg ggagcggctg gcggctggcg tggagtacac cttcagcctg  7020
accgtgtgga aggccggccg caaggaggag gccaccaacc agacggtgct gatccggagt  7080
ggccgggtgc ccattgtgtc cttggagtgt gtgtcctgca aggcacaggc cgtgtacgaa  7140
gtgagccgca gctcctacgt gtacttggag ggccgctgcc tcaattgcag cagcggctcc  7200
aagcgagggc ggtgggctgc acgtacgttc agcaacaaga cgctggtgct ggatgagacc  7260
accacatcca cgggcagtgc aggcatgcga ctggtgctgc ggcggggcgt gctgcgggac  7320
ggcgagggat acaccttcac gctcacggtg ctgggccgct ctggcgagga ggagggctgc  7380
gcctccatcc gcctgtcccc caaccgcccg ccgctggggg gctcttgccg cctcttccca  7440
ctgggcgctg tgcacgccct caccaccaag gtgcacttcg aatgcacggg ctggcatgac  7500
gcggaggatg ctggcgcccc gctggtgtac gccctgctgc tgcggcgctg tcgccagggc  7560
cactgcgagg agttctgtgt ctacaagggc agcctctcca gctacggagc cgtgctgccc  7620
ccgggtttca ggccacactt cgaggtgggc ctggccgtgg tggtgcagga ccagctggga  7680
gccgctgtgg tcgccctcaa caggtctttg gccatcaccc tcccagagcc caacggcagc  7740
gcaacggggc tcacagtctg gctgcacggg ctcaccgcta gtgtgctccc agggctgctg  7800
cggcaggccg atccccagca cgtcatcgag tactcgttgg ccctggtcac cgtgctgaac  7860
gagtacgagc gggccctgga cgtggcggca gagcccaagc acgagcggca gcaccgagcc  7920
cagatacgca agaacatcac ggagactctg gtgtccctga gggtccacac tgtggatgac  7980
atccagcaga tcgctgctgc gctggcccag tgcatggggc ccagcaggga gctcgtatgc  8040
cgctcgtgcc tgaagcagac gctgcacaag ctggaggcca tgatgctcat cctgcaggca  8100
gagaccaccg cgggcaccgt gacgcccacc gccatcggag acagcatcct caacatcaca  8160
ggagacctca tccacctggc cagctcggac gtgcgggcac cacagccctc agagctggga  8220
gccgagtcac catctcggat ggtggcgtcc caggcctaca acctgacctc tgccctcatg  8280
cgcatcctca tgcgctcccg cgtgctcaac gaggagcccc tgacgctggc gggcgaggag  8340
atcgtggccc agggcaagcg ctcggacccg cggagcctgc tgtgctatgg cggcgcccca  8400
gggcctggct gccacttctc catccccgag gctttcagcg ggcccctggc caacctcagt  8460
gacgtggtgc agctcatctt tctggtggac tccaatccct ttccctttgg ctatatcagc  8520
aactacaccg tctccaccaa ggtggcctcg atggcattcc agacacaggc cggcgcccag  8580
```

```
atccccatcg agcggctggc ctcagagcgc gccatcaccg tgaaggtgcc caacaactcg  8640
gactgggctg cccggggcca ccgcagctcc gccaactccg ccaactccgt tgtggtccag  8700
ccccaggcct ccgtcggtgc tgtggtcacc ctggacagca gcaaccctgc ggccgggctg  8760
catctgcagc tcaactatac gctgctggac ggccactacc tgtctgagga acctgagccc  8820
tacctggcag tctacctaca ctcggagccc cggcccaatg agcacaactg ctcggctagc  8880
aggaggatcc gcccagagtc actccagggt gctgaccacc ggccctacac cttcttcatt  8940
tccccgggga gcagagaccc agcggggagt taccatctga acctctccag ccacttccgc  9000
tggtcggcgc tgcaggtgtc cgtgggcctg tacacgtccc tgtgccagta cttcagcgag  9060
gaggacatgg tgtggcggac agaggggctg ctgcccctgg aggagacctc gccccgccag  9120
gccgtctgcc tcacccgcca cctcaccgcc ttcggcgcca gcctcttcgt gcccccaagc  9180
catgtccgct ttgtgtttcc tgagccgaca gcggatgtaa actacatcgt catgctgaca  9240
tgtgctgtgt gcctggtgac ctacatggtc atggccgcca tcctgcacaa gctggaccag  9300
ttggatgcca gccggggccg cgccatccct ttctgtgggc agcggggccg cttcaagtac  9360
gagatcctcg tcaagacagg ctggggccgg ggctcaggta ccacggccca cgtgggcatc  9420
atgctgtatg gggtggacag ccggagcggc caccggcacc tggacggcga cagagccttc  9480
caccgcaaca gcctggacat cttccggatc gccaccccgc acagcctggg tagcgtgtgg  9540
aagatccgag tgtggcacga caacaaaggg ctcagccctg cctggttcct gcagcacgtc  9600
atcgtcaggg acctgcagac ggcacgcagc gccttcttcc tggtcaatga ctggctttcg  9660
gtggagacgg aggccaacgg gggcctggtg gagaaggagg tgctggccgc gagcgacgca  9720
gcccttttgc gcttccggcg cctgctggtg gctgagctgc agcgtggctt ctttgacaag  9780
cacatctggc tctccatatg ggaccggccg cctcgtagcc gtttcactcg catccagagg  9840
gccacctgct gcgttctcct catctgcctc ttcctgggcg ccaacgccgt gtggtacggg  9900
gctgttggcg actctgccta cagcacgggg catgtgtcca ggctgagccc gctgagcgtc  9960
gacacagtcg ctgttggcct ggtgtccagc gtggttgtct atcccgtcta cctggccatc  10020
ctttttctct tccggatgtc ccggagcaag gtggctggga gcccgagccc cacacctgcc  10080
gggcagcagg tgctggacat cgacagctgc ctggactcgt ccgtgctgga cagctccttc  10140
ctcacgttct caggcctcca cgctgaggcc tttgttggac agatgaagag tgacttgttt  10200
ctggatgatt ctaagagtct ggtgtgctgg ccctccggcg agggaacgct cagttggccg  10260
gacctgctca gtgacccgtc cattgtgggt agcaatctgc ggcagctggc acggggccag  10320
gcgggccatg ggctgggccc agaggaggac ggcttctccc tggccagccc ctactcgcct  10380
gccaaatcct tctcagcatc agatgaagac ctgatccagc aggtccttgc cgaggggggtc  10440
agcagcccag cccctaccca agacacccac atggaaacgg acctgctcag cagcctgtcc  10500
agcactcctg gggagaagac agagacgctg gcgctgcaga ggctggggga gctggggcca  10560
cccagcccag gcctgaactg ggaacagccc caggcagcga ggctgtccag gacaggactg  10620
gtggagggtc tgcggaagcg cctgctgccg gcctggtgtg cctccctggc ccacgggctc  10680
agcctgctcc tggtggctgt ggctgtggct gtctcagggt gggtgggtgc gagcttcccc  10740
ccgggcgtga gtgttgcgtg gctcctgtcc agcagcgcca gcttcctggc ctcattcctc  10800
ggctgggagc cactgaaggt cttgctggaa gccctgtact tctcactggt ggccaagcgg  10860
ctgcacccgg atgaagatga caccctggta gagagcccgg ctgtgacgcc tgtgagcgca  10920
cgtgtgcccc gcgtacggcc accccacggc tttgcactct tcctggccaa ggaagaagcc  10980
cgcaaggtca agaggctaca tggcatgctg cggagcctcc tggtgtacat gctttttctg  11040
ctggtgaccc tgctggccag ctatggggat gcctcatgcc atgggcacgc ctaccgtctg  11100
caaagcgcca tcaagcagga gctgcacagc cgggccttcc tggccatcac gcggtctgag  11160
gagctctggc catggatggc ccacgtgctg ctgccctacg tccacgggaa ccagtccagc  11220
ccagagctgg ggcccccacg gctgcggcag gtgcggctgc aggaagcact ctacccagac  11280
cctcccggcc ccagggtcca cacgtgctcg gccgcaggag gcttcagcac cagcgattac  11340
gacgttggct gggagagtcc tcacaatggc tcggggacgt gggcctattc agcgccggat  11400
ctgctggggg catggtcctg gggctcctgt gccgtgtatg acagcggggg ctacgtgcag  11460
gagctgggcc tgagcctgga ggagagccgc gaccggctgc gcttcctgca gctgcacaac  11520
tggctggaca acaggagccg cgctgtgttc ctggagctca cgcgctacag cccggccgtg  11580
gggctgcacg ccgccgtcac gctgcgcctc gagttcccgg cggccggccg cgccctggcc  11640
gccctcagcg tccgcccctt tgcgctgcgc cgcctcagcg cgggcctctc gctgcctctg  11700
ctcacctcgg tgtgcctgct gctgttcgcc gtgcacttcg ccgtggccga ggcccgtact  11760
tggcacaggg aagggcgctg gcgcgtgctg cggctcggag cctgggcgcg gtggctgctg  11820
gtggcgctga cggcggccac ggcactggta cgcctcgccc agctgggtgc cgctgaccgc  11880
cagtggaccc gtttcgtgcg cggccgcccg cgccgcttca ctagcttcga ccaggtggcg  11940
cagctgagct ccgcagcccg tggcctggcg gcctcgctgc tcttcctgct tttggtcaag  12000
gctgcccagc agctacgctt cgtgcgccag tggtccgtct ttggcaagac attatgccga  12060
gctctgccag agctcctggg ggtcaccttg ggcctggtgg tgctcggggt agcctacgcc  12120
cagctggcca tcctgctcgt gtcttcctgt gtggactccc tctggagcgt ggcccaggcc  12180
ctgttggtgc tgtgccctgg gactgggctc tctaccctgt gtcctgccga gtcctggcac  12240
ctgtcacccc tgctgtgtgt ggggctctgg gcactgcggc tgtggggcgc cctacggctg  12300
ggggctgtta ttctccgctg gcgctaccac gccttgcgtg gagagctgta ccggccggcc  12360
tgggagcccc aggactacga gatggtggag ttgttcctgc gcaggctgcg cctctggatg  12420
ggcctcagca aggtcaagga gttccgccac aaagtccgct ttgaagggat ggagccgctg  12480
ccctctcgct cctccagggg ctccaaggta tccccggatg tgcccccacc cagcgctggc  12540
tccgatgcct cgcacccctc cacctcctcc agccagctgg atgggctgag cgtgagcctg  12600
ggccggctgg ggacaaggtg tgagcctgag ccctcccgcc tccaagccgt gttcgaggcc  12660
ctgctcaccc agtttgaccg actcaaccag gccacagagg acgtctacca gctggagcag  12720
cagctgcaca gcctgcaagg ccgcaggagc agccgggcgc ccgccggatc ttcccgtggc  12780
ccatccccgg gcctgcggcc agcactgccc agccgccttg cccgggccag tcggggtgtg  12840
gacctggcca ctggccccag caggacaccc cttcgggcca agaacaaggt ccaccccagc  12900
agcacttag                                                          12909
```

```
SEQ ID NO: 10          moltype = DNA  length = 2907
FEATURE                Location/Qualifiers
source                 1..2907
                       mol_type = unassigned DNA
                       organism = Homo sapiens
```

SEQUENCE: 10
atggtgaact ccagtcgcgt gcagcctcag cagcccgggg acgccaagcg gccgcccgcg 60
ccccgcgcgc cggacccggg ccggctgatg gctggctgcg cggccgtggg cgccagcctc 120
gccgccccgg gcggcctctg cgagcagcgg ggcctggaga tcgagatgca gcgcatccgg 180
caggcggccg cgcgggaccc cccggccgga gccgcggcct ccccttctcc tccgctctcg 240
tcgtgctccc ggcaggcgtg gagccgcgat aaccccggct tcgaggccga ggaggaggag 300
gaggaggtgg aaggggaaga aggcggaatg gtggtggaga tggacgtaga gtggcgcccg 360
ggcagccgga ggtcggccgc ctcctcggcc gtgagctccg tgggcgcgcg gagccggggg 420
cttgggggct accacggcgc gggccacccg agcgggaggc ggcgccggcg agaggaccag 480
ggcccgccgt gccccagccc agtcggcggc ggggacccgc tgcatcgcca cctccccctg 540
gaagggcagc cgccccgagt ggcctgggcg gagaggctgg ttcgcgggct gcgaggtctc 600
tggggaacaa gactcatgga ggaaagcagc actaaccgag agaaatacct taaaagtgtt 660
ttacgggaac tggtcacata cctccttttt ctcatagtct tgtgcatctt gacctacggc 720
atgatgagct ccaatgtgta ctactacacc cggatgatgt cacagctctt cctagacacc 780
cccgtgtcca aaacggagaa aactaacttt aaaactctgt cttccatgga agacttctgg 840
aagttcacag aaggctcctt attggatggg ctgtactgga agatgcagcc cagcaaccag 900
actgaagctg acaaccgaag tttcatcttc tatgagaacc tgctgttagg ggttccacga 960
atacggcaac tccgagtcag aaatggatcc tgctctatcc cccaggactt gagagatgaa 1020
attaaagagt gctatgatgt ctactctgtc agtagtgaag atagggctcc ctttgggccc 1080
cgaaatggaa ccgcttggat ctacacaagt gaaaaagact tgaatggtag tagccactgg 1140
ggaatcattg caacttatag tggagctggc tattatctgg atttgtcaag aacaagagag 1200
gaaacagctg cacaagttgc tagcctcaag aaaaatgtct ggctggaccg aggaaccagg 1260
gcaactttta ttgacttctc agtgtacaac gccaacatta acctgttctg tgtggtcagg 1320
ttattggttg aattcccagc aacaggtggt gtgattccat cttggcaatt tcagccttta 1380
aagctgatcc gatatgtcac aacttttgat ttcttcctgg cagcctgtga gattatcttt 1440
tgtttcttta tcttttacta tgtggtggaa gagatattgg aaattcgcat tcacaaacta 1500
cactatttca ggagtttctg gaattgtctg gatgttgtga tcgttgtgct gtcagtggta 1560
gctataggaa ttaacatata cagaacatca aatgtggagg tgctactaca gtttctggaa 1620
gatcaaaata ctttccccaa ctttgagcat ctggcatatt ggcagataca gttcaacaat 1680
atagctgctg tcacagtatt ttttgtctgg attaagctct tcaaattcat caattttaac 1740
aggaccatga gccagctctc gacaaccatg tctcgatgtg ccaaagacct gtttggcttt 1800
gctattatgt tcttcattat tttcctagcg tatgctcagt tggcatacct tgtctttggc 1860
actcaggtcg atgacttcag tactttccaa gagtgtatct tcactcaatt ccgtatcatt 1920
ttgggcgata tcaactttgc agagattgag gaagctaatc gagttttggg accaatttat 1980
ttcactacat ttgtgttctt tatgttcttc attcttttga atatgttttt ggctatcatc 2040
aatgatactt actctgaagt gaaatctgac ttggcacagc agaaagctga aatggaactc 2100
tcagatctta tcagaaaggg ctaccataaa gctttggtca aactaaaact gaaaaaaaat 2160
accgtggatg acatttcaga gagtctgcgg caaggaggag gcaagttaaa ctttgacgaa 2220
cttcgacaag atctcaaagg gaagggccat actgatgcag agattgaggc aatattcaca 2280
aagtacgacc aagatggaga ccaagaactg accgaacatg aacatcagca gatgagagac 2340
gacttggaga aagagaggga ggacctggat ttggatcaca gttctttacc acgtcccatg 2400
agcagccgaa gtttccctcg aagcctggat gactctgagg aggatgacga tgaagatagc 2460
ggacatagct ccagaaggag gggaagcatt tctagtggcg tttcttacga agagtttcaa 2520
gtcctggtga gacgagtgga ccggatggag cattccatcg gcagcatagt gtccaagatt 2580
gacgccgtga tcgtgaagct agagattatg gagcgagcca aactgaagag gagggaggtg 2640
ctgggaaggc tgttggatgg ggtggccgag gatgaaaggc tgggtcgtga cagtgaaatc 2700
catagggaac agatggaacg gctagtacgt gaagagttgg aacgctggga atccgatgat 2760
gcagcttccc agatcagtca tggtttaggc acgccagtgg gactaaatgg tcaacctcgc 2820
cccagaagct cccgcccatc ttcctcccaa tctacagaag gcatggaagg tgcaggtgga 2880
aatgggagtt ctaatgtcca cgtatga 2907

SEQ ID NO: 11 moltype = AA length = 4302
FEATURE Location/Qualifiers
source 1..4302
mol_type = protein
organism = Homo sapiens SEQUENCE: 11
MPPAAPARLA LALGLGLWLG ALAGGPGRGC GPCEPPCLCG PAPGAACRVN CSGRGLRTLG 60
PALRIPADAT ALDVSHNLLR ALDVGLLANL SALAELDISN NKISTLEEGI FANLFNLSEI 120
NLSGNPFECD CGLAWLPRWA EEQQVRVVQP EAATCAGPGS LAGQPLLGIP LLDSGCGEEY 180
VACLPDNSSG TVAAVSFSAA HEGLLQPEAC SAFCFSTGQG LAALSEQGWC LCGAAQPSSA 240
SFACLSLCSG PPPPPAPTCR GPTLLQHVFP ASPGATLVGP HGPLASGQLA AFHIAAPLPV 300
TATRWDFGDG SAEVDAAGPA ASHRYVLPGR YHVTAVLALG AGSALLGTDV QVEAAPAALE 360
LVCPSSVQSD ESLDLSIQNR GGSGLEAAYS IVALGEEPAR AVHPLCPSDT EIFPGNGHCY 420
RLVVEKAAWL QAQEQCQAWA GAALAMVDSP AVQRFLVSRV TRSLDVWIGF STVQGVEVGP 480
APQGEAFSLE SCQNWLPGEP HPATAEHCVR LGPTGWCNTD LCSAPHSYVC ELQPGGPVQD 540
AENLLVGAPS GDLQGPLTPL AQQDGLSAPH EPVEVMVFPG LRLSREAFLT TAEFGTQELR 600
RPAQLRLQVY RLLSTAGTPE NGSEPESRSP DNRTQLAPAC MPGGRWCPGA NICLPLDASC 660
HPQACANGCT SGPGLPGAPY ALWREFLFSV PAGPPAQYSV TLHGQDVLML PGDLVGLQHD 720
AGPGALLHCS PAPGHPGPRA PYLSANASSW LPHLPAQLEG TWACPACALR LLAATEQLTV 780
LLGLRPNPGL RLPGRYEVRA EVGNGVSRHN LSCSFDVVSP VAGLRVIYPA PRDGRLYVPT 840
NGSALVLQVD SGANATATAR WPGGSVSARF ENVCPALVAT FVPGCPWETN DTLFSVVALP 900
WLSEGEHVVD VVVENSASRA NLSLRVTAEE PICGLRATPS PEARVLQGVL VRYSPVVEAG 960
SDMVFRWTIN DKQSLTFQNV VFNVIYQSAA VFKLSLTASN HVSNVTVNYN VTVERMNRMQ 1020
GLQVSTVPAV LSPNATLALT AGVLVDSAVE VAFLWTFGDG EQALHQFQPP YNESFPVPDP 1080
SVAQVLVEHN VMHTYAAPGE YLLTVLASNA FENLTQQVPV SVRASLPSVA VGVSDGVLVA 1140
GRPVTFYPHP LPSPGGVLYT WDFGDGSPVL TQSQPAANHT YASRGTYHVR LEVNNTVSGA 1200
AAQADVRVFE ELRGLSVDMS LAVEQGAPVV VSAAVQTGDN ITWTFDMGDG TVLSGPEATV 1260
EHVYLRAQNC TVTVGAASPA GHLARSLHVL VFVLEVLRVE PAACIPTQPD ARLTAYVTGN 1320

-continued

```
PAHYLFDWTF GDGSSNTTVR GCPTVTHNFT RSGTFPLALV LSSRVNRAHY FTSICVEPEV  1380
GNVTLQPERQ FVQLGDEAWL VACAWPPFPY RYTWDFGTEE AAPTRARGPE VTFIYRDPGS  1440
YLVTVTASNN ISAANDSALV EVQEPVLVTS IKVNGSLGLE LQQPYLFSAV GRGRPASYLW  1500
DLGDGGWLEG PEVTHAYNST GDFTVRVAGW NEVSRSEAWL NVTVKRRVRG LVVNASRTVV  1560
PLNGSVSFST SLEAGSDVRY SWVLCDRCTP IPGGPTISYT FRSVGTFNII VTAENEVGSA  1620
QDSIFVYVLQ LIEGLQVVGG GRYFPTNHTV QLQAVVRDGT NVSYSWTAWR DRGPALAGSG  1680
KGFSLTVLEA GTYHVQLRAT NMLGSAWADC TMDFVEPVGW LMVAASPNPA AVNTSVTLSA  1740
ELAGGSGVVY TWSLEEGLSW ETSEPFTTHS FPTPGLHLVT MTAGNPLGSA NATVEVDVQV  1800
PVSGLSIRAS EPGGSFVAAG SSVPFWGQLA TGTNVSWCWA VPGGSSKRGP HVTMVFPDAG  1860
TFSIRLNASN AVSWVSATYN LTAEEPIVGL VLWASSKVVA PGQLVHFQIL LAAGSAVTFR  1920
LQVGGANPEV LPGPRFSHSF PRVGDHVVSV RGKNHVSWAQ AQVRIVVLEA VSGLQVPNCC  1980
EPGIATGTER NFTARVQRGS RVAYAWYFSL QKVQGDSLVI LSGRDVTYTP VAAGLLEIQV  2040
RAFNALGSEN RTLVLEVQDA VQYVALQSGP CFTNRSAQFE AATSPSPRRV AYHWDFGDGS  2100
PGQDTDEPRA EHSYLRPGDY RVQVNASNLV SFFVAQATVT VQVLACREPE VDVVLPLQVL  2160
MRRSQRNYLE AHVDLRDCVT YQTEYRWEVY RTASCQRPGR PARVALPGVD VSRPRLVLPR  2220
LALPVGHYCF VFVVSFGDTP LTQSIQANVT VAPERLVPII EGGSYRVWSD TRDLVLDGSE  2280
SYDPNLEDGD QTPLSFHWAC VASTQREAGG CALNFGPRGS STVTIPRERL AAGVEYTFSL  2340
TVWKAGRKEE ATNQTVLIRS GRVPIVSLEC VSCKAQAVYE VSRSSYVYLE GRCLNCSSGS  2400
KRGRWAARTF SNKTLVLDET TTSTGSAGMR LVLRRGVLRD GEGYTFTLTV LGRSGEEEGC  2460
ASIRLSPNRP PLGGSCRLFP LGAVHALTTK VHFECTGWHD AEDAGAPLVY ALLLRRCRQG  2520
HCEEFCVYKG SLSSYGAVLP PGFRPHFEVG LAVVVQDQLG AAVVALNRSL AITLPEPNGS  2580
ATGLTVWLHG LTASVLPGLL RQADPQHVIE YSLALVTVLN EYERALDVAA EPKHERQHRA  2640
QIRKNITETL VSLRVHTVDD IQQIAAALAQ CMGPSRELVC RSCLKQTLHK LEAMMLILQA  2700
ETTAGTVTPT AIGDSILNIT GDLIHLASSD VRAPQPSELG AESPSRMVAS QAYNLTSALM  2760
RILMRSRVLN EEPLTLAGEE IVAQGKRSDP RSLLCYGGAP GPGCHFSIPE AFSGALANLS  2820
DVVQLIFLVD SNPFPFGYIS NYTVSTKVAS MAFQTQAGAQ IPIERLASER AITVKVPNNS  2880
DWAARGHRSS ANSANSVVVQ PQASVGAVVT LDSSNPAAGL HLQLNYTLLD GHYLSEEPEP  2940
YLAVYLHSEP RPNEHNCSAS RRIRPESLQG ADHRPYTFFI SPGSRDPAGS YHLNLSSHFR  3000
WSALQVSVGL YTSLCQYFSE EDMVWRTEGL LPLEETSPRQ AVCLTRHLTA FGASLFVPPS  3060
HVRFVFPEPT ADVNYIVMLT CAVCLVTYMV MAAILHKLDQ LDASRGRAIP FCGQRGRFKY  3120
EILVKTGWGR GSGTTAHVGI MLYGVDSRSG HRHLDGDRAF HRNSLDIFRI ATPHSLGSVW  3180
KIRVWHDNKG LSPAWFLQHV IVRDLQTARS AFFLVNDWLS VETEANGGLV EKEVLAASDA  3240
ALLRFRRLLV AELQRGFFDK HIWLSIWDRP PRSRFTRIQR ATCCVLLICL FLGANAVWYG  3300
AVGDSAYSTG HVSRLSPLSV DTVAVGLVSS VVVYPVYLAI LFLFRMSRSK VAGSPSPTPA  3360
GQQVLDIDSC LDSSVLDSSF LTFSGLHAEA FVGQMKSDLF LDDSKSLVCW PSGEGTLSWP  3420
DLLSDPSIVG SNLRQLARGQ AGHGLGPEED GFSLASPYSP AKSFSASDED LIQQVLAEGV  3480
SSPAPTQDTH METDLLSSLS STPGEKTETL ALQRLGELGP PSPGLNWEQP QAARLSRTGL  3540
VEGLRKRLLP AWCASLAHGL SLLLVAVAVA VSGWVGASFP PGVSVAWLLS SSASFLASFL  3600
GWEPLKVLLE ALYFSLVAKR LHPDEDDTLV ESPAVTPVSA RVPRVRPPHG FALFLAKEEA  3660
RKVKRLHGML RSLLVYMLFL LVTLLASYGD ASCHGHAYRL QSAIKQELHS RAFLAITRSE  3720
ELWPWMAHVL LPYVHGNQSS PELGPPRLRQ VRLQEALYPD PPGPRVHTCS AAGGFSTSDY  3780
DVGWESPHNG SGTWAYSAPD LLGAWSWGSC AVYDSGGYVQ ELGLSLEESR DRLRFLQLHN  3840
WLDNRSRAVF LELTRYSPAV GLHAAVTLRL EFPAAGRALA ALSVRPFALR RLSAGLSLPL  3900
LTSVCLLLFA VHFAVAEART WHREGRWRVL RLGAWARWLL VALTAATALV RLAQLGAADR  3960
QWTRFVRGRP RRFTSFDQVA QLSSAARGLA ASLLFLLLVK AAQQLRFVRQ WSVFGKTLCR  4020
ALPELLGVTL GLVVLGVAYA QLAILLVSSC VDSLWSVAQA LLVLCPGTGL STLCPAESWH  4080
LSPLLCVGLW ALRLWGALRL GAVILRWRYH ALRGELYRPA WEPQDYEMVE LFLRRLRLWM  4140
GLSKVKEFRH KVRFEGMEPL PSRSSRGSKV SPDVPPPSAG SDASHPSTSS SQLDGLSVSL  4200
GRLGTRCEPE PSRLQAVFEA LLTQFDRLNQ ATEDVYQLEQ QLHSLQGRRS SRAPAGSSRG  4260
PSPGLRPALP SRLARASRGV DLATGPSRTP LRAKNKVHPS ST                    4302

SEQ ID NO: 12           moltype = AA  length = 968
FEATURE                 Location/Qualifiers
source                  1..968
                        mol_type = protein
                        organism = Homo sapiens
SEQUENCE: 12
MVNSSRVQPQ QPGDAKRPPA PRAPDPGRLM AGCAAVGASL AAPGGLCEQR GLEIEMQRIR  60
QAAARDPPAG AAASPSPPLS SCSRQAWSRD NPGFEAEEEE EEVEGEEGGM VVEMDVEWRP  120
GSRRSAASSA VSSVGARSRG LGGYHGAGHP SGRRRRREDQ GPPCPSPVGG GDPLHRHLPL  180
EGQPPRVAWA ERLVRGLRGL WGTRLMEESS TNREKYLKSV LRELVTYLLF LIVLCILTYG  240
MMSSNVYYYT RMMSQLFLDT PVSKTEKTNF KTLSSMEDFW KFTEGSLLDG LYWKMQPSNQ  300
TEADNRSFIF YENLLLGVPR IRQLRVRNGS CSIPQDLRDE IKECYDVYSV SSEDRAPFGP  360
RNGTAWIYTS EKDLNGSSHW GIIATYSGAG YYLDLSRTRE ETAAQVASLK KNVWLDRGTR  420
ATFIDFSVYN ANINLFCVVR LLVEFPATGG VIPSWQFQPL KLIRYVTTFD FFLAACEIIF  480
CFFIFYYVVE EILEIRIHKL HYFRSFWNCL DVVIVVLSVV AIGINIYRTS NVEVLLQFLE  540
DQNTFPNFEH LAYWQIQFNN IAAVTVFFVW IKLFKFINFN RTMSQLSTTM SRCAKDLFGF  600
AIMFFIIFLA YAQLAYLVFG TQVDDFSTFQ ECIFTQFRII LGDINFAEIE EANRVLGPIY  660
FTTFVFFMFF ILLNMFLAII NDTYSEVKSD LAQQKAEMEL SDLIRKGYHK ALVKLKLKKN  720
TVDDISESLR QGGGKLNFDE LRQDLKGKGH TDAEIEAIFT KYDQDGDQEL TEHEHQQMRD  780
DLEKEREDLD LDHSSLPRPM SSRSFPRSLD DSEEDDDEDS GHSSRRRGSI SSGVSYEEFQ  840
VLVRRVDRME HSIGSIVSKI DAVIVKLEIM ERAKLKRREV LGRLLDGVAE DERLGRDSEI  900
HREQMERLVR EELERWESDD AASQISHGLG TPVGLNGQPR PRSSRPSSSQ STEGMEGAGG  960
NGSSNVHV                                                          968

SEQ ID NO: 13           moltype = DNA  length = 2559
FEATURE                 Location/Qualifiers
source                  1..2559
                        mol_type = unassigned DNA
```

```
                        organism = Homo sapiens
SEQUENCE: 13
atggcggcgg tagcggcagt ggcggcgcgt aggaggcggc tttctgtctc tggtcgtgat  60
gagaacagtg tggagttaac catggctgag ggaccctaca agatcatctt gacagcacgg  120
ccattccgcc ttgacctact agaggaccga agtcttttgc ttagtgtcaa tgcccgagga  180
ctcttggagt ttgagcatca gagggcccct agggtctctt tctcggataa ggttaatctc  240
acgcttggta gcatatggga taagatcaag aaccttttct ctaggcaagg atcaaaagac  300
ccagctgagg gcgatggggc ccagcctgag gaaacaccca gggatggcga caagccagag  360
gagactcagg ggaaggcaga gaaagatgag ccaggagcct gggaggagac attcaaaact  420
cactctgaca gcaagccgta tggccccatg tctgtgggtt tggacttctc tctgccaggc  480
atggagcatg tctatgggat ccctgagcat gcagacaacc tgaggctgaa ggtcactgag  540
ggtggggagc catatcgcct ctacaatttg gatgtgttcc agtatgagct gtacaaccca  600
atggccttgt atgggtctgt gcctgtgctc ctggcacaca accctcatcg cgacttgggc  660
atcttctggc tcaatgctgc agagacctgg gttgatatat cttccaacac tgccgggaag  720
accctgtttg ggaagatgat ggactacctg cagggctctg ggagaccccc acagacagat  780
gttcgctgga tgtcagagac tggcatcatt gacgtcttcc tgctgctggg gccctccatc  840
tctgatgttt tccggcaata tgctagtctc acaggaaccc aggcgttgcc ccccactcttc  900
tccctcggct accaccagag ccgttggaac taccgggacg aggctgatgt gctggaagtg  960
gatcagggct ttgatgatca caacctgccc tgtgatgtca tctggctaga cattgaacat  1020
gctgatggca agcggtattt cacctgggac cccagtcgct tccctcagcc ccgcaccatg  1080
cttgagcgct tggcttctaa gaggcggaag ctggtggcca tcgtagaccc ccacatcaag  1140
gtggactccg gctaccgagt tcacgaggag ctgcggaacc tggggctgta tgttaaaacc  1200
cgggatggct ctgactatga gggctggtgc tggccaggct cagctggtta ccctgacttc  1260
actaatccca cgatgagggc ctggtgggct aacatgttca gctatgacaa ttatgagggc  1320
tcagctccca acctctttgt ctggaatgac atgaacgaac catctgtgtt caatggtcct  1380
gaggtcacca tgctcaagga tgcccagcat tatggggggct gggagcaccg ggatgtgcat  1440
aacatctatg gcctttatgt gcacatggcg actgctgatg ggctgagaca gcgctctggg  1500
ggcatggaac gcccctttgt cctggccagg gccttcttcg ctggctccca gcgctttgga  1560
gccgtgtgga caggggacaa cactgccgag tgggaccatt tgaagatctc tattcctatg  1620
tgtctcagct tggggctggt gggactttcc ttctgtgggg cggatgtggg tggcttcttc  1680
aaaaacccag agccagagct gcttgtgcgc tggtaccaga tgggtgctta ccagccattc  1740
ttccgggcac atgcccactt ggacactggg cgacgagagc catggctgtt accatctcag  1800
cacaatgata taatccgaga tgccttgggc cagcgatatt ctttgctgcc cttctggtac  1860
accctcttat atcaggccca tcgggaaggc attcctgtca tgaggcccct gtgggtgcag  1920
taccctcagg atgtgactac cttcaatata gatgatcagt acttgcttgg ggatgcgttg  1980
ctggttcacc ctgtatcaga ctctggagcc catggtgtcc aggtctatct gcctggccaa  2040
ggggaggtgt ggtatgacat tcaaagctac cagaagcatc atggtcccca gaccctgtac  2100
ctgcctgtaa ctctaagcag tatccctgtg ttccagcgtg gagggacaat cgtgcctcga  2160
tggatgcgag tgcggcggtc ttcagaatgt atgaaggatg accccatcac tctctttgtt  2220
gcacttagcc ctcagggtac agctcaagga gagctctttc tggatgatgg gcacacgttc  2280
aactatcaga ctcgccaaga gttcctgctg cgtcgattct cattctctgg caacaccctt  2340
gtctccagct cagcagaccc tgaaggacac tttgagacac caatctggat tgagcgggtg  2400
gtgataatag gggctggaaa gccagcagct gtggtactcc agacaaaagg atctccagaa  2460
agccgcctgt ccttccagca tgaccctgag acctctgtgt tggtcctgcg caagcctggc  2520
atcaatgtgg catctgattg gagtattcac ctgcgataa                        2559

SEQ ID NO: 14           moltype = AA  length = 852
FEATURE                 Location/Qualifiers
source                  1..852
                        mol_type = protein
                        organism = Homo sapiens
SEQUENCE: 14
MAAVAAVAAR RRRLSVSGRD ENSVELTMAE GPYKIILTAR PFRLDLLEDR SLLLSVNARG  60
LLEFEHQRAP RVSFSDKVNL TLGSIWDKIK NLFSRQGSKD PAEGDGAQPE ETPRDGDKPE  120
ETQGKAEKDE PGAWEETFKT HSDSKPYGPM SVGLDFSLPG MEHVYGIPEH ADNLRLKVTE  180
GGEPYRLYNL DVFQYELYNP MALYGSVPVL LAHNPHRDLG IFWLNAAETW VDISSNTAGK  240
TLFGKMMDYL QGSGETPQTD VRWMSETGII DVFLLLGPSI SDVFRQYASL TGTQALPPLF  300
SLGYHQSRWN YRDEADVLEV DQGFDDHNLP CDVIWLDIEH ADGKRYFTWD PSRFPQPRTM  360
LERLASKRRK LVAIVDPHIK VDSGYRVHEE LRNLGLYVKT RDGSDYEGWC WPGSAGYPDF  420
TNPTMRAWWA NMFSYDNYEG SAPNLFVWND MNEPSVFNGP EVTMLKDAQH YGGWEHRDVH  480
NIYGLYVHMA TADGLRQRSG GMERPFVLAR AFFAGSQRFG AVWTGDNTAE WDHLKISIPM  540
CLSLGLVGLS FCGADVGGFF KNPEPELLVR WYQMGAYQPF FRAHAHLDTG RREPWLLPSQ  600
HNDIIRDALG QRYSLLPFWY TLLYQAHREG IPVMRPLWVQ YPQDVTTFNI DDQYLLGDAL  660
LVHPVSDSGA HGVQVYLPGQ GEVWYDIQSY QKHHGPQTLY LPVTLSSIPV FQRGGTIVPR  720
WMRVRRSSEC MKDDPITLFV ALSPQGTAQG ELFLDDGHTF NYQTRQEFLL RRFSFSGNTL  780
VSSSADPEGH FETPIWIERV VIIGAGKPAA VVLQTKGSPE SRLSFQHDPE TSVLVLRKPG  840
INVASDWSIH LR                                                     852

SEQ ID NO: 15           moltype = AA  length = 13
FEATURE                 Location/Qualifiers
source                  1..13
                        mol_type = protein
                        organism = synthetic construct
SEQUENCE: 15
SVAGPSNMAV QGR                                                    13

SEQ ID NO: 16           moltype = AA  length = 4
FEATURE                 Location/Qualifiers
source                  1..4
```

```
                         mol_type = protein
                         organism = synthetic construct
SEQUENCE: 16
EFAW                                                                 4

SEQ ID NO: 17            moltype = DNA  length = 2307
FEATURE                  Location/Qualifiers
source                   1..2307
                         mol_type = unassigned DNA
                         organism = Mus musculus
SEQUENCE: 17
cattaacaaa gcacagcgct cagcaagaca cctttctacc tctgtccctg ctggaaagca  60
ccaggaagag ctacacaggg tagacatgga tgaggacaaa ggcaagagag accccatcca  120
aatgagtttg aagggatgcc gaaccaataa cgggtttgtc caaaatgaag acattccgga  180
gcaggaccca gacccaggct ccagggacac ccccacagccc aacgccgtga gtatccctgc  240
tccagaggag cctcacctaa aggcggtgcg gccctatgca gggatgccca aggaagtact  300
cttccagttc tccggccagg ctcgctaccg ggtgccccga gagatcctct tctggctcac  360
cgtggtttcc gtgttcctgc tcattggagc caccatagcc atcatcgtca tctctccaaa  420
atgccttgac tggtggcaag caggtcccat ataccagatc tacccgaggt cttttaagga  480
cagtgacaag gatgggaatg gagacctgaa aggtatccag gagaagctgg actatatcac  540
tgctttaaac ataaagactc tttggatcac ttccttttat aaatcatctt tgaaagactt  600
cagatacgct gttgaggatt tcaaagaaat tgaccctatt tttggaacaa tgaaagattt  660
tgagaatttg gttgctgcca tccatgacaa aggtttaaaa ttaataattg atttcatacc  720
aaaccacact agtgacaaac atccttggtt ccaatcgagt aggacacgga gcggaaaata  780
caccgattac tacatctggc acaactgtac ccatgtcaac ggtgtaacca cccctcccaa  840
caactggctg agtgtgtatg gaaactccag ctggcacttt gatgaagtac gaaagcaatg  900
ttattttcac cagtttttga aagagcaacc agatttaaat ttccgaaatc ctgctgttca  960
agaggaaata aaggaaataa taacgttctg gctctcgaag ggtgttgatg ggtttagttt  1020
tgatgcagtt aaatttcttc tggaagcgaa ggatctgaga aatgaaatcc aagtgaatac  1080
atcccaaatt ccggacacgg tcacccacta ctcagagctg taccatgact tcaccacaac  1140
tcaggtggga atgcatgaca tcgtccgaga cttccggcag accatgaacc agtacagcag  1200
ggagcctggc agataccggt tcatgggggc cgaagcctca gctgagagca tcgagaggac  1260
catgatgtac tatggcttgc catttatcca ggaagccgac tttcctttca acaagtactt  1320
caccacaata ggcactctct ctgggcatac tgtctatgaa gttatcacat cctggatgga  1380
aaacatgcct gaaggaaaat ggcccaattg gatgactggc ggaccggaga ctcctcggct  1440
gacttctcga gtagggagtg agtatgtcaa cgccatgcac atgctcctgt tcacactccc  1500
gggaacgccc atcacttact atggagagga aatcgggatg ggagacattt ccgttacaaa  1560
tttcaacgag agctatgata gtactaccct tgtctccaag tcaccgatgc agtgggacaa  1620
tagttccaat gctgggttta ctgaggccaa ccacacctgg ctacccacaa actctgacta  1680
ccacaccgtc aatgtggatg tccaaaagac ccagccgagc tcagcactga ggctgtatca  1740
ggatctgagt ctactccatg ccacagagct ggtcctcagc cggggctggt tttgcctctt  1800
gagagacgac agtcactctg tggtgtacac aagagagctg gacggcatag ataacgtctt  1860
cctcgtggtt ctgaattttg gagaatcatc aactgtgcta aatctacagg ggatcatttc  1920
agatcttcct ccagagctga gaataaggtt aagtaccaac tcagcctcca aaggcagtgc  1980
tgttgacacc cgtgccattt ctctggagaa gggagagggc ctggtcttgg agcacagcac  2040
gaaggctccc ctccatcagc aggccgcttt cagagacaga tgctttgttt ccagtcgggc  2100
gtgctactcc agtgcactgg acatcctcta tagctcgtgt taggaaggaa gctccctaag  2160
agatggccac ccagaacatc acgtacgcac agggctgagc agactcatga atggcatcaa  2220
ttcttagata tttctgtagc acgaatgcac tgtttttaaa gtgtttaaaa gattatgcca  2280
aaatactaaa gcatttaaat atgaaaa                                      2307

SEQ ID NO: 18            moltype = AA  length = 685
FEATURE                  Location/Qualifiers
source                   1..685
                         mol_type = protein
                         organism = Mus musculus
SEQUENCE: 18
MDEDKGKRDP IQMSLKGCRT NNGFVQNEDI PEQDPDPGSR DTPQPNAVSI PAPEEPHLKA  60
VRPYAGMPKE VLFQFSGQAR YRVPREILFW LTVVSVFLLI GATIAIIVIS PKCLDWWQAG  120
PIYQIYPRSF KDSDKDGNGD LKGIQEKLDY ITALNIKTLW ITSFYKSSLK DFRYAVEDFK  180
EIDPIFGTMK DFENLVAAIH DKGLKLIIDF IPNHTSDKHP WFQSSRTRSG KYTDYYIWHN  240
CTHVNGVTTP PNNWLSVYGN SSWHFDEVRK QCYFHQFLKE QPDLNFRNPA VQEEIKEIIT  300
FWLSKGVDGF SFDAVKFLLE AKDLRNEIQV NTSQIPDTVT HYSELYHDFT TTQVGMHDIV  360
RDFRQTMNQY SREPGRYRFM GAEASAESIE RTMMYYGLPF IQEADFPFNK YFTTIGTLSG  420
HTVYEVITSW MENMPEGKWP NWMTGGPETP RLTSRVGSEY VNAMHMLLFT LPGTPITYYG  480
EEIGMGDISV TNFNESYDST TLVSKSPMQW DNSSNAGFTE ANHTWLPTNS DYHTVNVDVQ  540
KTQPSSALRL YQDLSLLHAT ELVLSRGWFC LLRDDSHSVV YTRELDGIDN VFLVVLNFGE  600
SSTVLNLQGI ISDLPPELRI RLSTNSASKG SAVDTRAISL EKGEGLVLEH STKAPLHQQA  660
AFRDRCFVSS RACYSSALDI LYSSC                                        685
```